US011497770B2

(12) United States Patent
Schneider et al.

(10) Patent No.: US 11,497,770 B2
(45) Date of Patent: Nov. 15, 2022

(54) COMPOSITIONS AND METHODS FOR TREATING CANCER WITH TSLPR-CD19 OR TSLPR-CD22 IMMUNOTHERAPY

(71) Applicants: Lentigen Technology, Inc., Gaithersburg, MD (US); University of Colorado, Denver, CO (US)

(72) Inventors: Dina Schneider, Potomac, MD (US); Boro Dropulic, Ellicott City, MD (US); Terry James Fry, Denver, CO (US)

(73) Assignees: Lentigen Technology, Inc., Gaithersburg, MD (US); The Regemts of the University of Colorado, Denver, CO (US)

( * ) Notice: Subject to any disclaimer, the term of this patent is extended or adjusted under 35 U.S.C. 154(b) by 0 days.

(21) Appl. No.: 17/354,624

(22) Filed: Jun. 22, 2021

(65) Prior Publication Data

US 2021/0379110 A1 Dec. 9, 2021

Related U.S. Application Data

(60) Provisional application No. 63/042,437, filed on Jun. 22, 2020.

(51) Int. Cl.

| | |
|---|---|
| ***C12N 15/63*** | (2006.01) |
| ***C12N 15/13*** | (2006.01) |
| ***C07K 14/47*** | (2006.01) |
| ***A61K 39/395*** | (2006.01) |
| ***A61K 35/17*** | (2015.01) |
| ***C07K 14/725*** | (2006.01) |
| ***C07K 14/705*** | (2006.01) |
| ***C07K 16/28*** | (2006.01) |
| *A61K 38/00* | (2006.01) |

(52) U.S. Cl.

CPC .......... *A61K 35/17* (2013.01); *C07K 14/7051* (2013.01); *C07K 14/70521* (2013.01); *C07K 16/2803* (2013.01); *A61K 38/00* (2013.01); *C07K 2317/622* (2013.01); *C07K 2319/03* (2013.01)

(58) Field of Classification Search

None

See application file for complete search history.

(56) References Cited

U.S. PATENT DOCUMENTS

2016/0311910 A1* 10/2016 Qin .................... C07K 14/7051
2018/0355052 A1* 12/2018 Orentas ............ C07K 14/70517
2020/0147134 A1* 5/2020 Qin .................... C07K 16/2803

FOREIGN PATENT DOCUMENTS

WO WO 2015/084513 6/2015
WO WO 2016/149578 9/2016
WO WO 2018/028647 2/2018
WO WO 2018/045325 3/2018
WO WO 2019178382 * 9/2019
WO WO 2020/069184 4/2020

OTHER PUBLICATIONS

Albinger et al, Current status and perspective of CAR-T and CAR-NK cell therapy trials in Germany, Gene Therapy, 2020, pp. 1-15.*

Hollingsworth and Jansen, Turning the comer on therapeutic cancer vaccines, npj Vaccines (2019), pp. 1-10.*

Durgeau et al, Recent Advances in Targeting CD8 T-Cell Immunity for More Effective Cancer Immunotherapy, Front. Immunol., Jan. 22, 2018, pp. 1-14.*

Cadhila etal, Enabling T Cell Recruitment to Tumours as a Strategy for Improving Adoptive T Cell Therapy, European Oncology & Haematology, 2017, pp. 66-73.*

Qin et al., "Eradication of B-ALL using chimeric antigen receptor-expressing T cells targeting the TSLPR oncoprotein," Blood, The Journal of the American Society of Hematology, Jul. 30, 2015, 126(5):629-639.

Qin et al., "Preclinical development of bivalent chimeric antigen receptors targeting both CD19 and CD22," Molecular Therapy Oncolytics, Dec. 21, 2018, 11:127-137.

Walsh et al., "Multi-specific CAR targeting to prevent antigen escape. Current hematologic malignancy reports," Oct. 2019, 14(5):451-459.

* cited by examiner

*Primary Examiner* — Maria Marvich

(74) *Attorney, Agent, or Firm* — Serge Sira; Gregory J. Hwa, Esq.; Fish & Richardson P.C.

(57) ABSTRACT

Chimeric antigen receptors containing TSLPR-CD19 and TSLPR-CD22 antigen binding domains are disclosed. Nucleic acids, recombinant expression vectors, host cells, antigen binding fragments, and pharmaceutical compositions, relating to the chimeric antigen receptors are also disclosed. Methods of treating or preventing cancer in a subject, and methods of making chimeric antigen receptor T cells are also disclosed.

5 Claims, 16 Drawing Sheets

Specification includes a Sequence Listing.

COMPOSITIONS AND METHODS FOR TREATING CANCER WITH TSLPR-CD19 OR TSLPR-CD22 IMMUNOTHERAPY

CROSS-REFERENCE TO RELATED APPLICATIONS

This application claims the benefit of priority under 35 U.S.C. Section 119(e) to U.S. Provisional Patent Application No. 63/042,437, filed on Jun. 22, 2020, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Jun. 21, 2021, is named Sequence Listing.txt and is 285 kilobytes in size.

FIELD OF THE DISCLOSURE

This application relates to the field of cancer, particularly to CARs targeting TSLPR and CD19 or CD22 B cell antigens simultaneously, via TSLPR-CD19 or TSLPR-CD22 antigen-targeting domains and chimeric antigen receptors (CARs) containing such TSLPR-CD19 or TSLPR-CD22 antigen targeting domains and methods of use thereof.

BACKGROUND

Cancer is one of the most deadly threats to human health. In the U.S. alone, cancer affects nearly 1.3 million new patients each year, and is the second leading cause of death after cardiovascular disease, accounting for approximately 1 in 4 deaths. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making treatment extremely difficult.

CD19 is a 85-95 kDa transmembrane cell surface glycoprotein receptor. CD19 is a member of immunoglobulin (Ig) superfamily of proteins, and contains two extracellular Ig-like domains, a transmembrane, and an intracellular signaling domain (Tedder T F, Isaacs, C M, 1989, J Immunol 143:712-171). CD19 modifies B cell receptor signaling, lowering the triggering threshold for the B cell receptor for antigen (Carter, R H, and Fearon, D T, 1992, Science, 256:105-107), and co-ordinates with CD81 and CD21 to regulate this essential B cell signaling complex (Bradbury, L E, Kansas G S, Levy S, Evans R L, Tedder T F, 1992, J Immunol, 149:2841-50). During B cell ontogeny CD19 is able to signal at the pro-B, pre-pre-B cell, pre-B, early B cell stages independent of antigen receptor, and is associated with Src family protein tyrosine kinases, is tyrosine phosphorylated, inducing both intracellular calcium mobilization and inositol phospholipid signaling (Uckun F M, Burkhardt A L, Jarvis L, Jun X, Stealy B, Dibirdik I, Myers D E, Tuel-Ahlgren L, Bolen J B, 1983, J Biol Chem 268:21172-84). The key point of relevance for treatment of B cell malignancies is that CD19 is expressed in a tightly regulated manner on normal B cells, being restricted to early B cell precursors at the stage of IgH gene rearrangement, mature B cells, but not expressed on hematopoietic stem cells, or mature plasma cells (Anderson, K C, Bates, M P, Slaughenhout B L, Pinkus G S, Schlossman S F, Nadler L M, 1984, Blood 63:1424-1433).

CD22, also known as SIGLEC-2 (sialic acid-binding immunoglobulin-likelectin-2), is 95 kDa transmembrane surface glycoprotein and contains 6 Ig-like C2-type domains and one Ig-like V-type domain (uniprot.org/uniprot/P20273 #structure, accessed Jul. 12, 2017). During B-cell ontogeny, CD22 is expressed on the B-cell surface starting at the pre-B cell stage, persists on mature B cells and is lost on plasma cells (Nitschke L, 2009, Immunological Reviews, 230:128-143). CD22 contains intracellular ITIM (immunoreceptor tyrosine-based inhibition motifs) domains which following the engagement of the B cell receptor for antigen serve to down-modulate cellular activation. Antibody binding of CD22 induces co-localization with SHP-1, and intracellular phosphatase that also serves to down-modulate phosorylation-based signal transduction (Lumb S, Fleishcer S J, Wiedemann A, Daridon C, Maloney A, Shock A, Dorner T, 2016, Journal of Cell Communication and Signaling, 10:143-151). The key point of relevance for treatment of B cell malignancies is that CD22 is expressed in a tightly regulated manner on normal B cells, but not expressed on hematopoietic stem cells, or mature plasma cells, making it a suitable target antigen for B cell leukemias. The expression of CD22 on both adult and pediatric (pre-B-ALL) B cell malignancies has led to exploiting this target for both antibody and chimeric antigen receptor (CAR)-T cell-based therapy (Haso W, Lee D W, Shah N N, Stetler-Stevenson M, Yuan C M, Pastan I H, Dimitrov D S, Morgan R A, FitzGerlad D J, Barrett D M, Wayne A S, Mackall C L, Orentas R J, 2013, Blood, 121:1165-1174) (Wayne A S, Kreitman R J, Findley H W, Lew G, Delbrook C, Steinberg S M, Stetler-Stevenson M, FitzGerald D J, Pastan I, 2010, Clinical Cancer Research, 16:1894-1903. Recently, the CD22 CAR was shown high efficacy in Phase I clinical trial of ALL, demonstration the feasibility and the benefits of CD22 targeting in B-All patients that are naïve to CAR therapy or have developed resistance to CD19-targeted therapies (Fry T J, Shah N N, Orentas R J, et al. *Nat Med.* 2018124(1).20-28. doi:10.1038/nm.4441).

Thymic stromal lymphopoietin (TSLP) is a cytokine that shares CD127 but utilizes a second receptor chain, TSLPR (gene name CRLF2) as part of the heterodimeric signaling complex. Overexpression of TSLPR has been identified in 5-10% of pediatric and adult Acute lymphoblastic leukemia (ALL), largely due to translocations or deletions resulting in alternative promoters. Overexpression of TSLPR appears to be associated with poor prognosis in both children and adults with ALL, and it appears that activation of the TSLPR pathway as biologically important for ALL blasts. Also, in approximately 50% of cases, increased TSLPR expression is associated with mutations in the IKZF gene, a particularly high risk subgroup of patients. TSLPR seems to have restricted normal tissue expression. A number of novel approaches to treat B cell leukemia and lymphoma have been developed, including anti-CD22 antibodies linked to bacterial toxins or chemotherapeutic agents (Wayne A S, FitzGerald D J, Kreitman R J, Pastan I, 2014, Immunotoxins for leukemia, Blood, 123:2470-2477). Inotuzumab Ozogamicin (CMC-544, a humanized version of the murine monoclonal antibody G5/44) is an antibody drug conjugate and is currently being evaluated in clinical trials, either as a single agent or given in combination with chemotherapy (NCT01664910, sponsor: M.D. Anderson Cancer Center) (DiJoseph J F, et al., 2004, Blood, 103:1807-1814). As a single agent, outcomes exceeded those seen with standard therapy, although significant liver toxicity was noted (Kantarjian H, et al., 2016, Inotuzumb ozogamicin versus standard therapy for acute lymphoblastic leukemia, New England Journal of Medicine, 375:740-753). Unmodified CD22 therapeutic antibody, Epratuzumab, is also being tested in combination with chemotherapy (NCT01219816, sponsor: Nantes University Hospital). Epratuzumab is a chimeric protein composed of murine CDRs grafted onto a human antibody framework. Although effective in some leukemias, Moxetumomab pasudotox in not in broad clinical development due to problems with both immunogenicity of the bacterial toxin to which the antibody is fused and modest or comparable levels of activity with other agents (see NCT01829711, sponsor: MedImmune, LLC). To date, many of the binding moieties for CD22 employed in CAR constructs utilize a domain derived from these murine antibodies and do not effectively activate T cells that target this CD22 domain (such as the HA22 anti-CD22 binder used as the basis for Moxetumomab pasudotox, see James S E, Greenberg P D, Jensen M C, Lin Y, Wang J, Till B G, Raubitschek A A, Forman S J, Press O W, 2008, Journal of Immunology 180:7028-7038). One anti-CD22 binder that is effective as an anti-CD22 CAR is currently in clinical trial at the National Institutes of Health (NIH), although results have not been published (ClinicalTrials.gov Identifier: NCT02315612, Anti-CD22 Chimeric Receptor T Cells in Pediatric and Young Adults with Recurrent or Refractory CD22-expressing B Cell Malignancies, sponsor: NCI). This binder is based on the m971 fully human antibody developed in the laboratory of Dr. Dimiter Dimitrov (Xiao X, Ho M, Zhu Z, Pastan I, Dimitrov D, 2009, Identification and characterization of fully human anti-CD22 monoclonal antibodies, MABS, 1:297-303). The m971 domain was proven effective as a CAR (Haso W, et al., 2013, Anti-CD22-chimeric antigen receptors targeting B-cell precursor acute lymphoblastic leukemia, Blood, 121:1165-1174). Single-targeting TSLPR CAR has been previously developed by Dr. Terry Fry's group, and demonstrated efficacy against TSLPR-positive tumors in preclinical models of B-ALL. (Qin, Haiying, et al. "Eradication of B-ALL using chimeric antigen receptor-expressing T cells targeting the TSLPR oncoprotein." Blood, The Journal of the American Society of Hematology 126.5 (2015): 629-639.).

The traditional treatment approaches for B-lineage leukemias and lymphomas may involve chemotherapy, and stem cells transplant (see the world wide web at www.cancer.gov). High toxicity associated with these treatments, as well as the risk of complications, such as relapse, secondary malignancy, or GVHD, motivate the search for better therapeutic alternatives. The expression of CD19 on both adult and pediatric (pre-B-ALL) B cell malignancies has led to exploiting this target for both antibody and chimeric antigen receptor (CAR)-T cell-based therapy (Kochenderfer J N, Wilson W H, Janik J E, Dudley M E, Stetler-Stevenson M, Feldman S A, Maric I, Raffeld M, Nathan D A, Lanier B J, Morgan R A, Rosenberg S A, 2010, Blood 116:4099-102; Lee D W, Kochenderfer J N, Stetler-Stevenson M, Cui Y K, Delbrook C, Feldman S A, Orentas R, Sabatino M, Shah N N, Steinberg S M, Stroncek D, Tschernia N, Yuan C, Zhang H, Zhang L, Rosenberg S A, Wayne A S, Mackall C L, 2015, Lancet 385:517-28). Moreover, the presence of CD22 antigen on lymphomas (DLBCL, FL), and leukemias (CLL) make it an attractive additional target for efficient tumor elimination and for the prevention of tumor antigen escape.

The present standard of care for B-lineage leukemias may consists of remission induction treatment by high dose of chemotherapy or radiation, followed by consolidation, and may feature stem cell transplantation and additional courses of chemotherapy as needed (see the world wide web at cancer.gov). High toxicity associated with these treatments, as well as the risk of complications, such as relapse, secondary malignancy, or GVHD, motivate the search for better therapeutic alternatives. The expression of CD19 on both adult and pediatric (pre-B-ALL) B cell malignancies has led to exploiting this target for both antibody and chimeric antigen receptor (CAR)-T cell-based therapy (Kochenderfer J N, Wilson W H, Janik J E, Dudley M E, Stetler-Stevenson M, Feldman S A, Maric I, Raffeld M, Nathan D A, Lanier B J, Morgan R A, Rosenberg S A, 2010, Blood 116:4099-102; Lee D W, Kochenderfer J N, Stetler-Stevenson M, Cui Y K, Delbrook C, Feldman S A, Orentas R, Sabatino M, Shah N N, Steinberg S M, Stroncek D, Tschernia N, Yuan C, Zhang H, Zhang L, Rosenberg S A, Wayne A S, Mackall C L, 2015, Lancet 385:517-28).

A number of novel approaches to treat B cell leukemia and lymphoma have been developed, including bi-specific antibodies that link an anti-CD19 or anti-CD22 binding motif to a T cell binding motif (i.e. Blinatumomab, Blincyto® indicated for the treatment of Philadelphia chromosome-negative relapsed or refractory B-cell precursor acute lymphoblastic leukemia (ALL). To date, many of the binding moieties for CD19 or CD22 employed in CAR constructs utilize a domain derived from murine antibodies. A number of these products are currently being considered for approval including those developed by Novartis and Kite Pharmaceuticals. In April of 2017 Novartis announced that CTL019 (tisagenlecleucel) received FDA breakthrough designation for treatment of adult patients with refractory or recurrent (r/r) DLBCL (diffuse large B cell lymphoma) who failed two or more prior therapies, adding this designation to that for r/r B-cell acute lymphoblastic leukemia (ALL). These indications were based on the Phase II JULIET study (NCT02445248) and the ELIANA study (NCT02435849), respectively. The JULIET trial showed and overall response rate (ORR) of 45%, with a 37% complete response (CR), and an 8% partial response (PR) at three months. In the ELIANA study, 82% of patients infused with the product achieved CR or CR with incomplete count recovery, and the relapse free survival rate at 6 months was 60%. The CAR-T product from Kite Pharmaceuticals (KTE-C19, axicabtagene ciloleucel) was granted breakthrough designation for diffuse large B-cell lymphoma (DLBLC), transformed follicular lymphoma (TFL), and primary mediastinal B-cell lymphoma (PMBCL). In the Kite ZUMA-3 phase II trial of KTE-C19 in r/r ALL, a 73% CR was reported (at 2 months or greater). Whether antibody of CAR-T therapies are utilized, there are still a significant number of patients who are not helped by these therapies, and there is considerable room for improved therapeutic approaches.

Chimeric Antigen Receptors (CARs) are hybrid molecules comprising three essential units: (1) an extracellular antigen-binding motif, (2) linking/transmembrane motifs, and (3) intracellular T-cell signaling motifs (Long A H, Haso W M, Orentas R J. Lessons learned from a highly-active CD22-specific chimeric antigen receptor. Oncoimmunology. 2013; 2 (4):e23621). The antigen-binding motif of a CAR is commonly fashioned after an single chain Fragment variable (ScFv), the minimal binding domain of an immunoglobulin (Ig) molecule. Alternate antigen-binding motifs, such as receptor ligands (i.e., IL-13 has been engineered to bind tumor expressed IL-13 receptor), intact immune receptors, library-derived peptides, and innate immune system effector molecules (such as NKG2D) also have been engineered. Alternate cell targets for CAR expression (such as NK or gamma-delta T cells) are also under development (Brown C E et al. Clin Cancer Res. 2012; 18(8):2199-209; Lehner M et al. PLoS One. 2012; 7 (2):e31210). There remains significant work to be done with regard to defining the most active T-cell population to transduce with CAR vectors, determining the optimal culture and expansion techniques, and defining the molecular details of the CAR protein structure itself.

The linking motifs of a CAR can be a relatively stable structural domain, such as the constant domain of IgG, or designed to be an extended flexible linker. Structural motifs, such as those derived from IgG constant domains, can be used to extend the ScFv binding domain away from the T-cell plasma membrane surface. This may be important for some tumor targets where the binding domain is particularly close to the tumor cell surface membrane (such as for the disialoganglioside GD2; Orentas et al., unpublished observations). To date, the signaling motifs used in CARs always include the CD3-ζ chain because this core motif is the key signal for T cell activation. The first reported second-generation CARs featured CD28 signaling domains and the CD28 transmembrane sequence. This motif was used in third-generation CARs containing CD137 (4-1BB) signaling motifs as well (Zhao Y et al. J Immunol. 2009; 183 (9): 5563-74). With the advent of new technology, the activation of T cells with beads linked to anti-CD3 and anti-CD28 antibody, and the presence of the canonical "signal 2" from CD28 was no longer required to be encoded by the CAR itself. Using bead activation, third-generation vectors were found to be not superior to second-generation vectors in in vitro assays, and they provided no clear benefit over second-generation vectors in mouse models of leukemia (Haso W, Lee D W, Shah N N, Stetler-Stevenson M, Yuan C M, Pastan I H, Dimitrov D S, Morgan R A, FitzGerald D J, Barrett D M, Wayne A S, Mackall C L, Orentas R J. Anti-CD22-chimeric antigen receptors targeting B cell precursor acute lymphoblastic leukemia, Blood. 2013; 121 (7):1165-74; Kochenderfer J N et al. Blood. 2012; 119 (12):2709-20). This is borne out by the clinical success of CD19-specific CARs that are in a second generation CD28/CD3-ζ (Lee D W et al. American Society of Hematology Annual Meeting. New Orleans, La.; Dec. 7-10, 2013) and a CD137/CD3-signaling format (Porter D L et al. N Engl J Med. 2011; 365 (8): 725-33). In addition to CD137, other tumor necrosis factor receptor superfamily members such as OX40 also are able to provide important persistence signals in CAR-transduced T cells (Yvon E et al. Clin Cancer Res. 2009; 15(18):5852-60). Equally important are the culture conditions under which the CAR T-cell populations were cultured, for example the inclusion of the cytokines IL-2, IL-7, and/or IL-15 (Kaiser A D et al. Cancer Gene Ther. 2015; 22(2):72-78).

Current challenges in the more widespread and effective adaptation of CAR therapy for cancer relate to a paucity of compelling targets. Creating binders to cell surface antigens is now readily achievable, but discovering a cell surface antigen that is specific for tumor while sparing normal tissues remains a formidable challenge. One potential way to imbue greater target cell specificity to CAR-expressing T cells is to use combinatorial CAR approaches. In one system, the CD3-ζ and CD28 signal units are split between two different CAR constructs expressed in the same cell; in another, two CARs are expressed in the same T cell, but one has a lower affinity and thus requires the alternate CAR to be engaged first for full activity of the second (Lanitis E et al. Cancer Immunol Res. 2013; 1(1):43-53; Kloss C C et al. Nat Biotechnol. 2013; 31(1):71-5). A second challenge for the generation of a single ScFv-based CAR as an immunotherapeutic agent is tumor cell heterogeneity. At least one group has developed a CAR strategy for glioblastoma whereby the effector cell population targets multiple antigens (HER2, IL-13Ra, EphA2) at the same time in the hope of avoiding the outgrowth of target antigen-negative populations. (Hegde M et al. Mol Ther. 2013; 21(11):2087-101).

T-cell-based immunotherapy has become a new frontier in synthetic biology; multiple promoters and gene products are envisioned to steer these highly potent cells to the tumor microenvironment, where T cells can both evade negative regulatory signals and mediate effective tumor killing. The elimination of unwanted T cells through the drug-induced dimerization of inducible caspase 9 constructs with chemical-based dimerizers, such as AP1903, demonstrates one way in which a powerful switch that can control T-cell populations can be initiated pharmacologically (Di Stasi A et al. N Engl J Med. 2011; 365(18):1673-83). The creation of effector T-cell populations that are immune to the negative regulatory effects of transforming growth factor-β by the expression of a decoy receptor further demonstrates the degree to which effector T cells can be engineered for optimal antitumor activity (Foster A E et al. J Immunother. 2008; 31(5):500-5). Thus, while it appears that CARs can trigger T-cell activation in a manner similar to an endogenous T-cell receptor, a major impediment to the clinical application of this technology to date has been limited in vivo expansion of CAR+ T cells, rapid disappearance of the cells after infusion, and disappointing clinical activity. This may be due in part to the murine origin of some of the CAR sequences employed.

The use of Blinatumomab (bi-specific anti-CD19 and anti-CD3 antibody) has shown impressive results for the gravely ill patients who have received this therapy. Nevertheless the durable remission rate is less than 40%, and at best only 50% of responders can be salvaged to hematopoietic stem cell transplant (HSCT) (see Gore et al., 2014, NCT01471782 and Von Stackelberg, et al., 2014, NCT01471782, summarized in: Benjamin, J E, Stein A S, 2016, Therapeutic Advances in Hematology 7:142-156). The requirement of patients who have received either bi-specific antibody or CAR-T therapy to subsequently undergo HSCT in order to maintain durable responses remains an area of active debate. Although high responses are reported for CD19 CAR-T trials, some even greater than 90%, if the trials are re-cast as "intent to treat" trials the number may be closer to 70% (Davis K L, Mackall C L, 2016, Blood Advances 1:265-268). The best results at 12 months post-CAR19 treatment reported show a RFS of 55% and OS of 79% in patients who were able to receive the T cell product at the University of Pennsylvania (Maude S L, Teachey D T, Rheingold S R, Shaw P A, Aplenc R, Barrett D M, Barker C S, Callahan C, Frey N V, Farzana N, Lacey S F, Zheng A, Levine B, Melenhorst J J, Motley L, Prter D L, June C H, Grupp S A, 2016, J Clin Oncol 34, no15_suppl (May 2016) 3011-3011).

Accordingly, there is an urgent and long felt need in the art for discovering novel compositions and methods for treatment of B-ALL and other TSLPR, CD19 and/or CD22-expressing malignancies using an approach that can exhibit specific and efficacious anti-tumor effect without the aforementioned shortcomings.

The present invention addresses these needs by providing CAR compositions and therapeutic methods that can be used to treat cancers and other diseases and/or conditions. In particular, the present invention as disclosed and described herein provides CARs that may be used for the treatment of diseases, disorders or conditions associated with dysregulated expression of TSLPR, CD19 and/or CD22 and which CARs contain TSLPR-CD19 and/or TSLPR-CD22 antigen binding domains that exhibit a high surface expression on transduced T cells, exhibit a high degree of cytolysis of TSLPR, CD19, and/or CD22-expressing cells, and in which the transduced T cells demonstrate in vivo expansion and persistence.

SUMMARY OF THE INVENTION

Novel TSLPR-CD19, TSLPR-CD22, TSLPR-CD19-CD22 and TSLPR-CD22-CD19-targeting antibodies or antigen binding domains thereof in which the TSLPR-targeting moiety is positioned either before or after the respective CD19 or CD22 targeting moiety in the amino acid sequence (hereinafter termed "TSLPR-CD19" and "TSLPR-CD22," respectively), and chimeric antigen receptors (CARs) that contain such TSLPR-CD19, TSLPR-CD22, TSLPR-CD19-CD22 and/or TSLPR-CD22-CD19 antigen binding domains are provided herein, as well as host cells (e.g., T cells) expressing the receptors, and nucleic acid molecules encoding the receptors. The CARs exhibit a high surface expression on transduced T cells, with a high degree of cytolysis, and with transduced T cell expansion and persistence in vivo. Methods of using the disclosed CARs, host cells, and nucleic acid molecules are also provided, for example, to treat a cancer in a subject.

In one aspect, an isolated nucleic acid molecule encoding a TSLPR-CD19, TSLPR-CD22, TSLPR-CD19-CD22 or TSLPR-CD22-CD19 chimeric antigen receptor (CAR) is provided comprising, from N-terminus to C-terminus, at least one CD19 and/or CD22 antigen binding domain, at least one TSLPR antigen binding domain, at least one transmembrane domain, and at least one intracellular signaling domain, wherein the TSLPR-CD19, TSLPR-CD22, TSLPR-CD19-CD22 or TSLPR-CD22-CD19 CAR comprises a nucleic acid sequence selected from the group consisting of SEQ ID NOs: 1, 3, 60, 62, 64, 66, 68, 70, 72, 74, 76, 78, 80, 82, 84, 86, 88, 90, 92, 94, 96, and 98.

In one aspect, an isolated nucleic acid molecule encoding a TSLPR-CD19, TSLPR-CD22, TSLPR-CD19-CD22 or TSLPR-CD22-CD19 chimeric antigen receptor (CAR) is provided comprising, from N-terminus to C-terminus, at least one CD19 or CD22 antigen binding domain, at least one TSLPR antigen binding domain, at least one transmembrane domain, and at least one intracellular signaling domain, wherein the TSLPR-CD19, TSLPR-CD22, TSLPR-CD19-CD22 or TSLPR-CD22-CD19 CAR encoded by the nucleic acid sequence selected from the group consisting of SEQ ID NOs: 1, 3, 60, 62, 64, 66, 68, 70, 72, 74, 76, 78, 80, 82, 84, 86, 88, 90, 92, 94, 96, and 98 encodes a TSLPR-CD19, TSLPR-CD22, TSLPR-CD19-CD22 or TSLPR-CD22-CD19 CAR comprising the amino acid sequence selected from the group consisting of SEQ ID NOs: 2, 4, 61, 63, 65, 67, 69, 71, 73, 75, 77, 79, 81, 83, 85, 87, 89, 91, 93, 95, 97, and 99.

In one embodiment, an isolated nucleic acid molecule encoding the CAR is provided wherein the encoded extracellular TSLPR-CD19, TSLPR-CD22, TSLPR-CD19-CD22 or TSLPR-CD22-CD19 antigen binding domain comprises at least one single chain variable fragment of an antibody that binds to TSLPR, CD19, or CD22.

In another embodiment, an isolated nucleic acid molecule encoding the CAR is provided wherein the encoded extracellular TSLPR-CD19, TSLPR-CD22, TSLPR-CD19-CD22 or TSLPR-CD22-CD19 antigen binding domain comprises at least one heavy chain variable region of an antibody that binds to TSLPR, CD19 or CD22.

In yet another embodiment, an isolated nucleic acid molecule encoding the CAR is provided wherein the encoded CAR extracellular TSLPR-CD19, TSLPR-CD22, TSLPR-CD19-CD22 or TSLPR-CD22-CD19 antigen binding domain further comprises at least one lipocalin-based antigen binding antigen (anticalins) that binds to TSLPR, CD19, or CD22.

In one embodiment, an isolated nucleic acid molecule is provided wherein the encoded extracellular T SLPR-CD19, T SLPR-CD22, T SLPR-CD19-CD22 or T SLPR-CD22-CD19 antigen binding domain is connected to the transmembrane domain by a linker domain.

In another embodiment, an isolated nucleic acid molecule encoding the CAR is provided wherein the encoded TSLPR-CD19, TSLPR-CD22, TSLPR-CD19-CD22 or TSLPR-CD22-CD19 extracellular antigen binding domain is preceded by a sequence encoding a leader or signal peptide.

In yet another embodiment, an isolated nucleic acid molecule encoding the CAR is provided comprising at least one TSLPR-CD19, TSLPR-CD22, TSLPR-CD19-CD22 or TSLPR-CD22-CD19 antigen binding domain encoded by a nucleotide sequence comprising a TSLPR-CD19, TSLPR-CD22, TSLPR-CD19-CD22 or TSLPR-CD22-CD19 nucleotide sequence contained within SEQ ID Nos: 1, 3, 60, 62, 64, 66, 68, 70, 72, 74, 76, 78, 80, 82, 84, 86, 88, 90, 92, 94, 96, and 98 respectively, and wherein the CAR additionally encodes an extracellular antigen binding domain targets an antigen that includes, but is not limited to, CD22, ROR1, mesothelin, CD33, CD38, CD123 (IL3RA), CD138, BCMA (CD269), GPC2, GPC3, FGFR4, c-Met, PSMA, Glycolipid F77, EGFRvIII, GD-2, NY-ESO-1 TCR, MAGE A3 TCR, or any combination thereof.

In one embodiment, the CAR construct is comprised of two CAR chains co-expressed in the same cell via a 2A ribosomal skip element, one CAR chain comprises a targeting domain directed toward CD19 antigen, and another CAR chain comprises a CAR targeting domain directed toward TSLPR antigen. Fused in frame to the targeting domain, each chain comprises a hinge/linker/spacer domain, a transmembrane domain, and a CD3z activation domain. None, one or more co-stimulatory domains may be included in frame in each CAR chain.

In one embodiment, the CAR construct is comprised of two CAR chains co-expressed in the same cell via a 2A ribosomal skip element, one CAR chain comprises a targeting domain directed toward CD22 antigen, and another CAR chain comprises a CAR targeting domain directed toward TSLPR antigen fused in frame to the targeting domain, each chain comprises a hinge/linker/spacer domain, a transmembrane domain, and a CD3z activation domain. None, one or more co-stimulatory domains may be included in frame in each CAR chain.

In one embodiment, the CAR construct is comprised of two CAR chains co-expressed in the same cell via a 2A ribosomal skip element, one CAR chain comprises a targeting domain directed toward CD19 antigen, another CAR chain comprises a CAR targeting domain directed toward CD22, and another CAR chain comprises a CAR targeting domain directed toward TSLPR antigen. Fused in frame to the targeting domain, each chain comprises a hinge/linker/spacer domain, a transmembrane domain, and a CD3z activation domain. None, one or more co-stimulatory domains may be included in frame in each CAR chain.

In one embodiment, the CAR chain comprises two co-stimulatory domains linked sequentially (a third generation CAR).

In certain embodiments, an isolated nucleic acid molecule encoding the CAR is provided wherein the additionally encoded extracellular antigen binding domain comprises an anti-CD22 ScFv antigen binding domain, an anti CD19 scFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, an anti-TSLPR ScFv antigen binding domain an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESO-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In one aspect, the CARs provided herein further comprise a linker or spacer domain.

In one embodiment, an isolated nucleic acid molecule encoding the CAR is provided wherein the extracellular TSLPR-CD19, TSLPR-CD22, TSLPR-CD19-CD22 or TSLPR-CD22-CD19 antigen binding domain, the intracellular signaling domain, or both are connected to the transmembrane domain by a linker or spacer domain.

In one embodiment, an isolated nucleic acid molecule encoding the CAR is provided wherein the encoded linker domain is derived from the extracellular domain of CD8 or CD28, and is linked to a transmembrane domain.

In another embodiment, an isolated nucleic acid molecule encoding the CAR is provided wherein the encoded CAR further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD83, CD86, CD134, CD137 and CD154, or a combination thereof.

In yet another embodiment, an isolated nucleic acid molecule encoding the CAR is provided wherein the encoded intracellular signaling domain further comprises a CD3 zeta intracellular domain.

In one embodiment, an isolated nucleic acid molecule encoding the CAR is provided wherein the encoded intracellular signaling domain is arranged on a C-terminal side relative to the CD3 zeta intracellular domain.

In another embodiment, an isolated nucleic acid molecule encoding the CAR is provided wherein the encoded at least one intracellular signaling domain comprises a costimulatory domain, a primary signaling domain, or a combination thereof.

In further embodiments, an isolated nucleic acid molecule encoding the CAR is provided wherein the encoded at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, an isolated nucleic acid molecule encoding the CAR is provided that further contains a leader sequence or signal peptide wherein the leader or signal peptide nucleotide sequence comprises the nucleotide sequence of SEQ ID NO: 11.

In yet another embodiment, an isolated nucleic acid molecule encoding the CAR is provided wherein the encoded leader sequence comprises the amino acid sequence of SEQ ID NO: 12.

In one aspect, a chimeric antigen receptor (CAR) is provided herein comprising, from N-terminus to C-terminus, at least one CD19 and/or CD22 antigen binding domain, at least one TSLPR antigen binding domain, at least one transmembrane domain, and at least one intracellular signaling domain.

In one embodiment, a CAR is provided wherein the extracellular TSLPR-CD19, TSLPR-CD22, TSLPR-CD19-CD22 or TSLPR-CD22-CD19 antigen binding domain comprises at least one single chain variable fragment of an antibody that binds to the antigen, or at least one heavy chain variable region of an antibody that binds to the antigen, or a combination thereof.

In another embodiment, a CAR is provided wherein the at least one transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, TNFRSF19, or a combination thereof.

In some embodiments, the CAR is provided wherein CAR additionally encodes an extracellular antigen binding domain comprising CD22, ROR1, mesothelin, CD33, CD38, CD123 (IL3RA), CD138, BCMA (CD269), GPC2, GPC3, FGFR4, TSLPR, c-Met, PSMA, Glycolipid F77, EGFRvIII, GD-2, NY-ESO-1 TCR, MAGE A3 TCR, or an amino acid sequence with 85%, 90%, 95%, 96%, 97%, 98% or 99% identity thereof, or any combination thereof.

In one embodiment, the CAR is provided wherein the extracellular antigen binding domain comprises an anti-CD22 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESO-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In another embodiment, a CAR is provided wherein the at least one intracellular signaling domain comprises a costimulatory domain and a primary signaling domain.

In yet another embodiment, a CAR is provided wherein the at least one intracellular signaling domain comprises a costimulatory domain comprising a functional signaling domain of a protein selected from the group consisting of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, the nucleic acid sequence encoding a CAR comprising the nucleic acid sequence of SEQ ID NO: 84.

In one embodiment, the nucleic acid sequence encodes a CAR comprising the amino acid sequence of SEQ ID NO: 85.

In one embodiment, the nucleic acid sequence encoding a CAR comprising the nucleic acid sequence of SEQ ID NO: 86.

In one embodiment, the nucleic acid sequence encodes a CAR comprising the amino acid sequence of SEQ ID NO: 87.

In one embodiment, the nucleic acid sequence encoding a CAR comprising the nucleic acid sequence of SEQ ID NO: 88.

In one embodiment, the nucleic acid sequence encodes a CAR comprising the amino acid sequence of SEQ ID NO: 89.

In one embodiment, the nucleic acid sequence encoding a CAR comprising the nucleic acid sequence of SEQ ID NO: 90.

In one embodiment, the nucleic acid sequence encodes a CAR comprising the amino acid sequence of SEQ ID NO: 91.

In one embodiment, the nucleic acid sequence encoding a CAR comprising the nucleic acid sequence of SEQ ID NO: 92.

In one embodiment, the nucleic acid sequence encodes a CAR comprising the amino acid sequence of SEQ ID NO: 93.

In one embodiment, the nucleic acid sequence encoding a CAR comprising the nucleic acid sequence of SEQ ID NO: 94.

In one embodiment, the nucleic acid sequence encodes a CAR comprising the amino acid sequence of SEQ ID NO: 95.

In one embodiment, the nucleic acid sequence encoding a CAR comprising the nucleic acid sequence of SEQ ID NO: 96.

In one embodiment, the nucleic acid sequence encodes a CAR comprising the amino acid sequence of SEQ ID NO: 97.

In one embodiment, the nucleic acid sequence encoding a CAR comprising the nucleic acid sequence of SEQ ID NO: 98.

In one embodiment, the nucleic acid sequence encodes a CAR comprising the amino acid sequence of SEQ ID NO: 99.

In one aspect, the CARs disclosed herein are modified to express or contain a detectable marker for use in diagnosis, monitoring, and/or predicting the treatment outcome such as progression free survival of cancer patients or for monitoring the progress of such treatment.

In one embodiment, the nucleic acid molecule encoding the disclosed CARs can be contained in a vector, such as a viral vector. The vector is a DNA vector, an RNA vector, a plasmid vector, a cosmid vector, a herpes virus vector, a measles virus vector, a lentivirus vector, adenoviral vector, or a retrovirus vector, or a combination thereof.

In certain embodiments, the vector further comprises a promoter wherein the promoter is an inducible promoter, a tissue specific promoter, a constitutive promoter, a suicide promoter or any combination thereof.

In yet another embodiment, the vector expressing the CAR can be further modified to include one or more operative elements to control the expression of CAR T cells, or to eliminate CAR-T cells by virtue of a suicide switch. The suicide switch can include, for example, an apoptosis inducing signaling cascade or a drug that induces cell death. In a preferred embodiment, the vector expressing the CAR can be further modified to express an enzyme such thymidine kinase (TK) or cytosine deaminase (CD).

In another aspect, host cells including the nucleic acid molecule encoding the CAR are also provided. In some embodiments, the host cell is a T cell, such as a primary T cell obtained from a subject. In one embodiment, the host cell is a $CD8^+$ T cell.

In yet another aspect, a pharmaceutical composition is provided comprising an anti-tumor effective amount of a population of human T cells, wherein the T cells comprise a nucleic acid sequence that encodes a chimeric antigen receptor (CAR) comprising the amino acid sequence of SEQ ID NO. 2, 4, 61, 63, 65, 67, 69, 71, 73, 75, 77, 79, 81, 83, 85, 87, 89, 91, 93, 95, 97, and 99 wherein the CAR comprises at least one extracellular antigen binding domain comprising a T SLPR-CD19, T SLPR-CD22, T SLPR-CD19-CD22 or T SLPR-CD22-CD19 antigen binding domain, at least one linker domain, at least one transmembrane domain, and at least one intracellular signaling domain, wherein the T cells are T cells of a human having a cancer. The cancer includes, inter alia, a hematological cancer such as leukemia (e.g., chronic lymphocytic leukemia (CLL), acute lymphocytic leukemia (ALL), or chronic myelogenous leukemia (CIVIL), lymphoma (e.g., mantle cell lymphoma, non-Hodgkin's lymphoma or Hodgkin's lymphoma) or multiple myeloma, or a combination thereof.

In one embodiment, a pharmaceutical composition is provided wherein the at least one transmembrane domain of the CAR contains a transmembrane domain of a protein selected from the group consisting of the alpha, beta or zeta chain of the T-cell receptor, CD28, CD3 epsilon, CD45, CD4, CD5, CD8, CD9, CD16, CD22, Mesothelin, CD33, CD37, CD64, CD80, CD83, CD86, CD134, CD137, CD154, TNFRSF19, or a combination thereof.

In another embodiment, a pharmaceutical composition is provided wherein the human cancer includes an adult carcinoma comprising oral and pharynx cancer (tongue, mouth, pharynx, head and neck), digestive system cancers (esophagus, stomach, small intestine, colon, rectum, anus, liver, interhepatic bile duct, gallbladder, pancreas), respiratory system cancers (larynx, lung and bronchus), bones and joint cancers, soft tissue cancers, skin cancers (melanoma, basal and squamous cell carcinoma), pediatric tumors (neuroblastoma, rhabdomyosarcoma, osteosarcoma, Ewing's sarcoma), tumors of the central nervous system (brain, astrocytoma, glioblastoma, glioma), and cancers of the breast, the genital system (uterine cervix, uterine corpus, ovary, vulva, vagina, prostate, testis, penis, endometrium), the urinary system (urinary bladder, kidney and renal pelvis, ureter), the eye and orbit, the endocrine system (thyroid), and the brain and other nervous system, or any combination thereof.

In yet another embodiment, a pharmaceutical composition is provided comprising an anti-tumor effective amount of a population of human T cells of a human having a cancer wherein the cancer is a refractory cancer non-responsive to one or more chemotherapeutic agents. The cancer includes hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (Chronic lymphocytic leukemia), CML (chronic myelogenous leukemia), non-Hodgkin's lymphoma (NHL), pediatric B cell malignancies (including B lineage ALL (acute lymphocytic leukemia)), multiple myeloma lung cancer, breast cancer, ovarian cancer, prostate cancer, colon cancer, melanoma or other hematological cancer and solid tumors, or any combination thereof.

In another aspect, methods of making CAR-containing T cells (hereinafter "CAR-T cells") are provided. The methods include transducing a T cell with a vector or nucleic acid molecule encoding a disclosed CAR that specifically binds TSLPR, CD19, and/or CD22, thereby making the CAR-T cell.

In yet another aspect, a method of generating a population of RNA-engineered cells is provided that comprises introducing an in vitro transcribed RNA or synthetic RNA of a nucleic acid molecule encoding a disclosed CAR into a cell of a subject, thereby generating a CAR cell.

In one embodiment, the disease, disorder or condition associated with the expression of TSLPR, CD19, and/or CD22 is cancer including hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (Chronic lymphocytic leukemia), CIVIL (chronic myelogenous leukemia), non-Hodgkin's lymphoma (NHL), pediatric B cell malignancies (including B lineage ALL (acute lymphocytic leukemia)), multiple myeloma lung cancer, breast cancer, ovarian cancer, prostate cancer, colon cancer, melanoma or other hematological cancer and solid tumors, or any combination thereof.

In another embodiment, a method of blocking T-cell inhibition mediated by a TSLPR-CD19, TSLPR-CD22, TSLPR-CD19-CD22 or TSLPR-CD22-CD19 expressing cell and altering the tumor microenvironment to inhibit tumor growth in a mammal, is provided comprising administering to the mammal an effective amount of a composition comprising a CAR comprising the amino acid sequence selected from the group consisting of SEQ ID NOs: 2, 4, 61, 63, 65, 67, 69, 71, 73, 75, 77, 79, 81, 83, 85, 87, 89, 91, 93, 95, 97, and 99. In one embodiment, the cell is selected from the group consisting of a TSLPR, CD19 and/or CD22-expressing tumor cell, a tumor-associated macrophage, and any combination thereof.

In another embodiment, a method of inhibiting, suppressing or preventing immunosuppression of an anti-tumor or anti-cancer immune response in a mammal, is provided comprising administering to the mammal an effective amount of a composition comprising a CAR selected from the group consisting of SEQ ID NOs: 2, 4, 61, 63, 65, 67, 69, 71, 73, 75, 77, 79, 81, 83, 85, 87, 89, 91, 93, 95, 97, and 99. In one embodiment, the CAR inhibits the interaction between a first cell with a T cell, wherein the first cell is selected from the group consisting of a TSLPR, CD19 and/or CD22-expressing tumor cell, a tumor-associated macrophage, and any combination thereof.

In another aspect, a method is provided for inducing an anti-tumor immunity in a mammal comprising administering to the mammal a therapeutically effective amount of a T cell transduced with vector or nucleic acid molecule encoding a disclosed CAR.

In another embodiment, a method of treating or preventing cancer in a mammal is provided comprising administering to the mammal one or more of the disclosed CARs, in an amount effective to treat or prevent cancer in the mammal. The method includes administering to the subject a therapeutically effective amount of host cells expressing a disclosed CAR that specifically binds TSLPR, CD19 and/or CD22 and/or one or more of the aforementioned antigens, under conditions sufficient to form an immune complex of the antigen binding domain on the CAR and the extracellular domain of TSLPR, CD19 and/or CD22 and/or one or more of the aforementioned antigens in the subject.

In yet another embodiment, a method is provided for treating a mammal having a disease, disorder or condition associated with an elevated expression of a tumor antigen, the method comprising administering to the subject a pharmaceutical composition comprising an anti-tumor effective amount of a population of T cells, wherein the T cells comprise a nucleic acid sequence that encodes a chimeric antigen receptor (CAR), wherein the CAR includes at least one extracellular TSLPR, CD19 and/or CD22 antigen binding domain, or any combination thereof, at least one linker or spacer domain, at least one transmembrane domain, at least one intracellular signaling domain, and wherein the T cells are T cells of the subject having cancer.

In yet another embodiment, a method is provided for treating cancer in a subject in need thereof comprising administering to the subject a pharmaceutical composition comprising an anti-tumor effective amount of a population of T cells, wherein the T cells comprise a nucleic acid sequence that encodes a chimeric antigen receptor (CAR), wherein the CAR comprises the amino acid sequence of SEQ ID NOs: 2, 4, 61, 63, 65, 67, 69, 71, 73, 75, 77, 79, 81, 83, 85, 87, 89, 91, 93, 95, 97, and 99, or any combination thereof, wherein the T cells are T cells of the subject having cancer. In some embodiments of the aforementioned methods, the at least one transmembrane domain comprises a transmembrane the alpha, beta or zeta chain of the T-cell receptor, CD28, CD3 epsilon, CD45, CD4, CD5, CD8, CD9, CD16, CD19, CD22, Mesothelin, CD33, CD37, CD64, CD80, CD83, CD86, CD134, CD137, CD154, TNFRSF16, TNFRSF19, or a combination thereof.

In yet another embodiment, a method is provided for generating a persisting population of genetically engineered T cells in a human diagnosed with cancer. In one embodiment, the method comprises administering to a human a T cell genetically engineered to express a CAR wherein the CAR comprises the amino acid sequence of SEQ ID NOs: 2, 4, 61, 63, 65, 67, 69, 71, 73, 75, 77, 79, 81, 83, 85, 87, 89, 91, 93, 95, 97, and 99, or any combination thereof, at least one transmembrane domain, and at least one intracellular signaling domain wherein the persisting population of genetically engineered T cells, or the population of progeny of the T cells, persists in the human for at least one month, two months, three months, four months, five months, six months, seven months, eight months, nine months, ten months, eleven months, twelve months, two years, or three years after administration.

In one embodiment, the progeny T cells in the human comprise a memory T cell. In another embodiment, the T cell is an autologous T cell.

In all of the aspects and embodiments of methods described herein, any of the aforementioned cancers, diseases, disorders or conditions associated with an elevated expression of a tumor antigen that may be treated or prevented or ameliorated using one or more of the CARs disclosed herein.

In yet another aspect, a kit is provided for making a chimeric antigen receptor T-cell as described supra or for preventing, treating, or ameliorating any of the cancers, diseases, disorders or conditions associated with an elevated expression of a tumor antigen in a subject as described supra, comprising a container comprising any one of the nucleic acid molecules, vectors, host cells, or compositions disclosed supra or any combination thereof, and instructions for using the kit.

It will be understood that the CARs, host cells, nucleic acids, and methods are useful beyond the specific aspects and embodiments that are described in detail herein. The foregoing features and advantages of the disclosure will become more apparent from the following detailed description, which proceeds with reference to the accompanying figures.

CAR constructs diagrams D0101 and D0102 depict the anti-CD19 and anti-TSLPR dual targeting CAR constructs utilizing the human CD19 scFv 19217-1 in conjunction with the murine TSLPR scFv 3G11, where the TSLPR scFv is placed in distal or proximal orientation to the T cell membrane, respectively.

CAR constructs diagrams D0103 and D0104 depict the anti-CD22 and anti-TSLPR dual targeting CAR constructs utilizing the human CD22 scFv 16P17 in conjunction with the murine TSLPR scFv 3G11, where the TSLPR scFv is placed in distal or proximal orientation to the T cell membrane, respectively.

CAR constructs diagrams D0111 and D0112 depict the anti-CD22 and anti-TSLPR dual targeting CAR constructs utilizing the human CD22 scFv m971 in conjunction with the murine TSLPR scFv 3G11, where the TSLPR scFv is placed in distal or proximal orientation to the T cell membrane, respectively.

CAR constructs diagrams D0205 and D0206 depict the anti-CD19 and anti-TSLPR dual targeting CAR constructs utilizing the murine CD19 scFv FMC63 in conjunction with the murine TSLPR scFv 3G11, where the TSLPR scFv is placed in distal or proximal orientation to the T cell membrane, respectively.

Figure 2:
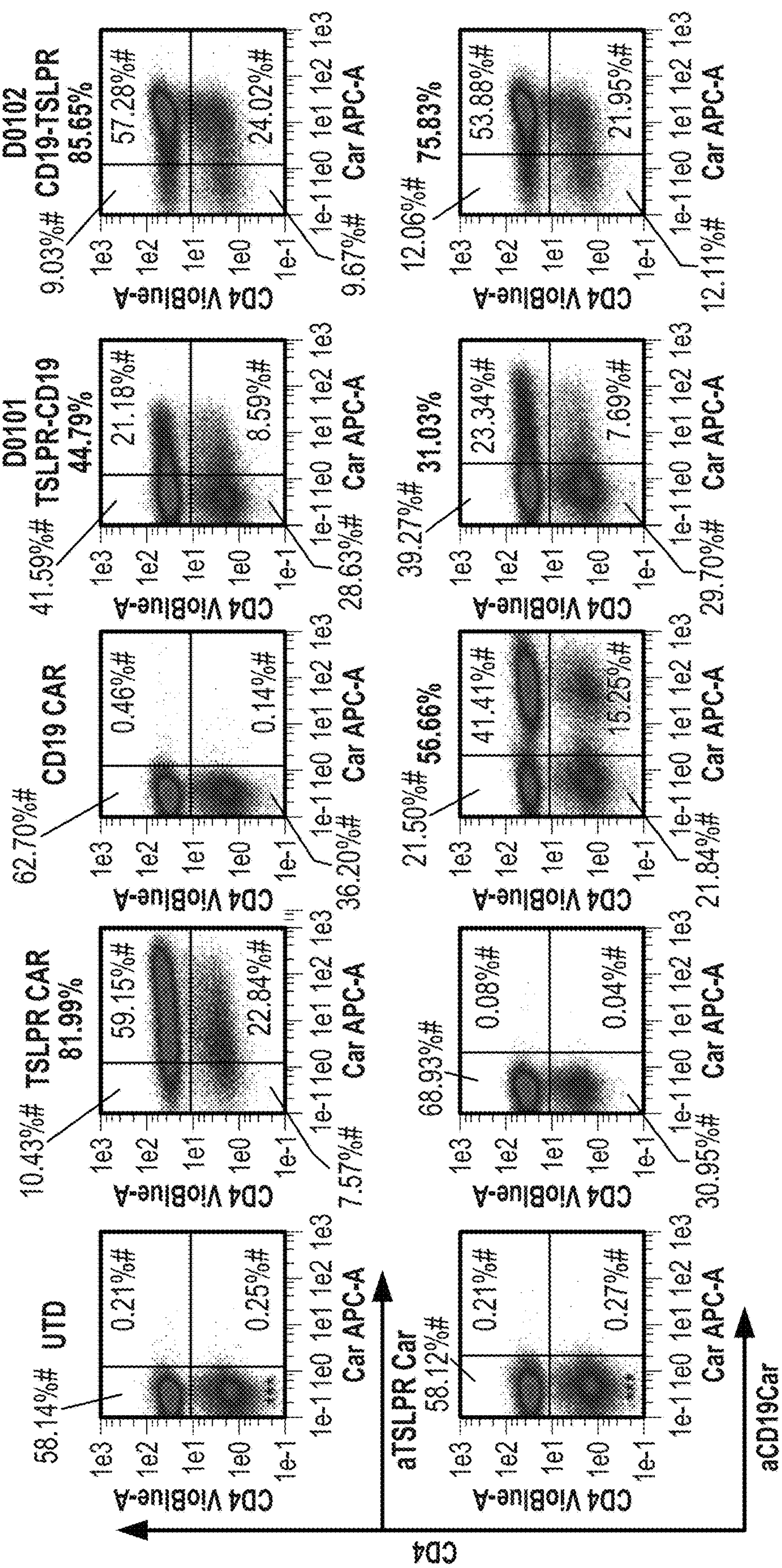

FIG. 2 depicts surface expression of tandem-CAR T constructs D0101(TSLPR-CD19) and D0102 (CD19-TSLPR), comprised of the CD22-targeting scFv sequence 19217_1 and the TSLPR targeting scFv sequence 3G11, on human primary T cells. CAR T expression was determined by flow cytometry. T cells were activated with Miltenyi Biotec TransAct™ CD3 CD28 reagent in the presence of IL-2, and transduced with LV as described in Materials and Methods. On culture day 8, viable transduced T cells (7-AAD negative) were assayed for CAR surface expression using one of two staining methods: TSLPR-Fc reagent followed by anti-Fc-AF647 staining (top panel), or CD19 Fc followed by anti-Fc-AF647 (bottom panel). The CD4 VioBlue antibody (Miltenyi Biotec) was included to differentiate between CAR expression in CD4+ and CD8+ T cells The LV used in transduction is listed on the top of each column. Transductions were performed in LV-saturating conditions. Percentage of CAR T-positive populations in relation to non-transduced T cell control (UTD) is noted above each histogram. Single-targeting CAR controls TSLPR CAR (LTG2282) and CD19 CAR (LTG2065), were included for comparison. Representative data of three separate donors is shown.

Figure 3A:
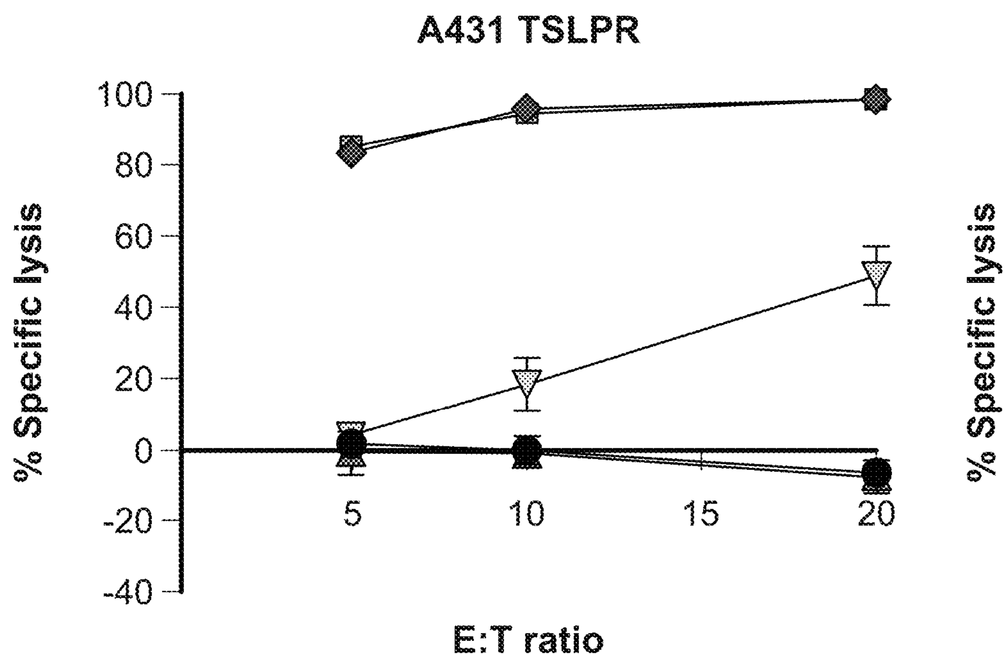
Figure 3B:
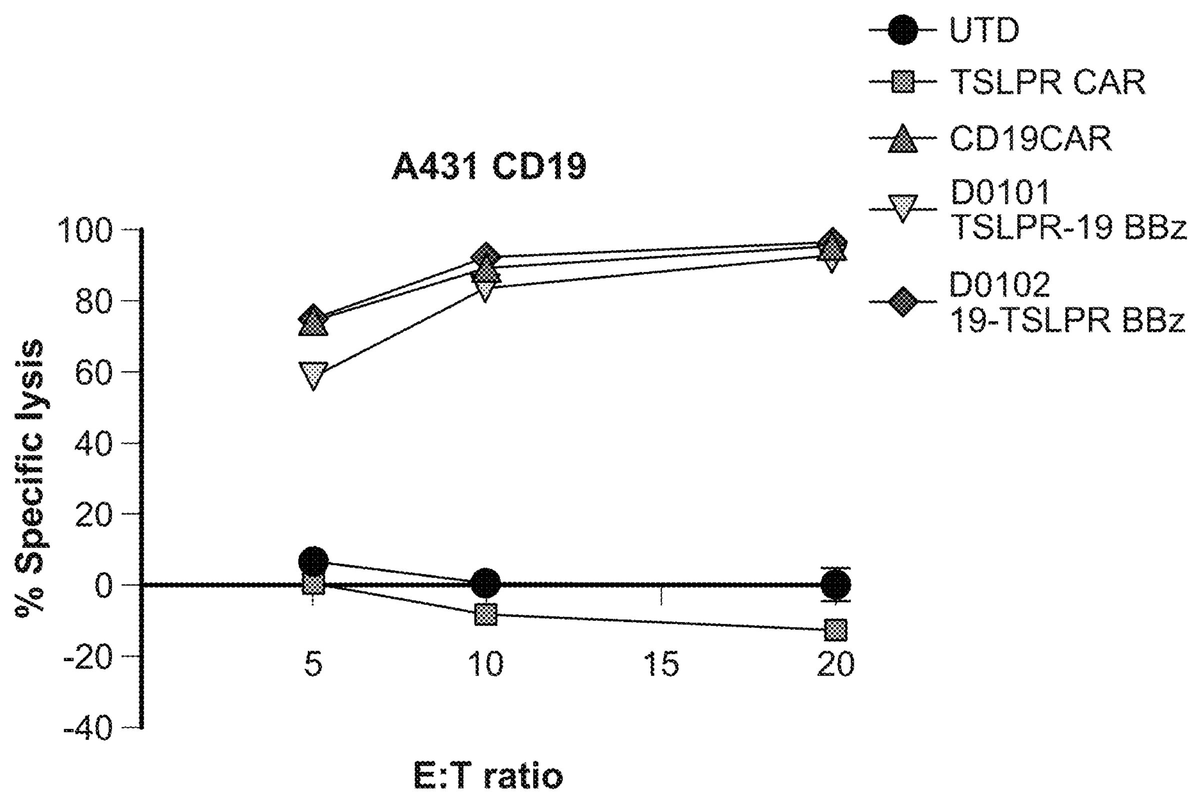
Figure 3C:
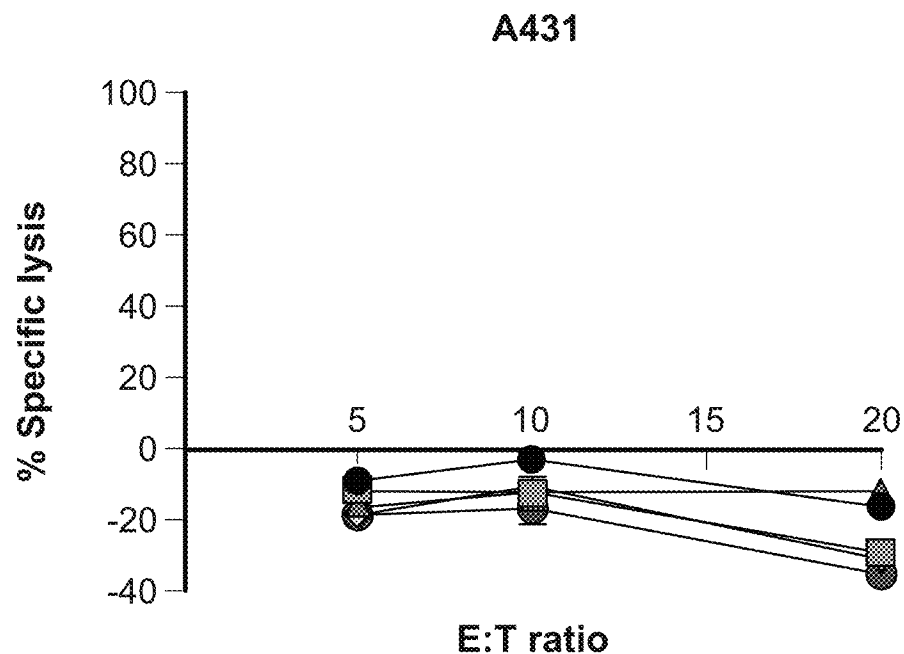

FIGS. 3A-C depict CAR T cytotoxicity in A431-luc tumor cell line clones engineered to stably express each one of the two targeted B-cell antigens. Luciferase-based cytotoxicity assays were performed using FIG. 3A: A431 TSLPR luc line, expressing the TSLPR protein on its surface, FIG. 3B: the A19 cell line stably expressing CD19, or FIG. 3C: the parental A431 cell line clone devoid of CD19 and TSLPR expression. All target lines were stably transduced with firefly luciferase to facilitate the detection of surviving target cells. A comparison between CAR TSLPR-19 BBz (D0101) and CAR 19-TSLPR BBz (D0102), which differ only in the order of antigen targeting domains. Comparator single-targeting CAR19 (pLTG2065) and CAR22 (pLTG2200), and negative control untransduced T cells were included. CAR T cells and target tumor cells were co-incubated overnight at the listed effector to target (E:T) ratios, x-axis. Error bars represent mean values±SEM from three technical replicates. One experiment representing three separate experiments in T cells from three donors, is shown.

FIGS. 4A-D depict CAR T cytotoxicity against the Reh and NALM-6 ALL B-cell tumor lines with or without overexpression of TSLPR. The parental B-cell ALL lines FIG. 4A: Reh and FIG. 4C: NALM-6 stably transduced to express firefly luciferase were engineered to express the TSLPR target protein, to generate FIG. 4B: Reh TSLPR and FIG. 4D: NALM TSLPR clonal lines, respectively. Tumor lysis by tandem TSLPR-19 BBz construct (D0101) (FIG. 4A and FIG. 4B) and 19-TSLPR BBz (D0102) (FIGS. 4A-D) in comparison to single CD19 CAR (LTG2065) or single TSLPR CAR (LTG2282), or untransduced T cells control is shown. Error bars represent mean values±SEM from three technical replicates. One experiment representing three separate experiments in T cells from three donors, is shown.

Figure 5:
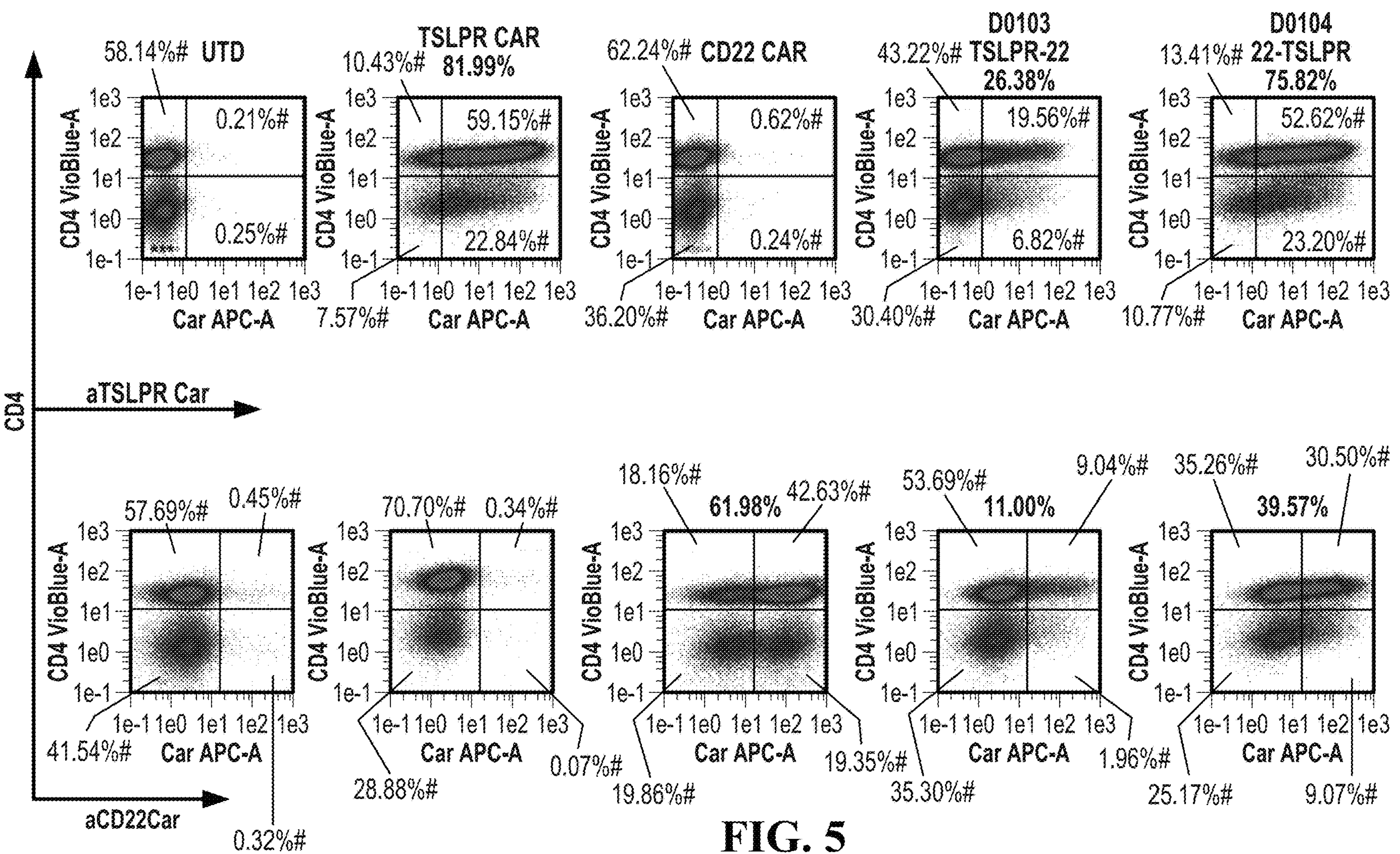

FIG. 5 depicts surface expression of tandem-CAR T constructs D0103(TSLPR-CD22) and D0104 (CD22-TSLPR), comprised of the CD22-targeting scFv sequence 16P17 and the TSLPR targeting scFv sequence 3G11, on human primary T cells. CAR T expression was determined by flow cytometry. T cells were activated with Miltenyi Biotec TransAct™ CD3 CD28 reagent in the presence of IL-2, and transduced with LV as described in Materials and Methods. On culture day 8, viable transduced T cells (7-AAD negative) were assayed for CAR surface expression using one of two staining methods: TSLPR-Fc reagent followed by anti-Fc-AF647 staining (top panel), or CD19 Fc followed by anti-Fc-AF647 (bottom panel). The CD4 VioBlue antibody (Miltenyi Biotec) was included to differentiate between CAR expression in CD4+ and CD8+ T cells. The LV used in transduction is listed on the top of each column. Transductions were performed in LV-saturating conditions. Percentage of CAR T-positive populations in relation to non-transduced T cell control (UTD) is noted above each histogram. Single-targeting CAR controls TSLPR CAR (LTG2282) and CD22 CAR (LTG2200), were included for comparison. Representative data of three separate donors is shown.

Figure 6A:
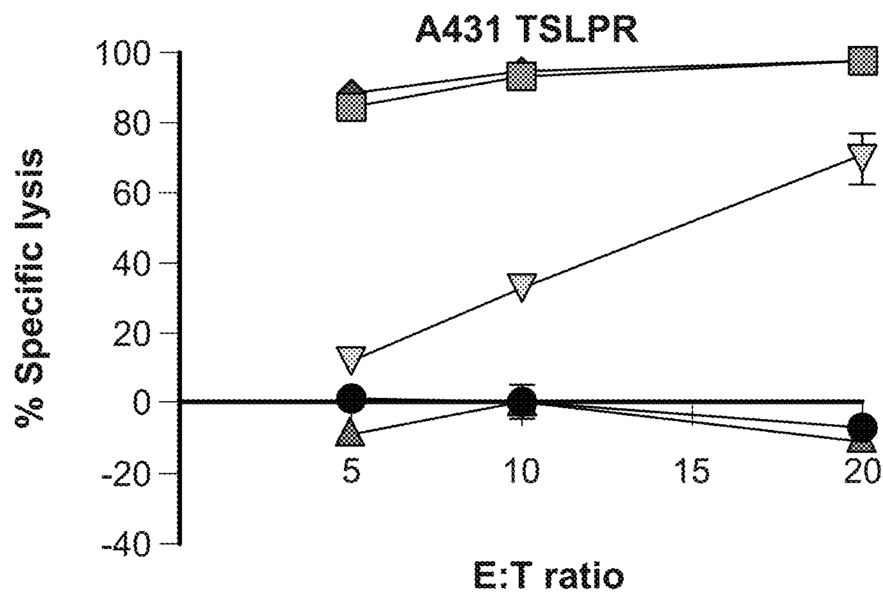
Figure 6B:
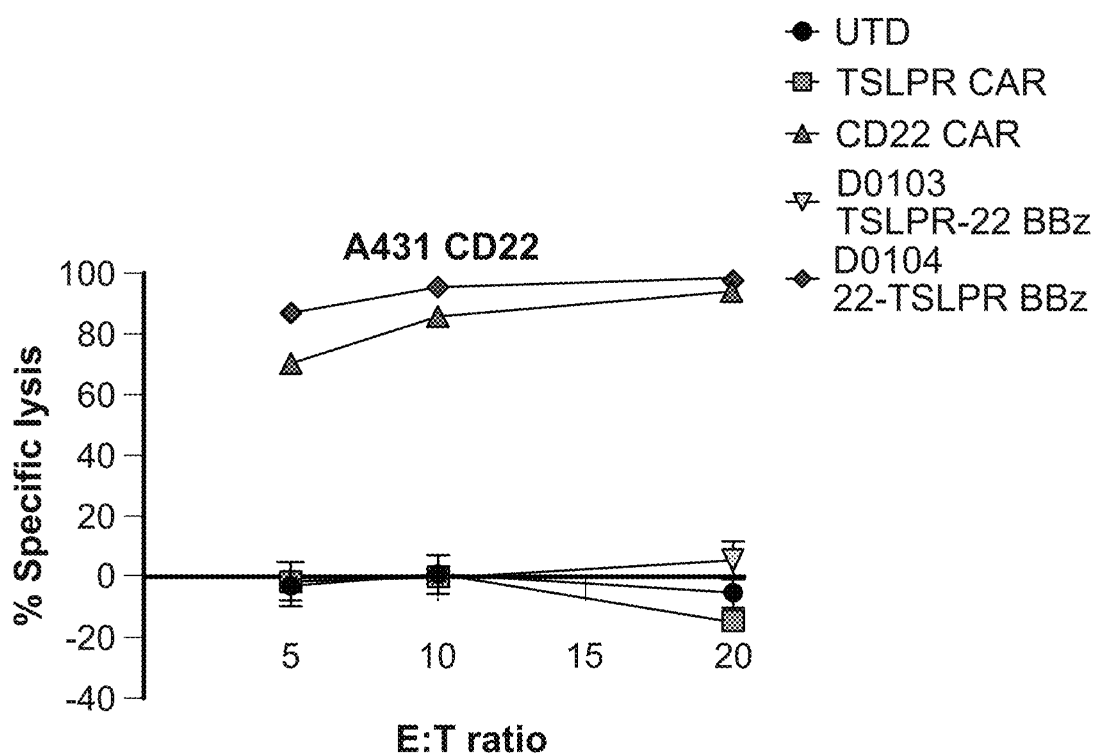
Figure 6C:
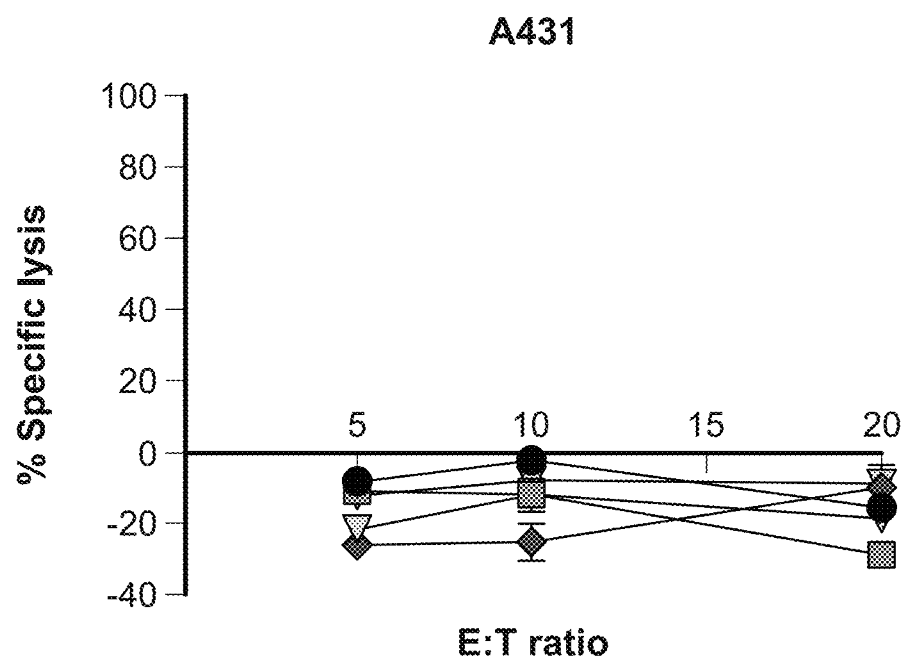

FIGS. 6A-C depict CAR T cytotoxicity in A431-luc tumor cell line clones engineered to stably express each one of the two targeted B-cell antigens, TSLPR and CD22. Luciferase-based cytotoxicity assays were performed using FIG. 6A: A431 TSLPR luc line, expressing the TSLPR protein on its surface, FIG. 6B: the A431 CD22 cell line stably expressing CD22, or FIG. 6C: the parental A431 cell line clone devoid of CD19 and TSLPR expression. All target lines were stably transduced with firefly luciferase to facilitate the detection of surviving target cells. A comparison between CAR TSLPR-22 BBz (D0103) and CAR 22-TSLPR BBz (D0104), which differ only in the order of antigen targeting domains. Comparator single-targeting TSLPR CAR (LTG2282) and CAR22 (LTG2200), and negative control untransduced T cells were included. CAR T cells and target tumor cells were co-incubated overnight at the listed effector to target (E:T) ratios, x-axis. Error bars represent mean values±SEM from three technical replicates. One experiment representing three separate experiments in T cells from three donors, is shown.

FIGS. 7A-D depict CAR T cytotoxicity against the Reh and NALM-6 ALL B-cell tumor lines with or without overexpression of TSLPR. The parental B-cell ALL lines FIG. 7A: Reh and FIG. 7C: NALM-6 stably transduced to express firefly luciferase were engineered to express the TSLPR target protein, to generate FIG. 7B: Reh TSLPR and FIG. 7D: NALM TSLPR clonal lines, respectively. Tumor lysis by tandem TSLPR-22 BBz construct (D0103) (FIG. 7A and FIG. 7B) and 22-TSLPR BBz (D0104) (FIGS. 7A-D) in comparison to single CD22 CAR (LTG2200) or single TSLPR CAR (LTG2282), or untransduced T cells control is shown. Error bars represent mean values±SEM from three technical replicates. One experiment representing three separate experiments in T cells from three donors, is shown.

Figure 8:
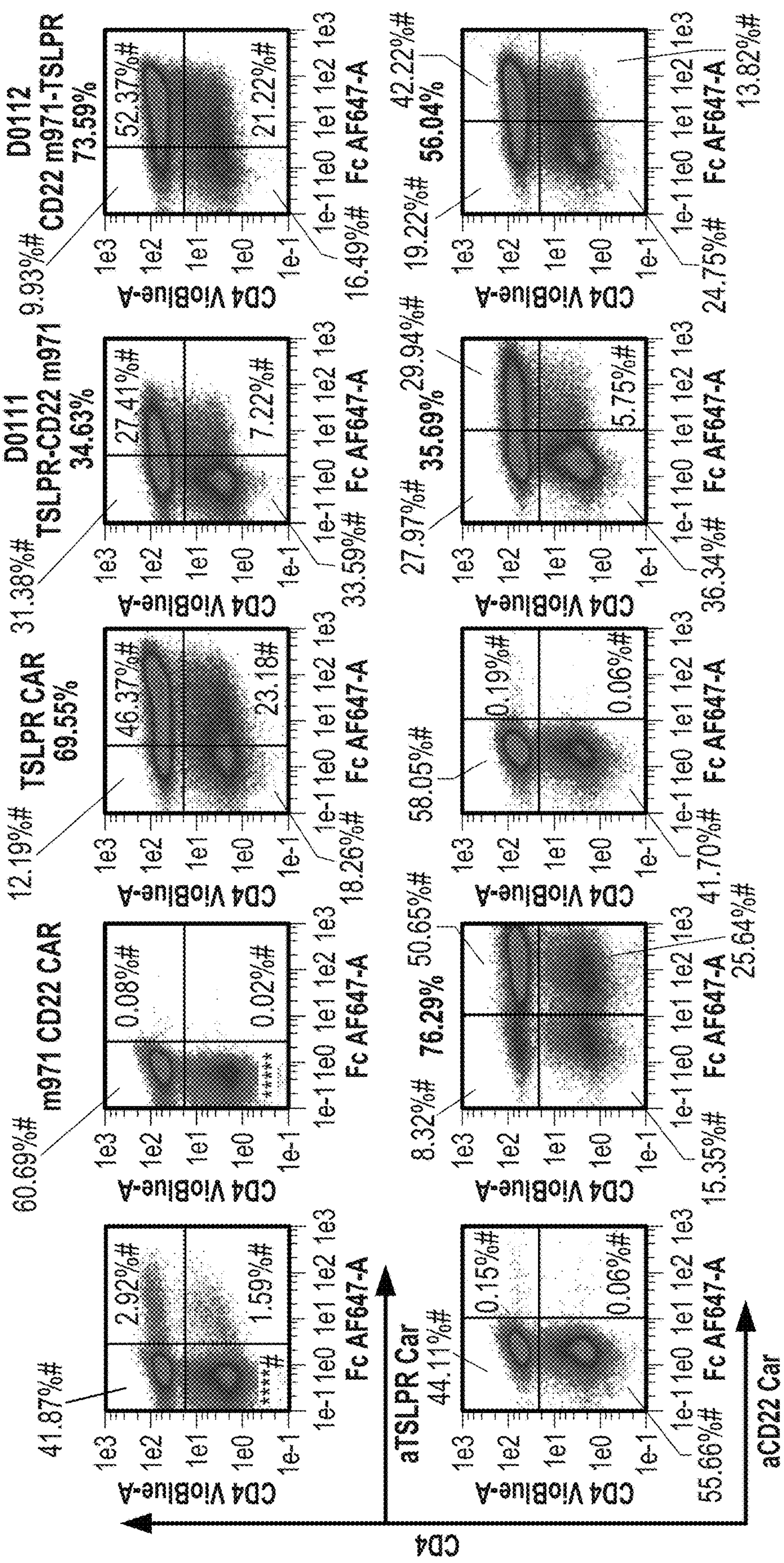

FIG. 8 depicts the surface expression of tandem-CAR T constructs D0111 (TSLPR-CD22) and D0112 (CD22-TSLPR), comprised of the CD22-targeting scFv sequence m971 and the TSLPR targeting scFv sequence 3G11, on human primary T cells. CAR T expression was determined by flow cytometry. T cells were activated with Miltenyi Biotec TransAct™ CD3 CD28 reagent in the presence of IL-2, and transduced with LV as described in Materials and Methods. On culture day 8, viable transduced T cells (7-AAD negative) were assayed for CAR surface expression using one of two staining methods: TSLPR-Fc reagent followed by anti-Fc-AF647 staining (top panel), or CD19 Fc followed by anti-Fc-AF647 (bottom panel). The CD4 VioBlue antibody (Miltenyi Biotec) was included to differentiate between CAR expression in CD4+ and CD8+ T cells. The LV used in transduction is listed on the top of each column. Transductions were performed in LV-saturating conditions. Percentage of CAR T-positive populations in relation to non-transduced T cell control (UTD) is noted above each histogram. Single-targeting CAR controls TSLPR CAR (LTG2282) and CD22 CAR (LTG2200), were included for comparison. Representative data of three separate donors is shown.

Figure 9A:
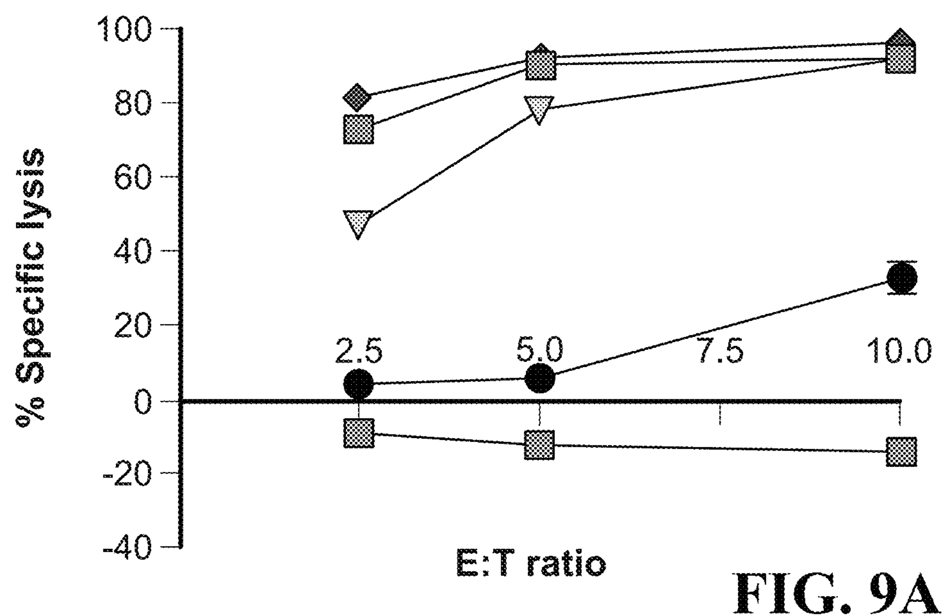
Figure 9B:
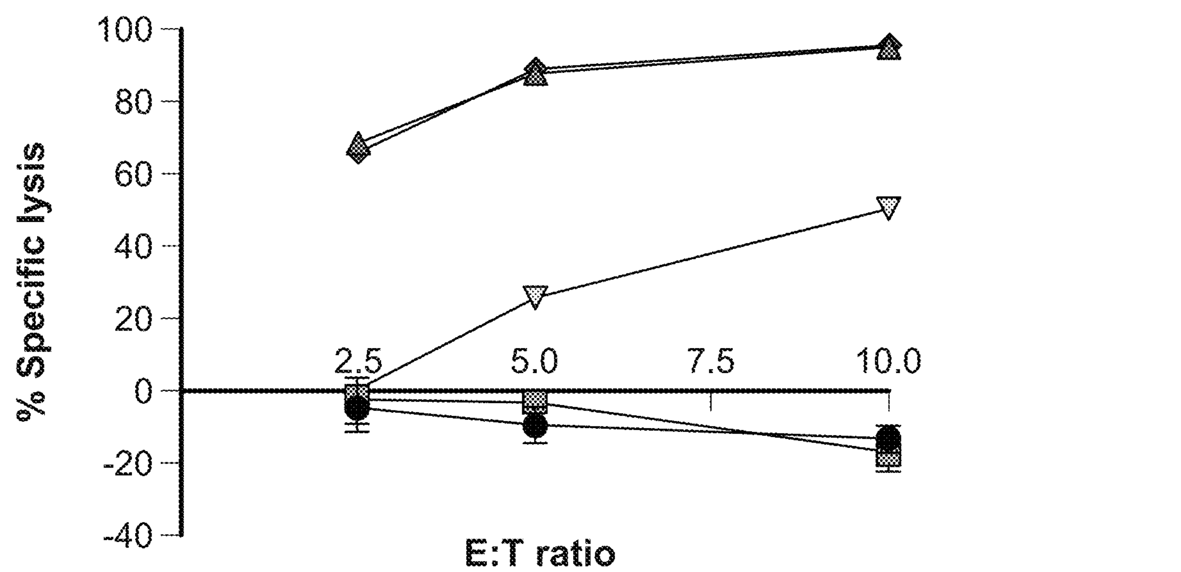
Figure 9C:
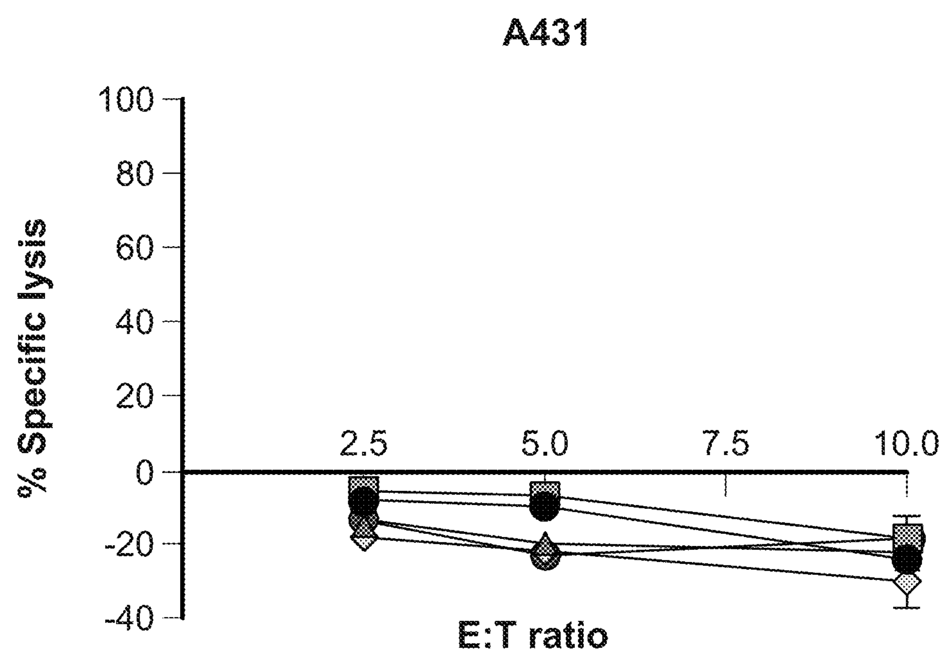

FIGS. 9A-C depict CAR T cytotoxicity in A431-luc tumor cell line clones engineered to stably express each one of the two targeted B-cell antigens, TSLPR and CD22. Luciferase-based cytotoxicity assays were performed using FIG. 9A: The A431 TSLPR luc line, expressing the TSLPR protein on its surface, FIG. 9B: the A431 CD22 cell line stably expressing CD22, or FIG. 9C: the parental A431 cell line clone devoid of CD22 and TSLPR expression. All target lines were stably transduced with firefly luciferase to facilitate the detection of surviving target cells.

A comparison between CAR TSLPR-22m971 BBz (D0111) and CAR 22m971-TSLPR BBz (D0112), which differ only in the order of antigen targeting domains. Comparator single-targeting TSLPR CAR (LTG2282) and CAR22 (LTG2200), and negative control untransduced T cells were included. CAR T cells and target tumor cells were co-incubated overnight at the listed effector to target (E:T) ratios, x-axis. Error bars represent mean values±SEM from three technical replicates. One experiment representing three separate experiments in T cells from three donors, is shown.

FIGS. 10A-D depict CAR T cytotoxicity against the Reh and NALM-6 ALL B-cell tumor lines with or without overexpression of TSLPR. The parental B-cell ALL lines FIG. 10A: Reh and FIG. 10C: NALM-6 stably transduced to express firefly luciferase were engineered to also express the TSLPR target protein, to generate FIG. 10B: Reh TSLPR and FIG. 10D. NALM TSLPR clonal lines, respectively. Tumor lysis by tandem TSLPR-22 BBz construct (D0111) (FIG. 10A and FIG. 10B) and 22-TSLPR BBz (D0112) (FIGS. 10A-D) in comparison to single CD22 CAR (LTG2200) or single TSLPR CAR (LTG2282), or untransduced T cells control is shown. Error bars represent mean values±SEM from three technical replicates. One experiment representing three separate experiments in T cells from three donors, is shown.

DETAILED DESCRIPTION OF THE INVENTION

Definitions

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements. The phrase "and/or" means "and" or "or." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

The term "about" when referring to a measurable value such as an amount, a temporal duration, and the like, is meant to encompass variations of .+−.20% or in some instances .+−.10%, or in some instances .+−.5%, or in some instances .+−.1%, or in some instances .+−.0.1% from the specified value, as such variations are appropriate to perform the disclosed methods.

Unless otherwise noted, the technical terms herein are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

The present disclosure provides for TSLPR-CD19, TSLPR-CD22, TSLPR-CD19-CD22 and TSLPR-CD22-CD19 antibodies or fragments thereof as well as chimeric antigen receptors (CARs) having such T SLPR-CD19, T SLPR-CD22, T SLPR-CD19-CD22 or T SLPR-CD22-CD19 antigen binding domains. The enhancement of the functional activity of the CAR directly relates to the enhancement of functional activity of the CAR-expressing T cell. As a result of one or more of these modifications, the CARs exhibit both a high degree of cytokine-induced cytolysis and cell surface expression on transduced T cells, along with an increased level of in vivo T cell expansion and persistence of the transduced CAR-expressing T cell. The CARs of the present disclosure are advantageous in that one CART lentiviral product may be utilized to treat multiple patient populations (i.e. $TSLPR^+$, $CD19^+$, $CD22^+$, double $CD19^+CD22^+$, or triple $TSLPR^+CD19^+CD22^+$ cancer patients), which allows flexibility in circumstances where resources are limited.

In the TSLPR-CD19-CD22 and TSLPR-CD22-CD19 CARs of the present disclosure, the TSLPR-CD19-CD22 antigen binding domains may be constructed on a single CAR (Triple CAR). Alternatively, the TSLPR-CD19-CD22 antigen binding domains may be constructed on a combination of single and tandem CARs, with the TSLPR-CD22-CD19 CAR antigen binding domains present in any of the possible combinations thereto. The anti-CD19/anti-CD22 antigen binders utilized in the TSLPR-CD19-CD22 and TSLPR-CD22-CD19 CARs are disclosed in Applicant's co-pending patent application Ser. No. 16/584,308, entitled Compositions and Methods for Treating Cancer with Anti-CD19/22 Immunotherapy, as filed on Sep. 26, 2019, and assigned Lentigen Technology, Inc. matter number LEN 025, which is incorporated by reference herein in its entirety.

The unique ability to combine functional moieties derived from different protein domains has been a key innovative feature of Chimeric Antigen Receptors (CARs). The choice of each of these protein domains is a key design feature, as is the way in which they are specifically combined. Each design domain is an essential component that can be used across different CAR platforms to engineer the function of lymphocytes. For example, the choice of the extracellular binding domain can make an otherwise ineffective CAR be effective.

The invariable framework components of the immunoglobulin-derived protein sequences used to create the extracellular antigen binding domain of a CAR can either be entirely neutral, or they can self-associate and drive the T cell to a state of metabolic exhaustion, thus making the therapeutic T cell expressing that CAR far less effective. This occurs independently of the antigen binding function of this CAR domain. Furthermore, the choice of the intracellular signaling domain(s) also can govern the activity and the durability of the therapeutic lymphocyte population used for immunotherapy. While the ability to bind target antigen and the ability to transmit an activation signal to the T cell through these extracellular and intracellular domains, respectively, are important CAR design aspects, what has also become apparent is that the choice of the source of the extracellular antigen binding fragments can have a significant effect on the efficacy of the CAR and thereby have a defining role for the function and clinical utility of the CAR.

The CARs disclosed herein are expressed at a high level in a cell. A cell expressing the CAR has a high in vivo proliferation rate, produces large amounts of cytokines, and has a high cytotoxic activity against a cell having, on its surface, a TSLPR-CD19, TSLPR-CD22, TSLPR-CD19-CD22 or TSLPR-CD22-CD19 antigen to which a CAR binds. The use of an extracellular T SLPR-CD19, T SLPR-CD22, T SLPR-CD19-CD22 or T SLPR-CD22-CD19 antigen binding domain results in generation of a CAR that functions better in vivo, while avoiding the induction of anti-CAR immunity in the host immune response and the killing of the CAR T cell population. The CARs expressing the extracellular TSLPR-CD19, TSLPR-CD22, TSLPR-CD19-CD22 or TSLPR-CD22-CD19 ScFv antigen binding domain exhibit superior activities/properties including i) prevention of poor CAR T persistence and function as seen with mouse-derived binding sequences; ii) lack of regional (i.e. intrapleural) delivery of the CAR to be efficacious; and iii) ability to generate CAR T cell designs based both on binders with high and low affinity to TSLPR-CD19, TSLPR-CD22, TSLPR-CD19-CD22 or TSLPR-CD22-CD19. This latter property allows investigators to better fine tune efficacy vs toxicity, and/or tissue specificity of the CAR T product, since lower-affinity binders may have higher specificity to tumors vs normal tissues due to higher expression of TSLPR, CD19 and/or CD22 on tumors than normal tissue, which may prevent on-target off tumor toxicity and bystander cell killing.

What follows is a detailed description of the inventive CARs including a description of their extracellular T SLPR-CD19, T SLPR-CD22, T SLPR-CD19-CD22 or T SLPR-CD22-CD19 antigen binding domain, the transmembrane domain and the intracellular domain, along with additional description of the CARs, antibodies and antigen binding fragments thereof, conjugates, nucleotides, expression, vectors, and host cells, methods of treatment, compositions, and kits employing the disclosed CARs.

A. Chimeric Antigen Receptors (CARs)

The CARs disclosed herein comprise at least one TSLPR-CD19, TSLPR-CD22, TSLPR-CD19-CD22 or TSLPR-CD22-CD19 antigen binding domain capable of binding to TSLPR, CD19, and/or CD22, at least one transmembrane domain, and at least one intracellular domain.

A chimeric antigen receptor (CAR) is an artificially constructed hybrid protein or polypeptide containing the antigen binding domains of an antibody (e.g., single chain variable fragment (ScFv)) linked to T-cell signaling domains via the transmembrane domain. Characteristics of CARs include their ability to redirect T-cell specificity and reactivity toward a selected target in a non-WIC-restricted manner, and exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

As disclosed herein, the intracellular T cell signaling domains of the CARs can include, for example, a T cell receptor signaling domain, a T cell costimulatory signaling domain, or both. The T cell receptor signaling domain refers to a portion of the CAR comprising the intracellular domain of a T cell receptor, such as, for example, and not by way of limitation, the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen.

1. Extracellular Domain

In one embodiment, the CAR comprises a target-specific binding element otherwise referred to as an antigen binding domain or moiety. The choice of domain depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen binding domain in the CAR include those associated with viral, bacterial and parasitic infections, autoimmune disease and cancer cells.

In one embodiment, the CAR can be engineered to target a tumor antigen of interest by way of engineering a desired antigen binding domain that specifically binds to an antigen on a tumor cell. Tumor antigens are proteins that are produced by tumor cells that elicit an immune response, particularly T-cell mediated immune responses. The selection of the antigen binding domain will depend on the particular type of cancer to be treated. Tumor antigens include, for example, a glioma-associated antigen, carcinoembryonic antigen (CEA), .beta.-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, insulin growth factor (IGF)-I, IGF-II, IGF-I receptor TSLPR, CD19 and CD22. The tumor antigens disclosed herein are merely included by way of example. The list is not intended to be exclusive and further examples will be readily apparent to those of skill in the art.

In one embodiment, the tumor antigen comprises one or more antigenic cancer epitopes associated with a malignant tumor. Malignant tumors express a number of proteins that can serve as target antigens for an immune attack. These molecules include, but are not limited to, tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD22, CD22, BCMA, ROR1, and CD37 are other candidates for target antigens in B-cell lymphoma. Some of these antigens (CEA, HER-2, CD19, CD22, idiotype) have been used as targets for passive immunotherapy with monoclonal antibodies with limited success.

In one preferred embodiment, the tumor antigens are TSLPR, CD19, and/or CD22 and the tumors associated with expression of TSLPR, CD19, and/or CD22 comprise blood cancers, lung mesothelioma, ovarian, and pancreatic cancers that express high levels of the extracellular proteins TSLPR, -CD19, and/or CD22, or any combination thereof.

The type of tumor antigen may also be a tumor-specific antigen (TSA) or a tumor-associated antigen (TAA). A TSA is unique to tumor cells and does not occur on other cells in the body. A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSAs or TAAs include the following: Differentiation antigens such as MART-1/MelanA (MART-I), gp100 (Pmel 17), tyrosinase, TRP-1, TRP-2 and tumor-specific multi-lineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In one embodiment, the antigen binding domain portion of the CAR targets an antigen that includes but is not limited to CD19, CD20, CD22, ROR1, CD33, CD38, CD123, CD138, BCMA, c-Met, PSMA, Glycolipid F77, EGFRvIII, GD-2, FGFR4, TSLPR, NY-ESO-1 TCR, MAGE A3 TCR, and the like.

In a preferred embodiment, the antigen binding domain portion of the CAR targets the extracellular TSLPR, CD19, and/or CD22 antigen.

Figure 1:
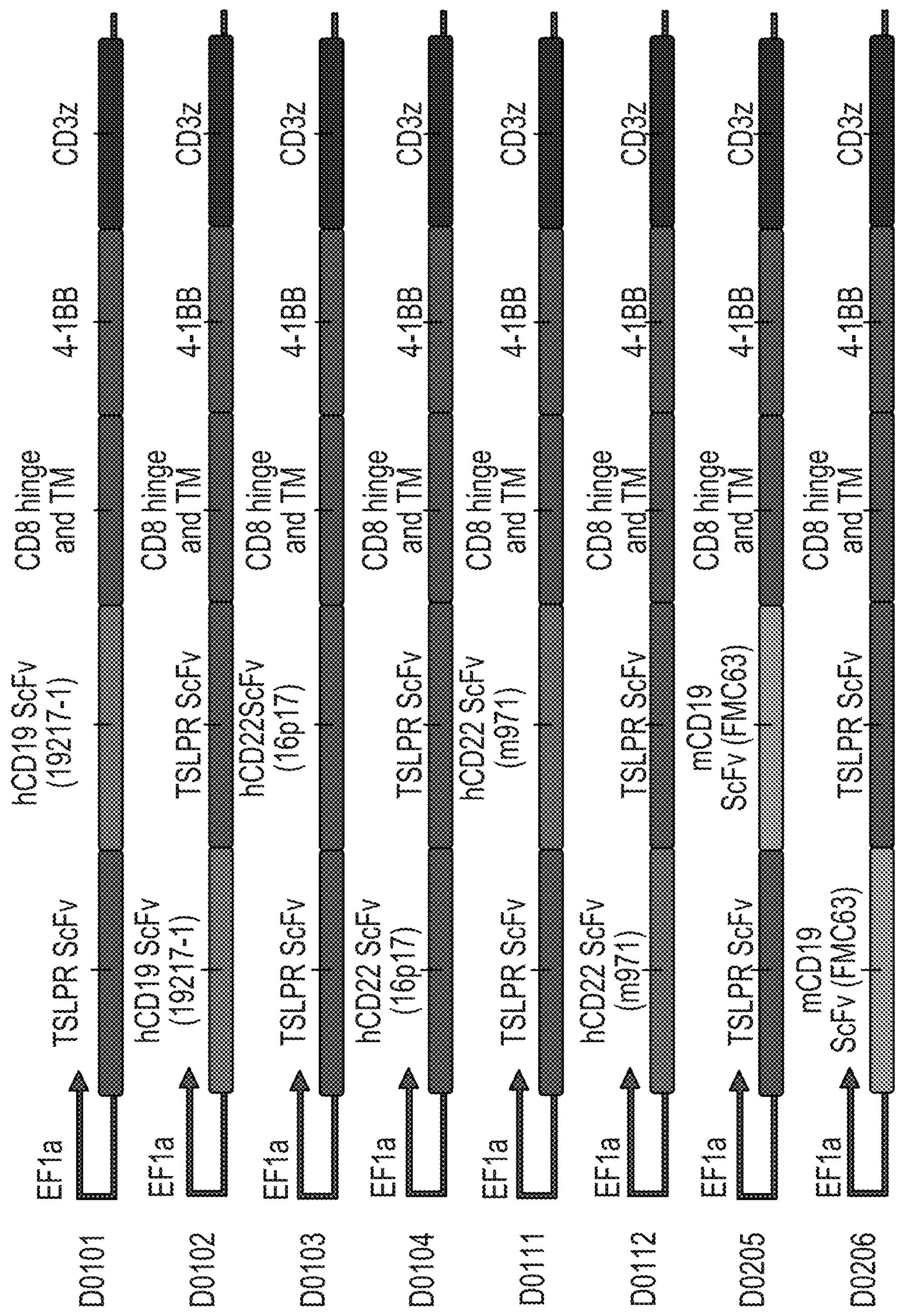
FIG. 1 depicts the construction of a tandem CARs targeting TSLPR and CD22 or TSLPR and CD19 simultaneously. The tandem scFv sequence, consisted of the two cognate scFv sequences connected in frame by a flexible Gly-Ser linker. The tandem scFv sequence was then cloned into a CAR backbone containing, in frame to the tandem binder, the CD8 hinge and transmembrane domain, 4-1BB co-stimulatory domain, and CD3ζ activation domain. Leader sequence derived from human GMCSF receptor was introduced in frame upstream of the tandem binding sequence to facilitate CAR expression at the T cell surface.

In the various embodiments of the TSLPR-CD19, TSLPR-CD22, TSLPR-CD19-CD22 and TSLPR-CD22-CD19-specific CARs disclosed herein, the general scheme is set forth in FIG. 1 and includes, from the N-terminus to the C-terminus, a signal or leader peptide, anti-CD19 or anti-CD22 ScFv, and an anti-TSLPR ScFv (where the CD19 or CD22 binder is distal to the T cell membrane and the TSLPR binder is proximal to the T cell membrane, or where the TSLPR binder is distal to the T cell membrane and the CD19 or CD22 binder is proximal to the T cell membrane), CD8 extracellular linker, CD8 transmembrane domain, 4-1BB costimulatory domain, CD3 zeta activation domain.

In one embodiment, the CAR comprises an anti-CD19 or anti-CD22 ScFv, and an anti-TSLPR ScFv.

In one preferred embodiment, the CAR comprises an anti-CD19 or anti-CD22 ScFv, and an anti-TSLPR ScFv, wherein the TSLPR binder is proximal to the T cell membrane.

In another embodiment, the CAR comprises an anti-CD19 ScFv, anti-CD22 ScFv, and an anti-TSLPR ScFv.

In one embodiment, the nucleic acid sequence encoding a CAR comprises the nucleic acid sequence of SEQ ID NO: 1 (Leader-CD22 VH-(GGGGS)-3 CD22 VL (GGGGS)-5 CD19 VH (GGGGS)-3 CD19 VL CD8 hinge+TM-4-1BB-CD3z (Construct 2219)), and encodes the CAR comprising the amino acid sequence as set forth in SEQ ID NO: 2 (Leader-CD22 VH-(GGGGS)-3 CD22 VL (GGGGS)-5 CD19 VH (GGGGS)-3 CD19 VL CD8 hinge+TM-4-1BB-CD3z (Construct 2219).

In one embodiment, the nucleic acid sequence encoding a CAR comprises the nucleic acid sequence of SEQ ID NO: 1, or a sequence with 85%, 90%, 95%, 96%, 97%, 98% or 99% identity thereof, and encodes the CAR comprising the amino acid sequence as set forth in SEQ ID NO: 2 or a sequence with 85%, 90%, 95%, 96%, 97%, 98% or 99% identity thereof Leader-CD22 VH-(GGGGS)-3 CD22 VL (GGGGS)-5 CD19 VH (GGGGS)-3 CD19 VL CD8 hinge+TM-4-1BB-CD3z (Construct 2219).

In another embodiment, the nucleic acid sequence encoding a CAR comprises the nucleic acid sequence of SEQ ID NO: 3 (Leader-CD19 VH (GGGGS)3-CD19 VL-(GGGGS)5-CD22 VL-(GGGGS)3-CD22 VH CD8 hinge+TM-4-1BB-CD3z (Construct 1922) (FIG. 2)), and encodes the CAR comprising the amino acid sequence as set forth in SEQ ID NO: 4 [Leader-CD19 VH (GGGGS)3-CD19 VL-(GGGGS)5-CD22 VL-(GGGGS)3-CD22 VH CD8 hinge+TM-4-1BB-CD3z (Construct 1922)].

In another embodiment, the nucleic acid sequence encoding a CAR comprises the nucleic acid sequence of SEQ ID NO: 3 or a sequence with 85%, 90%, 95%, 96%, 97%, 98% or 99% identity thereof, and encodes the CAR comprising the amino acid sequence as set forth in SEQ ID NO: 4 or a sequence with 85%, 90%, 95%, 96%, 97%, 98% or 99% identity thereof (Leader-CD19 VH (GGGGS)3-CD19 VL-(GGGGS)5-CD22 VL-(GGGGS)3-CD22 VH CD8 hinge+TM-4-1BB-CD3z (Construct 1922)).

The surface expression and cytolytic activity of the antigen binders of the anti-CD19 and anti-CD22 CARs is disclosed in Applicant's co-pending patent application Ser. No. 16/584,308, entitled Compositions and Methods for Treating Cancer with Anti-CD19/22 Immunotherapy, as filed on Sep. 26, 2019, and assigned Lentigen Technology, Inc. matter number LEN 025, which is incorporated by reference herein in its entirety.

In another embodiment, the nucleic acid sequence encoding a CAR comprises the nucleic acid sequence of SEQ ID NO: 60 [CD22-19 CD8 BBz (Construct LTG 2737)], and encodes the CAR comprising the amino acid sequence as set forth in SEQ ID NO: 61 [CD22-19 CD8 BBz (Construct LTG2737)].

In another embodiment, the nucleic acid sequence encoding a CAR comprises the nucleic acid sequence of SEQ ID NO: 60 or a sequence with 85%, 90%, 95%, 96%, 97%, 98% or 99% identity thereof, and encodes the CAR comprising the amino acid sequence as set forth in SEQ ID NO: 61 or a sequence with 85%, 90%, 95%, 96%, 97%, 98% or 99% identity thereof (CD22-19 CD8 BBz (Construct LTG2737)).

In another embodiment, the nucleic acid sequence encoding a CAR comprises the nucleic acid sequence of SEQ ID NO: 64 [CD22-19 CD8 ICOSz DNA (Construct D0136)], and encodes the CAR comprising the amino acid sequence as set forth in SEQ ID NO: 65 [CD22-19 CD8 ICOSz DNA (Construct D0136)].

In another embodiment, the nucleic acid sequence encoding a CAR comprises the nucleic acid sequence of SEQ ID NO: 64 or a sequence with 85%, 90%, 95%, 96%, 97%, 98% or 99% identity thereof, and encodes the CAR comprising the amino acid sequence as set forth in SEQ ID NO: 65 or a sequence with 85%, 90%, 95%, 96%, 97%, 98% or 99% identity thereof (CD22-19 CD8 ICOSz DNA (Construct D0136)).

In another embodiment, the nucleic acid sequence encoding a CAR comprises the nucleic acid sequence of SEQ ID NO: 70 [CD22-19 CD28 CD28z (Construct D0139)], and encodes the CAR comprising the amino acid sequence as set forth in SEQ ID NO: 71 [CD22-19 CD28 CD28z (Construct D0139)].

In another embodiment, the nucleic acid sequence encoding a CAR comprises the nucleic acid sequence of SEQ ID NO: 70 or a sequence with 85%, 90%, 95%, 96%, 97%, 98% or 99% identity thereof, and encodes the CAR comprising the amino acid sequence as set forth in SEQ ID NO: 71 or a sequence with 85%, 90%, 95%, 96%, 97%, 98% or 99% identity thereof (CD22-19 CD28 CD28z (Construct D0139)).

In another embodiment, the nucleic acid sequence encoding a CAR comprises the nucleic acid sequence of SEQ ID NO: 76 [CD19 CD8H&TM ICOS z_CD22 CD8H&TM 3z (Construct D0146)], and encodes the CAR comprising the amino acid sequence as set forth in SEQ ID NO: 77 [CD19 CD8H&TM ICOS z_CD22 CD8H&TM 3z (Construct D0146)].

In another embodiment, the nucleic acid sequence encoding a CAR comprises the nucleic acid sequence of SEQ ID NO: 76 or a sequence with 85%, 90%, 95%, 96%, 97%, 98% or 99% identity thereof, and encodes the CAR comprising the amino acid sequence as set forth in SEQ ID NO: 77 or a sequence with 85%, 90%, 95%, 96%, 97%, 98% or 99% identity thereof (CD19 CD8H&TM ICOS z_CD22 CD8H&TM 3z (Construct D0146)).

In another embodiment, the TSLPR-CD19-CD22 and TSLPR-CD22-CD19-specific CARs disclosed herein comprise a nucleic acid sequence as set forth in SEQ ID NOs: 1, 3, 60, 64, 70, 76, 84, 86, 88, 90, 92, 94, 96, or 98, or a sequence with 85%, 90%, 95%, 96%, 97%, 98% or 99% identity thereof, and encode the CAR comprising an amino acid sequence as set forth in SEQ ID NOs: 2, 4, 61, 65, 71, 77, 85, 87, 89, 91, 93, 95, 97, or 99, or a sequence with 85%, 90%, 95%, 96%, 97%, 98% or 99% identity thereof.

In another embodiment, the nucleic acid sequence encoding a CAR comprises the nucleic acid sequence of SEQ ID NO: 84 [EF-1a-TSLPR-CD19 (19217_1) CD8 BBz (Construct D0101)], and encodes the CAR comprising the amino acid sequence as set forth in SEQ ID NO: 85 [EF-1a-TSLPR-CD19 (19217_1) CD8 BBz (Construct D0101)].

In another embodiment, the nucleic acid sequence encoding a CAR comprises the nucleic acid sequence of SEQ ID NO: 84 or a sequence with 85%, 90%, 95%, 96%, 97%, 98% or 99% identity thereof, and encodes the CAR comprising the amino acid sequence as set forth in SEQ ID NO: 85 or a sequence with 85%, 90%, 95%, 96%, 97%, 98% or 99% identity thereof [EF-1a-TSLPR-CD19 (19217_1) CD8 BBz (Construct D0101)].

In another embodiment, the nucleic acid sequence encoding a CAR comprises the nucleic acid sequence of SEQ ID NO: 86 [EF-1a-CD19 (19217_1)-TSLPR CD8 BBz (Construct D0102)], and encodes the CAR comprising the amino acid sequence as set forth in SEQ ID NO: 87 [EF-1a-CD19 (19217_1)-TSLPR CD8 BBz (Construct D0102)].

In another embodiment, the nucleic acid sequence encoding a CAR comprises the nucleic acid sequence of SEQ ID NO: 86 or a sequence with 85%, 90%, 95%, 96%, 97%, 98% or 99% identity thereof, and encodes the CAR comprising the amino acid sequence as set forth in SEQ ID NO: 87 or a sequence with 85%, 90%, 95%, 96%, 97%, 98% or 99% identity thereof [EF-1a-CD19 (19217_1)-TSLPR CD8 BBz (Construct D0102)].

In another embodiment, the nucleic acid sequence encoding a CAR comprises the nucleic acid sequence of SEQ ID NO: 88 [EF-1a-TSLPR-CD22 (16P17) CD8 BBz (Construct D0103)], and encodes the CAR comprising the amino acid sequence as set forth in SEQ ID NO: 89 [EF-1a-TSLPR-CD22 (16P17) CD8 BBz (Construct D0103)].

In another embodiment, the nucleic acid sequence encoding a CAR comprises the nucleic acid sequence of SEQ ID NO: 88 or a sequence with 85%, 90%, 95%, 96%, 97%, 98% or 99% identity thereof, and encodes the CAR comprising the amino acid sequence as set forth in SEQ ID NO: 89 or a sequence with 85%, 90%, 95%, 96%, 97%, 98% or 99% identity thereof [EF-1a-TSLPR-CD22 (16P17) CD8 BBz (Construct D0103)).

In another embodiment, the nucleic acid sequence encoding a CAR comprises the nucleic acid sequence of SEQ ID NO: 90 [EF-1a-CD22 (16P17)-TSLPR CD8 BBz (Construct D0104)], and encodes the CAR comprising the amino acid sequence as set forth in SEQ ID NO: 91 [EF-1a-CD22 (16P17)-TSLPR CD8 BBz (Construct D0104)].

In another embodiment, the nucleic acid sequence encoding a CAR comprises the nucleic acid sequence of SEQ ID NO: 90 or a sequence with 85%, 90%, 95%, 96%, 97%, 98% or 99% identity thereof, and encodes the CAR comprising the amino acid sequence as set forth in SEQ ID NO: 91 or a sequence with 85%, 90%, 95%, 96%, 97%, 98% or 99% identity thereof [EF-1a-CD22 (16P17)-TSLPR CD8 BBz (Construct D0104)).

In another embodiment, the nucleic acid sequence encoding a CAR comprises the nucleic acid sequence of SEQ ID NO: 92 [EF-1a-TSLPR-CD22 (m971) CD8 BBz (Construct D0111)], and encodes the CAR comprising the amino acid sequence as set forth in SEQ ID NO: 93 [EF-1a-TSLPR-CD22 (m971) CD8 BBz (Construct D0111)].

In another embodiment, the nucleic acid sequence encoding a CAR comprises the nucleic acid sequence of SEQ ID NO: 92 or a sequence with 85%, 90%, 95%, 96%, 97%, 98% or 99% identity thereof, and encodes the CAR comprising the amino acid sequence as set forth in SEQ ID NO: 93 or a sequence with 85%, 90%, 95%, 96%, 97%, 98% or 99% identity thereof [EF-1a-TSLPR-CD22 (m971) CD8 BBz (Construct D0111)].

In another embodiment, the nucleic acid sequence encoding a CAR comprises the nucleic acid sequence of SEQ ID NO: 94 [EF-1a-CD22 (m971)-TSLPR CD8 BBz (Construct D0112)], and encodes the CAR comprising the amino acid sequence as set forth in SEQ ID NO: 95 [EF-1a-CD22 (m971)-TSLPR CD8 BBz (Construct D0112)].

In another embodiment, the nucleic acid sequence encoding a CAR comprises the nucleic acid sequence of SEQ ID NO: 94 or a sequence with 85%, 90%, 95%, 96%, 97%, 98% or 99% identity thereof, and encodes the CAR comprising the amino acid sequence as set forth in SEQ ID NO: 95 or a sequence with 85%, 90%, 95%, 96%, 97%, 98% or 99% identity thereof [EF-1a-CD22 (m971)-TSLPR CD8 BBz (Construct D0112)).

In another embodiment, the nucleic acid sequence encoding a CAR comprises the nucleic acid sequence of SEQ ID NO: 96 [EF-1a-CD19 (FMC63)-TSLPR-CD8 BBz (Construct D0205)], and encodes the CAR comprising the amino acid sequence as set forth in SEQ ID NO: 97 [EF-1a-CD19 (FMC63)-TSLPR-CD8 BBz (Construct D0205)].

In another embodiment, the nucleic acid sequence encoding a CAR comprises the nucleic acid sequence of SEQ ID NO: 96 or a sequence with 85%, 90%, 95%, 96%, 97%, 98% or 99% identity thereof, and encodes the CAR comprising the amino acid sequence as set forth in SEQ ID NO: 97 or a sequence with 85%, 90%, 95%, 96%, 97%, 98% or 99% identity thereof [EF-1a-CD19 (FMC63)-TSLPR-CD8 BBz (Construct D0205)].

In another embodiment, the nucleic acid sequence encoding a CAR comprises the nucleic acid sequence of SEQ ID NO: 98 [EF-1a-TSLPR-CD19 (FMC63)-CD8 BBz (Construct D0206)], and encodes the CAR comprising the amino acid sequence as set forth in SEQ ID NO: 99 [EF-1a-TSLPR-CD19 (FMC63)-CD8 BBz (Construct D0206)].

In another embodiment, the nucleic acid sequence encoding a CAR comprises the nucleic acid sequence of SEQ ID NO: 98 or a sequence with 85%, 90%, 95%, 96%, 97%, 98% or 99% identity thereof, and encodes the CAR comprising the amino acid sequence as set forth in SEQ ID NO: 99 or a sequence with 85%, 90%, 95%, 96%, 97%, 98% or 99% identity thereof [EF-1a-TSLPR-CD19 (FMC63)-CD8 BBz (Construct D0206)).

In another embodiment, the nucleic acid sequence encoding a CAR comprises the nucleic acid sequence of SEQ ID NO: 62, 66, 68, 72, 74, 78, 80, 82, 84, 86, 88, 90, 92, 94, 96, and 98 or a sequence with 85%, 90%, 95%, 96%, 97%, 98% or 99% identity thereof, and encodes the CAR comprising the amino acid sequence as set forth in SEQ ID NO: 63, 67, 69, 73, 75, 79, 81, 83, 85, 87, 89, 91, 93, 95, 97, and 99 or a sequence with 85%, 90%, 95%, 96%, 97%, 98% or 99% identity thereof.

The surface expression of anti-TSLPR-CD22 and anti-TSLPR-CD19 CARs incorporating single chain fragment variable (ScFv) sequences reactive with TSLPR-CD22 and TSLPR-CD19 antigen, is shown in Example 2 infra.

Without being intended to limit to any particular mechanism of action, it is believed that possible reasons for the enhanced therapeutic function associated with the exemplary TSLPR-CD19, TSLPR-CD22, TSLPR-CD19-CD22 and TSLPR-CD22-CD19 targeting CARs of the invention include, for example, and not by way of limitation, a) improved lateral movement within the plasma membrane allowing for more efficient signal transduction, b) superior location within plasma membrane microdomains, such as lipid rafts, and greater ability to interact with transmembrane signaling cascades associated with T cell activation, c) superior location within the plasma membrane by preferential movement away from dampening or down-modulatory interactions, such as less proximity to or interaction with phosphatases such as CD45, and d) superior assembly into T cell receptor signaling complexes (i.e. the immune synapse), or e) superior ability to engage with tumor antigen due to two distinct targeting domains present in each CAR molecule, or any combination thereof.

While the disclosure has been illustrated with an exemplary extracellular TSLPR, CD19, and/or CD22 variable heavy chain only and ScFv antigen binding domains, other nucleotide and/or amino acid variants within the TSLPR, CD19, and/or CD22 variable heavy chain only and ScFv antigen binding domains may be used to derive the TSLPR-CD19, TSLPR-CD22, TSLPR-CD19-CD22 or TSLPR-CD22-CD19 antigen binding domains for use in the CARs described herein.

Depending on the desired antigen to be targeted, the CAR can be additionally engineered to include the appropriate antigen binding domain that is specific to the desired antigen target. For example, if TSLPR, CD19 and/or CD22 are the desired antigens that are to be targeted, an antibody for TSLPR, CD19 and/or CD22 can be used as the antigen binding domain incorporated into the CAR.

In one exemplary embodiment, the antigen binding domain portion of the CAR additionally targets CD33. Preferably, the antigen binding domain in the CAR is anti-CD33 ScFv, wherein the nucleic acid sequence of the anti-CD33 ScFv comprises the sequence set forth in SEQ ID NO: 46. In one embodiment, the anti-CD33 ScFv comprises the nucleic acid sequence that encodes the amino acid sequence of SEQ ID NO: 46. In another embodiment, the anti-CD33 ScFv portion of the CAR comprises the amino acid sequence set forth in SEQ ID NO: 47.

In one exemplary embodiment, the antigen binding domain portion of the CAR additionally targets mesothelin. Preferably, the antigen binding domain in the CAR is anti-mesothelin ScFv, wherein the nucleic acid sequence of the anti-mesothelin ScFv comprises the sequence set forth in SEQ ID NO: 48. In one embodiment, the anti-mesothelin ScFv comprises the nucleic acid sequence that encodes the amino acid sequence of SEQ ID NO: 48. In another embodiment, the anti-mesothelin ScFv portion of the CAR comprises the amino acid sequence set forth in SEQ ID NO: 49.

In one aspect of the present invention, there is provided a CAR capable of binding to a non-TSA or non-TAA including, for example and not by way of limitation, an antigen derived from Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus, or any combination thereof.

In another aspect of the present invention, there is provided a CAR capable of binding to an antigen derived from a bacterial strain of Staphylococci, *Streptococcus, Escherichia coli, Pseudomonas*, or *Salmonella*. Particularly, there is provided a CAR capable of binding to an antigen derived from an infectious bacterium, for example, *Helicobacter pyloris, Legionella* pneumophilia, a bacterial strain of *Mycobacteria* sps. (e.g. *M. tuberculosis, M. avium, M. intracellulare, M. kansaii*, or *M. gordonea*), *Staphylococcus aureus, Neisseria gonorrhoeae, Neisseria meningitides, Listeria monocytogenes, Streptococcus pyogenes*, Group A *Streptococcus*, Group B *Streptococcus* (*Streptococcus agalactiae*), *Streptococcus pneumoniae*, or *Clostridium tetani*, or a combination thereof 2. Transmembrane Domain With respect to the transmembrane domain, the CAR comprises one or more transmembrane domains fused to the extracellular TSLPR-CD19, TSLPR-CD22, TSLPR-CD19-CD22 or TSLPR-CD22-CD19 antigen binding domain of the CAR.

The transmembrane domain may be derived either from a natural or from a synthetic source. Where the source is natural, the domain may be derived from any membrane-bound or transmembrane protein.

Transmembrane regions of particular use in the CARs described herein may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, mesothelin, CD33, CD37, CD64, CD80, CD83, CD86, CD134, CD137, CD154, TNFRSF16, or TNFRSF19. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain that naturally is associated with one of the domains in the CAR is used in addition to the transmembrane domains described supra.

In some instances, the transmembrane domain can be selected or by amino acid substitution to avoid binding of such domains to the transmembrane domains of the same or different surface membrane proteins to minimize interactions with other members of the receptor complex.

In one embodiment, the transmembrane domain in the CAR of the invention is the CD8 transmembrane domain. In one embodiment, the CD8 transmembrane domain comprises the nucleic acid sequence of SEQ ID NO: 35. In one embodiment, the CD8 transmembrane domain comprises the nucleic acid sequence that encodes the amino acid sequence of SEQ ID NO: 36. In another embodiment, the CD8 transmembrane domain comprises the amino acid sequence of SEQ ID NO: 36.

In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO: 28, or a sequence with 95-99% identity to an amino acid sequence of SEQ ID NO: 28.

In some instances, the transmembrane domain of the CAR comprises the CD8.alpha.hinge domain. In one embodiment, the CD8 hinge domain comprises the nucleic acid sequence of SEQ ID NO: 37. In one embodiment, the CD8 hinge domain comprises the nucleic acid sequence that encodes the amino acid sequence of SEQ ID NO: 38. In another embodiment, the CD8 hinge domain comprises the amino acid sequence of SEQ ID NO: 38, or a sequence with 95-99% identify thereof.

In one embodiment, an isolated nucleic acid molecule is provided wherein the encoded linker domain is derived from the extracellular domain of CD8, and is linked to the transmembrane CD8 domain, the transmembrane CD28 domain, or a combination thereof 3. Spacer Domain In the CAR, a spacer domain can be arranged between the extracellular domain and the transmembrane domain, or between the intracellular domain and the transmembrane domain. The spacer domain means any oligopeptide or polypeptide that serves to link the transmembrane domain with the extracellular domain and/or the transmembrane domain with the intracellular domain. The spacer domain comprises up to 300 amino acids, preferably 10 to 100 amino acids, and most preferably 25 to 50 amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

The spacer domain preferably has a sequence that promotes binding of a CAR with an antigen and enhances signaling into a cell. Examples of an amino acid that is expected to promote the binding include cysteine, a charged amino acid, and serine and threonine in a potential glycosylation site, and these amino acids can be used as an amino acid constituting the spacer domain.

As the spacer domain, the entire or a part of amino acid numbers 137-206 (SEQ ID NO: 39) which is a hinge region of CD8.alpha. (NCBI RefSeq: NP.sub.-001759.3), amino acid numbers 135 to 195 of CD8.beta. (GenBank: AAA35664.1), amino acid numbers 315 to 396 of CD4 (NCBI RefSeq: NP.sub.-000607.1), or amino acid numbers 137 to 152 of CD28 (NCBI RefSeq: NP.sub.-006130.1) can be used. Also, as the spacer domain, a part of a constant region of an antibody H chain or L chain can be used. Further, the spacer domain may be an artificially synthesized sequence.

Further, in the CAR, a signal peptide sequence can be linked to the N-terminus. The signal peptide sequence exists at the N-terminus of many secretory proteins and membrane proteins, and has a length of 15 to 30 amino acids. Since many of the protein molecules mentioned above as the intracellular domain have signal peptide sequences, the signal peptides can be used as a signal peptide for the CAR. In one embodiment, the signal peptide comprises the amino acid sequence shown in SEQ ID NO: 18.

4. Intracellular Domain

The cytoplasmic domain or otherwise the intracellular signaling domain of the CAR is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the CARs disclosed herein include those derived from TCR zeta (CD3 Zeta), FcR gamma, FcR beta, CD3 gamma, CD3 delta, CD3 epsilon, CD5, CD22, CD79a, CD79b, and CD66d. Specific, non-limiting examples, of the ITAM include peptides having sequences of amino acid numbers 51 to 164 of CD3 zeta. (NCBI RefSeq: NP.sub.-932170.1), amino acid numbers 45 to 86 of Fc epsilon RI gamma. (NCBI RefSeq: NP.sub.-004097.1), amino acid numbers 201 to 244 of Fc epsilon RI beta. (NCBI RefSeq: NP.sub.-000130.1), amino acid numbers 139 to 182 of CD3 gamma. (NCBI RefSeq: NP.sub.-000064.1), amino acid numbers 128 to 171 of CD3 delta. (NCBI RefSeq: NP.sub.-000723.1), amino acid numbers 153 to 207 of CD3.epsilon. (NCBI RefSeq: NP.sub.-000724.1), amino acid numbers 402 to 495 of CD5 (NCBI RefSeq: NP.sub.-055022.2), amino acid numbers 707 to 847 of 0022 (NCBI RefSeq: NP.sub.-001762.2), amino acid numbers 166 to 226 of CD79a (NCBI RefSeq: NP.sub.-001774.1), amino acid numbers 182 to 229 of CD79b (NCBI RefSeq: NP.sub.-000617.1), and amino acid numbers 177 to 252 of CD66d (NCBI RefSeq: NP.sub.-001806.2), and their variants having the same function as these peptides have. The amino acid number based on amino acid sequence information of NCBI RefSeq ID or GenBank described herein is numbered based on the full length of the precursor (comprising a signal peptide sequence etc.) of each protein. In one embodiment, the cytoplasmic signaling molecule in the CAR comprises a cytoplasmic signaling sequence derived from CD3 zeta.

In a preferred embodiment, the intracellular domain of the CAR can be designed to comprise the CD3-zeta signaling domain by itself or combined with any other desired cytoplasmic domain(s) useful in the context of the CAR. For example, the intracellular domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such costimulatory molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Specific, non-limiting examples, of such costimulatory molecules include peptides having sequences of amino acid numbers 236 to 351 of CD2 (NCBI RefSeq: NP.sub.-001758.2), amino acid numbers 421 to 458 of CD4 (NCBI RefSeq: NP.sub.-000607.1), amino acid numbers 402 to 495 of CD5 (NCBI RefSeq: NP.sub.-055022.2), amino acid numbers 207 to 235 of CD8 alpha. (NCBI RefSeq: NP.sub.-001759.3), amino acid numbers 196 to 210 of CD83 (GenBank: AAA35664.1), amino acid numbers 181 to 220 of CD28 (NCBI RefSeq: NP.sub.-006130.1), amino acid numbers 214 to 255 of CD137 (4-1BB, NCBI RefSeq: NP.sub.-001552.2), amino acid numbers 241 to 277 of CD134 (OX40, NCBI RefSeq: NP.sub.-003318.1), and amino acid numbers 166 to 199 of ICOS (NCBI RefSeq: NP.sub.-036224.1), and their variants having the same function as these peptides have. Thus, while the disclosure herein is exemplified primarily with 4-1BB as the co-stimulatory signaling element, other costimulatory elements are within the scope of the disclosure.

The cytoplasmic signaling sequences within the cytoplasmic signaling portion of the CAR may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In another embodiment, the intracellular domain is designed to comprise the signaling domain of CD3-zeta and the signaling domain of 4-1BB. In yet another embodiment, the intracellular domain is designed to comprise the signaling domain of CD3-zeta and the signaling domain of CD28 and 4-1BB.

In one embodiment, the intracellular domain in the CAR is designed to comprise the signaling domain of 4-1BB and the signaling domain of CD3-zeta, wherein the signaling domain of 4-1BB comprises the nucleic acid sequence set forth in SEQ ID NO: 40 and the signaling domain of CD3-zeta comprises the nucleic acid sequence set forth in SEQ ID NO: 42.

In one embodiment, the intracellular domain in the CAR is designed to comprise the signaling domain of 4-1BB and the signaling domain of CD3-zeta, wherein the signaling domain of 4-1BB comprises the nucleic acid sequence that encodes the amino acid sequence of SEQ ID NO: 41 and the signaling domain of CD3-zeta comprises the nucleic acid sequence that encodes the amino acid sequence of SEQ ID NO: 43.

In one embodiment, the intracellular domain in the CAR is designed to comprise the signaling domain of 4-1BB and the signaling domain of CD3-zeta, wherein the signaling domain of 4-1BB comprises the amino acid sequence set forth in SEQ ID NO: 41 and the signaling domain of CD3-zeta comprises the amino acid sequence set forth in SEQ ID NO: 43.

5. Additional Description of CARs

Also expressly included within the scope of the invention are functional portions of the CARs disclosed herein. The term "functional portion" when used in reference to a CAR refers to any part or fragment of one or more of the CARs disclosed herein, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the disclosure are functional variants of the CARs disclosed herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a non-polar side chain (e.g., Ala, Gly, Val, He, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., He, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, -amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, -aminocyclopentane carboxylic acid, a-aminocyclohexane carboxylic acid, a-aminocycloheptane carboxylic acid, a-(2-amino-2-norbornane)-carboxylic acid, γ-diaminobutyric acid, β-diaminopropionic acid, homophenylalanine, and a-tert-butylglycine.

The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs (including functional portions and functional variants thereof) can be obtained by methods known in the art. The CARs may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, N Y, 1994. Further, some of the CARs (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs described herein (including functional portions and functional variants thereof) can be commercially synthesized by companies. In this respect, the CARs can be synthetic, recombinant, isolated, and/or purified.

B. Antibodies and Antigen Binding Fragments

One embodiment further provides a CAR, a T cell expressing a CAR, an antibody, or antigen binding domain or portion thereof, which specifically binds to one or more of the antigens disclosed herein. As used herein, a "T cell expressing a CAR," or a "CAR T cell" means a T cell expressing a CAR, and has antigen specificity determined by, for example, the antibody-derived targeting domain of the CAR.

As used herein, and "antigen binding domain" can include an antibody and antigen binding fragments thereof. The term "antibody" is used herein in the broadest sense and encompasses various antibody structures, including but not limited to monoclonal antibodies, polyclonal antibodies, multi-specific antibodies (e.g., bispecific antibodies), and antigen binding fragments thereof, so long as they exhibit the desired antigen-binding activity. Non-limiting examples of antibodies include, for example, intact immunoglobulins and variants and fragments thereof known in the art that retain binding affinity for the antigen.

A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. In some examples, a monoclonal antibody is an antibody produced by a single clone of B lymphocytes or by a cell into which nucleic acid encoding the light and heavy variable regions of the antibody of a single antibody (or an antigen binding fragment thereof) have been transfected, or a progeny thereof. In some examples monoclonal antibodies are isolated from a subject. Monoclonal antibodies can have conservative amino acid substitutions which have substantially no effect on antigen binding or other immunoglobulin functions. Exemplary methods of production of monoclonal antibodies are known, for example, see Harlow & Lane, Antibodies, A Laboratory Manual, 2nd ed. Cold Spring Harbor Publications, New York (2013).

Typically, an immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, 6th ed., W.H. Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). References to "VH" or "VH" refer to the variable region of an antibody heavy chain, including that of an antigen binding fragment, such as Fv, ScFv, dsFv or Fab. References to "VL" or "VL" refer to the variable domain of an antibody light chain, including that of an Fv, ScFv, dsFv or Fab.

Light and heavy chain variable regions contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, Md., 1991; "Kabat" numbering scheme), Al-Lazikani et al., (JMB 273,927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a VH CDR3 is the CDR3 from the variable domain of the heavy chain of the antibody in which it is found, whereas a VL CDR1 is the CDR1 from the variable domain of the light chain of the antibody in which it is found. Light chain CDRs are sometimes referred to as LCDR1, LCDR2, and LCDR3. Heavy chain CDRs are sometimes referred to as LCDR1, LCDR2, and LCDR3.

An "antigen binding fragment" is a portion of a full length antibody that retains the ability to specifically recognize the cognate antigen, as well as various combinations of such portions. Non-limiting examples of antigen binding fragments include Fv, Fab, Fab', Fab'-SH, F(ab')2; diabodies; linear antibodies; single-chain antibody molecules (e.g. ScFv); and multi-specific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2nd Ed., Springer Press, 2010).

A single-chain antibody (ScFv) is a genetically engineered molecule containing the VH and VL domains of one or more antibody(ies) linked by a suitable polypeptide linker as a genetically fused single chain molecule (see, for example, Bird et al., Science, 242:423 426, 1988; Huston et al., Proc. Natl. Acad. Sci., 85:5879 5883, 1988; Ahmad et al., Clin. Dev. Immunol., 2012, doi:10.1155/2012/980250; Marbry, IDrugs, 13:543-549, 2010). The intramolecular orientation of the VH-domain and the VL-domain in a ScFv, is typically not decisive for ScFvs. Thus, ScFvs with both possible arrangements (VH-domain-linker domain-VL-domain; VL-domain-linker domain-VH-domain) may be used.

In a dsFv, the heavy and light chain variable chains have been mutated to introduce a disulfide bond to stabilize the association of the chains. Diabodies also are included, which are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., Proc. Natl. Acad. Sci., 90:6444 6448, 1993; Poljak et al., Structure, 2:1121 1123, 1994).

Antibodies also include genetically engineered forms such as chimeric antibodies (such as humanized murine antibodies) and heteroconjugate antibodies (such as bispecific antibodies). See also, Pierce Catalog and Handbook, 1994-1995 (Pierce Chemical Co., Rockford, Ill.); Kuby, J., Immunology, 3rd Ed., W.H. Freeman & Co., New York, 1997.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. Phage display: A Laboratory Manuel. 1st Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Methods of testing antibodies for the ability to bind to any functional portion of the CAR are known in the art and include any antibody-antigen binding assay, such as, for example, radioimmunoassay (MA), ELISA, Western blot, immunoprecipitation, and competitive inhibition assays (see, e.g., Janeway et al., infra, U.S. Patent Application Publication No. 2002/0197266 A1, and U.S. Pat. No. 7,338, 929).

Also, a CAR, a T cell expressing a CAR, an antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

C. Conjugates

A CAR, a T cell expressing a CAR, or monoclonal antibodies, or antigen binding fragments thereof, specific for one or more of the antigens disclosed herein, can be conjugated to an agent, such as an effector molecule or detectable marker, using any number of means known to those of skill in the art. Both covalent and noncovalent attachment means may be used. Conjugates include, but are not limited to, molecules in which there is a covalent linkage of an effector molecule or a detectable marker to an antibody or antigen binding fragment that specifically binds one or more of the antigens disclosed herein. One of skill in the art will appreciate that various effector molecules and detectable markers can be used, including (but not limited to) chemotherapeutic agents, anti-angiogenic agents, toxins, radioactive agents such as $^{125}I$, $^{32}P$, $^{14}C$, $^{3}H$ and $^{35}S$ and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a tumor cell).

The procedure for attaching an effector molecule or detectable marker to an antibody or antigen binding fragment varies according to the chemical structure of the effector. Polypeptides typically contain a variety of functional groups; such as carboxylic acid (COOH), free amine (—$NH_2$) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, Ill. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239, 104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15 amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker is not cleavable and the effector molecule or detectable marker is released by antibody degradation. (See U.S. Publication No. 2005/0238649 incorporated by reference herein in its entirety).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317, each of which is incorporated by reference herein in its entirety.

In several embodiments, conjugates of a CAR, a T cell expressing a CAR, an antibody, or antigen binding portion thereof, and one or more small molecule toxins, such as a calicheamicin, maytansinoids, dolastatins, auristatins, a trichothecene, and CC1065, and the derivatives of these toxins that have toxin activity, are provided.

Maytansine compounds suitable for use as maytansinoid toxin moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, each of which is incorporated herein by reference. Conjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference.

Additional toxins can be employed with a CAR, a T cell expressing a CAR, an antibody, or antigen binding portion thereof. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.). Contemplated toxins also include variants of the toxins (see, for example, see, U.S. Pat. Nos. 5,079,163 and 4,689,401).

Saporin is a toxin derived from *Saponaria officinalis* that disrupts protein synthesis by inactivating the 60S portion of the ribosomal complex (Stirpe et al., Bio/Technology, 10:405-412, 1992). However, the toxin has no mechanism for specific entry into cells, and therefore requires conjugation to an antibody or antigen binding fragment that recognizes a cell-surface protein that is internalized in order to be efficiently taken up by cells.

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used in human clinical trials. See, U.S. Pat. Nos. 5,792,458 and 5,208,021.

Ricin is the lectin RCA60 from *Ricinus communis* (Castor bean). For examples of ricin, see, U.S. Pat. Nos. 5,079,163 and 4,689,401. *Ricinus communis* agglutinin (RCA) occurs in two forms designated RCA60 and RCA120 according to their molecular weights of approximately 65 and 120 kD, respectively (Nicholson & Blaustein, J. Biochim. Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87,1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

A CAR, a T cell expressing a CAR, monoclonal antibodies, antigen binding fragments thereof, specific for one or more of the antigens disclosed herein, can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-naphthalenesulfonyl chloride, phycoerythrin, lanthanide phosphors and the like. Bioluminescent markers are also of use, such as luciferase, Green fluorescent protein (GFP), Yellow fluorescent protein (YFP). A CAR, a T cell expressing a CAR, an antibody, or antigen binding portion thereof, can also be conjugated with enzymes that are useful for detection, such as horseradish peroxidase, 0-galactosidase, luciferase, alkaline phosphatase, glucose oxidase and the like. When a CAR, a T cell expressing a CAR, an antibody, or antigen binding portion thereof, is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. A CAR, a T cell expressing a CAR, an antibody, or antigen binding portion thereof, may also be conjugated with biotin, and detected through indirect measurement of avidin or streptavidin binding. It should be noted that the avidin itself can be conjugated with an enzyme or a fluorescent label.

A CAR, a T cell expressing a CAR, an antibody, or antigen binding portion thereof, may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

A CAR, a T cell expressing a CAR, an antibody, or antigen binding portion thereof, can also be conjugated with a radiolabeled amino acid. The radiolabel may be used for both diagnostic and therapeutic purposes. For instance, the radiolabel may be used to detect one or more of the antigens disclosed herein and antigen expressing cells by x-ray, emission spectra, or other diagnostic techniques. Further, the radiolabel may be used therapeutically as a toxin for treatment of tumors in a subject, for example for treatment of a neuroblastoma. Examples of labels for polypeptides include, but are not limited to, the following radioisotopes or radionucleotides: $^{3}H$, $^{14}C$, $^{15}N$, $^{35}S$, $^{90}Y$, $^{99}Te$, $^{111}In$, $^{125}I$, and $^{131}I$.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

D. Nucleotides, Expression, Vectors, and Host Cells

Further provided by an embodiment of the invention is a nucleic acid comprising a nucleotide sequence encoding any of the CARs, an antibody, or antigen binding portion thereof, described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

In some embodiments, the nucleotide sequence may be codon-modified. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

In an embodiment of the invention, the nucleic acid may comprise a codon-modified nucleotide sequence that encodes the antigen binding domain of the inventive CAR. In another embodiment of the invention, the nucleic acid may comprise a codon-modified nucleotide sequence that encodes any of the CARs described herein (including functional portions and functional variants thereof).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carb oxymethyl amino methyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Integrated DNA Technologies (Coralville, Iowa, USA).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

Also provided is a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids can be incorporated into a recombinant expression vector. In this regard, an embodiment provides recombinant expression vectors comprising any of the nucleic acids. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors are not naturally-occurring as a whole.

However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.).

Bacteriophage vectors, such as λϋTIO, λϋTI 1, λZapII (Stratagene), EMBL4, and λNMI 149, also can be used. Examples of plant expression vectors include pBIOI, pBI101.2, pBH01.3, pBI121 and pBIN19 (Clontech). Examples of animal expression vectors include pEUK-C1, pMAM, and pMAMneo (Clontech). The recombinant expression vector may be a viral vector, e.g., a retroviral vector or a lentiviral vector. A lentiviral vector is a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include, for example, and not by way of limitation, the LENTIVECTOR® gene delivery technology from Oxford BioMedica plc, the LENTIMAX™ vector system from Lentigen and the like. Nonclinical types of lentiviral vectors are also available and would be known to one skilled in the art.

A number of transfection techniques are generally known in the art (see, e.g., Graham et al., Virology, 52: 456-467 (1973); Sambrook et al., supra; Davis et al., Basic Methods in Molecular Biology, Elsevier (1986); and Chu et al, Gene, 13: 97 (1981).

Transfection methods include calcium phosphate co-precipitation (see, e.g., Graham et al., supra), direct micro injection into cultured cells (see, e.g., Capecchi, Cell, 22: 479-488 (1980)), electroporation (see, e.g., Shigekawa et al., BioTechniques, 6: 742-751 (1988)), liposome mediated gene transfer (see, e.g., Mannino et al., BioTechniques, 6: 682-690 (1988)), lipid mediated transduction (see, e.g., Feigner et al., Proc. Natl. Acad. Sci. USA, 84: 7413-7417 (1987)), and nucleic acid delivery using high velocity microprojectiles (see, e.g., Klein et al, Nature, 327: 70-73 (1987)).

In an embodiment, the recombinant expression vectors can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

An embodiment further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5a cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupTl, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4+/CD8+ double positive T cells, CD4+ helper T cells, e.g., Th1 and Th2 cells, CD8+ T cells (e.g., cytotoxic T cells), tumor infiltrating cells, memory T cells, memory stem cells, i.e. Tscm, naive T cells, and the like. The T cell may be a CD8+ T cell or a CD4+ T cell.

In an embodiment, the CARs as described herein can be used in suitable non-T cells. Such cells are those with an immune-effector function, such as, for example, NK cells, and T-like cells generated from pluripotent stem cells.

Also provided by an embodiment is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

CARs (including functional portions and variants thereof), nucleic acids, recombinant expression vectors, host cells (including populations thereof), and antibodies (including antigen binding portions thereof), can be isolated and/or purified. For example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

E. Methods of Treatment

It is contemplated that the CARs disclosed herein can be used in methods of treating or preventing a disease in a mammal. In this regard, an embodiment provides a method of treating or preventing cancer in a mammal, comprising administering to the mammal the CARs, the nucleic acids, the recombinant expression vectors, the host cells, the population of cells, the antibodies and/or the antigen binding portions thereof, and/or the pharmaceutical compositions in an amount effective to treat or prevent cancer in the mammal.

An embodiment further comprises lymphodepleting the mammal prior to administering the CARs disclosed herein. Examples of lymphodepletion include, but may not be limited to, nonmyeloablative lymphodepleting chemotherapy, myeloablative lymphodepleting chemotherapy, total body irradiation, etc.

For purposes of the methods, wherein host cells or populations of cells are administered, the cells can be cells that are allogeneic or autologous to the mammal. Preferably, the cells are autologous to the mammal. As used herein, allogeneic means any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically. As used herein, "autologous" means any material derived from the same individual to whom it is later to be re-introduced into the individual.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, non-Hodgkin lymphoma, B-chronic lymphocytic leukemia, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the methods can provide any amount or any level of treatment or prevention of cancer in a mammal.

Furthermore, the treatment or prevention provided by the method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment provides a method of detecting the presence of cancer in a mammal, comprising: (a) contacting a sample comprising one or more cells from the mammal with the CARs, the nucleic acids, the recombinant expression vectors, the host cells, the population of cells, the antibodies, and/or the antigen binding portions thereof, or the pharmaceutical compositions, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the method of detecting the presence of a proliferative disorder, e.g., cancer, in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

The contacting can take place in vitro or in vivo with respect to the mammal. Preferably, the contacting is in vitro.

Also, detection of the complex can occur through any number of ways known in the art. For instance, the CARs disclosed herein, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles) as disclosed supra.

Methods of testing a CAR for the ability to recognize target cells and for antigen specificity are known in the art. For instance, Clay et al., J. Immunol, 163: 507-513 (1999), teaches methods of measuring the release of cytokines (e.g., interferon-γ, granulocyte/monocyte colony stimulating factor (GM-CSF), tumor necrosis factor a (TNF-a) or interleukin 2 (IL-2)). In addition, CAR function can be evaluated by measurement of cellular cytotoxicity, as described in Zhao et al, J. Immunol, 174: 4415-4423 (2005).

Another embodiment provides for the use of the CARs, nucleic acids, recombinant expression vectors, host cells, populations of cells, antibodies, or antigen binding portions thereof, and/or pharmaceutical compositions of the invention, for the treatment or prevention of a proliferative disorder, e.g., cancer, in a mammal. The cancer may be any of the cancers described herein.

Any method of administration can be used for the disclosed therapeutic agents, including local and systemic administration. For example topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used; for example, a chemotherapeutic agent may be administered orally and an antibody or antigen binding fragment or conjugate or composition may be administered intravenously. Methods of administration include injection for which the CAR, CAR T Cell, conjugates, antibodies, antigen binding fragments, or compositions are provided in a nontoxic pharmaceutically acceptable carrier such as water, saline, Ringer's solution, dextrose solution, 5% human serum albumin, fixed oils, ethyl oleate, or liposomes. In some embodiments, local administration of the disclosed compounds can be used, for instance by applying the antibody or antigen binding fragment to a region of tissue from which a tumor has been removed, or a region suspected of being prone to tumor development. In some embodiments, sustained intra-tumoral (or near-tumoral) release of the pharmaceutical preparation that includes a therapeutically effective amount of the antibody or antigen binding fragment may be beneficial. In other examples, the conjugate is applied as an eye drop topically to the cornea, or intravitreally into the eye.

The disclosed therapeutic agents can be formulated in unit dosage form suitable for individual administration of precise dosages. In addition, the disclosed therapeutic agents may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

Typical dosages of the antibodies or conjugates can range from about 0.01 to about 30 mg/kg, such as from about 0.1 to about 10 mg/kg.

In particular examples, the subject is administered a therapeutic composition that includes one or more of the conjugates, antibodies, compositions, CARs, CAR T cells or additional agents, on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, the disclosed methods include providing surgery, radiation therapy, and/or chemotherapeutics to the subject in combination with a disclosed antibody, antigen binding fragment, conjugate, CAR or T cell expressing a CAR (for example, sequentially, substantially simultaneously, or simultaneously). Methods and therapeutic dosages of such agents and treatments are known to those skilled in the art, and can be determined by a skilled clinician. Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

In some embodiments, the combination therapy can include administration of a therapeutically effective amount of an additional cancer inhibitor to a subject. Non-limiting examples of additional therapeutic agents that can be used with the combination therapy include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. These agents (which are administered at a therapeutically effective amount) and treatments can be used alone or in combination. For example, any suitable anti-cancer or anti-angiogenic agent can be administered in combination with the CARS, CAR-T cells, antibodies, antigen binding fragment, or conjugates disclosed herein. Methods and therapeutic dosages of such agents are known to those skilled in the art, and can be determined by a skilled clinician.

Additional chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masoprocol, mitotane, pegaspargase, tamoxifen, sorafenib, sunitinib, vemurafinib, vandetanib, and tretinoin. Selection and therapeutic dosages of such agents are known to those skilled in the art, and can be determined by a skilled clinician.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

In one embodiment, an effective amount of an antibody or antigen binding fragment that specifically binds to one or more of the antigens disclosed herein or a conjugate thereof is administered to a subject having a tumor following anti-cancer treatment. After a sufficient amount of time has elapsed to allow for the administered antibody or antigen binding fragment or conjugate to form an immune complex with the antigen expressed on the respective cancer cell, the immune complex is detected. The presence (or absence) of the immune complex indicates the effectiveness of the treatment. For example, an increase in the immune complex compared to a control taken prior to the treatment indicates that the treatment is not effective, whereas a decrease in the immune complex compared to a control taken prior to the treatment indicates that the treatment is effective.

F. Biopharmaceutical Compositions

Biopharmaceutical or biologics compositions (hereinafter, "compositions") are provided herein for use in gene therapy, immunotherapy and/or cell therapy that include one or more of the disclosed CARs, or T cells expressing a CAR, antibodies, antigen binding fragments, conjugates, CARs, or T cells expressing a CAR that specifically bind to one or more antigens disclosed herein, in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenus) or local (such as intra-tumor) administration. In one example, a disclosed CARs, or T cells expressing a CAR, antibody, antigen binding fragment, conjugate, is formulated for parenteral administration, such as intravenous administration. Compositions including a CAR, or T cell expressing a CAR, a conjugate, antibody or antigen binding fragment as disclosed herein are of use, for example, for the treatment and detection of a tumor, for example, and not by way of limitation, a neuroblastoma. In some examples, the compositions are useful for the treatment or detection of a carcinoma. The compositions including a CAR, or T cell expressing a CAR, a conjugate, antibody or antigen binding fragment as disclosed herein are also of use, for example, for the detection of pathological angiogenesis.

The compositions for administration can include a solution of the CAR, or T cell expressing a CAR, conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents, adjuvant agents, and the like, for example, sodium acetate, sodium chloride, potassium chloride, calcium chloride, sodium lactate and the like. The concentration of a CAR, or T cell expressing a CAR, antibody or antigen binding fragment or conjugate in these formulations can vary widely, and will be selected primarily based on fluid volumes, viscosities, body weight and the like in accordance with the particular mode of administration selected and the subject's needs. Actual methods of preparing such dosage forms for use in in gene therapy, immunotherapy and/or cell therapy are known, or will be apparent, to those skilled in the art.

A typical composition for intravenous administration includes about 0.01 to about 30 mg/kg of antibody or antigen binding fragment or conjugate per subject per day (or the corresponding dose of a CAR, or T cell expressing a CAR, conjugate including the antibody or antigen binding fragment). Actual methods for preparing administrable compositions will be known or apparent to those skilled in the art and are described in more detail in such publications as *Remington's Pharmaceutical Science, 19th ed.*, Mack Publishing Company, Easton, Pa. (1995).

A CAR, or T cell expressing a CAR, antibodies, antigen binding fragments, or conjugates may be provided in lyophilized form and rehydrated with sterile water before administration, although they are also provided in sterile solutions of known concentration. The CARs, or T cells expressing a CAR, antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of antibody or antigen binding fragment and conjugate drugs; for example, antibody drugs have been marketed in the U.S. since the approval of RITUXAN® in 1997. A CAR, or T cell expressing a CAR, antibodies, antigen binding fragments and conjugates thereof can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres, the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, J., Colloidal Drug Delivery Systems, J. Kreuter, ed., Marcel Dekker, Inc., New York, N.Y., pp. 219-342 (1994); and Tice & Tabibi, Treatise on Controlled Drug Delivery, A. Kydonieus, ed., Marcel Dekker, Inc. New York, N.Y., pp. 315-339, (1992).

Polymers can be used for ion-controlled release of the CARs, or T cells expressing a CAR, antibody or antigen binding fragment or conjugate compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

G. Kits

In one aspect, kits employing the CARs disclosed herein are also provided. For example, kits for treating a tumor in a subject, or making a CAR T cell that expresses one or more of the CARs disclosed herein. The kits will typically include a disclosed antibody, antigen binding fragment, conjugate, nucleic acid molecule, CAR or T cell expressing a CAR as disclosed herein. More than one of the disclosed antibodies, antigen binding fragments, conjugates, nucleic acid molecules, CARs or T cells expressing a CAR can be included in the kit.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, CARs or T cells expressing a CAR. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed antibodies, antigen binding fragments, conjugates, nucleic acid molecules, CARs or T cells expressing a CAR, for example, in a method of treating or preventing a tumor or of making a CAR T cell. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1A

Isolation of CD19-Specific Antibodies from a Fully Human Phage and Yeast-Displayed ScFv library Materials and Methods:

a) Production of Human ScFv and CD19-Specific Antibodies

A naïve human ScFv (recombinant single chain fragment variable of immunoglobulin) phage display library (approximate diversity, $10^{10}$ unique specificities), constructed from peripheral blood B cells of 50 healthy donors (Z. Y. Zhu and D. S. Dimitrov, unpublished data), were used for selection of ScFvs for recombinant human CD19 protein (Miltenyi Biotec, unpublished). Amplified libraries of $10^{12}$ phage-displayed ScFv were incubated with 5, 3, and 1, μg of coated CD19 in a 5×100-μl volume, distributed equally in 5 wells of a 96-well plate for 2 h at room temperature during the first, second and third rounds of biopanning, respectively. After each round of incubation the wells were washed 5 times for the first round and 10 times for the later rounds with phosphate-buffered saline containing 0.05% Tween 20 (PBST) to remove nonspecifically bound phage, the bound phage were mixed with TG1 competent cells for 1 hour at 37° C., and the phage was amplified from the infected cells and used in the next round of biopanning. After the third round of biopanning, 380 clones were randomly picked from the infected TG1 cells and each inoculated into 150 μl 2YT medium containing 100 μg/ml carbenicillin and 0.2% glucose in 96-well plates by using the automated BioRobotics BioPick colony picking system (Genomic Solutions, Ann Arbor, Mich.). After the bacterial cultures reached an optical density at 600 nm (OD600) of 0.5, helper phage M13K07 at a multiplicity of infection (MOI) of 10 and kanamycin at 50 μg/ml (final concentration) were added to the medium, and the plates were further incubated at 30° C. overnight in a shaker at 250 rpm. The phage supernatants were mixed with 3% nonfat milk in PBS at a 4:1 volume ratio and used for enzyme-linked immunosorbent assay (ELISA) to identify clones of phage displaying ScFvs or VHs with high CD19 binding affinity. The supernatants were incubated for 2 h at room temperature with recombinant human CD19 coated at 50 ng per well in 96-well plates and washed five times with PBST, (after overnight incubation at 4° C. it was blocked with 3% nonfat milk in PBS and washed three times with PBS containing 0.05% Tween 20.) CD19-bound phage were detected using horseradish peroxidase-conjugated goat anti-M13 antibody. After incubation with the antibody, the nonspecifically bound antibody was removed by washing wells, and the 3,3,'5,5'-tetramethylbenzidine (TMB) substrate was added, and solution absorbance at 450 nm (A450) measured. Clones that bound to CD19 with A450 of >1.0 were selected for further characterization.

b) Expression and Purification of Selected Soluble ScFvs.

The VH and VL of the selected clones were DNA sequenced, and the ScFvs encoded by clones with unique sequences were expressed and purified as described below. Plasmids extracted from these clones were used for transformation of HB2151 cells. A single colony was picked from the plate containing freshly transformed cells, inoculated into 200 ml 2YT medium containing 100 μg/ml ampicillin and 0.2% glucose, and incubated at 37° C. with shaking at 250 rpm. When the culture OD at 600 nm reached 0.90, isopropyl-β-d-thiogalactopyranoside at a 0.5 mM final concentration was added, and the culture was further incubated overnight at 30° C. The bacterial pellet was collected after centrifugation at 8,000×g for 20 min and resuspended in PBS buffer containing 0.5 mU polymixin B (Sigma-Aldrich, St. Louis, Mo.). After 30 min incubation with rotation at 50 rpm at room temperature, the resuspended pellet was centrifuged at 25,000×g for 25 min at 4° C., and the supernatant was used for ScFv purification using the Ni-NTA resin following vendor protocol (Qiagen).

c) ELISA Binding Assay

ELISA binding assay 50 μl of the diluted recombinant human CD19 in PBS at 2 ug/ml was coated in a 96-well plate at 4° C. overnight. Purified ScFv with His and Flag tags were serially diluted and added into the target protein coated wells. After washing, a 1:3000 diluted HRP conjugated anti-Flag antibody was added for 1 hr at RT. After washing, 3, 3, 5, 5'-Tetramethylbenzidine (TMB) substrate was added, 1N $H_2SO_4$ was added to stop the reaction after incubation at room temperature for 10 minutes, and the O.D. was read at 450 nm to quantify the relative ability of ScFv to bind CD19.

d) Yeast Display of scFv Library.

The same ScFv starting material as for phage display was also incorporated into a yeast ScFv display system. To supplement phage-based scFv analysis, yeast libraries expressing the human scFv library were also screened. To enrich the yeast expressing scFvs that bind to both the recombinant CD19-Fc and the CD19 expressed on the cell surface of the CHOK1 cells, cell panning on CHOK1 transfected with CD19 cells was performed. For the first round of panning on the cell surface, two days prior to panning, the CHOK1-CD19 cells were seeded into 6-well plates and grown to 50% confluency in F12 K medium. $5\times10^7$ yeast cells were then washed 2× with PBSA buffer and resuspended into 3 mL F12 K medium, and then gently added dropwise to the CHOK1-CD19 cells. After rocking gently on ice for 2 hours, the CHOK1-CD19 cells were then washed 3 times with ice-cold PBSA to remove the yeast cells that did not bind to the CHOK1-CD19, and 0.05% Trypsin-EDTA (Gibco) was then used to dissociate the CHOK1-CD19 cells and bound yeast cells from the plate. The cell mix containing both the yeast and CHOK1 cells were then inoculated into 10 mL SDCAA medium and amplified overnight at 30° C. and then induced in SGCAA medium at 30° C. for 16 hours. For the second round of cell panning, a similar protocol as above was performed, but more stringent wash conditions were used. This method of panning yielded the m19217 binder. Further characterization of this binder as well as others from phage display indicated that affinity maturation was required, as the biological characteristics of the CAR created from this hit were still not optimal.

To increase the affinity of m19217, a yeast-display m19217 mutant scFv library was created by using error-prone PCR to create random point mutations in scFv gene sequences. After electroporation, the resulting mutant library was then grown overnight at 30° C. for 16 hours in SDCAA medium and then switched into SGCAA medium at 30° C. for another 16 hours. The mutant library was then sorted through MACS (immunomagentic column, Miltenyi Biotec) with CD19-Fc as the capture antigen to downsize the library and to increase the population of mutants that could bind to CD19-Fc. The strongest binders were then selected by double staining the pools with Anti-c-Myc-Alexa 488 and CD19-Fc/Anti-Hu-Fc and selecting for the binders that had the highest binding affinities as well as c-Myc expression levels. This process was then repeated two more times, until flow cytometry of yeast particles with fluorescently tagged antigen yielded average binding affinities of the mutant pools that were increased over the starting construct. Binding affinities were estimated by flow cytometry of yeast pools using decreasing amounts of labeled CD19. This process resulted in an increase of EC50 (Effective concentration for 50% binding of labeled CD19 on yeast displaying ScFv) for M19217 of 0.5 ug/ml to an affinity of <0.01 ug/ml for the affinity matured binders (M19217-1, 19217-2, M19217-7, M19217-23, M19217-29, M19217-38, M19217-40).

Results:

Due to the unique challenges of CD19 structure, phage display candidates did not yield biologically functional CAR constructs and thus ScFv identification that yielded biologically active binders were generated by yeast display. Based upon flow cytometry analysis of yeast-displayed ScFv, eight ScFv clones specific for recombinant human CD19 were identified and labeled as human anti-CD19 ScFv binders M19217 (LTG2050, founder clone, EC50 of 0.5 ug/ml), and the following affinity matured binders (EC50<0.01 ug/ml): M19217-1 (LTG2065), M19217-2 (LTG2066), M19217-7 (LTG2067), M19217-23 (LTG2068), M19217-29 (LTG2069), M19217-38 (LTG2070), and M19217-40 (LTG2071) respectively.

Example 1B

Isolation of CD22-Specific Antibodies from a Fully Human Phage and Yeast-Displayed ScFv Library Materials and Methods:

a) Production of Human ScFv and CD22-Specific Antibodies

A naïve human ScFv (recombinant single chain fragment variable of immunoglobulin) phage display library (approximate diversity, $10^{10}$ unique specificities), constructed from peripheral blood B cells of 50 healthy donors (Z. Y. Zhu and D. S. Dimitrov, unpublished data), were used for selection of ScFvs for recombinant human CD19 protein (Miltenyi Biotec, unpublished). Amplified libraries of $10^{12}$ phage-displayed ScFv were incubated with 5, 3, and 1, pg of coated CD22 in a 5×100-μl volume, distributed equally in 5 wells of a 96-well plate for 2 h at room temperature during the first, second and third rounds of biopanning, respectively. After each round of incubation the wells were washed 5 times for the first round and 10 times for the later rounds with phosphate-buffered saline containing 0.05% Tween 20 (PBST) to remove nonspecifically bound phage, the bound phage were mixed with TG1 competent cells for 1 hour at 37° C., and the phage was amplified from the infected cells and used in the next round of biopanning. After the third round of biopanning, 380 clones were randomly picked from the infected TG1 cells and each inoculated into 150 μl 2YT medium containing 100 μg/ml carbenicillin and 0.2% glucose in 96-well plates by using the automated BioRobotics BioPick colony picking system (Genomic Solutions, Ann Arbor, Mich.). After the bacterial cultures reached an optical density at 600 nm (OD600) of 0.5, helper phage M13K07 at a multiplicity of infection (MOI) of 10 and kanamycin at 50 μg/ml (final concentration) were added to the medium, and the plates were further incubated at 30° C. overnight in a shaker at 250 rpm. The phage supernatants were mixed with 3% nonfat milk in PBS at a 4:1 volume ratio and used for enzyme-linked immunosorbent assay (ELISA) to identify clones of phage displaying ScFvs or VHs with high CD22 binding affinity. The supernatants were incubated for 2 h at room temperature with recombinant human CD22 coated at 50 ng per well in 96-well plates and washed five times with PBST, (after overnight incubation at 4° C. it was blocked with 3% nonfat milk in PBS and washed three times with PBS containing 0.05% Tween 20.) CD22-bound phage were detected using horseradish peroxidase-conjugated goat anti-M13 antibody. After incubation with the antibody, the nonspecifically bound antibody was removed by washing wells, and the 3,3',5,5'-tetramethylbenzidine (TMB) substrate was added, and solution absorbance at 450 nm (A450) measured. Clones that bound to CD22 with A450 of >1.0 were selected for further characterization.

b) Expression and Purification of Selected Soluble ScFvs

The VH and VL of the selected clones were DNA sequenced, and the ScFvs encoded by clones with unique sequences were expressed and purified as described below. Plasmids extracted from these clones were used for transformation of HB2151 cells. A single colony was picked from the plate containing freshly transformed cells, inoculated into 200 ml 2YT medium containing 100 μg/ml ampicillin and 0.2% glucose, and incubated at 37° C. with shaking at 250 rpm. When the culture OD at 600 nm reached 0.90, isopropyl-β-d-thiogalactopyranoside at a 0.5 mM final concentration was added, and the culture was further incubated overnight at 30° C. The bacterial pellet was collected after centrifugation at 8,000×g for 20 min and resuspended in PBS buffer containing 0.5 mU polymixin B (Sigma-Aldrich, St. Louis, Mo.). After 30 min incubation with rotation at 50 rpm at room temperature, the resuspended pellet was centrifuged at 25,000×g for 25 min at 4° C., and the supernatant was used for ScFv purification using the Ni-NTA resin following vendor protocol (Qiagen).

c) ELISA Binding Assay

For ELISA analysis 50 μl of the diluted recombinant human CD22 in PBS at 2 ug/ml was coated in a 96-well plate at 4° C. overnight. Purified ScFv with His and Flag tags were serially diluted and added into the target protein coated wells. After washing, a 1:3000 diluted HRP conjugated anti-Flag antibody was added for 1 hr at RT. After washing, 3, 3, 5, 5'-Tetramethylbenzidine (TMB) substrate was added, 1N $H_2SO_4$ was added to stop the reaction after incubation at room temperature for 10 minutes, and the O.D. was read at 450 nm to quantify the relative ability of ScFv to bind CD22.

d) Yeast Display of scFv Library

The same ScFv starting material as for phage display was also incorporated into a yeast ScFv display system. To supplement phage-based scFv analysis, yeast libraries expressing the human scFv library were also screened. To enrich the yeast expressing scFvs that bind to both the recombinant CD22-Fc and the CD19 expressed on the cell surface of the CHOK1 cells, cell panning on CHOK1 transfected with CD22 cells was performed. For the first round of panning on the cell surface, two days prior to panning, the CHOK1-CD22 cells were seeded into 6-well plates and grown to 50% confluency in F12 K medium. $5\times10^7$ yeast cells were then washed 2× with PBSA buffer and resuspended into 3 mL F12 K medium, and then gently added dropwise to the CHOK1-CD22 cells. After rocking gently on ice for 2 hours, the CHOK1-CD22 cells were then washed 3 times with ice-cold PBSA to remove the yeast cells that did not bind to the CHOK1-CD22, and 0.05% Trypsin-EDTA (Gibco) was then used to dissociate the CHOK1-CD22 cells and bound yeast cells from the plate. The cell mix containing both the yeast and CHOK1 cells were then inoculated into 10 mL SDCAA medium and amplified overnight at 30° C. and then induced in SGCAA medium at 30° C. for 16 hours. For the second round of cell panning, a similar protocol as above was performed, but more stringent wash conditions were used. This method of panning yielded the 16P, 24P, 25P, 11S and 12S binders. Binder sequences were incorporated into CART constructs as described in Example 2, infra, in a series of in vitro CART functional assays. Characterization of these binders from phage display in CART format revealed that only 16P binder had specific tumor-lytic activity in vitro, but it was low as compared to CAR positive control. Further, when 16P-based CART cells were tested in in vivo xenograft model, its antitumor function was very weak (Example 2, infra). Taken together, these results indicated that affinity maturation of anti-CD22 ScFv binders was required, as the biological characteristics of the CAR created from this binder set were still not optimal.

To increase the affinity of 16P, a yeast-display mutant scFv library was created by using error-prone PCR to create random point mutations in scFv gene sequences. After electroporation, the resulting mutant library was then grown overnight at 30° C. for 16 hours in SDCAA medium and then switched into SGCAA medium at 30° C. for another 16 hours. The mutant library was then sorted through MACS (immunomagnetic column, Miltenyi Biotec) with CD22-Fc as the capture antigen to downsize the library and to increase the population of mutants that could bind to CD22-Fc. The strongest binders were then selected by double staining the pools with Anti-c-Myc-Alexa 488 and CD19-Fc/Anti-Hu-Fc and selecting for the binders that had the highest binding affinities as well as c-Myc expression levels. This process was then repeated two more times, until flow cytometry of yeast particles with fluorescently tagged antigen yielded average binding affinities of the mutant pools that were increased over the starting construct. Binding affinities were estimated by flow cytometry of yeast pools using decreasing amounts of labeled CD22. This process resulted in an increase of EC50 (Effective concentration for 50% binding of labeled CD19 on yeast displaying ScFv) for 16P of 0.5 ug/ml to an affinity of <0.01 ug/ml for the affinity matured binders (16P1, 16P2, 16P3, 16P3v2, 16P6, 16P8, 16P10, 16P13, 16P15, 16P16, 16P17, 16P20, 16P20v2).

Results:

Due to the unique challenges of CD22 structure, phage display candidates did not yield sufficient functional CAR constructs with high biological activity and specificity. Thus, ScFv for biologically active and highly specific binders were generated by yeast display. Based upon flow cytometry analysis of yeast-displayed ScFv, thirteen ScFv clones specific for recombinant human CD22 were identified and labeled as human anti-CD22 ScFv binders 16P (LTG2202, founder clone, EC50 of 0.5 ug/ml), and the following affinity matured binders (EC50<0.01 ug/ml): 16P1, 16P2, 16P3, 16P3v2, 16P6, 16P8, 16P10, 16P13, 16P15, 16P17, 16P20, and 16P20v2 respectively.

Example 1C

Isolation of TSLPR-Specific Antibodies

The sequence for the TSLPR-binding scFv domain used in the CD19 and TSP was derived from an anti-TSLPR producing hybridoma 3G11, as described in the Supplemental Methods section of the manuscript titled "Eradication of B-ALL using chimeric antigen receptor-expressing T cells targeting the TSLPR oncoprotein" (Qin H et al., *Blood* (2015) 126 (5): 629-6)9.)

TSLPR binding single chain fragment variable (scFv) sequences were determined from the anti-TSLPR producing hybridoma 3G11 obtained from the MD Anderson Cancer Center. 3G11 was cultured in RPMI 1640 medium with Sodium Pyruvate (1 mM), Penicillin streptomycin (pen/strep) and 10% fetal bovine serum (FBS). When the cells were in the logarithmic phase of growth, their culture medium was changed to RPMI 1640 with sodium pyruvate, pen/strep, and 5% of ultra-low IgG FBS from GIBCO (Cat #16250) for antibody production. Some cells were harvested for total RNA extraction. 3G11 total RNA was extracted with RNeasy Mini kit (Qiagen), then reverse transcribed into cDNA with SuperScript III (Invitrogen). The cDNA was subsequently used for PCR amplification with combination of the degenerated primers from the variable region of the heavy chain and the constant gamma chain for the variable region of the heavy chain (VH) or with the degenerated primer from the kappa variable region and the specific primer from the kappa chain constant region for the kappa light chain (VL) 43. The PCR buffer set and One Taq polymerase were purchased from Roche Diagnostics and New England BioLabs, respectively. The following PCR conditions were used for the amplification: 950 C for 1 minutes (min), 35 cycles of 950 C for 15 seconds (sec), 500 C for 30 sec, 680 C for 45 sec, and final extension at 680 C for 5 min. The resulting PCR products were gel-purified and cloned into TOPO vector (TOPO TA Cloning Kit for Sequencing) and then transformed into One Shot® TOP10 Chemically Competent *E. coli* (Life Technologies). Single clones were picked for mini-prep, and the resulting plasmids were sent for sequencing analysis. To overcome the secondary structure at the beginning of the heavy chain variable region, a new antibody subtype specific reverse primer was designed, which is closer to the beginning of the 5' to combine with the degenerated primer at the 5' end for amplification of the 5' region of the VH. A betaine PCR enhancer was used at 1M to facilitate the PCR reaction. For construction of the long CAR constructs, the CH2CH3 domains from IgG1 (Gene ID: 3500 IGHG1, aa 176-407) were included. The leader sequence for the ScFv codes for T-cell surface glycoprotein CD8 alpha chain. The CAR-encoding amino acid sequences were reverse translated, codon optimized, and synthesized as single constructs (DNA 2.0). These constructs were then subcloned into a third generation lentiviral plasmid (pELNS-19BBzeta) containing a CD8 transmembrane domain, a 41BB (CD137) signaling domain and a CD3zeta domain (kindly provided by Dr. Carl June at the University of Pennsylvania).

Example 2

Generation and Testing of tandem TSLPR and CD19-targeting or TSLPR and CD22-targeting CAR Constructs Materials and Methods Creation of Chimeric Antigen Receptor (CAR)-Expressing Vectors Tandem CARs were created by linking the murine TSLPR scFv 3G11 (Ref 1) in tandem to either CD19-targeting scFv or CD22-targeting scFv. For CD19 targeting, mouse scFv FMC63 or human scFv 19217_1 were used. For CD22 targeting, either human scFv 16p1'7, or the human scFv m971 (Ref 2) were used.

CARs were generated by linking scFv of each antibody in frame to CD8 hinge and transmembrane domains (aa 138-191, Ref sequence ID NP_001759.3), 4-1BB (CD137, aa 214-255, UniProt sequence ID Q07011) transactivation domain and CD3 zeta signaling domain (CD247, aa 52-163, Ref sequence ID: NP_000725.1.). the scFvs were connected by a flexible linker (GGGGS)5. Leader sequence from human granulocyte macrophage colony stimulating factor receptor alpha subunit was included in all constructs. CAR constructs sequences were synthesized as gblock (IDT, Coralville, Iowa), cloned with InFusion HD cloning kit (Takara, Mountain View, Calif.) into a third generation lentiviral plasmid backbone (Lentigen Technology Inc., Gaithersburg, Md.) under the control of elongation factor-1α (EF-1α) promoter.

Cell lines used to demonstrate CAR activity

The acute lymphocytic leukemia cell lines Reh (ATCC, Manassas, Va.) and NALM-6 (ACC-128 DSMZ, Leibniz Institute DSMZ, Braunschweig, Germany) were cultured in RPMI-1640 with GlutaGro (Corning, Tewksbury, Mass.) supplemented with 10% heat-inactivated fetal bovine serum (FBS, Hyclone, Logan, Utah). The epidermoid carcinoma cell line A-431 (ATCC Manassas, Va.) was propagated in Dulbecco's modified Eagle medium with Glutamine (Hyclone, Logan, Utah) supplemented with 10% heat-inactivated FBS. All these cell lines were further developed into luciferase-expressing cell lines by stably transducing wild-type tumor lines with lentiviral vector encoding firefly luciferase (Lentigen Technology, Inc., Gaithersburg, Md.), followed by single cell cloning and selection of luciferase-positive clones.

TSLPR, CD19, or CD22 single surface marker expression lines were generated by stably transducing luciferase-expressing cell lines with lentiviral vector encoding TSLPR or CD19 or CD22 fused with puromycin by P2A peptide. The pools of transduced cell lines were selected with puromycin at 1 μg/ml for 2 weeks. Surface expression of target molecules were verified by flow cytometry. TSLPR antibody 1F11 labeled with PE (BD Biosciences, San Jose, Calif.), CD19 antibody LT19 conjugated withPE-Vio770 and CD22 antibody REA340 conjugated with APC (Miltenyi Biotec, Bergisch Gladbach, Germany) were used to detect TSLPR, CD19 or CD22 over-expression respectively.

Primary Human T Cells Purification

Whole blood was collected from healthy volunteers at Oklahoma Blood Institute (OBI) with donors' written consent. Processed buffy coats were purchased from OBI (Oklahoma City, Okla.). The CD4-positive and CD8-positive human T cells were purified from buffy coats via positive selection using a 1:1 mixture of CD4- and CD8-MicroBeads (Miltenyi Biotec, Bergisch Gladbach, Germany) according to manufacturer's protocol.

Primary T Cells Transduction

Human primary $CD4^+$ and $CD8^+$ T cells from normal donors were cultivated in TexMACS medium supplemented with 30 IU/ml IL-2 at a density of $1\times10^6$ cells/ml, activated with CD3/CD28 MACS® GMP T Cell TransAct reagent on day 0 (all reagents from Miltenyi Biotec), and transduced on day 1 with LV encoding CAR constructs either by 5% volume or by indicated MOI for 2 days. Cultures were washed on day 3 and propagated until harvest on day 8-10.

Surface CAR Detection by Flow Cytometric Analysis

Flow cytometric analysis was performed to detect the CAR molecule surface expression. Half million of harvested primary T cells were washed and stained with cold AutoMACS buffer supplemented with 0.5% bovine serum albumin (Miltenyi Biotec, Bergisch Gladbach, Germany), and resuspended in 200 ul Running Buffer before acquired by MACSQuant®10 Analyzer (Miltenyi Biotec Bergisch Gladbach, Germany). For CAR surface expression, TSLPR Fc, CD19Fc and CD22Fc peptide (R&D systems, Minneapolis, Minn.) were used followed anti Fc-AF647 (Jackson ImmunoResearch, West Grove, Pa.). T cell subtypes was further identified with anti-CD4 antibody conjugated to VioBlue fluorophore (Miltenyi Biotec Bergisch Gladbach, Germany). Dead cells in all studies were excluded by 7AAD staining (BD Biosciences, San Jose, Calif.). Flow data were analyzed with MACSQuantify software.

Cell-Mediated Cytotoxicity

To determine cell-mediated cytotoxicity (CTL assay), 5,000 target cells stably transduced with firefly luciferase were combined with CAR T cells at various effector to target ratios (E:T) and incubated overnight. SteadyGlo reagent (Promega, Madison Wis.) was added to each well and the resulting luminescence was analyzed on an EnSpire plate reader (Perkin Elmer, Shelton, Conn.) and recorded as counts per second (sample CPS). Target only wells (max CPS) and target only wells plus 1% Tween-20 (min CPS) were used to determine assay range. Percent specific lysis was calculated as: (1-(sample CPS-min CP S)/(max CPS-min CPS)).

Results

Example 2 describes the generation and in vitro evaluation of tandem CAR T cells targeting the B-cell tumor antigen TSLPR simultaneously with either CD19 or CD22 for the treatment of B-cell malignancies.

Schematic representations of the tandem CAR constructs targeting the TSLPR antigen together with either the CD19 or the CD22 B-cell antigens are shown in FIG. 1. The tandem scFv domain was comprised of two scFv sequences linked in frame by a Gly-Ser flexible linker. The tandem targeting domain was linked in frame to CD8 hinge and transmembrane domain, 4-1BB costimulatory domain and CD3 zeta activation domain. CAR variants with both cell membrane-proximal and cell membrane-distal positioning of the TSLPR-targeting domain were constructed (TABLE 1). Single CAR controls targeting B-cell antigens CD19, CD22 or TSLPR were also included (TABLE 2). CAR sequences were incorporated into a third-generation lentiviral vectors and transduced into human primary T cells at saturation, to generate the tandem TSLPR×CD19 or tandem TSLPR×CD22 CAR T cells under the control of the mammalian EF-1α promoter.

TABLE 1

Tandem TSLPR × CD19 and TSLPR × CD22 CAR constructs

| Construct Number | ScFv1 | ScFv2 | Construct designation |
|---|---|---|---|
| D0101 | TSLPR (3A11) | CD19 19217_1 | D0101 (EF-1a-TSLPR-CD19 (19217_1) CD8 BBz) |
| D0102 | CD19 (19217_1) | TSLPR (3A11) | D0102 (EF-1a-CD19 (19217_1)-TSLPR CD8 BBz) |
| D0103 | TSLPR (3A11) | CD22 (16P17) | D0103 (EF-1a-TSLPR-CD22 (16P17) CD8 BBz) |
| D0104 | CD22 (16P17) | TSLPR (3A11) | D0104 (EF-1a-CD22 (16P17)-TSLPR CD8 BBz) |
| D0111 | TSLPR (3A11) | CD22 (m971) | D0111 (EF-1a-TSLPR-CD22 (m971) CD8 BBz) |
| D0112 | CD22 (m971) | TSLPR (3A11) | D0112 (EF-1a-CD22 (m971)-TSLPR CD8 BBz) |
| D0205 | CD19 (FMC63) | TSLPR (3A11) | D0205 (EF-1a-CD19 (FMC63)-TSLPR- CD8 BBz) |
| D0206 | TSLPR (3A11) | CD19 (FMC63) | D0206 (EF-1a-TSLPR-CD19 (FMC63)- CD8 BBz) |

Lentiviral vectors encoding the tandem TSLPR CAR constructs were used for CAR transduction into human primary T cells. Single CAR controls targeting TSLPR, CD19, or CD22 individually were included as appropriate for each construct set (TABLE 2). Untransduced T cells derived form same donor as the CAR-expressing cells (UTD) were used as a negative control.

TABLE 2

Single-targeting CAR controls

| Construct Number | scFv | Construct designation |
|---|---|---|
| LTG2282 | TSLPR (3A11) | EF-1a TSLPR (3A11) CD8 BBz tEGFR |
| LTG2065 | CD19 (19217_1) | EF-1a CD19 (19217_1) CD8 BBz |
| LTG2200 | CD22 (m971) | EF-1a CD22 (m971) CD8 BBz |

CAR constructs combining TSLPR-targeting with CD19 targeting were constructed using either the 19217_1 CD19-targeting ScFv domain (D0101, D0102), or the FMC63 CD19-targeting domain (D0205, D0206), as shown in TABLE 1 and FIG. 1. LTG2282 (TSLPR (3A11) EF-1a TSLPR (3A11) CD8 BBz tEGFR) (SEQ ID NOs: 100 and 101, respectively), LTG2065 (CD19 (19217_1) EF-1a CD19 (19217_1) CD8 BBz) (SEQ ID NOs: 5 and 6, respectively), and LTG2200 (CD22 (m971) EF-1a CD22 (m971) CD8 BBz) (SEQ ID NOs: 58 and 59, respectively) served as the controls for the TSLPR-CD19 and TSLPR-CD22 CARS tested in this Example 2. The surface expression of the tandem TSLPR×CD19 CAR incorporating the human CD19 ScFv 19217_1 and the TSLPR scFv 3A11, when the TSLPR scFv is in membrane-distal orientation (D0101), and in the membrane-proximal orientation (D0102) is shown in FIG. 2. Specific detection of each scFv domain within the CAR structure was facilitated by CAR T cell staining with TSLPR-Fc peptide, or CD19-Fc peptide, followed by a secondary staining with anti-Fc AF647-labeled reagent, and fluorescence was detected in the APC channel. In CAR construct D0101, in which CD19 scFv was membrane-proximal and the TSLPR scFv was membrane-distal, the TSLPR scFv was detected at 44% of the transduced cells, and CD19 scFv was detected at 31%. In CAR construct D0102 with the reverse binder orientation (i.e. the TSLPR scFv membrane-proximal, and CD19 scFv membrane-distal), the detection levels were 85% and 75% for scFv TSLPR and CD19, respectively (FIG. 2).

Results from both methods were taken into account when analyzing CAR expression. Both CAR constructs D0101 and D0102 were successfully expressed in human primary T cells, however the CAR construct D0102, with membrane-proximal TSLPR orientation, was detected at a greater percentage of transduced cells at vector-saturating transduction conditions, and was expressed with a greater intensity.

Next, the cytolytic function of the tandem TSLPR×CD19 CARs was evaluated in a luciferase-based killing assay (FIG. 3). To determine the tandem TSLPR×CD19 CAR reactivity to each of the two antigens, CAR T cells were incubated with skin carcinoma cell line A431-luc stably expressing firefly luciferase, and engineered to express either the CD19 antigen (A431 CD19), or the TSLPR antigen (A431 TSLPR). The parental antigen-negative cell line A431 served as a control for non-specific CAR activation (FIG. 3). The single CAR controls CD19 CAR, and TSLPR CAR, were included as a target-specific positive controls. Effector CAR T cells and tumor cells were combined at effector to target (E:T) ratio of 5:1, 10:1 or 20:1, in order to compare and contrast the potency of the different CAR constructs (FIG. 3).

A431-TSLPR tumor cell line, expressing the B-cell antigen TSLPR, was efficiently lysed by the tandem D0102 CD19×TSLPR CAR, and the single TSLPR CAR control (FIG. 3A). By contrast, A431-TSLPR target cells were lysed to a lesser degree by the tandem D0101 TSLPR×CD19 CAR. No lysis occurred in A431-TSLPR combination with the negative control UTD, or the CD19 CAR not targeting the TSLPR antigen, as expected (FIG. 3A).

Target Line A431 CD19, expressing only the CD19 surface antigen, but not the TSLPR surface antigen, was potently lysed by the tandem CAR constructs D0101, and D0102, and by the single CD19 CAR control (FIG. 3B). The tandem CARs were equally lytic to A431 CD19 target cells at E:T ratios of 10:1 and 20:1, but D0101 was slightly less potent than D0102 at the low E:T ratio of 5 (FIG. 3B). As expected, the negative control UTD, and the single TSLPR CAR had no lytic effect against this target line, demonstrating CAR target specificity (FIG. 3B). Lastly, no lysis was detected by any of the CAR constructs or controls against the parental A431 target line, negative for both the CD19 and the TSLPR antigens (FIG. 3C).

Then, the tandem TSLPR×CD19 CAR T cells D0101 and D0102 were tested in a killing assay against a panel of native leukemia lines with natural CD19 expression with or without overexpression of TSLPR. Luciferase-expressing B-ALL parental lines, Reh and NALM-6, and their respective TSLPR-overexpressing subclones were used to test the potency of the TSLPR×CD19 tandem CAR T cells (FIG. 4).

In the Reh line, most potent killing was achieved by the single CD19 CAR, followed by the tandem D0102 CAR construct, and then, the tandem D0101 tandem CAR (FIG.

Figure 4A:
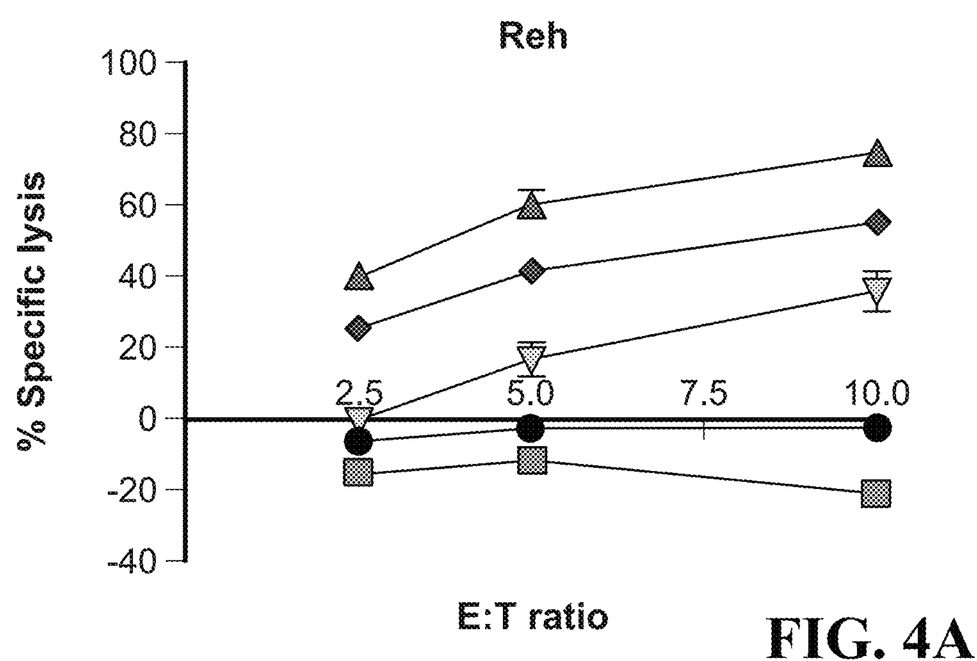
Figure 4B:
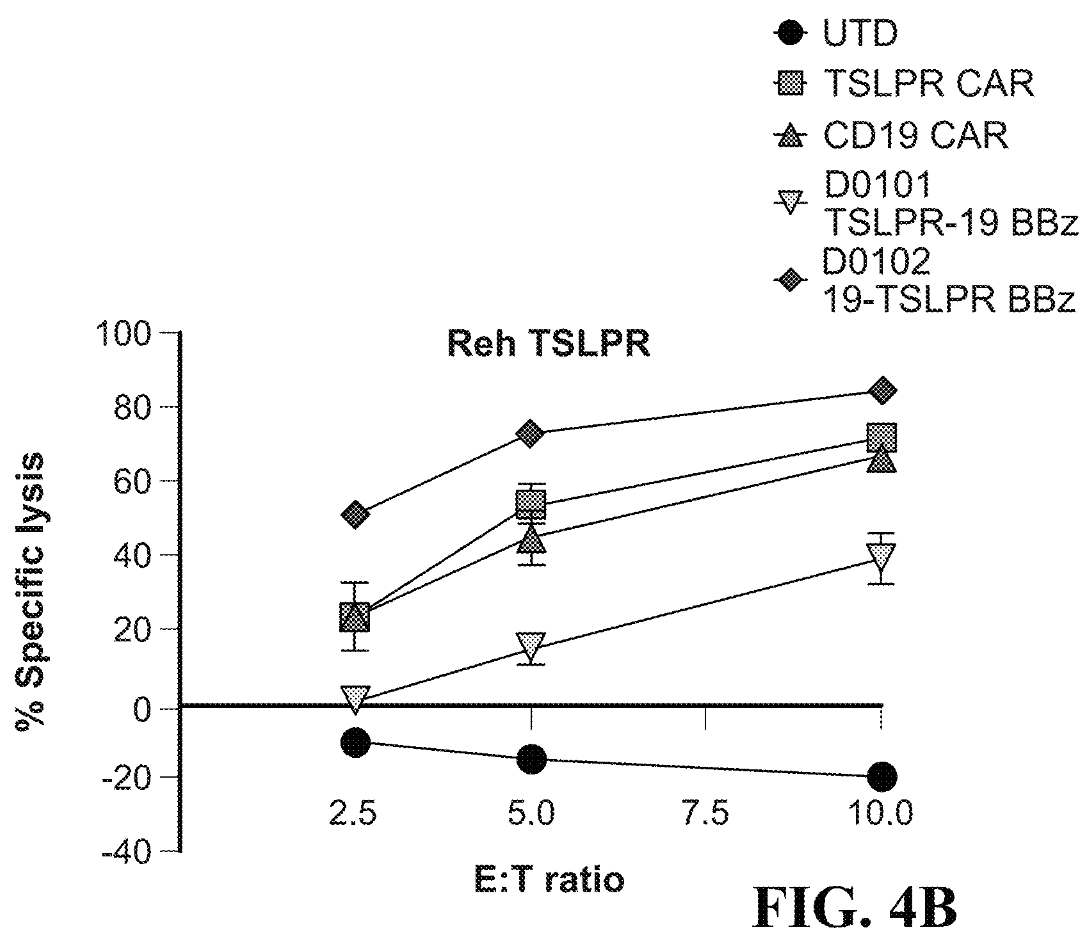

4A). By contrast, in the Reh TSLPR clone, positive for both TSLPR and CD19 antigens, the tandem CAR D0102 was the most potent in target cell lysis, followed by the single-targeting controls CAR19 and CAR TSLPR, and then the tandem CAR D0101 (FIG. 4B). This finding demonstrates the superior function of the tandem CAR D0102 as compared to the single CAR controls against target lines expressing both targeted tumor antigens, CD19 and TSLPR (FIG. 4B).

Figure 4C:
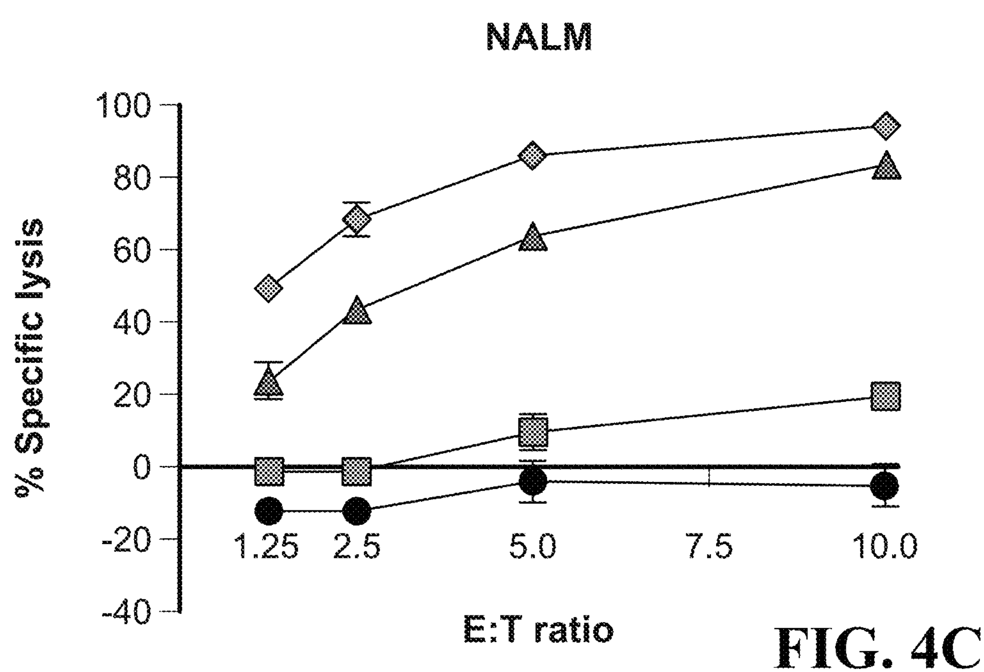
Figure 4D:
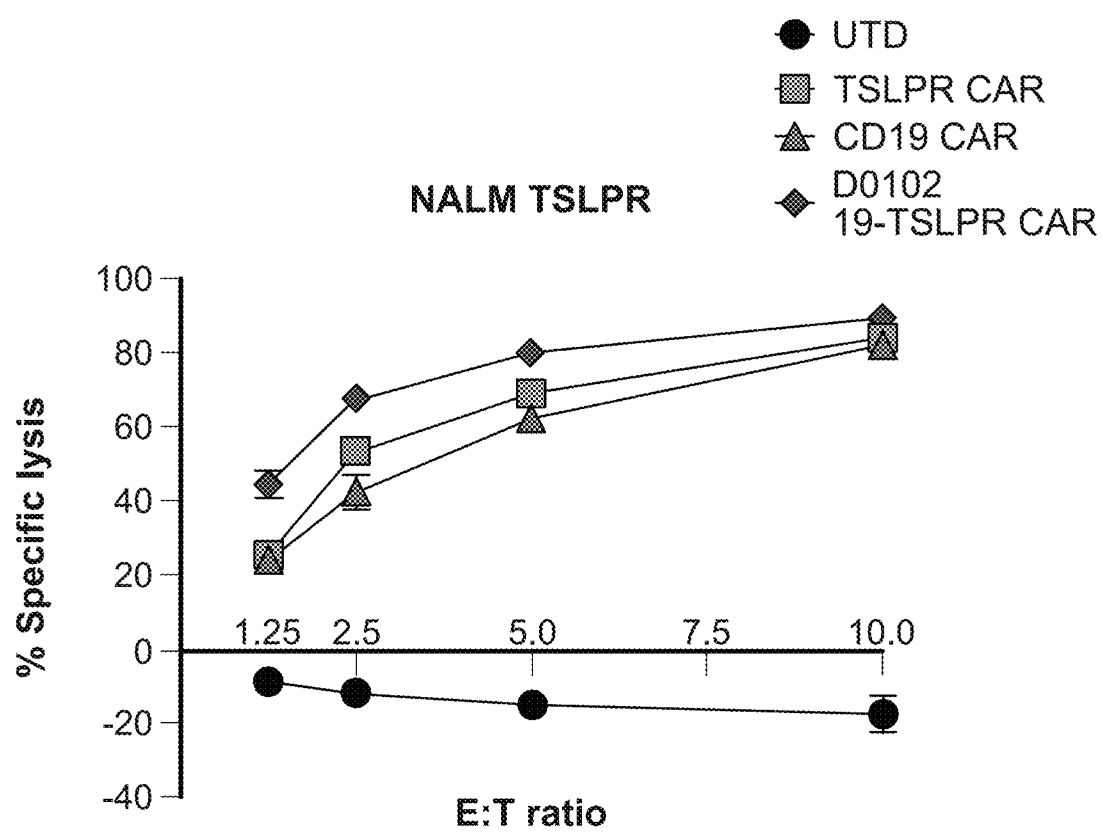

To verify the high potency of tandem D0102 CAR which was observed against the Reh cell lines, in a different target line, D0102 CAR was tested against the NALM-6 B-ALL tumor, with or without overexpression of TSLPR (FIG. 4C). Again, CAR D0102 was more lytic than the single CAR 19 or the single CAR TSLPR against the parental NALM-6 cells (FIG. 4C). Moreover, when the TSLPR-overexpressing CD19+ cell line NALM TSLPR was targeted, the D0102 CAR was more potent than the single CD19 CAR or the single TSLPR CAR against the TSLPR-overexpressing tumor cell line (FIG. 4D).

Overall, the tandem CAR D0102 was expressed at a higher level following transduction of primary human T cells at vector-saturating conditions and mediated greater antigen-specific target cell lysis than the tandem CAR construct D0101. This finding indicates that the optimal orientation of the targeting domains within the CAR architecture was not obvious, and that empirical testing was necessary for the identification of the optimal configuration for the tandem CD19×TSLPR CAR T constructs.

To develop the tandem CD22 and TSLPR targeting CARs, CD22-directed scFv 16P17 was used in either membrane-proximal or membrane-distal orientation (construct D0103 and D0104, respectively). For TSLPR-targeting, scFv 3G11 was used. Surface expression of the tandem TSLPR×CD22 CAR incorporating the human ScFv 16P17 together with the TSLPR scFv 3G11, when the TSLPR scFv is positioned in the membrane-distal orientation (D0103), or in the membrane-proximal orientation (D0104) is shown in FIG. 5. Specific detection of each scFv domain within the CAR structure was facilitated by CAR T cell staining with TSLPR-Fc peptide, or CD22-Fc peptide, followed by a secondary staining with anti-Fc AF647-labeled reagent, and detected in the APC channel by flow cytometry. In CAR construct D0103, in which CD22 scFv was membrane-proximal and the TSLPR scFv was membrane-distal, the TSLPR scFv was detected at 26% of the transduced cells, and CD22 scFv was detected at 11%. In CAR construct D0104 with the opposite binder orientation (i.e. the CD22 scFv was membrane-distal, and the TSLPR scFv was membrane-proximal), the detection levels were 75% and 39% for scFv TSLPR and CD22, respectively (FIG. 5).

Results from both methods were taken into account when analyzing CAR expression. Both CAR constructs D0103 and D0104 were successfully expressed in human primary T cells, however the CAR construct D0104, with membrane-proximal TSLPR orientation, was detected at a greater percentage of transduced cells at vector-saturating transduction conditions, and was expressed with a greater intensity.

Next, the cytolytic function of the tandem TSLPR×22 CARs was evaluated in a luciferase-based killing assay (FIG. 6). To determine the tandem TSLPR×CD22 CAR reactivity to each of the two antigens, CAR T cells were incubated with skin carcinoma cell line A431-luc stably expressing firefly luciferase, and engineered to express either the CD22 antigen (A431 CD22), or the TSLPR antigen (A431 TSLPR). The parental antigen-negative cell line A431 served as a control for non-specific CAR activation (FIG. 6). The single antigen-targeting CARs CD22 CAR, and TSLPR CAR, were included as a target-specific positive controls. Effector CAR T cells and tumor cells were combined at effector to target (E:T) ratio of 5:1, 10:1 or 20:1, in order to compare and contrast the potency of the different CAR constructs (FIG. 6).

The A431-TSLPR tumor cell line, derived from the A431-luc parental line stably transduced to express the B-cell antigen TSLPR, was efficiently lysed by the tandem D0104 CD22×TSLPR CAR, and the single TSLPR CAR control (FIG. 6A). By contrast, A431-TSLPR target cells were lysed to a lesser degree by the tandem D0103 TSLPR×CD22 CAR. No lysis occurred in A431-TSLPR combination with the negative control UTD, or the CD22 CAR not targeting the TSLPR antigen, indicating that the CAR-mediated cell lysis was specific to the targeted antigen (FIG. 6A).

Target cell line A431 CD22, expressing only the CD22 surface antigen, but not the TSLPR surface antigen, was potently lysed by the tandem CAR constructs D0104 and the single CD22 CAR control, but not by the tandem CAR D0102, (FIG. 5B). The negative control UTD, and the single TSLPR CAR had no lytic effect against this target line, demonstrating CAR target specificity (FIG. 3B). Lastly, no lysis was detected by any of the CAR constructs or controls against the parental A431 target line, negative for both the CD19 and the TSLPR antigens (FIG. 3C). Therefore, the tandem CAR D0104 was more potent than the tandem CAR D0103 in lysing A431-based target lines expressing the single TSLPR or CD22 antigens.

Then, the CAR T cells bearing the D0103 and D0104 tandem TSLPR×CD22 CAR constructs were tested in a killing assay against a panel of native leukemia lines with natural CD22 expression with or without overexpression of TSLPR. Luciferase-expressing B-ALL parental lines, Reh and NALM-6, and their respective TSLPR-overexpressing subclones were used to test the potency of TSLPR×CD22 tandem CAR T cells (FIG. 7).

Figure 7A:
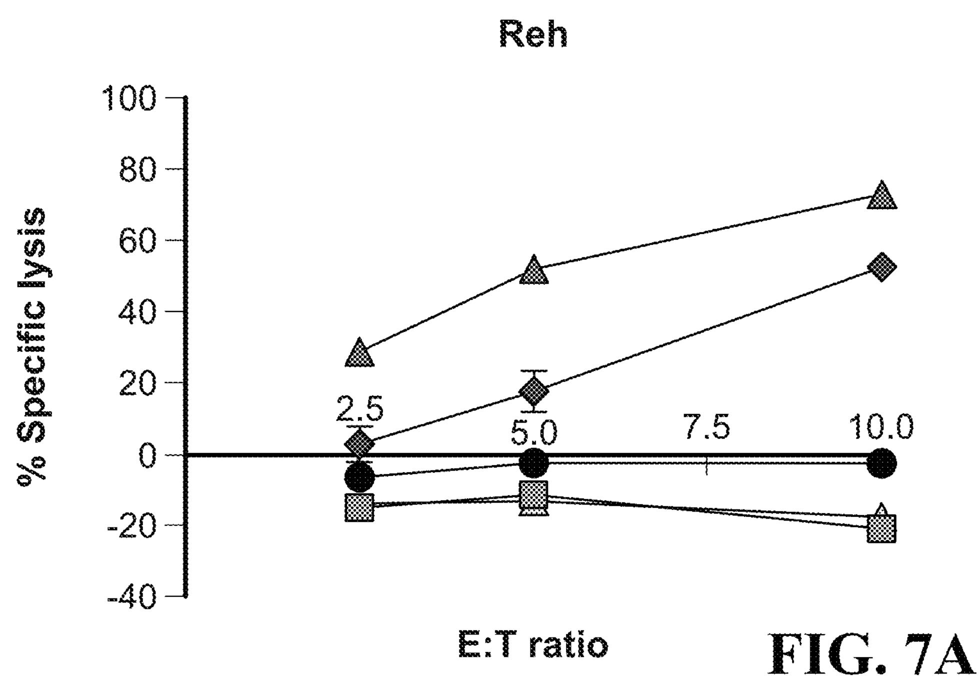
Figure 7B:
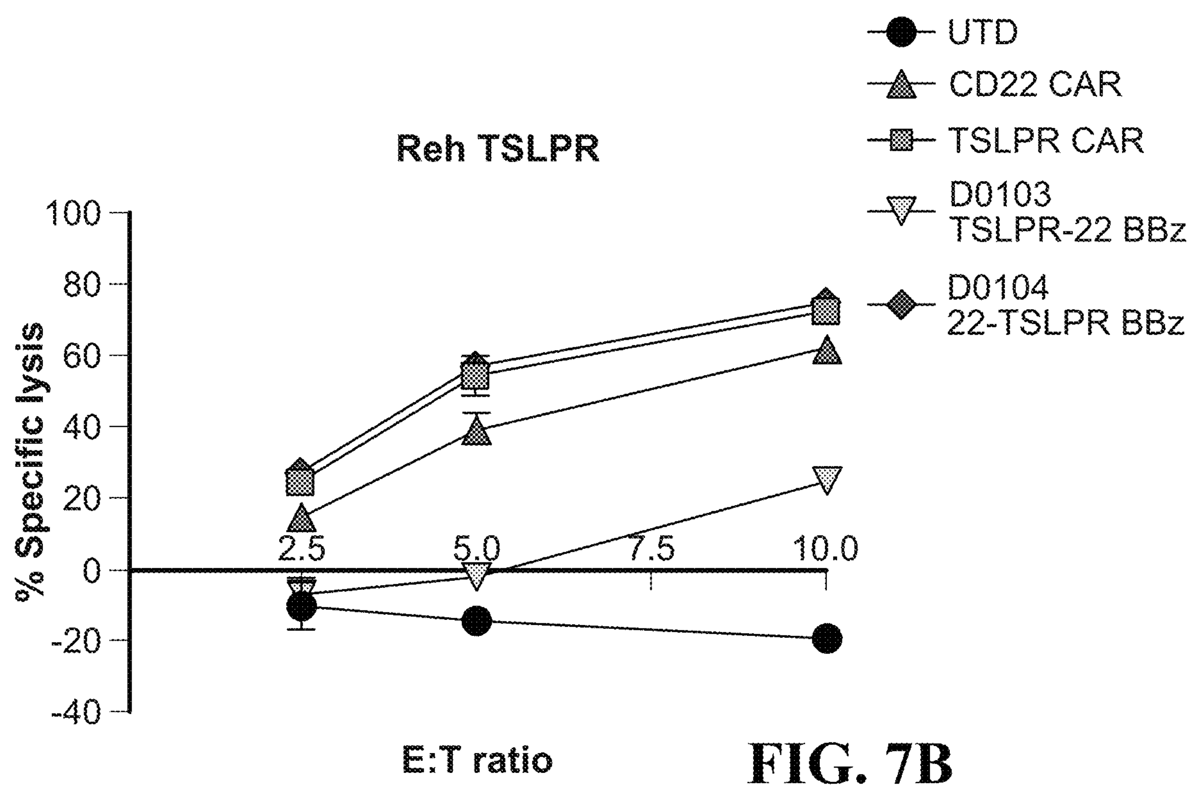

In the Reh line, most potent killing was achieved by the single CD22 CAR, followed by the tandem D0104 CAR construct, whereas the tandem D0101 tandem CAR was not lytic against Reh cells (FIG. 7A). In the Reh TSLPR clone, positive for both TSLPR and CD22 antigens, the tandem CAR D0104 was as potent as the single TSLPR CAR in target cell lysis, followed by the single-targeting control CD22 CAR, whereas the lytic activity of the tandem CAR D0103 was weaker, and target lysis (of 20%) was achieved only at the highest E:T ratio of 10 (FIG. 7B). This finding demonstrates the superior function of the tandem CAR D0104 as compared to the tandem CAR D0103 against Reh target cells expressing CD22, with or without overexpression of TSLPR (FIG. 7A-7B).

Figure 7C:
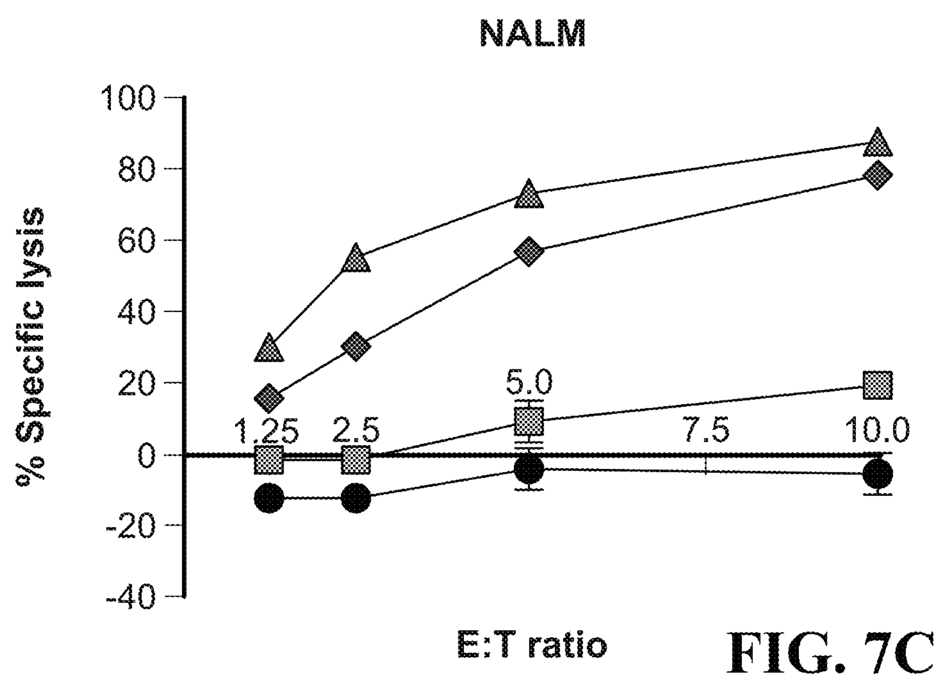
Figure 7D:
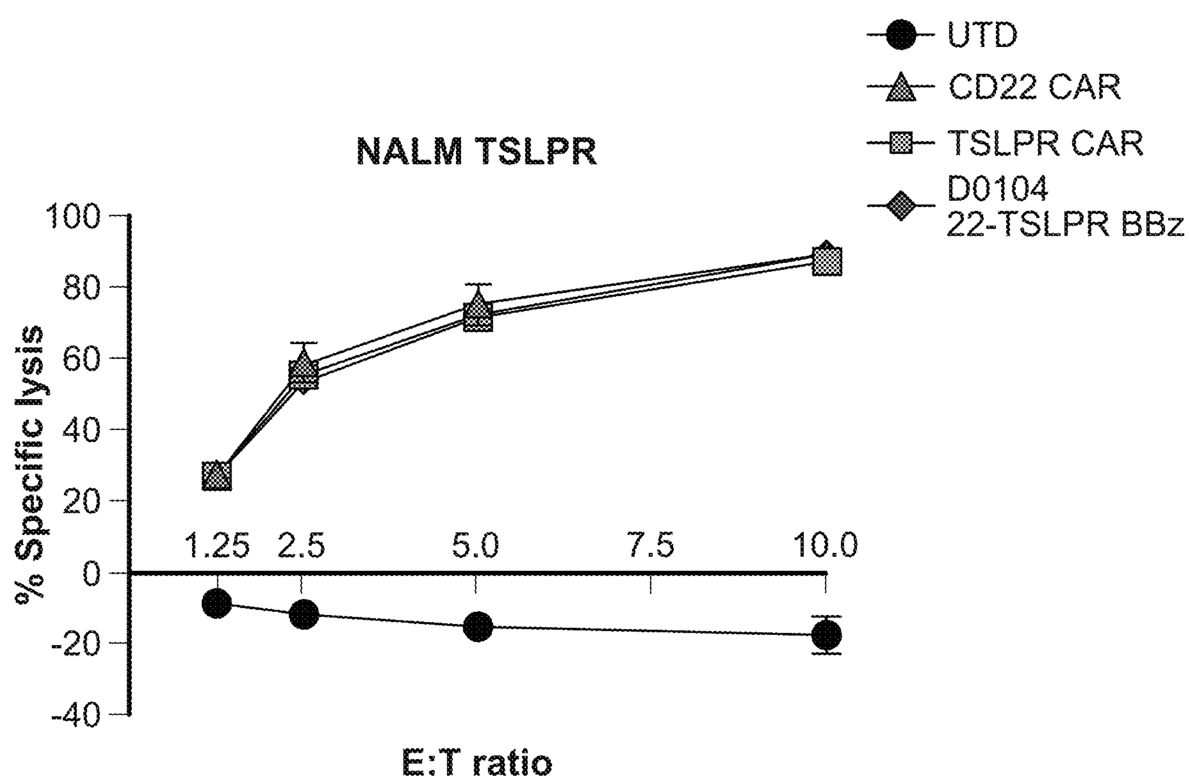

To verify the high potency of tandem D0104 CAR which was observed against the Reh cell lines, in a different target line, this tandem CAR was tested against the NALM-6 B-ALL tumor cell lines, with or without overexpression of TSLPR (FIG. 7C). Here, CAR D0104 was only slightly less potent than the single CD22 CAR against the parental NALM luc line (FIG. 7C), and was equally potent to the single CD22 CAR or single TSLPR CAR against the TSLPR-overexpressing NALM luc TSLPR cell line (FIG. 7D).

Overall, the tandem CAR D0104, in which the TSLPR-targeting scFv domain is positioned proximal to the T cell membrane, and the CD22-targeting scFv domain is distal to the T cell membrane, was more readily expressed on T cells surface at vector-saturating conditions, and mediated greater antigen-specific target cell lysis, than the tandem CAR construct D0103, with the reverse orientation of the targeting domains. This finding indicates that the optimal orientation of the targeting domains within the CAR architecture was not obvious and that empirical testing was necessary for the identification of the optimal configuration for the tandem CD22 (16P17)×TSLPR CAR T constructs.

The CD22-targeting scFv m971 has been previously developed in a single CAR format and evaluated clinically (Fry et al., Nature Medicine 2018). Tandem CAR constructs combining the TSLPR 3G11 targeting scFv domain with the CD22-targeting m971 scFv were generated (FIG. 1 and TABLE 1). In the tandem CAR construct D0111 the CD22 scFv m971 was positioned proximally to T cell membrane, and TSLPR scFv distal to cell membrane. By contrast, in the tandem CAR construct D0112, the m971 scFv was in the membrane-distal orientation, and the TSLPR scFv was in the membrane-proximal orientation (FIG. 1 and TABLE 1).

The surface expression of the tandem TSLPR×CD22 CAR incorporating the human ScFv m971 in membrane-proximal orientation (D0111), and in the membrane-distal orientation (D0112) is shown in FIG. 8. Specific detection of each scFv domain within the CAR structure was facilitated by CAR T cell staining with TSLPR-Fc peptide, or CD22-Fc peptide, followed by a secondary staining with anti-Fc AF647-labeled reagent and detection in the APC channel by flow cytometry. In CAR construct D0111, in which CD22 scFv was membrane-proximal and the TSLPR scFv was membrane-distal, the TSLPR scFv was detected at 34% of the transduced cells, and CD22 scFv was detected at 11%. In CAR construct D0112 with the reverse binder orientation, the detection levels were 73% and 39% for scFv TSLPR and CD22, respectively (FIG. 8).

Results from both methods were taken into account when analyzing CAR expression. Both CAR constructs D0111 and D0112 were successfully expressed in human primary T cells, however the CAR construct D0112, with membrane-proximal TSLPR orientation, was detected at a greater percentage of transduced cells at vector-saturating transduction conditions, and was expressed with greater intensity.

Next, the cytolytic function of the tandem TSLPR×22 CARs bearing the m971 CD22 scFv and the 3G11 TSLPR scFv, was evaluated in a luciferase-based killing assay (FIG. 9). To determine the tandem TSLPR×CD22 CAR reactivity to each of the two antigens, CAR T cells were incubated with skin carcinoma cell line A431-luc stably expressing firefly luciferase, and engineered to express either the CD22 antigen (A431 CD22), or the TSLPR antigen (A431 TSLPR). The parental antigen-negative cell line A431 served as a control for non-specific CAR activation (FIG. 9). The single antigen-targeting CARs CD22 CAR, and TSLPR CAR, were included as a target-specific positive controls. Effector CAR T cells and tumor cells were combined at effector to target (E:T) ratio of 5:1, 10:1 or 20:1, in order to compare and contrast the potency of the different CAR constructs (FIG. 9).

A431-TSLPR tumor cell line, derived from A431-luc parental line stably transduced to express the B-cell antigen TSLPR, was efficiently lysed by the tandem D0112 CD22×TSLPR CAR, and the single TSLPR CAR control, but was lysed less effectively by the D0111 tandem CAR in which the CD22 scFv was cell membrane-proximal (FIG. 9A).

Furthermore, the A431-TSLPR target cells expressing the TSLPR antigen only, were potently lysed by the tandem D0112 TSLPR×CD22 CAR, as well as the single TSLPR CAR control, but not by the single CD22 CAR (FIG. 9B). The tandem D0111 CAR, with the opposite orientation of scFv domains, was less potent than the tandem CAR D0112 against A431 TSLR target line at the lower E:T ratios of 2.5:1 and 5:1, but equally potent at the ratio of 10:1. (FIG. 9B). No lysis occurred in A431-TSLPR combination with the negative control UTD, as expected (FIG. 9A, 9B).

Lastly, no lysis was detected by any of the CAR constructs or controls against the parental A431 target line, negative for both the CD22 and the TSLPR antigens (FIG. 3C). Therefore, the tandem CAR D0112 was more potent than the tandem CAR D0111 in lysing A431-based target lines expressing the single TSLPR or CD22 antigens.

Then, the tandem TSLPR×CD22 CAR T cells D0111 and D0112 were tested in a killing assay against a panel of native leukemia lines with natural CD22 expression with or without overexpression of TSLPR. Luciferase-expressing B-ALL parental lines, Reh and NALM-6, and their respective TSLPR-overexpressing subclones were used to test the potency of TSLPR×CD19 tandem CAR T cells (FIG. 10).

Figure 10A:
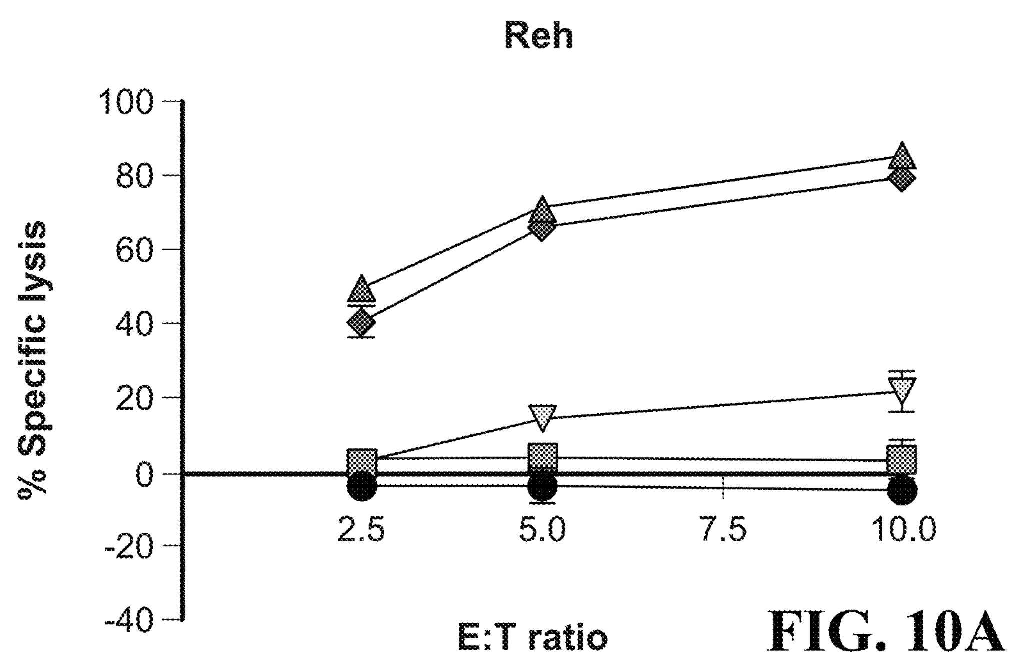
Figure 10B:
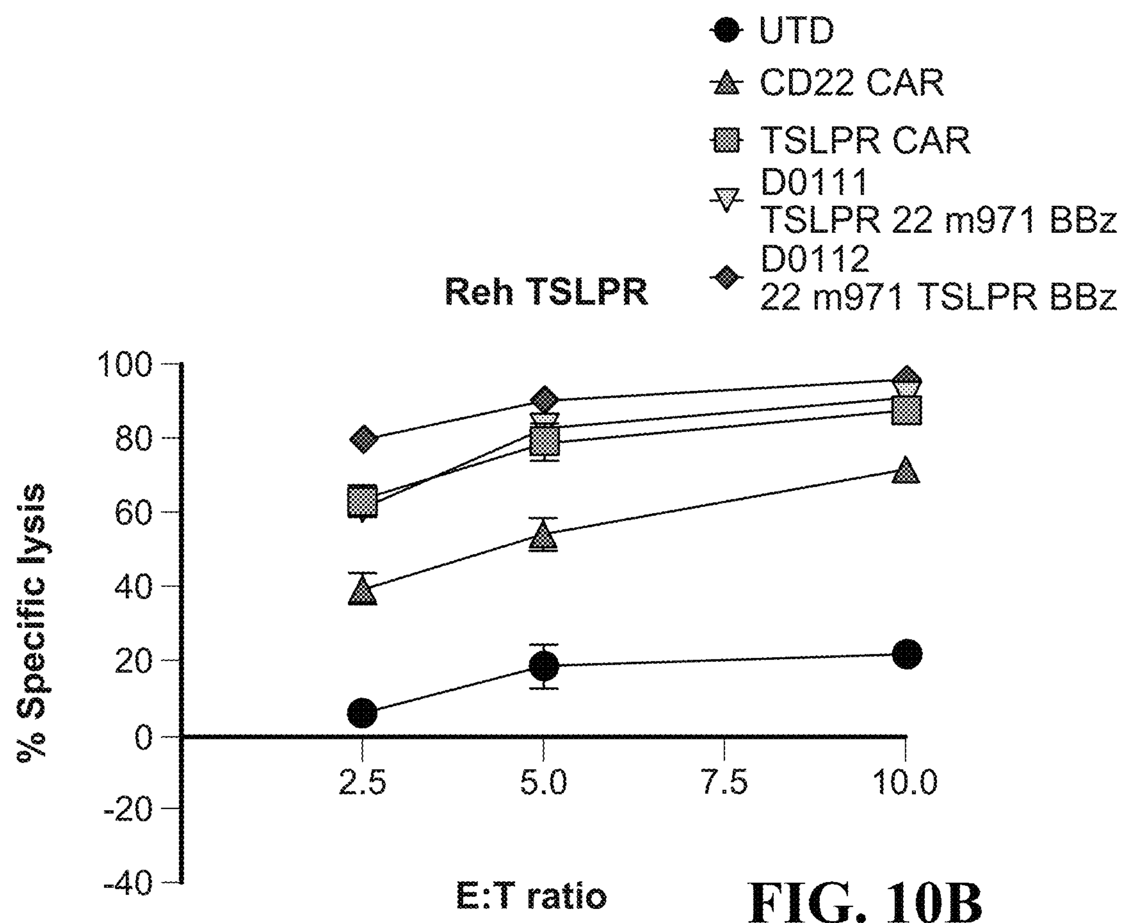

In the Reh Luc line, robust and equally potent killing was achieved by the single CD22 CAR, and the tandem D0112 CAR construct, whereas the tandem D0111 tandem CAR exhibited only a weak lytic activity against Reh Luc cells, which was seen only at the highest E:T ratio of 10 (FIG. 10A). In the Reh TSLPR clone, positive for both TSLPR and CD22 antigens, the tandem CAR D0112 was more potent than the single TSLPR CAR or the single CD22 CAR in target cell lysis, whereas the tandem CAR D0111 with the opposite orientation of scFv domains achieved only a modest lysis of Reh TSLPR target cell line at E:T ratios of 10:1 and 5:1 (FIG. 10B).

Figure 10C:
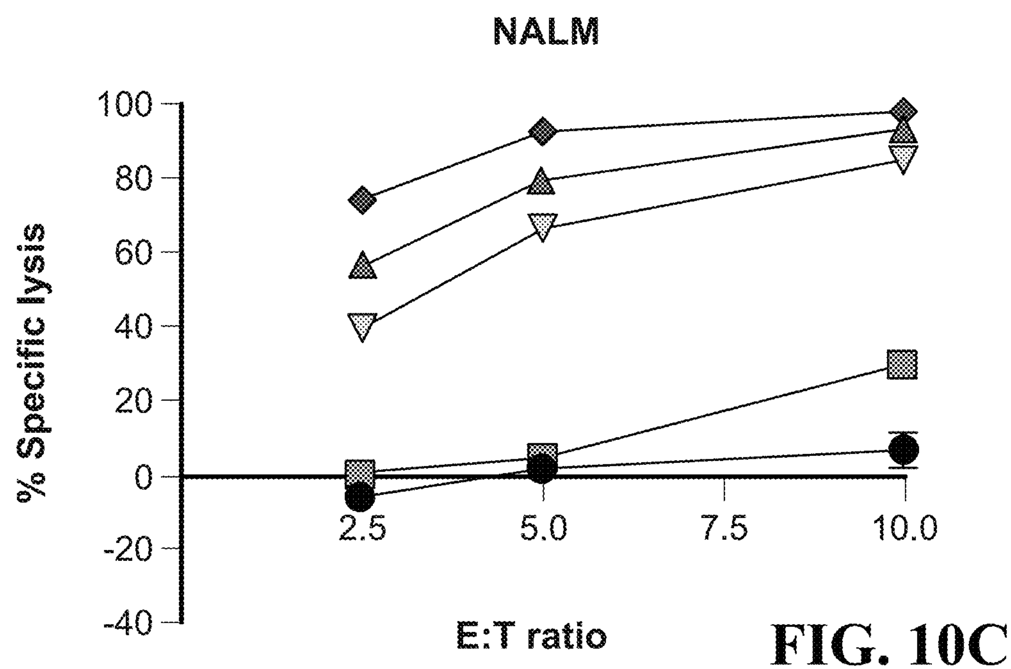
Figure 10D:
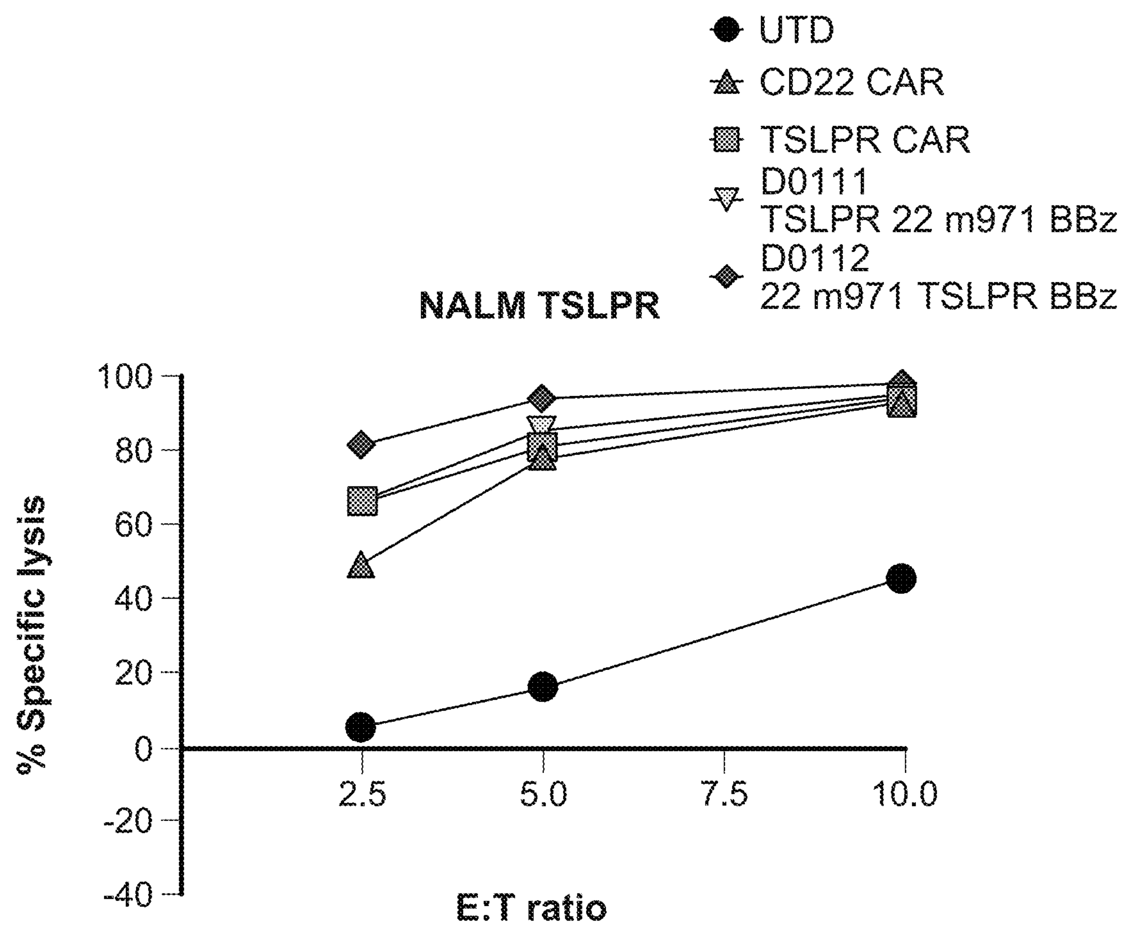

To verify the potency of tandem D0112 CAR observed against the Reh cell lines in a different target line, this tandem CAR was tested against the NALM-6 B-ALL tumor cell lines, with or without overexpression of TSLPR (FIG. 10C). When combined with the NALM Luc line, CAR D0112 was the most potent CAR in this set, followed by the single CD22 CAR, and the tandem D0111 CAR against the parental NALM luc line, whereas the single TSLPR CAR only showed a modest target cell lysis of 20% at the highest E:T ratio of 10:1 (FIG. 10C). In the NALM TSLPR target line overexpressing TSLPR, the tandem CAR D0112 was the most potent in the set, followed by the tandem D0111, the single TSLPR CAR, and the single CD22 CAR (FIG. 10D).

Overall, the tandem CAR D0112 was more readily expressed on T cells surface at LV-saturating conditions, and mediated greater antigen-specific target cell lysis than the tandem CAR construct D0111.

Thus it was found that positioning the TSLPR scFv proximal to target cell membrane was preferred, and yielded greater CAR expression and stronger tumor-lytic activity for both CD19-targeting and CD22-targeting CAR constructs, and did not depend on the scFv sequence that was used. This finding was not expected, and required empirical testing of each scFv sequence incorporated in the tandem TSLPR×CD19 and TSLPR×CD22 CAR constructs, in both membrane-proximal and membrane-distal orientations.

EQUIVALENTS

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

SEQUENCE LISTING

The nucleic and amino acid sequences listed below are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

nucleotide sequence of LTG2681 D0023 Leader-CD22 VH-(GGGGS)-3 CD22 VL (GGGGS)-5 CD19 VH (GGGGS)-3 CD19 VL CD8 hinge + TM-4-1BB-CD3z (Construct CAR 2219)

SEQ ID NO: 1

```
ATGCTCTTGCTCGTGACTTCTTTGCTTTTGTGCGAACTTCCGCACCCAGCCTTCCT

TTTGATACCTCAGGTACAGCTTCAACAAAGCGGACCGGGACTTGTTAAGCATTCC

CAAACCCTTTCTCTCACGTGTGCAATTAGCGGCGATAGTGTATCCTCTAATTCTGC

GGCCTGGAACTGGATACGACAATCACCAAGCCGGGGACTCGAGTGGTTGGGCCG

AACCTACTATCGGTCCAAATGGTATAATGACTACGCAGTATCCGTGAAATCTCGC

ATTACGATCAATCCAGACACCTCCAAAAATCAATTTTCTCTGCAGTTGAATAGCG

TGACTCCCGAGGACACGGCCGTTTACTATTGCGCCCAGGAAGTTGAACCCCACG

ATGCATTTGATATTTGGGGCCAGGGAACCATGGTGACAGTGAGTAGTGGGGGTG

GAGGATCTGGAGGAGGCGGTAGCGGCGGGGGCGGCAGTGATATCCAGATGACG

CAGTCACCTTCCAGCGTGTATGCGAGTGTGGGGGACAAGGTCACCATAACCTGTC

GCGCTAGCCAAGATGTCAGCGGGTGGCTGGCTTGGTACCAGCAGAAACCAGGTT

TGGCTCCTCAGCTTTTGATCTCAGGAGCGAGCACGCTTCAGGGTGAGGTCCCAAG

TCGCTTTAGTGGCTCTGGCTCCGGGACAGACTTCACGTTGACGATCAGCAGTTTG

CAGCCTGAGGATTTCGCGACCTACTACTGCCAGCAAGCGAAATATTTTCCGTACA

CTTTCGGTCAGGGGACCAAATTGGAGATCAAAGGTGGGGGTGGTTCAGGCGGCG

GAGGCTCAGGCGGCGGCGGTAGCGGAGGAGGCGGAAGCGGGGGTGGCGGATCA

GAAGTGCAACTCGTTCAGAGTGGCGCGGAGGTTAAGAAACCCGGTGCATCTGTA

AAGGTTAGCTGTAAGGCATCAGGATACACTTTTACCAGCTATTACATGCATTGGG

TGAGACAGGCTCCCGGTCAGGGGCTCGAATGGATGGGGTTGATCAACCCGAGTG

GTGGTTCAACATCTTACGCCCAGAAGTTTCAGGGCCGAGTAACAATGACTCGGG

ACACGTCTACCTCAACTGTGTATATGGAGCTTTCCAGCCTGCGCTCAGAGGATAC

AGCAGTCTATTACTGCGCACGGTCAGACAGAGGTATAACGGCCACTGATGCGTT

CGATATCTGGGGACAAGGGACTATGGTAACTGTGTCTTCCGGAGGAGGAGGTAG

TGGAGGGGGAGGAAGCGGTGGGGGGGGCTCACAGTCCGTTTTGACTCAGCCACC

AAGCGTCTCAGTCGCACCGGGGCGAATGGCGAAAATTACTTGCGGCGGGAGCGA
```

-continued

CATAGGCAACAAGAATGTGCATTGGTACCAACAGAAACCAGGTCAAGCACCTGT

TCTCGTGGTGTATGATGACTACGATCGCCCAAGCGGGATCCCGGAGCGGTTCTCT

GGATCAAATTCTGGTGATGCAGCCACTCTGACAATATCAACGGTGGAAGTCGGT

GACGAGGCTGATTACTTCTGCCAAGTATGGGATGGCAGCGGAGATCCCTACTGG

ATGTTTGGAGGAGGTACTCAACTGACAGTTCTGGGCGCGGCCGCAACGACCACT

CCTGCACCCCGCCCTCCGACTCCGGCCCCAACCATTGCCAGCCAGCCCCTGTCCC

TGCGGCCGGAAGCCTGCAGACCGGCTGCCGGCGGAGCCGTCCATACCCGGGGAC

TGGATTTCGCCTGCGATATCTATATCTGGGCACCACTCGCCGGAACCTGTGGAGT

GCTGCTGCTGTCCCTTGTGATCACCCTGTACTGCAAGCGCGGACGGAAGAAACTC

TTGTACATCTTCAAGCAGCCGTTCATGCGCCCTGTGCAAACCACCCAAGAAGAGG

ACGGGTGCTCCTGCCGGTTCCCGGAAGAGGAAGAGGGCGGCTGCGAACTGCGCG

TGAAGTTTTCCCGGTCCGCCGACGCTCCGGCGTACCAGCAGGGGCAAAACCAGC

TGTACAACGAACTTAACCTCGGTCGCCGGGAAGAATATGACGTGCTGGACAAGC

GGCGGGGAAGAGATCCCGAGATGGGTGGAAAGCCGCGGCGGAAGAACCCTCAG

GAGGGCTTGTACAACGAGCTGCAAAAGGACAAAATGGCCGAAGCCTACTCCGAG

ATTGGCATGAAGGGAGAGCGCAGACGCGGGAAGGGACACGATGGACTGTACCA

GGGACTGTCAACCGCGACTAAGGACACTTACGACGCCCTGCACATGCAGGCCCT

GCCCCCGCGC amino acid sequence of LTG2681 D0023 Leader-CD22 VH-(GGGGS)-3 CD22 VL (GGGGS)-5 CD19 VH (GGGGS)-3 CD19 VL CD8 hinge + TM-4-1BB-CD3z (Construct CAR 2219)

SEQ ID NO: 2

MLLLVTSLLLCELPHPAFLLIPQVQLQQSGPGLVKHSQTLSLTCAISGDSVSSNSAAW

NWIRQSPSRGLEWLGRTYYRSKWYNDYAVSVKSRITINPDTSKNQFSLQLNSVTPED

TAVYYCAQEVEPHDAFDIWGQGTMVTVSSGGGGSGGGGSGGGGSDIQMTQSPSSV

YASVGDKVTITCRASQDVSGWLAWYQQKPGLAPQLLISGASTLQGEVPSRFSGSGSG

TDFTLTISSLQPEDFATYYCQQAKYFPYTFGQGTKLEIKGGGGSGGGGSGGGGSGGG

GSGGGGSEVQLVQSGAEVKKPGASVKVSCKASGYTFTSYYMHWVRQAPGQGLEW

MGLINPSGGSTSYAQKFQGRVTMTRDTSTSTVYMELSSLRSEDTAVYYCARSDRGIT

ATDAFDIWGQGTMVTVSSGGGGSGGGGSGGGGSQSVLTQPPSVSVAPGRMAKITCG

GSDIGNKNVHWYQQKPGQAPVLVVYDDYDRPSGIPERFSGSNSGDAATLTISTVEVG

DEADYFCQVWDGSGDPYWMFGGGTQLTVLGAAATTTPAPRPPTPAPTIASQPLSLRP

EACRPAAGGAVHTRGLDFACDIYIWAPLAGTCGVLLLSLVITLYCKRGRKKLLYIFK

QPFMRPVQTTQEEDGCSCRFPEEEEGGCELRVKFSRSADAPAYQQGQNQLYNELNL

GRREEYDVLDKRRGRDPEMGGKPRRKNPQEGLYNELQKDKMAEAYSEIGMKGERR

RGKGHDGLYQGLSTATKDTYDALHMQALPPR nucleotide sequence of LTG2791 D0024 Leader-CD19 VH (GGGGS)3-CD19 VL-(GGGGS)5-CD22 VH (GGGGS)3-CD22 VH CD8 hinge + TM-4-1BB-CD3z (Construct CAR 1922)

SEQ ID NO: 3

ATGTTGCTTCTGGTTACTTCCCTTCTTCTTTGCGAGCTTCCACACCCAGCATTCCT

GCTCATTCCGGAGGTGCAACTCGTCCAATCCGGGGCCGAAGTTAAGAAGCCGGG

AGCATCTGTTAAAGTATCCTGTAAGGCCAGTGGGTATACTTTCACCTCATATTAT

ATGCACTGGGTGAGGCAGGCTCCAGGCCAAGGGTTGGAGTGGATGGGACTGATA

-continued

```
AACCCATCTGGGGGATCAACTTCTTATGCGCAAAAGTTCCAAGGTCGGGTCACTA

TGACAAGGGACACATCCACCAGCACTGTTTATATGGAACTGAGCAGCCTGAGAT

CTGAGGATACCGCAGTATATTACTGTGCACGCAGTGATAGAGGCATAACGGCGA

CTGACGCCTTCGACATTTGGGGCCAAGGGACAATGGTCACGGTTTCAAGTGGAG

GTGGAGGGTCTGGTGGCGGGGGGTCTGGTGGTGGAGGCAGTCAGAGCGTCCTGA

CCCAGCCGCCTAGCGTCAGTGTGGCCCCCGGCCGCATGGCCAAGATAACGTGTG

GCGGAAGCGATATTGGGAATAAGAACGTCCACTGGTATCAGCAGAAGCCAGGGC

AGGCTCCCGTCCTCGTAGTATACGACGATTATGATCGGCCCAGTGGAATCCCCGA

GAGATTTAGCGGGAGTAACTCTGGGGATGCAGCGACACTTACTATCTCCACTGTT

GAAGTAGGAGACGAGGCTGACTATTTTTGTCAGGTTTGGGACGGATCCGGAGAT

CCTTATTGGATGTTTGGCGGAGGTACTCAATTGACCGTGCTTGGAGGTGGCGGAG

GGAGCGGGGGTGGGGGCTCAGGGGGAGGTGGGTCAGGCGGGGGCGGAAGTGGT

GGCGGGGGTTCCCAAGTCCAACTCCAGCAGTCAGGACCTGGACTGGTAAAACAC

TCTCAAACCCTGTCTCTCACGTGTGCCATATCTGGCGATAGTGTATCTTCAAACTC

TGCTGCATGGAACTGGATCAGGCAAAGTCCATCCCGCGGCCTTGAGTGGCTCGGT

CGAACCTATTACCGAAGCAAATGGTACAACGATTATGCGGTTTCAGTCAAGTCA

AGAATTACGATCAACCCTGATACGAGTAAGAACCAGTTTAGTTTGCAATTGAAC

AGTGTAACTCCCGAGGACACGGCGGTGTACTATTGTGCGCAAGAAGTCGAACCG

CATGATGCGTTCGATATCTGGGGGCAGGGCACAATGGTGACCGTATCTTCTGGCG

GCGGCGGCTCTGGAGGAGGAGGAAGCGGCGGAGGGGGATCTGACATACAAATG

ACACAATCCCCAAGTTCAGTATATGCTAGCGTCGGGGATAAAGTGACAATTACTT

GTAGGGCTTCTCAAGACGTAAGTGGCTGGTTGGCGTGGTACCAGCAAAAGCCGG

GTCTCGCCCCTCAACTCCTTATCAGCGGAGCTTCAACTCTTCAGGGAGAGGTCCC

AAGTCGATTCTCAGGCTCTGGCTCCGGGACAGATTTCACCTTGACAATTAGTTCA

CTGCAACCCGAGGATTTCGCAACTTACTACTGTCAACAGGCCAAGTACTTCCCGT

ATACGTTTGGTCAAGGCACAAAACTGGAGATTAAGGCGGCCGCAACGACCACTC

CTGCACCCCGCCCTCCGACTCCGGCCCCAACCATTGCCAGCCAGCCCCTGTCCCT

GCGGCCGGAAGCCTGCAGACCGGCTGCCGGCGGAGCCGTCCATACCCGGGGACT

GGATTTCGCCTGCGATATCTATATCTGGGCACCACTCGCCGGAACCTGTGGAGTG

CTGCTGCTGTCCCTTGTGATCACCCTGTACTGCAAGCGCGGACGGAAGAAACTCT

TGTACATCTTCAAGCAGCCGTTCATGCGCCCTGTGCAAACCACCCAAGAAGAGG

ACGGGTGCTCCTGCCGGTTCCCGGAAGAGGAAGAGGGCGGCTGCGAACTGCGCG

TGAAGTTTTCCCGGTCCGCCGACGCTCCGGCGTACCAGCAGGGGCAAAACCAGC

TGTACAACGAACTTAACCTCGGTCGCCGGGAAGAATATGACGTGCTGGACAAGC

GGCGGGGAAGAGATCCCGAGATGGGTGGAAAGCCGCGGCGGAAGAACCCTCAG

GAGGGCTTGTACAACGAGCTGCAAAAGGACAAAATGGCCGAAGCCTACTCCGAG

ATTGGCATGAAGGGAGAGCGCAGACGCGGGAAGGGACACGATGGACTGTACCA

GGGACTGTCAACCGCGACTAAGGACACTTACGACGCCCTGCACATGCAGGCCCT

GCCCCCGCGC
```

amino acid sequence of LTG2719 D0024 Leader-CD19 VH (GGGGS)3-CD19 VL-(GGGGS)5-CD22 VH (GGGGS)3-CD22 VH CD8 hinge + TM-4-1BB- CD3z (Construct CAR 1922)

-continued

SEQ ID NO: 4

MLLLVTSLLLCELPHPAFLLIPEVQLVQSGAEVKKPGASVKVSCKASGYTFTSYYMH

WVRQAPGQGLEWMGLINPSGGSTSYAQKFQGRVTMTRDTSTSTVYMELSSLRSEDT

AVYYCARSDRGITATDAFDIWGQGTMVTVSSGGGGSGGGGSGGGGSQSVLTQPPSV

SVAPGRMAKITCGGSDIGNKNVHWYQQKPGQAPVLVVYDDYDRPSGIPERFSGSNS

GDAATLTISTVEVGDEADYFCQVWDGSGDPYWMFGGGTQLTVLGGGGGSGGGGS

GGGGSGGGGSGGGGSQVQLQQSGPGLVKHSQTLSLTCAISGDSVSSNSAAWNWIRQ

SPSRGLEWLGRTYYRSKWYNDYAVSVKSRITINPDTSKNQFSLQLNSVTPEDTAVYY

CAQEVEPHDAFDIWGQGTMVTVSSGGGGSGGGGSGGGGSDIQMTQSPSSVYASVG

DKVTITCRASQDVSGWLAWYQQKPGLAPQLLISGASTLQGEVPSRFSGSGSGTDFTL

TISSLQPEDFATYYCQQAKYFPYTFGQGTKLEIKAAATTTPAPRPPTPAPTIASQPLSL

RPEACRPAAGGAVHTRGLDFACDIYIWAPLAGTCGVLLLSLVITLYCKRGRKKLLYI

FKQPFMRPVQTTQEEDGCSCRFPEEEEGGCELRVKFSRSADAPAYQQGQNQLYNEL

NLGRREEYDVLDKRRGRDPEMGGKPRRKNPQEGLYNELQKDKMAEAYSEIGMKGE

RRRGKGHDGLYQGLSTATKDTYDALHMQALPPR nucleotide sequence of fully human CAR19 LTG2065 (M19217-1-CD8 TM-4-1BB zeta)

SEQ ID NO: 5

ATGCTGCTGCTGGTGACCAGCCTGCTGCTGTGCGAACTGCCGCATCCGGCGTTTC

TGCTGATTCCGGAGGTCCAGCTGGTACAGTCTGGAGCTGAGGTGAAGAAGCCTG

GGGCCTCAGTGAAGGTCTCCTGCAAGGCTTCTGGATACACCTTCACCAGCTACTA

TATGCACTGGGTGCGACAGGCCCCTGGACAAGGGCTTGAGTGGATGGGATTAAT

CAACCCTAGTGGTGGTAGCACAAGCTACGCACAGAAGTTCCAGGGCAGAGTCAC

CATGACCAGGGACACGTCCACGAGCACAGTCTACATGGAGCTGAGCAGCCTGAG

ATCTGAGGACACGGCCGTGTATTACTGTGCGAGATCGGATCGGGGAATTACCGC

CACGGACGCTTTTGATATCTGGGGCCAAGGGACAATGGTCACCGTCTCTTCAGGC

GGAGGAGGCTCCGGGGGAGGAGGTTCCGGGGGCGGGGGTTCCCAGTCTGTGCTG

ACTCAGCCACCCTCGGTGTCAGTGGCCCCAGGGCGGATGGCCAAGATTACCTGT

GGGGGAAGTGACATTGGAAATAAAAATGTCCACTGGTATCAGCAGAAGCCAGGC

CAGGCCCCTGTCCTGGTTGTCTATGATGATTACGACCGGCCCTCAGGGATCCCTG

AGCGATTCTCTGGCTCCAACTCTGGGGACGCGGCCACCCTGACGATCAGCACGGT

CGAAGTCGGGGATGAGGCCGACTATTTCTGTCAGGTGTGGGACGGTAGTGGTGA

TCCTTATTGGATGTTCGGCGGAGGGACCCAGCTCACCGTTTTAGGTGCGGCCGCA

ACTACCACCCCTGCCCCTCGGCCGCCGACTCCGGCCCCAACCATCGCAAGCCAAC

CCCTCTCCTTGCGCCCCGAAGCTTGCCGCCCGGCCGCGGGTGGAGCCGTGCATAC

CCGGGGGCTGGACTTTGCCTGCGATATCTACATTTGGGCCCCGCTGGCCGGCACT

TGCGGCGTGCTCCTGCTGTCGCTGGTCATCACCCTTTACTGCAAGAGGGGCCGGA

AGAAGCTGCTTTACATCTTCAAGCAGCCGTTCATGCGGCCCGTGCAGACGACTCA

GGAAGAGGACGGATGCTCGTGCAGATTCCCTGAGGAGGAAGAGGGGGGATGCG

AACTGCGCGTCAAGTTCTCACGGTCCGCCGACGCCCCCGCATATCAACAGGGCC

AGAATCAGCTCTACAACGAGCTGAACCTGGGAAGGAGAGAGGAGTACGACGTG

CTGGACAAGCGACGCGGACGCGACCCGGAGATGGGGGGGAAACCACGGCGGAA

AAACCCTCAGGAAGGACTGTACAACGAACTCCAGAAAGACAAGATGGCGGAAG

-continued

CCTACTCAGAAATCGGGATGAAGGGAGAGCGGAGGAGGGGAAAGGGTCACGAC

GGGCTGTACCAGGGACTGAGCACCGCCACTAAGGATACCTACGATGCCTTGCAT

ATGCAAGCACTCCCACCCCGG amino acid sequence of fully human CAR19 LTG2065
(M19217-1-CD8 TM-4-1BB zeta)

SEQ ID NO: 6

MLLLVTSLLLCELPHPAFLLIPEVQLVQSGAEVKKPGASVKVSCKASGYTFTSYYMH

WVRQAPGQGLEWMGLINPSGGSTSYAQKFQGRVTMTRDTSTSTVYMELSSLRSEDT

AVYYCARSDRGITATDAFDIWGQGTMVTVSSGGGGSGGGGSGGGGSQSVLTQPPSV

SVAPGRMAKITCGGSDIGNKNVHWYQQKPGQAPVLVVYDDYDRPSGIPERFSGSNSG

DAATLTISTVEVGDEADYFCQVWDGSGDPYWMFGGGTQLTVLGAAATTTPAPRPPT

PAPTIASQPLSLRPEACRPAAGGAVHTRGLDFACDIYIWAPLAGTCGVLLLSLVITLYC

KRGRKKLLYIFKQPFMRPVQTTQEEDGCSCRFPEEEEGGCELRVKFSRSADAPAYQQ

GQNQLYNELNLGRREEYDVLDKRRGRDPEMGGKPRRKNPQEGLYNELQKDKMAEA

YSEIGMKGERRRGKGHDGLYQGLSTATKDTYDALHMQALPPR nucleotide sequence of mouse scFv CAR19 LTG1538

SEQ ID NO: 7

ATGCTTCTCCTGGTCACCTCCCTGCTCCTCTGCGAACTGCCTCACCCTGCCTTCCT

TCTGATTCCTGACATTCAGATGACTCAGACCACCTCTTCCTTGTCCGCGTCACTG

GGAGACAGAGTGACCATCTCGTGTCGCGCAAGCCAGGATATCTCCAAGTACCTG

AACTGGTACCAACAGAAGCCCGACGGGACTGTGAAGCTGCTGATCTACCACACC

TCACGCCTGCACAGCGGAGTGCCAAGCAGATTCTCCGGCTCCGGCTCGGGAACC

GATTACTCGCTTACCATTAGCAACCTCGAGCAGGAGGACATCGCTACCTACTTCT

GCCAGCAAGGAAATACCCTGCCCTACACCTTCGGCGGAGGAACCAAATTGGAAA

TCACCGGCGGAGGAGGCTCCGGGGGAGGAGGTTCCGGGGGCGGGGGTTCCGAA

GTGAAGCTCCAGGAGTCCGGCCCCGGCCTGGTGGCGCCGTCGCAATCACTCTCT

GTGACCTGTACCGTGTCGGGAGTGTCCCTGCCTGATTACGGCGTGAGCTGGATTC

GGCAGCCGCCGCGGAAGGGCCTGGAATGGCTGGGTGTCATCTGGGGATCCGAGA

CTACCTACTACAACTCGGCCCTGAAGTCCCGCCTGACTATCATCAAAGACAACTC

GAAGTCCCAGGTCTTTCTGAAGATGAACTCCCTGCAAACTGACGACACCGCCAT

CTATTACTGTGCTAAGCACTACTACTACGGTGGAAGCTATGCTATGGACTACTGG

GGGCAAGGCACTTCGGTGACTGTGTCAAGCGCGGCCGCAACTACCACCCCTGCC

CCTCGGCCGCCGACTCCGGCCCCAACCATCGCAAGCCAACCCCTCTCCTTGCGCC

CCGAAGCTTGCCGCCCGGCCGCGGGTGGAGCCGTGCATACCCGGGGGCTGGACT

TTGCCTGCGATATCTACATTTGGGCCCCGCTGGCCGGCACTTGCGGCGTGCTCCT

GCTGTCGCTGGTCATCACCCTTTACTGCAAGAGGGGCCGGAAGAAGCTGCTTTAC

ATCTTCAAGCAGCCGTTCATGCGGCCCGTGCAGACGACTCAGGAAGAGGACGGA

TGCTCGTGCAGATTCCCTGAGGAGGAAGAGGGGGGATGCGAACTGCGCGTCAAG

TTCTCACGGTCCGCCGACGCCCCCGCATATCAACAGGGCCAGAATCAGCTCTAC

AACGAGCTGAACCTGGGAAGGAGAGAGGAGTACGACGTGCTGGACAAGCGACG

CGGACGCGACCCGGAGATGGGGGGGAAACCACGGCGGAAAAACCCTCAGGAAG

GACTGTACAACGAACTCCAGAAAGACAAGATGGCGGAAGCCTACTCAGAAATC

GGGATGAAGGGAGAGCGGAGGAGGGGAAAGGGTCACGACGGGCTGTACCAGGG

-continued

ACTGAGCACCGCCACTAAGGATACCTACGATGCCTTGCATATGCAAGCACTCCC

ACCCCGG amino acid sequence of mouse scFv CAR19 LTG1538

SEQ ID NO: 8

MLLLVTSLLLCELPHPAFLLIPDIQMTQTTSSLSASLGDRVTISCRASQDISKYLNWYQ

QKPDGTVKLLIYHTSRLHSGVPSRFSGSGSGTDYSLTISNLEQEDIATYFCQQGNTLP

YTFGGGTKLEITGGGGSGGGGSGGGGSEVKLQESGPGLVAPSQSLSVTCTVSGVSLP

DYGVSWIRQPPRKGLEWLGVIWGSETTYYNSALKSRLTIIKDNSKSQVFLKMNSLQT

DDTAIYYCAKHYYYGGSYAMDYWGQGTSVTVSSAAATTTPAPRPPTPAPTIASQPL

SLRPEACRPAAGGAVHTRGLDFACDIYIWAPLAGTCGVLLLSLVITLYCKRGRKKLL

YIFKQPFMRPVQTTQEEDGCSCRFPEEEEGGCELRVKFSRSADAPAYQQGQNQLYNE

LNLGRREEYDVLDKRRGRDPEMGGKPRRKNPQEGLYNELQKDKMAEAYSEIGMKG

ERRRGKGHDGLYQGLSTATKDTYDALHMQALPP nucleotide sequence of CAR22 LTG2209

SEQ ID NO: 9

ATGCTTCTTTTGGTGACTTCCCTTTTGCTGTGCGAGTTGCCACACCCCGCCTTCCT

GCTTATTCCCCAGGTACAGCTTCAACAGAGTGGGCCGGGACTGGTGAAACACTC

CCAAACACTTTCTCTGACGTGCGCTATATCAGGTGACTCTGTTTCATCTAATTCTG

CTGCGTGGAACTGGATTCGACAATCTCCCAGTCGCGGGTTGGAATGGCTGGGAC

GAACATATTATCGGTCTAAGTGGTATAACGATTATGCTGTATCTGTTAAATCTCG

AATTACGATTAATCCTGACACCTCCAAGAACCAGTTCTCCCTCCAGTTGAACTCA

GTCACACCGGAAGACACTGCGGTCTACTATTGCGCTCAAGAAGTCGAGCCACAT

GATGCATTCGACATCTGGGGCCAGGGAACGATGGTCACCGTCAGCAGTGGCGGC

GGCGGATCTGGGGGTGGCGGTTCTGGCGGTGGAGGATCAGACATACAAATGACG

CAGAGTCCCTCAAGTGTGTACGCGAGTGTGGGGGATAAGGTAACTATTACGTGC

AGAGCGTCACAGGATGTTAGTGGATGGCTTGCCTGGTATCAGCAGAAGCCAGGC

CTTGCTCCACAGCTCCTTATCAGTGGTGCTTCTACACTTCAGGGCGAGGTTCCGA

GTAGATTCTCTGGTTCTGGATCTGGTACTGACTTCACTCTTACAATTTCTTCTTTG

CAACCAGAAGACTTTGCGACTTATTACTGCCAACAGGCCAAATACTTCCCTTATA

CATTTGGCCAAGGTACCAAGTTGGAGATAAAGGCGGCCGCAACTACCACCCCTG

CCCCTCGGCCGCCGACTCCGGCCCCAACCATCGCAAGCCAACCCCTCTCCTTGCG

CCCCGAAGCTTGCCGCCCGGCCGCGGGTGGAGCCGTGCATACCCGGGGGCTGGA

CTTTGCCTGCGATATCTACATTTGGGCCCCGCTGGCCGGCACTTGCGGCGTGCTC

CTGCTGTCGCTGGTCATCACCCTTTACTGCAAGAGGGGCCGGAAGAAGCTGCTTT

ACATCTTCAAGCAGCCGTTCATGCGGCCCGTGCAGACGACTCAGGAAGAGGACG

GATGCTCGTGCAGATTCCCTGAGGAGGAAGAGGGGGGATGCGAACTGCGCGTCA

AGTTCTCACGGTCCGCCGACGCCCCCGCATATCAACAGGGCCAGAATCAGCTCTA

CAACGAGCTGAACCTGGGAAGGAGAGAGGAGTACGACGTGCTGGACAAGCGAC

GCGGACGCGACCCGGAGATGGGGGGGAAACCACGGCGGAAAAACCCTCAGGAA

GGACTGTACAACGAACTCCAGAAAGACAAGATGGCGGAAGCCTACTCAGAAATC

GGGATGAAGGGAGAGCGGAGGAGGGGAAAGGGTCACGACGGGCTGTACCAGGG

ACTGAGCACCGCCACTAAGGATACCTACGATGCCTTGCATATGCAAGCACTCCCA

-continued

CCCCGG amino acid sequence of CAR22 LTG2209

SEQ ID NO: 10

MLLLVTSLLLCELPHPAFLLIPQVQLQQSGPGLVKHSQTLSLTCAISGDSVSSNSAA

WNWIRQSPSRGLEWLGRTYYRSKWYNDYAVSVKSRITINPDTSKNQFSLQLNSVTPEDT

AVYYCAQEVEPHDAFDIWGQGTMVTVSSGGGGSGGGGSGGGGSDIQMTQSPSSVYASV

GDKVTITCRASQDVSGWLAWYQQKPGLAPQLLISGASTLQGEVPSRFSGSGSGTDFTLTIS

SLQPEDFATYYCQQAKYFPYTFGQGTKLEIKAAATTTPAPRPPTPAPTIASQPLSLRPEACR

PAAGGAVHTRGLDFACDIYIWAPLAGTCGVLLLSLVITLYCKRGRKKLLYIFKQPFMRPV

QTTQEEDGCSCRFPEEEEGGCELRVKFSRSADAPAYQQGQNQLYNELNLGRREEYDVLD

KRRGRDPEMGGKPRRKNPQEGLYNELQKDKMAEAYSEIGMKGERRRGKGHDGLYQGL

STATKDTYDALHMQALPPR nucleotide sequence of leader/signal peptide sequence (LP)

SEQ ID NO: 11 atgctgctgctggtgaccagcctgctgctgtgcgaactgccgcatccggcgtttctgctgattccg amino acid sequence of leader/signal peptide sequence (LP)

SEQ ID NO: 12

MLLLVTSLLLCELPHPAFLLIP nucleotide sequence of DNA CD8 transmembrane domain

SEQ ID NO: 35 atttgggccccgctggccggcacttgCggcgtgctCctgctgtcgctggtcatcacccttt tactgc amino acid sequence of CD8 transmembrane domain

SEQ ID NO: 36

Ile Trp Ala Pro Leu Ala Gly Thr Cys Gly Val Leu Leu Leu Ser Leu

Val Ile Thr Leu Tyr Cys nucleotide sequence of DNA CD8 hinge domain

SEQ ID NO: 37 actaccacccctgcccctcggccgccgactccggccccaaccatcgcaagccaacccctc tccttgcgccccgaagcttgccgcccggccgcgggtggagccgtgcatacccgggggctg gactttgcctgcgatatctac amino acid sequence of CD8 hinge domain

SEQ ID NO: 38

Thr Thr Thr Pro Ala Pro Arg Pro Pro Thr Pro Ala Pro Thr Ile Ala

Ser Gln Pro Leu Ser Leu Arg Pro Glu Ala Cys Arg Pro Ala Ala Gly

Gly Ala Val His Thr Arg Gly Leu Asp Phe Ala Cys Asp Ile Tyr amino acid sequence of amino acid numbers 137 to 206 hinge and transmembrane region of CD8.alpha. (NCBI RefSeq: NP.sub.--001759.3)

SEQ ID NO: 39

Thr Thr Thr Pro Ala Pro Arg Pro Pro Thr Pro Ala Pro Thr Ile Ala Ser Gln Pro Leu

Ser Leu Arg Pro Glu Ala Cys Arg Pro Ala Ala Gly Gly Ala Val His Thr Arg Gly Leu

Asp Phe Ala Cys Asp Ile Tyr Ile Trp Ala Pro Leu Ala Gly Thr Cys Gly Val Leu Leu

Leu Ser Leu Val Ile Thr Leu Tyr Cys nucleotide sequence of DNA signaling domain of 4-1BB

SEQ ID NO: 40 aagaggggccggaagaagctgctttacatcttcaagcagccgttcatgcggcccgtgcag acgactcaggaagaggacggatgctcgtgcagattccctgaggaggaagagggggggatgc gaactg amino acid sequence of signaling domain of 4-1BB

SEQ ID NO: 41

Lys Arg Gly Arg Lys Lys Leu Leu Tyr Ile Phe Lys Gln Pro Phe Met

-continued

Arg Pro Val Gln Thr Thr Gln Glu Glu Asp Gly Cys Ser Cys Arg Phe

Pro Glu Glu Glu Glu Gly Gly Cys Glu Leu nucleotide sequence of DNA signaling domain of CD3-zeta

SEQ ID NO: 42 cgcgtcaagttctcacggtccgccgacgcccccgcatatcaacagggccagaatcagctc tacaacgagctgaacctgggaaggagagaggagtacgacgtgctggacaagcgacgcgga cgcgacccggagatgggggggaaaccacggcggaaaaaccctcaggaaggactgtacaac gaactccagaaagacaagatggcggaagcctactcagaaatcgggatgaagggagagcgg aggaggggaaagggtcacgacgggctgtaccagggactgagcaccgccactaaggatacc tacgatgccttgcatatgcaagcactcccaccccgg amino acid sequence of CD3zeta

SEQ ID NO: 43

Arg Val Lys Phe Ser Arg Ser Ala Asp Ala Pro Ala Tyr Gln Gln Gly Gln Asn Gln Leu

Tyr Asn Glu Leu Asn Leu Gly Arg Arg Glu Glu Tyr Asp Val Leu Asp Lys Arg Arg

Gly Arg Asp Pro Glu Met Gly Gly Lys Pro Arg Arg Lys Asn Pro Gln Glu Gly Leu

Tyr Asn Glu Leu Gln Lys Asp Lys Met Ala Glu Ala Tyr Ser Glu Ile Gly Met Lys Gly

Glu Arg Arg Arg Gly Lys Gly His Asp Gly Leu Tyr Gln Gly Leu Ser Thr Ala Thr

Lys Asp Thr Tyr Asp Ala Leu His Met Gln Ala Leu Pro Pro Arg nucleotide sequence of ScFv CD19 (FMC63)

SEQ ID NO: 44 gacattcagatgactcagaccacctcttccttgtccgcgtcactgggagacagagtgaccat ctcgtgtcgcgcaagccaggatatctccaagtacctgaactggtaccaacagaagcccga cgggactgtgaagctgctgatctaccacacctcacgcctgcacagcggagtgccaagcag attctccggctccggctcgggaaccgattactcgcttaccattagcaacctcgagcagga ggacatcgctacctacttctgccagcaaggaaataccctgccctacaccttcggcggagg aaccaaattggaaatcaccggcggaggaggctccgggggaggaggttccgggggcggggg ttccgaagtgaagctccaggagtccggccccggcctggtggcgccgtcgcaatcactctc tgtgacctgtaccgtgtcgggagtgtccctgcctgattacggcgtgagctggattcggca gccgccgcggaagggcctggaatggctgggtgtcatctggggatccgagactacctacta caactcggccctgaagtcccgcctgactatcatcaaagacaactcgaagtcccaggtctt tctgaagatgaactccctgcaaactgacgacaccgccatctattactgtgctaagcacta ctactacggtggaagctatgctatggactactgggggcaaggcacttcggtgactgtgtc aagc amino acid sequence of ScFv CD19 (FMC63)

SEQ ID NO: 45

Asp Ile Gln Met Thr Gln Thr Thr Ser Ser Leu Ser Ala Ser Leu Gly Asp Arg Val Thr

Ile Ser Cys Arg Ala Ser Gln Asp Ile Ser Lys Tyr Leu Asn Trp Tyr Gln Gln Lys Pro

Asp Gly Thr Val Lys Leu Leu Ile Tyr His Thr Ser Arg Leu His Ser Gly Val Pro Ser

Arg Phe Ser Gly Ser Gly Ser Gly Thr Asp Tyr Ser Leu Thr Ile Ser Asn Leu Glu Gln

Glu Asp Ile Ala Thr Tyr Phe Cys Gln Gln Gly Asn Thr Leu Pro Tyr Thr Phe Gly Gly

Gly Thr Lys Leu Glu Ile Thr Gly Gly Gly GlySer Gly Gly Gly Gly Ser G1 yGly Gly

Gly Ser Glu Val Lys Leu Gln Glu Ser Gly Pro Gly Leu Val Ala Pro Ser Gln Ser Leu

Ser Val Thr Cys Thr Val Ser Gly Val Ser Leu Pro Asp Tyr Gly Val Ser Trp Ile Arg

Gln Pro Pro Arg Lys Gly Leu Glu Trp Leu Gly Val Ile Trp Gly Ser Glu Thr Thr Tyr

Tyr Asn Ser Ala Leu Lys Ser Arg Leu Thr Ile Ile Lys Asp Asn Ser Lys Ser Gln Val

-continued

Phe Leu Lys Met Asn Ser Leu Gln Thr Asp Asp Thr Ala Ile Tyr Tyr Cys Ala Lys His

Tyr Tyr Tyr Gly Gly Ser Tyr Ala Met Asp Tyr Trp Gly Gln Gly Thr Ser Val Thr Val

Ser Ser nucleotide sequence of anti-CD33 CAR (LTG1936)

SEQ ID NO: 46

ATGCTGCTGCTGGTGACCAGCCTGCTGCTGTGCGAACTGCCGCATCCGGCGTTTC

TGCTGATTCCGCAGGTGCAGCTGGTGCAATCTGGGGCAGAGGTGAAAAAGCCCG

GGGAGTCTCTGAGGATCTCCTGTAAGGGTTCTGGATTCAGTTTTCCCACCTACTG

GATCGGCTGGGTGCGCCAGATGCCCGGGAAAGGCCTGGAGTGGATGGGGATCAT

CTATCCTGGTGACTCTGATACCAGATACAGCCCGTCCTTCCAAGGCCAGGTCACC

ATCTCAGCCGACAAGTCCATCAGCACCGCCTACCTGCAGTGGAGCAGCCTGAAG

GCCTCGGACACCGCCATGTATTACTGTGCGAGACTAGTTGGAGATGGCTACAATA

CGGGGGCTTTTGATATCTGGGGCCAAGGGACAATGGTCACCGTCTCTTCAGGAG

GTGGCGGGTCTGGTGGTGGCGGTAGCGGTGGTGGCGGATCCGATATTGTGATGA

CCCACACTCCACTCTCTCTGTCCGTCACCCCTGGACAGCCGGCCTCCATCTCCTGC

AAGTCTAGTCAGAGCCTCCTGCATAGTAATGGAAAGACCTATTTGTATTGGTACC

TGCAGAAGCCAGGCCAGCCTCCACAGCTCCTGATCTATGGAGCTTCCAACCGGTT

CTCTGGAGTGCCAGACAGGTTCAGTGGCAGCGGGTCAGGGACAGATTTCACACT

GAAAATCAGCCGGGTGGAGGCTGAGGATGTTGGGGTTTATTACTGCATGCAAAG

TATACAGCTTCCTATCACCTTCGGCCAAGGGACACGACTGGAGATTAAAGCGGC

CGCAACTACCACCCCTGCCCCTCGGCCGCCGACTCCGGCCCCAACCATCGCAAGC

CAACCCCTCTCCTTGCGCCCCGAAGCTTGCCGCCCGGCCGCGGGTGGAGCCGTGC

ATACCCGGGGGCTGGACTTTGCCTGCGATATCTACATTTGGGCCCCGCTGGCCGG

CACTTGCGGCGTGCTCCTGCTGTCGCTGGTCATCACCCTTTACTGCAAGAGGGGC

CGGAAGAAGCTGCTTTACATCTTCAAGCAGCCGTTCATGCGGCCCGTGCAGACG

ACTCAGGAAGAGGACGGATGCTCGTGCAGATTCCCTGAGGAGGAAGAGGGGGG

ATGCGAACTGCGCGTCAAGTTCTCACGGTCCGCCGACGCCCCCGCATATCAACAG

GGCCAGAATCAGCTCTACAACGAGCTGAACCTGGGAAGGAGAGAGGAGTACGA

CGTGCTGGACAAGCGACGCGGACGCGACCCGGAGATGGGGGGGAAACCACGGC

GGAAAAACCCTCAGGAAGGACTGTACAACGAACTCCAGAAAGACAAGATGGCG

GAAGCCTACTCAGAAATCGGGATGAAGGGAGAGCGGAGGAGGGGAAAGGGTCA

CGACGGGCTGTACCAGGGACTGAGCACCGCCACTAAGGATACCTACGATGCCTT

GCATATGCAAGCACTCCCACCCCGG amino acid sequence of anti-CD33 CAR (LTG1936)

SEQ ID NO: 47

MLLLVTSLLLCELPHPAFLLIPQVQLVQSGAEVKKPGESLRISCKGSGFSFPTYWIGW

VRQMPGKGLEWMGIIYPGDSDTRYSPSFQGQVTISADKSISTAYLQWSSLKASDTAM

YYCARLVGDGYNTGAFDIWGQGTMVTVSSGGGGSGGGGSGGGGSDIVMTHTPLSL

SVTPGQPASISCKSSQSLLHSNGKTYLYWYLQKPGQPPQLLIYGASNRFSGVPDRFSG

SGSGTDFTLKISRVEAEDVGVYYCMQSIQLPITFGQGTRLEIKAAATTTPAPRPPTPAP

TIASQPLSLRPEACRPAAGGAVHTRGLDFACDIYIWAPLAGTCGVLLLSLVITLYCKR

GRKKLLYIFKQPFMRPVQTTQEEDGCSCRFPEEEEGGCELRVKFSRSADAPAYQQGQ

-continued

NQLYNELNLGRREEYDVLDKRRGRDPEMGGKPRRKNPQEGLYNELQKDKMAEAYS

EIGMKGERRRGKGHDGLYQGLSTATKDTYDALHMQALPP nucleotide sequence of anti-mesothelin CAR (LTG1904)

SEQ ID NO: 48

ATGCTGCTGCTGGTGACCAGCCTGCTGCTGTGCGAACTGCCGCATCCGGCGTTTC

TGCTGATTCCGGAGGTCCAGCTGGTACAGTCTGGGGGAGGCTTGGTACAGCCTG

GGGGGTCCCTGAGACTCTCCTGTGCAGCCTCTGGATTCACCTTTGATGATTATGC

CATGCACTGGGTCCGGCAAGCTCCAGGGAAGGGCCTGGAGTGGGTCTCAGGTAT

TAGTTGGAATAGTGGTAGCATAGGCTATGCGGACTCTGTGAAGGGCCGATTCAC

CATCTCCAGAGACAACGCCAAGAACTCCCTGTATCTGCAAATGAACAGTCTGAG

AGCTGAGGACACGGCCTTGTATTACTGTGCAAAAGATTTATCGTCAGTGGCTGG

ACCCTTTAACTACTGGGGCCAGGGCACCCTGGTCACCGTCTCCTCAGGAGGTGGC

GGGTCTGGTGGAGGCGGTAGCGGCGGTGGCGGATCCTCTTCTGAGCTGACTCAG

GACCCTGCTGTGTCTGTGGCCTTGGGACAGACAGTCAGGATCACATGCCAAGGA

GACAGCCTCAGAAGCTATTATGCAAGCTGGTACCAGCAGAAGCCAGGACAGGCC

CCTGTACTTGTCATCTATGGTAAAAACAACCGGCCCTCAGGGATCCCAGACCGAT

TCTCTGGCTCCAGCTCAGGAAACACAGCTTCCTTGACCATCACTGGGGCTCAGGC

GGAGGATGAGGCTGACTATTACTGTAACTCCCGGGACAGCAGTGGTAACCATCT

GGTATTCGGCGGAGGCACCCAGCTGACCGTCCTCGGTGCGGCCGCAACTACCAC

CCCTGCCCCTCGGCCGCCGACTCCGGCCCCAACCATCGCAAGCCAACCCCTCTCC

TTGCGCCCCGAAGCTTGCCGCCCGGCCGCGGGTGGAGCCGTGCATACCCGGGGG

CTGGACTTTGCCTGCGATATCTACATTTGGGCCCCGCTGGCCGGCACTTGCGGCG

TGCTCCTGCTGTCGCTGGTCATCACCCTTTACTGCAAGAGGGGCCGGAAGAAGCT

GCTTTACATCTTCAAGCAGCCGTTCATGCGGCCCGTGCAGACGACTCAGGAAGA

GGACGGATGCTCGTGCAGATTCCCTGAGGAGGAAGAGGGGGGATGCGAACTGC

GCGTCAAGTTCTCACGGTCCGCCGACGCCCCCGCATATCAACAGGGCCAGAATC

AGCTCTACAACGAGCTGAACCTGGGAAGGAGAGAGGAGTACGACGTGCTGGAC

AAGCGACGCGGACGCGACCCGGAGATGGGGGGGAAACCACGGCGGAAAAACCC

TCAGGAAGGACTGTACAACGAACTCCAGAAAGACAAGATGGCGGAAGCCTACT

CAGAAATCGGGATGAAGGGAGAGCGGAGGAGGGGAAAGGGTCACGACGGGCTG

TACCAGGGACTGAGCACCGCCACTAAGGATACCTACGATGCCTTGCATATGCAA

GCACTCCCACCCCGG amino acid sequence of anti-mesothelin CAR (LTG1904)

SEQ ID NO: 49

MLLLVTSLLLCELPHPAFLLIPEVQLVQSGGGLVQPGGSLRLSCAASGFTFDDYAMH

WVRQAPGKGLEWVSGISWNSGSIGYADSVKGRFTISRDNAKNSLYLQMNSLRAEDT

ALYYCAKDLSSVAGPFNYWGQGTLVTVSSGGGGSGGGGSGGGGSSSELTQDPAVS

VALGQTVRITCQGDSLRSYYASWYQQKPGQAPVLVIYGKNNRPSGIPDRFSGSSSGN

TASLTITGAQAEDEADYYCNSRDSSGNHLVFGGGTQLTVLGAAATTTPAPRPPTPAP

TIASQPLSLRPEACRPAAGGAVHTRGLDFACDIYIWAPLAGTCGVLLLSLVITLYCKR

GRKKLLYIFKQPFMRPVQTTQEEDGCSCRFPEEEEGGCELRVKFSRSADAPAYQQGQ

NQLYNELNLGRREEYDVLDKRRGRDPEMGGKPRRKNPQEGLYNELQKDKMAEAY

SEIGMKGERRRGKGHDGLYQGLSTATKDTYDALHMQALPPR

-continued nucleotide sequence of heavy chain scFv 16P17

SEQ ID NO: 50

CAGGTACAGCTTCAACAGAGTGGGCCGGGACTGGTGAAACACTCCCAAACACTT
TCTCTGACGTGCGCTATATCAGGTGACTCTGTTTCATCTAATTCTGCTGCGTGGA
ACTGGATTCGACAATCTCCCAGTCGCGGGTTGGAATGGCTGGGACGAACATATT
ATCGGTCTAAGTGGTATAACGATTATGCTGTATCTGTTAAATCTCGAATTACGAT
TAATCCTGACACCTCCAAGAACCAGTTCTCCCTCCAGTTGAACTCAGTCACACCG
GAAGACACTGCGGTCTACTATTGCGCTCAAGAAGTCGAGCCACATGATGCATTC
GACATCTGGGGCCAGGGAACGATGGTCACCGTCAGCAGT amino acid sequence of heavy chain scFv 16P17

SEQ ID NO: 51

QVQLQQSGPGLVKHSQTLSLTCAISGDSVSSNSAAWNWIRQSPSRGLEWLGRTYYR
SKWYNDYAVSVKSRITINPDTSKNQFSLQLNSVTPEDTAVYYCAQEVEPHDAFDIW
GQGTMVTVSS nucleotide sequence of light chain scFv 16P17

SEQ ID NO: 52

GACATACAAATGACGCAGAGTCCCTCAAGTGTGTACGCGAGTGTGGGGGATAAG
GTAACTATTACGTGCAGAGCGTCACAGGATGTTAGTGGATGGCTTGCCTGGTATC
AGCAGAAGCCAGGCCTTGCTCCACAGCTCCTTATCAGTGGTGCTTCTACACTTCA
GGGCGAGGTTCCGAGTAGATTCTCTGGTTCTGGATCTGGTACTGACTTCACTCTT
ACAATTTCTTCTTTGCAACCAGAAGACTTTGCGACTTATTACTGCCAACAGGCCA
AATACTTCCCTTATACATTTGGCCAAGGTACCAAGTTGGAGATAAAG amino acid sequence of light chain scFv 16P17

SEQ ID NO: 53

DIQMTQSPSSVYASVGDKVTITCRASQDVSGWLAWYQQKPGLAPQLLISGASTLQG
EVPSRFSGSGSGTDFTLTISSLQPEDFATYYCQQAKYFPYTFGQGTKLEIK nucleotide sequence of heavy chain scFv M19217-1

SEQ ID NO: 54

GAGGTCCAGCTGGTACAGTCTGGAGCTGAGGTGAAGAAGCCTGGGGCCTCAGTG
AAGGTCTCCTGCAAGGCTTCTGGATACACCTTCACCAGCTACTATATGCACTGGG
TGCGACAGGCCCCTGGACAAGGGCTTGAGTGGATGGGATTAATCAACCCTAGTG
GTGGTAGCACAAGCTACGCACAGAAGTTCCAGGGCAGAGTCACCATGACCAGGG
ACACGTCCACGAGCACAGTCTACATGGAGCTGAGCAGCCTGAGATCTGAGGACA
CGGCCGTGTATTACTGTGCGAGATCGGATCGGGGAATTACCGCCACGGACGCTT
TTGATATCTGGGGCCAAGGGACAATGGTCACCGTCTCTTCA nucleotide sequence of heavy chain scFv M19217-1

SEQ ID NO: 55

EVQLVQSGAEVKKPGASVKVSCKASGYTFTSYYMHWVRQAPGQGLEWMGLINPSG
GSTSYAQKFQGRVTMTRDTSTSTVYMELSSLRSEDTAVYYCARSDRGITATDAFDI
WGQGTMVTVSS nucleotide sequence of light chain scFv M19217-1

SEQ ID NO: 56

CAGTCTGTGCTGACTCAGCCACCCTCGGTGTCAGTGGCCCCAGGGCGGATGGCC
AAGATTACCTGTGGGGGAAGTGACATTGGAAATAAAAATGTCCACTGGTATCAG
CAGAAGCCAGGCCAGGCCCCTGTCCTGGTTGTCTATGATGATTACGACCGGCCCT
CAGGGATCCCTGAGCGATTCTCTGGCTCCAACTCTGGGGACGCGGCCACCCTGA
CGATCAGCACGGTCGAAGTCGGGGATGAGGCCGACTATTTCTGTCAGGTGTGGG

-continued

ACGGTAGTGGTGATCCTTATTGGATGTTCGGCGGAGGGACCCAGCTCACCGTTTT

AGGT amino acid sequence of light chain scFv M19217-1

SEQ ID NO: 57

QSVLTQPPSVSVAPGRMAKITCGGSDIGNKNVHWYQQKPGQAPVLVVYDDYDRPS

GIPERFSGSNSGDAATLTISTVEVGDEADYFCQVWDGSGDPYWMFGGGTQLTVLG nucleotide sequence of CAR22 LTG2200 (M971-CD8TM-4-1BB-zeta)

SEQ ID NO: 58

ATGCTTCTTTTGGTGACTTCCCTTTTGCTGTGCGAGTTGCCACACCCCGCCTTCCT

GCTTATTCCCCAGGTACAGCTCCAGCAGAGTGGCCCAGGGCTCGTGAAGCCAAG

CCAGACGCTGTCCCTGACTTGTGCAATTTCAGGGGATTCAGTTTCATCAAATAGC

GCGGCGTGGAATTGGATTCGACAATCTCCTTCCCGAGGGTTGGAATGGCTTGGA

CGAACATATTACAGATCCAAATGGTATAACGACTATGCGGTATCAGTAAAGTCA

AGAATAACCATTAACCCCGACACAAGCAAGAACCAATTCTCTTTGCAGCTTAAC

TCTGTCACGCCAGAAGACACGGCAGTCTATTATTGCGCTCGCGAGGTAACGGGT

GACCTGGAAGACGCTTTTGACATTTGGGGGCAGGGTACGATGGTGACAGTCAGT

TCAGGGGGCGGTGGGAGTGGGGGAGGGGGTAGCGGGGGGGGAGGGTCAGACAT

TCAGATGACCCAGTCCCCTTCATCCTTGTCTGCCTCCGTCGGTGACAGGGTGACA

ATAACATGCAGAGCAAGCCAAACAATCTGGAGCTATCTCAACTGGTACCAGCAG

CGACCAGGAAAAGCGCCAAACCTGCTGATTTACGCTGCTTCCTCCCTCCAATCAG

GCGTGCCTAGTAGATTTAGCGGTAGGGGCTCCGGCACCGATTTTACGCTCACTAT

AAGCTCTCTTCAAGCAGAAGATTTTGCGACTTATTACTGCCAGCAGTCCTATAGT

ATACCTCAGACTTTCGGACAGGGTACCAAGTTGGAGATTAAGGCGGCCGCAACT

ACCACCCCTGCCCCTCGGCCGCCGACTCCGGCCCCAACCATCGCAAGCCAACCC

CTCTCCTTGCGCCCCGAAGCTTGCCGCCCGGCCGCGGGTGGAGCCGTGCATACCC

GGGGGCTGGACTTTGCCTGCGATATCTACATTTGGGCCCCGCTGGCCGGCACTTG

CGGCGTGCTCCTGCTGTCGCTGGTCATCACCCTTTACTGCAAGAGGGGCCGGAAG

AAGCTGCTTTACATCTTCAAGCAGCCGTTCATGCGGCCCGTGCAGACGACTCAGG

AAGAGGACGGATGCTCGTGCAGATTCCCTGAGGAGGAAGAGGGGGGATGCGAA

CTGCGCGTCAAGTTCTCACGGTCCGCCGACGCCCCCGCATATCAACAGGGCCAG

AATCAGCTCTACAACGAGCTGAACCTGGGAAGGAGAGAGGAGTACGACGTGCT

GGACAAGCGACGCGGACGCGACCCGGAGATGGGGGGGAAACCACGGCGGAAAA

ACCCTCAGGAAGGACTGTACAACGAACTCCAGAAAGACAAGATGGCGGAAGCC

TACTCAGAAATCGGGATGAAGGGAGAGCGGAGGAGGGGAAAGGGTCACGACGG

GCTGTACCAGGGACTGAGCACCGCCACTAAGGATACCTACGATGCCTTGCATAT

GCAAGCACTCCCACCCCGG amino acid sequence of CAR22 LTG2200 (M971-CD8TM-4-1BB-zeta)

SEQ ID NO: 59

MLLLVTSLLLCELPHPAFLLIPQVQLQQSGPGLVKPSQTLSLTCAISGDSVSSNSAAW

NWIRQSPSRGLEWLGRTYYRSKWYNDYAVSVKSRITINPDTSKNQFSLQLNSVTPED

TAVYYCAREVTGDLEDAFDIWGQGTMVTVSSGGGGSGGGGSGGGGSDIQMTQSPS

SLSASVGDRVTITCRASQTIWSYLNWYQQRPGKAPNLLIYAASSLQSGVPSRFSGRGS

GTDFTLTISSLQAEDFATYYCQQSYSIPQTFGQGTKLEIKAAATTTPAPRPPTPAPTIAS

-continued

QPLSLRPEACRPAAGGAVHTRGLDFACDIYIWAPLAGTCGVLLLSLVITLYCKRGRK

KLLYIFKQPFMRPVQTTQEEDGCSCRFPEEEEGGCELRVKFSRSADAPAYQQGQNQL

YNELNLGRREEYDVLDKRRGRDPEMGGKPRRKNPQEGLYNELQKDKMAEAYSEIG

MKGERRRGKGHDGLYQGLSTATKDTYDALHMQALPPR nucleotide sequence of CAR LTG2737 (CD22-19 CD8 BBz)

SEQ ID NO: 60

ATGCTCTTGCTCGTGACTTCTTTGCTTTTGTGCGAACTTCCGCACCCAGCCTTCCT

TTTGATACCTCAGGTACAGCTTCAACAAAGCGGACCGGGACTTGTTAAGCATTC

CCAAACCCTTTCTCTCACGTGTGCAATTAGCGGCGATAGTGTATCCTCTAATTCT

GCGGCCTGGAACTGGATACGACAATCACCAAGCCGGGGACTCGAGTGGTTGGG

CCGAACCTACTATCGGTCCAAATGGTATAATGACTACGCAGTATCCGTGAAATC

TCGCATTACGATCAATCCAGACACCTCCAAAAATCAATTTTCTCTGCAGTTGAAT

AGCGTGACTCCCGAGGACACGGCCGTTTACTATTGCGCCCAGGAAGTTGAACCC

CACGATGCATTTGATATTTGGGGCCAGGGAACCATGGTGACAGTGAGTAGTGGG

GGTGGAGGATCTGGAGGAGGCGGTAGCGGCGGGGGCGGCAGTGATATCCAGAT

GACGCAGTCACCTTCCAGCGTGTATGCGAGTGTGGGGGACAAGGTCACCATAAC

CTGTCGCGCTAGCCAAGATGTCAGCGGGTGGCTGGCTTGGTACCAGCAGAAACC

AGGTTTGGCTCCTCAGCTTTTGATCTCAGGAGCGAGCACGCTTCAGGGTGAGGT

CCCAAGTCGCTTTAGTGGCTCTGGCTCCGGGACAGACTTCACGTTGACGATCAG

CAGTTTGCAGCCTGAGGATTTCGCGACCTACTACTGCCAGCAAGCGAAATATTT

TCCGTACACTTTCGGTCAGGGGACCAAATTGGAGATCAAAGGTGGGGGTGGTTC

AGGCGGCGGAGGCTCAGGCGGCGGCGGTAGCGGAGGAGGCGGAAGCGGGGGT

GGCGGATCAGAAGTGCAACTCGTTCAGAGTGGCGCGGAGGTTAAGAAACCCGG

TGCATCTGTAAAGGTTAGCTGTAAGGCATCAGGATACACTTTTACCAGCTATTA

CATGCATTGGGTGAGACAGGCTCCCGGTCAGGGGCTCGAATGGATGGGGTTGAT

CAACCCGAGTGGTGGTTCAACATCTTACGCCCAGAAGTTTCAGGGCCGAGTAAC

AATGACTCGGGACACGTCTACCTCAACTGTGTATATGGAGCTTTCCAGCCTGCG

CTCAGAGGATACAGCAGTCTATTACTGCGCACGGTCAGACAGAGGTATAACGG

CCACTGATGCGTTCGATATCTGGGGACAAGGGACTATGGTAACTGTGTCTTCCG

GAGGAGGAGGTAGTGGAGGGGGAGGAAGCGGTGGGGGGGGCTCACAGTCCGT

TTTGACTCAGCCACCAAGCGTCTCAGTCGCACCGGGGCGAATGGCGAAAATTAC

TTGCGGCGGGAGCGACATAGGCAACAAGAATGTGCATTGGTACCAACAGAAAC

CAGGTCAAGCACCTGTTCTCGTGGTGTATGATGACTACGATCGCCCAAGCGGGA

TCCCGGAGCGGTTCTCTGGATCAAATTCTGGTGATGCAGCCACTCTGACAATAT

CAACGGTGGAAGTCGGTGACGAGGCTGATTACTTCTGCCAAGTATGGGATGGCA

GCGGAGATCCCTACTGGATGTTTGGAGGAGGTACTCAACTGACAGTTCTGGGCG

CGGCCGCAACGACCACTCCTGCACCCCGCCCTCCGACTCCGGCCCCAACCATTG

CCAGCCAGCCCCTGTCCCTGCGGCCGGAAGCCTGCAGACCGGCTGCCGGCGGA

GCCGTCCATACCCGGGGACTGGATTTCGCCTGCGATATCTATATCTGGGCACCA

CTCGCCGGAACCTGTGGAGTGCTGCTGCTGTCCCTTGTGATCACCCTGTACTGCA

AGCGCGGACGGAAGAAACTCTTGTACATCTTCAAGCAGCCGTTCATGCGCCCTG

-continued

TGCAAACCACCCAAGAAGAGGACGGGTGCTCCTGCCGGTTCCCGGAAGAGGAA

GAGGGCGGCTGCGAACTGCGCGTGAAGTTTTCCCGGTCCGCCGACGCTCCGGCG

TACCAGCAGGGGCAAAACCAGCTGTACAACGAACTTAACCTCGGTCGCCGGGA

AGAATATGACGTGCTGGACAAGCGGCGGGGAAGAGATCCCGAGATGGGTGGAA

AGCCGCGGCGGAAGAACCCTCAGGAGGGCTTGTACAACGAGCTGCAAAAGGAC

AAAATGGCCGAAGCCTACTCCGAGATTGGCATGAAGGGAGAGCGCAGACGCGG

GAAGGGACACGATGGACTGTACCAGGGACTGTCAACCGCGACTAAGGACACTT

ACGACGCCCTGCACATGCAGGCCCTGCCCCCGCGC amino acid sequence of CAR LTG2737 CD22-19 CD8 BBz

SEQ ID NO: 61

MLLLVTSLLLCELPHPAFLLIPQVQLQQSGPGLVKHSQTLSLTCAISGDSVSSNSAA

WNWIRQSPSRGLEWLGRTYYRSKWYNDYAVSVKSRITINPDTSKNQFSLQLNSVTP

EDTAVYYCAQEVEPHDAFDIWGQGTMVTVSSGGGGSGGGGSGGGGSDIQMTQSPS

SVYASVGDKVTITCRASQDVSGWLAWYQQKPGLAPQLLISGASTLQGEVPSRFSGS

GSGTDFTLTISSLQPEDFATYYCQQAKYFPYTFGQGTKLEIKGGGGSGGGGSGGGGS

GGGGSGGGGSEVQLVQSGAEVKKPGASVKVSCKASGYTFTSYYMHWVRQAPGQG

LEWMGLINPSGGSTSYAQKFQGRVTMTRDTSTSTVYMELSSLRSEDTAVYYCARSD

RGITATDAFDIWGQGTMVTVSSGGGGSGGGGSGGGGSQSVLTQPPSVSVAPGRMA

KITCGGSDIGNKNVHWYQQKPGQAPVLVVYDDYDRPSGIPERFSGSNSGDAATLTI

STVEVGDEADYFCQVWDGSGDPYWMFGGGTQLTVLGAAATTTPAPRPPTPAPTIA

SQPLSLRPEACRPAAGGAVHTRGLDFACDIYIWAPLAGTCGVLLLSLVITLYCKRGR

KKLLYIFKQPFMRPVQTTQEEDGCSCRFPEEEEGGCELRVKFSRSADAPAYQQGQN

QLYNELNLGRREEYDVLDKRRGRDPEMGGKPRRKNPQEGLYNELQKDKMAEAYS

EIGMKGERRRGKGHDGLYQGLSTATKDTYDALHMQALPPR nucleotide sequence of CAR D0135 CD22-19 CD8 CD28z

SEQ ID NO: 62

ATGCTCTTGCTCGTGACTTCTTTGCTTTTGTGCGAACTTCCGCACCCAGCCTTCCT

TTTGATACCTCAGGTACAGCTTCAACAAAGCGGACCGGGACTTGTTAAGCATTC

CCAAACCCTTTCTCTCACGTGTGCAATTAGCGGCGATAGTGTATCCTCTAATTCT

GCGGCCTGGAACTGGATACGACAATCACCAAGCCGGGGACTCGAGTGGTTGGG

CCGAACCTACTATCGGTCCAAATGGTATAATGACTACGCAGTATCCGTGAAATC

TCGCATTACGATCAATCCAGACACCTCCAAAAATCAATTTTCTCTGCAGTTGAAT

AGCGTGACTCCCGAGGACACGGCCGTTTACTATTGCGCCCAGGAAGTTGAACCC

CACGATGCATTTGATATTTGGGGCCAGGGAACCATGGTGACAGTGAGTAGTGGG

GGTGGAGGATCTGGAGGAGGCGGTAGCGGCGGGGGCGGCAGTGATATCCAGAT

GACGCAGTCACCTTCCAGCGTGTATGCGAGTGTGGGGGACAAGGTCACCATAAC

CTGTCGCGCTAGCCAAGATGTCAGCGGGTGGCTGGCTTGGTACCAGCAGAAACC

AGGTTTGGCTCCTCAGCTTTTGATCTCAGGAGCGAGCACGCTTCAGGGTGAGGT

CCCAAGTCGCTTTAGTGGCTCTGGCTCCGGGACAGACTTCACGTTGACGATCAG

CAGTTTGCAGCCTGAGGATTTCGCGACCTACTACTGCCAGCAAGCGAAATATTT

TCCGTACACTTTCGGTCAGGGGACCAAATTGGAGATCAAAGGTGGGGGTGGTTC

AGGCGGCGGAGGCTCAGGCGGCGGCGGTAGCGGAGGAGGCGGAAGCGGGGGT

GGCGGATCAGAAGTGCAACTCGTTCAGAGTGGCGCGGAGGTTAAGAAACCCGG

-continued

TGCATCTGTAAAGGTTAGCTGTAAGGCATCAGGATACACTTTTACCAGCTATTA
CATGCATTGGGTGAGACAGGCTCCCGGTCAGGGGCTCGAATGGATGGGGTTGAT
CAACCCGAGTGGTGGTTCAACATCTTACGCCCAGAAGTTTCAGGGCCGAGTAAC
AATGACTCGGGACACGTCTACCTCAACTGTGTATATGGAGCTTTCCAGCCTGCG
CTCAGAGGATACAGCAGTCTATTACTGCGCACGGTCAGACAGAGGTATAACGG
CCACTGATGCGTTCGATATCTGGGGACAAGGGACTATGGTAACTGTGTCTTCCG
GAGGAGGAGGTAGTGGAGGGGGAGGAAGCGGTGGGGGGGGCTCACAGTCCGT
TTTGACTCAGCCACCAAGCGTCTCAGTCGCACCGGGGCGAATGGCGAAAATTAC
TTGCGGCGGGAGCGACATAGGCAACAAGAATGTGCATTGGTACCAACAGAAAC
CAGGTCAAGCACCTGTTCTCGTGGTGTATGATGACTACGATCGCCCAAGCGGGA
TCCCGGAGCGGTTCTCTGGATCAAATTCTGGTGATGCAGCCACTCTGACAATAT
CAACGGTGGAAGTCGGTGACGAGGCTGATTACTTCTGCCAAGTATGGGATGGCA
GCGGAGATCCCTACTGGATGTTTGGAGGAGGTACTCAACTGACAGTTCTGGGCG
CGGCCGCGACTACCACTCCTGCACCACGGCCACCTACCCCAGCCCCCACCATTG
CAAGCCAGCCACTTTCACTGCGCCCCGAAGCGTGTAGACCAGCTGCTGGAGGAG
CCGTGCATACCCGAGGGCTGGACTTCGCCTGTGACATCTACATCTGGGCCCCAT
TGGCTGGAACTTGCGGCGTGCTGCTCTTGTCTCTGGTCATTACCCTGTACTGCCG
GTCGAAGAGGTCCAGACTCTTGCACTCCGACTACATGAACATGACTCCTAGAAG
GCCCGGACCCACTAGAAAGCACTACCAGCCGTACGCCCCTCCTCGGGATTTCGC
CGCATACCGGTCCAGAGTGAAGTTCAGCCGCTCAGCCGATGCACCGGCCTACCA
GCAGGGACAGAACCAGCTCTACAACGAGCTCAACCTGGGTCGGCGGGAAGAAT
ATGACGTGCTGGACAAACGGCGCGGCAGAGATCCGGAGATGGGGGGAAAGCCG
AGGAGGAAGAACCCTCAAGAGGGCCTGTACAACGAACTGCAGAAGGACAAGAT
GGCGGAAGCCTACTCCGAGATCGGCATGAAGGGAGAACGCCGGAGAGGGAAG
GGTCATGACGGACTGTACCAGGGCCTGTCAACTGCCACTAAGGACACTTACGAT
GCGCTCCATATGCAAGCTTTGCCCCCGCGG amino acid sequence of CAR D0135 CD22-19 CD8 CD28z

SEQ ID NO: 63

MLLLVTSLLLCELPHPAFLLIPQVQLQQSGPGLVKHSQTLSLTCAISGDSVSSNSAA
WNWIRQSPSRGLEWLGRTYYRSKWYNDYAVSVKSRITINPDTSKNQFSLQLNSVTP
EDTAVYYCAQEVEPHDAFDIWGQGTMVTVSSGGGGSGGGGSGGGGSDIQMTQSPS
SVYASVGDKVTITCRASQDVSGWLAWYQQKPGLAPQLLISGASTLQGEVPSRFSGS
GSGTDFTLTISSLQPEDFATYYCQQAKYFPYTFGQGTKLEIKGGGGSGGGGSGGGGS
GGGGSGGGGSEVQLVQSGAEVKKPGASVKVSCKASGYTFTSYYMHWVRQAPGQG
LEWMGLINPSGGSTSYAQKFQGRVTMTRDTSTSTVYMELSSLRSEDTAVYYCARSD
RGITATDAFDIWGQGTMVTVSSGGGGSGGGGSGGGGSQSVLTQPPSVSVAPGRMA
KITCGGSDIGNKNVHWYQQKPGQAPVLVVYDDYDRPSGIPERFSGSNSGDAATLTI
STVEVGDEADYFCQVWDGSGDPYWMFGGGTQLTVLGAAATTTPAPRPPTPAPTIA
SQPLSLRPEACRPAAGGAVHTRGLDFACDIYIWAPLAGTCGVLLLSLVITLYCRSKR
SRLLHSDYMNMTPRRPGPTRKHYQPYAPPRDFAAYRSRVKFSRSADAPAYQQGQN
QLYNELNLGRREEYDVLDKRRGRDPEMGGKPRRKNPQEGLYNELQKDKMAEAYS

-continued

EIGMKGERRRGKGHDGLYQGLSTATKDTYDALHMQALPPR nucleotide sequence of CAR D0136 CD22-19 CD8 ICOSz DNA

SEQ ID NO: 64

ATGCTCTTGCTCGTGACTTCTTTGCTTTTGTGCGAACTTCCGCACCCAGCCTTCC

TTTTGATACCTCAGGTACAGCTTCAACAAAGCGGACCGGGACTTGTTAAGCATT

CCCAAACCCTTTCTCTCACGTGTGCAATTAGCGGCGATAGTGTATCCTCTAATT

CTGCGGCCTGGAACTGGATACGACAATCACCAAGCCGGGGACTCGAGTGGTTG

GGCCGAACCTACTATCGGTCCAAATGGTATAATGACTACGCAGTATCCGTGAA

ATCTCGCATTACGATCAATCCAGACACCTCCAAAAATCAATTTTCTCTGCAGTT

GAATAGCGTGACTCCCGAGGACACGGCCGTTTACTATTGCGCCCAGGAAGTTG

AACCCCACGATGCATTTGATATTTGGGGCCAGGGAACCATGGTGACAGTGAGT

AGTGGGGGTGGAGGATCTGGAGGAGGCGGTAGCGGCGGGGGCGGCAGTGATA

TCCAGATGACGCAGTCACCTTCCAGCGTGTATGCGAGTGTGGGGGACAAGGTC

ACCATAACCTGTCGCGCTAGCCAAGATGTCAGCGGGTGGCTGGCTTGGTACCA

GCAGAAACCAGGTTTGGCTCCTCAGCTTTTGATCTCAGGAGCGAGCACGCTTCA

GGGTGAGGTCCCAAGTCGCTTTAGTGGCTCTGGCTCCGGGACAGACTTCACGTT

GACGATCAGCAGTTTGCAGCCTGAGGATTTCGCGACCTACTACTGCCAGCAAG

CGAAATATTTTCCGTACACTTTCGGTCAGGGGACCAAATTGGAGATCAAAGGT

GGGGGTGGTTCAGGCGGCGGAGGCTCAGGCGGCGGCGGTAGCGGAGGAGGCG

GAAGCGGGGGTGGCGGATCAGAAGTGCAACTCGTTCAGAGTGGCGCGGAGGT

TAAGAAACCCGGTGCATCTGTAAAGGTTAGCTGTAAGGCATCAGGATACACTT

TTACCAGCTATTACATGCATTGGGTGAGACAGGCTCCCGGTCAGGGGCTCGAA

TGGATGGGGTTGATCAACCCGAGTGGTGGTTCAACATCTTACGCCCAGAAGTTT

CAGGGCCGAGTAACAATGACTCGGGACACGTCTACCTCAACTGTGTATATGGA

GCTTTCCAGCCTGCGCTCAGAGGATACAGCAGTCTATTACTGCGCACGGTCAG

ACAGAGGTATAACGGCCACTGATGCGTTCGATATCTGGGGACAAGGGACTATG

GTAACTGTGTCTTCCGGAGGAGGAGGTAGTGGAGGGGGAGGAAGCGGTGGGG

GGGGCTCACAGTCCGTTTTGACTCAGCCACCAAGCGTCTCAGTCGCACCGGGG

CGAATGGCGAAAATTACTTGCGGCGGGAGCGACATAGGCAACAAGAATGTGC

ATTGGTACCAACAGAAACCAGGTCAAGCACCTGTTCTCGTGGTGTATGATGAC

TACGATCGCCCAAGCGGGATCCCGGAGCGGTTCTCTGGATCAAATTCTGGTGA

TGCAGCCACTCTGACAATATCAACGGTGGAAGTCGGTGACGAGGCTGATTACT

TCTGCCAAGTATGGGATGGCAGCGGAGATCCCTACTGGATGTTTGGAGGAGGT

ACTCAACTGACAGTTCTGGGCGCGGCCGCGACTACCACTCCTGCACCACGGCC

ACCTACCCCAGCCCCCACCATTGCAAGCCAGCCACTTTCACTGCGCCCCGAAGC

GTGTAGACCAGCTGCTGGAGGAGCCGTGCATACCCGAGGGCTGGACTTCGCCT

GTGACATCTACATCTGGGCCCCATTGGCTGGAACTTGCGGCGTGCTGCTCTTGT

CTCTGGTCATTACCCTGTACTGCTGGCTGACAAAAAAGAAGTATTCATCTAGTG

TACATGATCCGAACGGTGAATACATGTTCATGCGCGCGGTGAACACGGCCAAG

AAGAGCAGACTGACCGACGTAACCCTTAGAGTGAAGTTCAGCCGCTCAGCCGA

TGCACCGGCCTACCAGCAGGGACAGAACCAGCTCTACAACGAGCTCAACCTGG

GTCGGCGGGAAGAATATGACGTGCTGGACAAACGGCGCGGCAGAGATCCGGA

-continued

GATGGGGGGAAAGCCGAGGAGGAAGAACCCTCAAGAGGGCCTGTACAACGAA

CTGCAGAAGGACAAGATGGCGGAAGCCTACTCCGAGATCGGCATGAAGGGAG

AACGCCGGAGAGGGAAGGGTCATGACGGACTGTACCAGGGCCTGTCAACTGCC

ACTAAGGACACTTACGATGCGCTCCATATGCAAGCTTTGCCCCCGCGG amino acid sequence of CAR D0136 CD22-19 CD8 ICOSz

SEQ ID NO: 65

MLLLVTSLLLCELPHPAFLLIPQVQLQQSGPGLVKHSQTLSLTCAISGDSVSSNSAA

WNWIRQSPSRGLEWLGRTYYRSKWYNDYAVSVKSRITINPDTSKNQFSLQLNSVTP

EDTAVYYCAQEVEPHDAFDIWGQGTMVTVSSGGGGSGGGGSGGGGSDIQMTQSPS

SVYASVGDKVTITCRASQDVSGWLAWYQQKPGLAPQLLISGASTLQGEVPSRFSGS

GSGTDFTLTISSLQPEDFATYYCQQAKYFPYTFGQGTKLEIKGGGGSGGGGSGGGGS

GGGGSGGGGSEVQLVQSGAEVKKPGASVKVSCKASGYTFTSYYMHWVRQAPGQG

LEWMGLINPSGGSTSYAQKFQGRVTMTRDTSTSTVYMELSSLRSEDTAVYYCARSD

RGITATDAFDIWGQGTMVTVSSGGGGSGGGGSGGGGSQSVLTQPPSVSVAPGRMA

KITCGGSDIGNKNVHWYQQKPGQAPVLVVYDDYDRPSGIPERFSGSNSGDAATLTI

STVEVGDEADYFCQVWDGSGDPYWMFGGGTQLTVLGAAATTTPAPRPPTPAPTIA

SQPLSLRPEACRPAAGGAVHTRGLDFACDIYIWAPLAGTCGVLLLSLVITLYCWLTK

KKYSSSVHDPNGEYMFMRAVNTAKKSRLTDVTLRVKFSRSADAPAYQQGQNQLY

NELNLGRREEYDVLDKRRGRDPEMGGKPRRKNPQEGLYNELQKDKMAEAYSEIG

MKGERRRGKGHDGLYQGLSTATKDTYDALHMQALPPR nucleotide sequence of CAR D0137 CD22-19 CD8 OX40TM OX40z

SEQ ID NO: 66

ATGCTCTTGCTCGTGACTTCTTTGCTTTTGTGCGAACTTCCGCACCCAGCCTTC

CTTTTGATACCTCAGGTACAGCTTCAACAAAGCGGACCGGGACTTGTTAAGCA

TTCCCAAACCCTTTCTCTCACGTGTGCAATTAGCGGCGATAGTGTATCCTCTAA

TTCTGCGGCCTGGAACTGGATACGACAATCACCAAGCCGGGGACTCGAGTGG

TTGGGCCGAACCTACTATCGGTCCAAATGGTATAATGACTACGCAGTATCCGT

GAAATCTCGCATTACGATCAATCCAGACACCTCCAAAAAATCAATTTTCTCTGC

AGTTGAATAGCGTGACTCCCGAGGACACGGCCGTTTACTATTGCGCCCAGGAA

GTTGAACCCCACGATGCATTTGATATTTGGGGCCAGGGAACCATGGTGACAGT

GAGTAGTGGGGGTGGAGGATCTGGAGGAGGCGGTAGCGGCGGGGGCGGCAG

TGATATCCAGATGACGCAGTCACCTTCCAGCGTGTATGCGAGTGTGGGGGACA

AGGTCACCATAACCTGTCGCGCTAGCCAAGATGTCAGCGGGTGGCTGGCTTGG

TACCAGCAGAAACCAGGTTTGGCTCCTCAGCTTTTGATCTCAGGAGCGAGCAC

GCTTCAGGGTGAGGTCCCAAGTCGCTTTAGTGGCTCTGGCTCCGGGACAGACT

TCACGTTGACGATCAGCAGTTTGCAGCCTGAGGATTTCGCGACCTACTACTGC

CAGCAAGCGAAATATTTTCCGTACACTTTCGGTCAGGGGACCAAATTGGAGAT

CAAAGGTGGGGGTGGTTCAGGCGGCGGAGGCTCAGGCGGCGGCGGTAGCGGA

GGAGGCGGAAGCGGGGGTGGCGGATCAGAAGTGCAACTCGTTCAGAGTGGCG

CGGAGGTTAAGAAACCCGGTGCATCTGTAAAGGTTAGCTGTAAGGCATCAGG

ATACACTTTTACCAGCTATTACATGCATTGGGTGAGACAGGCTCCCGGTCAGG

GGCTCGAATGGATGGGGTTGATCAACCCGAGTGGTGGTTCAACATCTTACGCC

-continued

CAGAAGTTTCAGGGCCGAGTAACAATGACTCGGGACACGTCTACCTCAACTGT
GTATATGGAGCTTTCCAGCCTGCGCTCAGAGGATACAGCAGTCTATTACTGCG
CACGGTCAGACAGAGGTATAACGGCCACTGATGCGTTCGATATCTGGGGACA
AGGGACTATGGTAACTGTGTCTTCCGGAGGAGGAGGTAGTGGAGGGGGAGGA
AGCGGTGGGGGGGGCTCACAGTCCGTTTTGACTCAGCCACCAAGCGTCTCAGT
CGCACCGGGGCGAATGGCGAAAATTACTTGCGGCGGGAGCGACATAGGCAAC
AAGAATGTGCATTGGTACCAACAGAAACCAGGTCAAGCACCTGTTCTCGTGGT
GTATGATGACTACGATCGCCCAAGCGGGATCCCGGAGCGGTTCTCTGGATCAA
ATTCTGGTGATGCAGCCACTCTGACAATATCAACGGTGGAAGTCGGTGACGAG
GCTGATTACTTCTGCCAAGTATGGGATGGCAGCGGAGATCCCTACTGGATGTT
TGGAGGAGGTACTCAACTGACAGTTCTGGGCGCGGCCGCAACGACCACTCCA
GCACCGAGACCGCCAACCCCCGCGCCTACCATCGCAAGTCAACCACTTTCTCT
CAGGCCTGAAGCGTGCCGACCTGCAGCTGGTGGGGCAGTACATACCAGGGGT
TTGGACTTCGCATGTGACGTGGCGGCAATTCTCGGCCTGGGACTTGTCCTTGG
TCTGCTTGGTCCGCTCGCAATACTTCTGGCCTTGTACCTGCTCCGCAGAGACCA
AAGACTTCCGCCCGACGCCCACAAGCCCCCAGGAGGAGGTTCCTTCAGAACG
CCTATACAAGAAGAACAAGCAGATGCCCACTCTACCCTGGCTAAAATCAGGG
TGAAGTTTAGCCGGTCAGCTGATGCACCTGCATATCAGCAGGGACAGAACCA
GCTGTACAATGAGCTGAACCTCGGACGAAGAGAGGAGTACGACGTGTTGGAC
AAAAGACGAGGTAGAGACCCCGAGATGGGCGGCAAGCCGAGAAGAAAAAAC
CCACAAGAAGGGCTTTATAATGAGCTTCAGAAAGATAAGATGGCAGAGGCCT
ACAGTGAGATTGGCATGAAGGGCGAAAGAAGGAGGGGCAAAGGACACGACG
GTCTCTACCAAGGCCTCAGCACGGCTACCAAAGATACGTATGACGCATTGCAT
ATGCAGGCATTGCCGCCCCGC amino acid sequence of CAR D0137 CD22-19 CD8 OX40TM OX40z

SEQ ID NO: 67

LLLVTSLLLCELPHPAFLLIPQVQLQQSGPGLVKHSQTLSLTCAISGDSVSSNSAAW
NWIRQSPSRGLEWLGRTYYRSKWYNDYAVSVKSRITINPDTSKNQFSLQLNSVTP
EDTAVYYCAQEVEPHDAFDIWGQGTMVTVSSGGGGSGGGGSGGGGSDIQMTQS
PSSVYASVGDKVTITCRASQDVSGWLAWYQQKPGLAPQLLISGASTLQGEVPSRF
SGSGSGTDFTLTISSLQPEDFATYYCQQAKYFPYTFGQGTKLEIKGGGGSGGGGSG
GGGSGGGGSGGGGSEVQLVQSGAEVKKPGASVKVSCKASGYTFTSYYMHWVRQ
APGQGLEWMGLINPSGGSTSYAQKFQGRVTMTRDTSTSTVYMELSSLRSEDTAV
YYCARSDRGITATDAFDIWGQGTMVTVSSGGGGSGGGGSGGGGSQSVLTQPPSV
SVAPGRMAKITCGGSDIGNKNVHWYQQKPGQAPVLVVYDDYDRPSGIPERFSGS
NSGDAATLTISTVEVGDEADYFCQVWDGSGDPYWMFGGGTQLTVLGAAATTTP
APRPPTPAPTIASQPLSLRPEACRPAAGGAVHTRGLDFACDVAAILGLGLVLGLLG
PLAILLALYLLRRDQRLPPDAHKPPGGGSFRTPIQEEQADAHSTLAKIRVKFSRSAD
APAYQQGQNQLYNELNLGRREEYDVLDKRRGRDPEMGGKPRRKNPQEGLYNEL
QKDKMAEAYSEIGMKGERRRGKGHDGLYQGLSTATKDTYDALHMQALPPR nucleotide sequence of CAR D0138 CD22-19 CD8 CD27z

SEQ ID NO: 68

ATGCTCTTGCTCGTGACTTCTTTGCTTTTGTGCGAACTTCCGCACCCAGCCTTC

CTTTTGATACCTCAGGTACAGCTTCAACAAAGCGGACCGGGACTTGTTAAGCA

TTCCCAAACCCTTTCTCTCACGTGTGCAATTAGCGGCGATAGTGTATCCTCTAA

TTCTGCGGCCTGGAACTGGATACGACAATCACCAAGCCGGGGACTCGAGTGG

TTGGGCCGAACCTACTATCGGTCCAAATGGTATAATGACTACGCAGTATCCGT

GAAATCTCGCATTACGATCAATCCAGACACCTCCAAAAATCAATTTTCTCTGC

AGTTGAATAGCGTGACTCCCGAGGACACGGCCGTTTACTATTGCGCCCAGGAA

GTTGAACCCCACGATGCATTTGATATTTGGGGCCAGGGAACCATGGTGACAGT

GAGTAGTGGGGGTGGAGGATCTGGAGGAGGCGGTAGCGGCGGGGGCGGCAG

TGATATCCAGATGACGCAGTCACCTTCCAGCGTGTATGCGAGTGTGGGGGACA

AGGTCACCATAACCTGTCGCGCTAGCCAAGATGTCAGCGGGTGGCTGGCTTGG

TACCAGCAGAAACCAGGTTTGGCTCCTCAGCTTTTGATCTCAGGAGCGAGCAC

GCTTCAGGGTGAGGTCCCAAGTCGCTTTAGTGGCTCTGGCTCCGGGACAGACT

TCACGTTGACGATCAGCAGTTTGCAGCCTGAGGATTTCGCGACCTACTACTGC

CAGCAAGCGAAATATTTTCCGTACACTTTCGGTCAGGGGACCAAATTGGAGAT

CAAAGGTGGGGGTGGTTCAGGCGGCGGAGGCTCAGGCGGCGGCGGTAGCGGA

GGAGGCGGAAGCGGGGGTGGCGGATCAGAAGTGCAACTCGTTCAGAGTGGCG

CGGAGGTTAAGAAACCCGGTGCATCTGTAAAGGTTAGCTGTAAGGCATCAGG

ATACACTTTTACCAGCTATTACATGCATTGGGTGAGACAGGCTCCCGGTCAGG

GGCTCGAATGGATGGGGTTGATCAACCCGAGTGGTGGTTCAACATCTTACGCC

CAGAAGTTTCAGGGCCGAGTAACAATGACTCGGGACACGTCTACCTCAACTGT

GTATATGGAGCTTTCCAGCCTGCGCTCAGAGGATACAGCAGTCTATTACTGCG

CACGGTCAGACAGAGGTATAACGGCCACTGATGCGTTCGATATCTGGGGACA

AGGGACTATGGTAACTGTGTCTTCCGGAGGAGGAGGTAGTGGAGGGGGAGGA

AGCGGTGGGGGGGGCTCACAGTCCGTTTTGACTCAGCCACCAAGCGTCTCAGT

CGCACCGGGGCGAATGGCGAAAATTACTTGCGGCGGGAGCGACATAGGCAAC

AAGAATGTGCATTGGTACCAACAGAAACCAGGTCAAGCACCTGTTCTCGTGGT

GTATGATGACTACGATCGCCCAAGCGGGATCCCGGAGCGGTTCTCTGGATCAA

ATTCTGGTGATGCAGCCACTCTGACAATATCAACGGTGGAAGTCGGTGACGAG

GCTGATTACTTCTGCCAAGTATGGGATGGCAGCGGAGATCCCTACTGGATGTT

TGGAGGAGGTACTCAACTGACAGTTCTGGGCGCGGCCGCGACTACCACTCCTG

CACCACGGCCACCTACCCCAGCCCCCACCATTGCAAGCCAGCCACTTTCACTG

CGCCCCGAAGCGTGTAGACCAGCTGCTGGAGGAGCCGTGCATACCCGAGGGC

TGGACTTCGCCTGTGACATCTACATCTGGGCCCCATTGGCTGGAACTTGCGGC

GTGCTGCTCTTGTCTCTGGTCATTACCCTGTACTGCCAACGGCGCAAATACCGC

TCCAATAAAGGCGAAAGTCCGGTAGAACCCGCAGAACCTTGCCACTACAGTT

GTCCCAGAGAAGAAGAGGGTTCTACAATACCTATTCAAGAGGACTATAGGAA

ACCAGAGCCCGCATGTAGTCCCAGAGTGAAGTTCAGCCGCTCAGCCGATGCA

CCGGCCTACCAGCAGGGACAGAACCAGCTCTACAACGAGCTCAACCTGGGTC

GGCGGGAAGAATATGACGTGCTGGACAAACGGCGCGGCAGAGATCCGGAGAT

-continued

GGGGGGAAAGCCGAGGAGGAAGAACCCTCAAGAGGGCCTGTACAACGAACT

GCAGAAGGACAAGATGGCGGAAGCCTACTCCGAGATCGGCATGAAGGGAGA

ACGCCGGAGAGGGAAGGGTCATGACGGACTGTACCAGGGCCTGTCAACTGCC

ACTAAGGACACTTACGATGCGCTCCATATGCAAGCTTTGCCCCCGCGG amino acid sequence of CAR D0138 CD22-19 CD8 CD27z

SEQ ID NO: 69

MLLLVTSLLLCELPHPAFLLIPQVQLQQSGPGLVKHSQTLSLTCAISGDSVSSNSAA

WNWIRQSPSRGLEWLGRTYYRSKWYNDYAVSVKSRITINPDTSKNQFSLQLNSVT

PEDTAVYYCAQEVEPHDAFDIWGQGTMVTVSSGGGGSGGGGSGGGGSDIQMTQ

SPSSVYASVGDKVTITCRASQDVSGWLAWYQQKPGLAPQLLISGASTLQGEVPSR

FSGSGSGTDFTLTISSLQPEDFATYYCQQAKYFPYTFGQGTKLEIKGGGGSGGGGS

GGGGSGGGGSGGGGSEVQLVQSGAEVKKPGASVKVSCKASGYTFTSYYMHWVR

QAPGQGLEWMGLINPSGGSTSYAQKFQGRVTMTRDTSTSTVYMELSSLRSEDTA

VYYCARSDRGITATDAFDIWGQGTMVTVSSGGGGSGGGGSGGGGSQSVLTQPPS

VSVAPGRMAKITCGGSDIGNKNVHWYQQKPGQAPVLVVYDDYDRPSGIPERFSG

SNSGDAATLTISTVEVGDEADYFCQVWDGSGDPYWMFGGGTQLTVLGAAATTT

PAPRPPTPAPTIASQPLSLRPEACRPAAGGAVHTRGLDFACDIYIWAPLAGTCGVL

LLSLVITLYCQRRKYRSNKGESPVEPAEPCHYSCPREEEGSTIPIQEDYRKPEPACSP

RVKFSRSADAPAYQQGQNQLYNELNLGRREEYDVLDKRRGRDPEMGGKPRRKN

PQEGLYNELQKDKMAEAYSEIGMKGERRRGKGHDGLYQGLSTATKDTYDALHM

QALPP nucleotide sequence of CAR D0139 CD22-19 CD28 CD28z

SEQ ID NO: 70

ATGCTCTTGCTCGTGACTTCTTTGCTTTTGTGCGAACTTCCGCACCCAGCCTTC

CTTTTGATACCTCAGGTACAGCTTCAACAAAGCGGACCGGGACTTGTTAAGCA

TTCCCAAACCCTTTCTCTCACGTGTGCAATTAGCGGCGATAGTGTATCCTCTAA

TTCTGCGGCCTGGAACTGGATACGACAATCACCAAGCCGGGGACTCGAGTGG

TTGGGCCGAACCTACTATCGGTCCAAATGGTATAATGACTACGCAGTATCCGT

GAAATCTCGCATTACGATCAATCCAGACACCTCCAAAAATCAATTTTCTCTGC

AGTTGAATAGCGTGACTCCCGAGGACACGGCCGTTTACTATTGCGCCCAGGAA

GTTGAACCCCACGATGCATTTGATATTTGGGGCCAGGGAACCATGGTGACAGT

GAGTAGTGGGGGTGGAGGATCTGGAGGAGGCGGTAGCGGCGGGGGCGGCAG

TGATATCCAGATGACGCAGTCACCTTCCAGCGTGTATGCGAGTGTGGGGGACA

AGGTCACCATAACCTGTCGCGCTAGCCAAGATGTCAGCGGGTGGCTGGCTTGG

TACCAGCAGAAACCAGGTTTGGCTCCTCAGCTTTTGATCTCAGGAGCGAGCAC

GCTTCAGGGTGAGGTCCCAAGTCGCTTTAGTGGCTCTGGCTCCGGGACAGACT

TCACGTTGACGATCAGCAGTTTGCAGCCTGAGGATTTCGCGACCTACTACTGC

CAGCAAGCGAAATATTTTCCGTACACTTTCGGTCAGGGGACCAAATTGGAGAT

CAAAGGTGGGGGTGGTTCAGGCGGCGGAGGCTCAGGCGGCGGCGGTAGCGGA

GGAGGCGGAAGCGGGGGTGGCGGATCAGAAGTGCAACTCGTTCAGAGTGGCG

CGGAGGTTAAGAAACCCGGTGCATCTGTAAAGGTTAGCTGTAAGGCATCAGG

ATACACTTTTACCAGCTATTACATGCATTGGGTGAGACAGGCTCCCGGTCAGG

GGCTCGAATGGATGGGGTTGATCAACCCGAGTGGTGGTTCAACATCTTACGCC

-continued

CAGAAGTTTCAGGGCCGAGTAACAATGACTCGGGACACGTCTACCTCAACTGT
GTATATGGAGCTTTCCAGCCTGCGCTCAGAGGATACAGCAGTCTATTACTGCG
CACGGTCAGACAGAGGTATAACGGCCACTGATGCGTTCGATATCTGGGGACA
AGGGACTATGGTAACTGTGTCTTCCGGAGGAGGAGGTAGTGGAGGGGGAGGA
AGCGGTGGGGGGGGCTCACAGTCCGTTTTGACTCAGCCACCAAGCGTCTCAGT
CGCACCGGGGCGAATGGCGAAAATTACTTGCGGCGGGAGCGACATAGGCAAC
AAGAATGTGCATTGGTACCAACAGAAACCAGGTCAAGCACCTGTTCTCGTGGT
GTATGATGACTACGATCGCCCAAGCGGGATCCCGGAGCGGTTCTCTGGATCAA
ATTCTGGTGATGCAGCCACTCTGACAATATCAACGGTGGAAGTCGGTGACGAG
GCTGATTACTTCTGCCAAGTATGGGATGGCAGCGGAGATCCCTACTGGATGTT
TGGAGGAGGTACTCAACTGACAGTTCTGGGCGCGGCCGCAATCGAAGTGATG
TATCCACCTCCGTACCTCGATAACGAGAAATCAAATGGAACGATCATTCATGT
GAAAGGGAAACATCTGTGCCCAAGCCCATTGTTCCCAGGTCCGTCAAAACCAT
TCTGGGTGCTTGTCGTTGTTGGGGGTGTACTCGCATGTTATTCTTTGCTGGTGA
CTGTGGCGTTTATCATCTTCTGGGTAAGGAGTAAACGCAGCCGCCTGCTGCAT
TCAGACTACATGAACATGACCCCACGGCGGCCCGGCCCAACGCGCAAACACT
ACCAACCTTACGCCCCACCGCGAGACTTTGCCGCCTACAGATCCCGCGTGAAG
TTTTCCCGGTCCGCCGACGCTCCGGCGTACCAGCAGGGGCAAAACCAGCTGTA
CAACGAACTTAACCTCGGTCGCCGGGAAGAATATGACGTGCTGGACAAGCGG
CGGGGAAGAGATCCCGAGATGGGTGGAAAGCCGCGGCGGAAGAACCCTCAG
GAGGGCTTGTACAACGAGCTGCAAAAGGACAAAATGGCCGAAGCCTACTCCG
AGATTGGCATGAAGGGAGAGCGCAGACGCGGGAAGGGACACGATGGACTGT
ACCAGGGACTGTCAACCGCGACTAAGGACACTTACGACGCCCTGCACATGCA
GGCCCTGCCCCCGCGC amino acid sequence of CAR D0139 CD22-19 CD28 CD28z

SEQ ID NO: 71

MLLLVTSLLLCELPHPAFLLIPQVQLQQSGPGLVKHSQTLSLTCAISGDSVSSNSAA
WNWIRQSPSRGLEWLGRTYYRSKWYNDYAVSVKSRITINPDTSKNQFSLQLNSVT
PEDTAVYYCAQEVEPHDAFDIWGQGTMVTVSSGGGGSGGGGSGGGGSDIQMTQ
SPSSVYASVGDKVTITCRASQDVSGWLAWYQQKPGLAPQLLISGASTLQGEVPSR
FSGSGSGTDFTLTISSLQPEDFATYYCQQAKYFPYTFGQGTKLEIKGGGGSGGGGS
GGGGSGGGGSGGGGSEVQLVQSGAEVKKPGASVKVSCKASGYTFTSYYMHWVR
QAPGQGLEWMGLINPSGGSTSYAQKFQGRVTMTRDTSTSTVYMELSSLRSEDTA
VYYCARSDRGITATDAFDIWGQGTMVTVSSGGGGSGGGGSGGGGSQSVLTQPPS
VSVAPGRMAKITCGGSDIGNKNVHWYQQKPGQAPVLVVYDDYDRPSGIPERFSG
SNSGDAATLTISTVEVGDEADYFCQVWDGSGDPYWMFGGGTQLTVLGAAAIEV
MYPPPYLDNEKSNGTIIHVKGKHLCPSPLFPGPSKPFWVLVVVGGVLACYSLLVT
VAFIIFWVRSKRSRLLHSDYMNMTPRRPGPTRKHYQPYAPPRDFAAYRSRVKFSR
SADAPAYQQGQNQLYNELNLGRREEYDVLDKRRGRDPEMGGKPRRKNPQEGLY
NELQKDKMAEAYSEIGMKGERRRGKGHDGLYQGLSTATKDTYDALHMQALPPR nucleotide sequence of CAR D0145 CD22-19 CD8 OX40z

SEQ ID NO: 72

-continued

ATGCTCTTGCTCGTGACTTCTTTGCTTTTGTGCGAACTTCCGCACCCAGCCTTC

CTTTTGATACCTCAGGTACAGCTTCAACAAAGCGGACCGGGACTTGTTAAGCA

TTCCCAAACCCTTTCTCTCACGTGTGCAATTAGCGGCGATAGTGTATCCTCTAA

TTCTGCGGCCTGGAACTGGATACGACAATCACCAAGCCGGGGACTCGAGTGG

TTGGGCCGAACCTACTATCGGTCCAAATGGTATAATGACTACGCAGTATCCGT

GAAATCTCGCATTACGATCAATCCAGACACCTCCAAAAATCAATTTTCTCTGC

AGTTGAATAGCGTGACTCCCGAGGACACGGCCGTTTACTATTGCGCCCAGGAA

GTTGAACCCCACGATGCATTTGATATTTGGGGCCAGGGAACCATGGTGACAGT

GAGTAGTGGGGGTGGAGGATCTGGAGGAGGCGGTAGCGGCGGGGGCGGCAG

TGATATCCAGATGACGCAGTCACCTTCCAGCGTGTATGCGAGTGTGGGGGACA

AGGTCACCATAACCTGTCGCGCTAGCCAAGATGTCAGCGGGTGGCTGGCTTGG

TACCAGCAGAAACCAGGTTTGGCTCCTCAGCTTTTGATCTCAGGAGCGAGCAC

GCTTCAGGGTGAGGTCCCAAGTCGCTTTAGTGGCTCTGGCTCCGGGACAGACT

TCACGTTGACGATCAGCAGTTTGCAGCCTGAGGATTTCGCGACCTACTACTGC

CAGCAAGCGAAATATTTTCCGTACACTTTCGGTCAGGGGACCAAATTGGAGAT

CAAAGGTGGGGGTGGTTCAGGCGGCGGAGGCTCAGGCGGCGGCGGTAGCGGA

GGAGGCGGAAGCGGGGGTGGCGGATCAGAAGTGCAACTCGTTCAGAGTGGCG

CGGAGGTTAAGAAACCCGGTGCATCTGTAAAGGTTAGCTGTAAGGCATCAGG

ATACACTTTTACCAGCTATTACATGCATTGGGTGAGACAGGCTCCCGGTCAGG

GGCTCGAATGGATGGGGTTGATCAACCCGAGTGGTGGTTCAACATCTTACGCC

CAGAAGTTTCAGGGCCGAGTAACAATGACTCGGGACACGTCTACCTCAACTGT

GTATATGGAGCTTTCCAGCCTGCGCTCAGAGGATACAGCAGTCTATTACTGCG

CACGGTCAGACAGAGGTATAACGGCCACTGATGCGTTCGATATCTGGGGACA

AGGGACTATGGTAACTGTGTCTTCCGGAGGAGGAGGTAGTGGAGGGGGAGGA

AGCGGTGGGGGGGGCTCACAGTCCGTTTTGACTCAGCCACCAAGCGTCTCAGT

CGCACCGGGGCGAATGGCGAAAATTACTTGCGGCGGGAGCGACATAGGCAAC

AAGAATGTGCATTGGTACCAACAGAAACCAGGTCAAGCACCTGTTCTCGTGGT

GTATGATGACTACGATCGCCCAAGCGGGATCCCGGAGCGGTTCTCTGGATCAA

ATTCTGGTGATGCAGCCACTCTGACAATATCAACGGTGGAAGTCGGTGACGAG

GCTGATTACTTCTGCCAAGTATGGGATGGCAGCGGAGATCCCTACTGGATGTT

TGGAGGAGGTACTCAACTGACAGTTCTGGGCGCGGCCGCAACAACCACTCCA

GCACCTAGACCGCCAACACCTGCACCTACCATCGCAAGTCAACCACTTTCTCT

CAGGCCTGAAGCGTGCCGACCTGCAGCTGGTGGGGCAGTACATACCAGGGGT

TTGGACTTCGCATGTGACATCTACATCTGGGCCCCATTGGCTGGAACTTGCGG

CGTGCTGCTCTTGTCTCTGGTCATTACCCTGTACTGCGCCTTGTACCTGCTCCG

CAGAGACCAAAGACTTCCGCCCGACGCCCACAAGCCCCCAGGAGGAGGTTCC

TTCAGAACGCCTATACAAGAAGAACAAGCAGATGCCCACTCTACCCTGGCTA

AAATCAGGGTGAAGTTTAGCCGGTCAGCTGATGCACCTGCATATCAGCAGGG

ACAGAACCAGCTGTACAATGAGCTGAACCTCGGACGAAGAGAGGAGTACGAC

GTGTTGGACAAAAGACGAGGTAGAGACCCCGAGATGGGCGGCAAGCCGAGA

AGAAAAAACCCACAAGAAGGGCTTTATAATGAGCTTCAGAAAGATAAGATGG

-continued

CAGAGGCCTACAGTGAGATTGGCATGAAGGGCGAAAGAAGGAGGGGCAAAG
GACACGACGGTCTCTACCAAGGCCTCAGCACGGCTACCAAAGATACGTATGA
CGCATTGCATATGCAGGCATTGCCGCCCCGC amino acid sequence of CAR D0145 CD22-19 CD8 OX40z

SEQ ID NO: 73

MLLLVTSLLLCELPHPAFLLIPQVQLQQSGPGLVKHSQTLSLTCAISGDSVSSNSA
AWNWIRQSPSRGLEWLGRTYYRSKWYNDYAVSVKSRITINPDTSKNQFSLQLNS
VTPEDTAVYYCAQEVEPHDAFDIWGQGTMVTVSSGGGGSGGGGSGGGGSDIQM
TQSPSSVYASVGDKVTITCRASQDVSGWLAWYQQKPGLAPQLLISGASTLQGEV
PSRFSGSGSGTDFTLTISSLQPEDFATYYCQQAKYFPYTFGQGTKLEIKGGGGSGG
GGSGGGGSGGGGSGGGGSEVQLVQSGAEVKKPGASVKVSCKASGYTFTSYYM
HWVRQAPGQGLEWMGLINPSGGSTSYAQKFQGRVTMTRDTSTSTVYMELSSLR
SEDTAVYYCARSDRGITATDAFDIWGQGTMVTVSSGGGGSGGGGSGGGGSQSV
LTQPPSVSVAPGRMAKITCGGSDIGNKNVHWYQQKPGQAPVLVVYDDYDRPSGI
PERFSGSNSGDAATLTISTVEVGDEADYFCQVWDGSGDPYWMFGGGTQLTVLG
AAATTTPAPRPPTPAPTIASQPLSLRPEACRPAAGGAVHTRGLDFACDIYIWAPLA
GTCGVLLLSLVITLYCALYLLRRDQRLPPDAHKPPGGGSFRTPIQEEQADAHSTL
AKIRVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDTYD
ALHMQALPPR

CAR nucleotide sequence of D0140 CD22-19 CD28 CD28 BBz

SEQ ID NO: 74

ATGCTCTTGCTCGTGACTTCTTTGCTTTTGTGCGAACTTCCGCACCCAGCCTTC
CTTTTGATACCTCAGGTACAGCTTCAACAAAGCGGACCGGGACTTGTTAAGC
ATTCCCAAACCCTTTCTCTCACGTGTGCAATTAGCGGCGATAGTGTATCCTCT
AATTCTGCGGCCTGGAACTGGATACGACAATCACCAAGCCGGGGACTCGAGT
GGTTGGGCCGAACCTACTATCGGTCCAAATGGTATAATGACTACGCAGTATC
CGTGAAATCTCGCATTACGATCAATCCAGACACCTCCAAAAATCAATTTTCTC
TGCAGTTGAATAGCGTGACTCCCGAGGACACGGCCGTTTACTATTGCGCCCA
GGAAGTTGAACCCCACGATGCATTTGATATTTGGGGCCAGGGAACCATGGTG
ACAGTGAGTAGTGGGGGTGGAGGATCTGGAGGAGGCGGTAGCGGCGGGGGC
GGCAGTGATATCCAGATGACGCAGTCACCTTCCAGCGTGTATGCGAGTGTGG
GGGACAAGGTCACCATAACCTGTCGCGCTAGCCAAGATGTCAGCGGGTGGCT
GGCTTGGTACCAGCAGAAACCAGGTTTGGCTCCTCAGCTTTTGATCTCAGGAG
CGAGCACGCTTCAGGGTGAGGTCCCAAGTCGCTTTAGTGGCTCTGGCTCCGG
GACAGACTTCACGTTGACGATCAGCAGTTTGCAGCCTGAGGATTTCGCGACC
TACTACTGCCAGCAAGCGAAATATTTTCCGTACACTTTCGGTCAGGGGACCA
AATTGGAGATCAAAGGTGGGGGTGGTTCAGGCGGCGGAGGCTCAGGCGGCG
GCGGTAGCGGAGGAGGCGGAAGCGGGGGTGGCGGATCAGAAGTGCAACTCG
TTCAGAGTGGCGCGGAGGTTAAGAAACCCGGTGCATCTGTAAAGGTTAGCTG
TAAGGCATCAGGATACACTTTTACCAGCTATTACATGCATTGGGTGAGACAG
GCTCCCGGTCAGGGGCTCGAATGGATGGGGTTGATCAACCCGAGTGGTGGTT

CAACATCTTACGCCCAGAAGTTTCAGGGCCGAGTAACAATGACTCGGGACAC
GTCTACCTCAACTGTGTATATGGAGCTTTCCAGCCTGCGCTCAGAGGATACAG
CAGTCTATTACTGCGCACGGTCAGACAGAGGTATAACGGCCACTGATGCGTT
CGATATCTGGGGACAAGGGACTATGGTAACTGTGTCTTCCGGAGGAGGAGGT
AGTGGAGGGGGAGGAAGCGGTGGGGGGGGCTCACAGTCCGTTTTGACTCAG
CCACCAAGCGTCTCAGTCGCACCGGGGCGAATGGCGAAAATTACTTGCGGCG
GGAGCGACATAGGCAACAAGAATGTGCATTGGTACCAACAGAAACCAGGTC
AAGCACCTGTTCTCGTGGTGTATGATGACTACGATCGCCCAAGCGGGATCCC
GGAGCGGTTCTCTGGATCAAATTCTGGTGATGCAGCCACTCTGACAATATCA
ACGGTGGAAGTCGGTGACGAGGCTGATTACTTCTGCCAAGTATGGGATGGCA
GCGGAGATCCCTACTGGATGTTTGGAGGAGGTACTCAACTGACAGTTCTGGG
CGCGGCCGCAATCGAAGTGATGTATCCACCTCCGTACCTCGATAACGAGAAA
TCAAATGGAACGATCATTCATGTGAAAGGGAAACATCTGTGCCCAAGCCCAT
TGTTCCCAGGTCCGTCAAAACCATTCTGGGTGCTTGTCGTTGTTGGGGGTGTA
CTCGCATGTTATTCTTTGCTGGTGACTGTGGCGTTTATCATCTTCTGGGTAAGG
AGTAAACGCAGCCGCCTGCTGCATTCAGACTACATGAACATGACCCCACGGC
GGCCCGGCCCAACGCGCAAACACTACCAACCTTACGCCCCACCGCGAGACTT
TGCCGCCTACAGATCCAAGCGCGGACGGAAGAAACTCTTGTACATCTTCAAG
CAGCCGTTCATGCGCCCTGTGCAAACCACCCAAGAAGAGGACGGGTGCTCCT
GCCGGTTCCCGGAAGAGGAAGAGGGCGGCTGCGAACTGCGCGTGAAGTTTTC
CCGGTCCGCCGACGCTCCGGCGTACCAGCAGGGGCAAAACCAGCTGTACAAC
GAACTTAACCTCGGTCGCCGGGAAGAATATGACGTGCTGGACAAGCGGCGGG
GAAGAGATCCCGAGATGGGTGGAAAGCCGCGGCGGAAGAACCCTCAGGAGG
GCTTGTACAACGAGCTGCAAAAGGACAAAATGGCCGAAGCCTACTCCGAGAT
TGGCATGAAGGGAGAGCGCAGACGCGGGAAGGGACACGATGGACTGTACCA
GGGACTGTCAACCGCGACTAAGGACACTTACGACGCCCTGCACATGCAGGCC
CTGCCCCCGCGC amino acid sequence of CAR D0140 CD22-19 CD28 CD28 BBz

SEQ ID NO: 75

MLLLVTSLLLCELPHPAFLLIPQVQLQQSGPGLVKHSQTLSLTCAISGDSVSSNSA
AWNWIRQSPSRGLEWLGRTYYRSKWYNDYAVSVKSRITINPDTSKNQFSLQLNS
VTPEDTAVYYCAQEVEPHDAFDIWGQGTMVTVSSGGGGSGGGGSGGGGSDIQM
TQSPSSVYASVGDKVTITCRASQDVSGWLAWYQQKPGLAPQLLISGASTLQGEV
PSRFSGSGSGTDFTLTISSLQPEDFATYYCQQAKYFPYTFGQGTKLEIKGGGGSGG
GGSGGGGSGGGGSGGGGSEVQLVQSGAEVKKPGASVKVSCKASGYTFTSYYM
HWVRQAPGQGLEWMGLINPSGGSTSYAQKFQGRVTMTRDTSTSTVYMELSSLR
SEDTAVYYCARSDRGITATDAFDIWGQGTMVTVSSGGGGSGGGGSGGGGSQSV
LTQPPSVSVAPGRMAKITCGGSDIGNKNVHWYQQKPGQAPVLVVYDDYDRPSGI
PERFSGSNSGDAATLTISTVEVGDEADYFCQVWDGSGDPYWMFGGGTQLTVLG
AAAIEVMYPPPYLDNEKSNGTIIHVKGKHLCPSPLFPGPSKPFWVLVVVGGVLAC
YSLLVTVAFIIFWVRSKRSRLLHSDYMNMTPRRPGPTRKHYQPYAPPRDFAAYRS
KRGRKKLLYIFKQPFMRPVQTTQEEDGCSCRFPEEEEGGCELRVKFSRSADAPAY

-continued

QQGQNQLYNELNLGRREEYDVLDKRRGRDPEMGGKPRRKNPQEGLYNELQKD

KMAEAYSEIGMKGERRRGKGHDGLYQGLSTATKDTYDALHMQALPPR nucleotide sequence of CAR D0146 CD19 CD8H & TM ICOS z-_CD22 CD8H & TM 3z

SEQ ID NO: 76

ATGCTGCTGCTGGTGACCAGCCTGCTGCTGTGCGAACTGCCGCATCCGGCGTT

TCTGCTGATTCCGGAGGTCCAGCTGGTACAGTCTGGAGCTGAGGTGAAGAAG

CCTGGGGCCTCAGTGAAGGTCTCCTGCAAGGCTTCTGGATACACCTTCACCA

GCTACTATATGCACTGGGTGCGACAGGCCCCTGGACAAGGGCTTGAGTGGAT

GGGATTAATCAACCCTAGTGGTGGTAGCACAAGCTACGCACAGAAGTTCCAG

GGCAGAGTCACCATGACCAGGGACACGTCCACGAGCACAGTCTACATGGAG

CTGAGCAGCCTGAGATCTGAGGACACGGCCGTGTATTACTGTGCGAGATCGG

ATCGGGGAATTACCGCCACGGACGCTTTTGATATCTGGGGCCAAGGGACAAT

GGTCACCGTCTCTTCAGGCGGAGGAGGCTCCGGGGGAGGAGGTTCCGGGGGC

GGGGGTTCCCAGTCTGTGCTGACTCAGCCACCCTCGGTGTCAGTGGCCCCAG

GGCGGATGGCCAAGATTACCTGTGGGGGAAGTGACATTGGAAATAAAAATGT

CCACTGGTATCAGCAGAAGCCAGGCCAGGCCCCTGTCCTGGTTGTCTATGAT

GATTACGACCGGCCCTCAGGGATCCCTGAGCGATTCTCTGGCTCCAACTCTGG

GGACGCGGCCACCCTGACGATCAGCACGGTCGAAGTCGGGGATGAGGCCGA

CTATTTCTGTCAGGTGTGGGACGGTAGTGGTGATCCTTATTGGATGTTCGGCG

GAGGGACCCAGCTCACCGTTTTAGGTGCGGCCGCAACGACCACTCCTGCACC

ACGGCCACCTACCCCAGCCCCCACCATTGCAAGCCAGCCACTTTCACTGCGC

CCCGAAGCGTGTAGACCAGCTGCTGGAGGAGCCGTGCATACCCGAGGGCTGG

ACTTCGCCTGTGACATCTACATCTGGGCCCCATTGGCTGGAACTTGCGGCGTG

CTGCTCTTGTCTCTGGTCATTACCCTGTACTGCTGGCTGACAAAAAAGAAGTA

TTCATCTAGTGTACATGATCCGAACGGTGAATACATGTTCATGCGCGCGGTGA

ACACGGCCAAGAAGAGCAGACTGACCGACGTAACCCTTAGAGTGAAGTTTAG

CCGCTCAGCCGATGCACCGGCCTACCAGCAGGGACAGAACCAGCTCTACAAC

GAGCTCAACCTGGGTCGGCGGGAAGAATATGACGTGCTGGACAAACGGCGC

GGCAGAGATCCGGAGATGGGGGGAAAGCCGAGGAGGAAGAACCCTCAAGAG

GGCCTGTACAACGAACTGCAGAAGGACAAGATGGCGGAAGCCTACTCCGAG

ATCGGCATGAAGGGAGAACGCCGGAGAGGGAAGGGTCATGACGGACTGTAC

CAGGGCCTGTCAACTGCCACTAAGGACACTTACGATGCGCTCCATATGCAAG

CTTTGCCCCCGCGGCGCGCGAAACGCGGCAGCGGCGCGACCAACTTTAGCCT

GCTGAAACAGGCGGGCGATGTGGAAGAAAACCCGGGCCCGCGAGCAAAGAG

GAATATTATGGCTCTGCCTGTTACGGCACTGCTCCTTCCGCTTGCATTGTTGTT

GCACGCAGCGCGGCCCCAAGTGCAGCTGCAGCAGTCCGGTCCTGGACTGGTC

AAGCCGTCCCAGACTCTGAGCCTGACTTGCGCAATTAGCGGGGACTCAGTCT

CGTCCAATTCGGCGGCCTGGAACTGGATCCGGCAGTCACCATCAAGGGGCCT

GGAATGGCTCGGGCGCACTTACTACCGGTCCAAATGGTATACCGACTACGCC

GTGTCCGTGAAGAATCGGATCACCATTAACCCCGACACCTCGAAGAACCAGT

TCTCACTCCAACTGAACAGCGTGACCCCCGAGGATACCGCGGTGTACTACTG

-continued

CGCACAAGAAGTGGAACCGCAGGACGCCTTCGACATTTGGGGACAGGGAAC

GATGGTCACAGTGTCGTCCGGTGGAGGAGGTTCCGGAGGCGGTGGATCTGGA

GGCGGAGGTTCGGATATCCAGATGACCCAGAGCCCCTCCTCGGTGTCCGCAT

CCGTGGGCGATAAGGTCACCATTACCTGTAGAGCGTCCCAGGACGTGTCCGG

ATGGCTGGCCTGGTACCAGCAGAAGCCAGGCTTGGCTCCTCAACTGCTGATC

TTCGGCGCCAGCACTCTTCAGGGGGAAGTGCCATCACGCTTCTCCGGATCCG

GTTCCGGCACCGACTTCACCCTGACCATCAGCAGCCTCCAGCCTGAGGACTTC

GCCACTTACTACTGCCAACAGGCCAAGTACTTCCCCTATACCTTCGGAAGAG

GCACTAAGCTGGAAATCAAGGCTAGCGCAACCACTACGCCTGCTCCGCGGCC

TCCAACGCCCGCGCCCACGATAGCTAGTCAGCCGTTGTCTCTCCGACCAGAG

GCGTGTAGACCGGCCGCTGGCGGAGCCGTACATACTCGCGGACTCGACTTCG

CTTGCGACATCTACATTTGGGCACCCTTGGCTGGGACCTGTGGGGTGCTGTTG

CTGTCCTTGGTTATTACGTTGTACTGCAGAGTCAAATTTTCCAGGTCCGCAGA

TGCCCCCGCGTACCAGCAAGGCCAGAACCAACTTTACAACGAACTGAACCTG

GGTCGCCGGGAGGAATATGATGTGCTGGATAAACGAAGGGGGAGGGACCCT

GAGATGGGAGGGAAACCTCGCAGGAAAAACCCGCAGGAAGGTTTGTACAAC

GAGTTGCAGAAGGATAAGATGGCTGAGGCTTACTCTGAAATAGGGATGAAG

GGAGAGAGACGGAGAGGAAAAGGCCATGATGGCCTTTACCAGGGCTTAAGC

ACAGCAACAAAGGATACTTACGACGCTCTTCACATGCAAGCTCTGCCACCAC

GG amino acid sequence of CAR D0146 CD19 CD8H & TM ICOS z_CD22 CD8H & TMz

SEQ ID NO: 77

MLLLVTSLLLCELPHPAFLLIPEVQLVQSGAEVKKPGASVKVSCKASGYTFTSYY

MHWVRQAPGQGLEWMGLINPSGGSTSYAQKFQGRVTMTRDTSTSTVYMELSS

LRSEDTAVYYCARSDRGITATDAFDIWGQGTMVTVSSGGGGSGGGGSGGGGSQ

SVLTQPPSVSVAPGRMAKITCGGSDIGNKNVHWYQQKPGQAPVLVVYDDYDRP

SGIPERFSGSNSGDAATLTISTVEVGDEADYFCQVWDGSGDPYWMFGGGTQLT

VLGAAATTTPAPRPPTPAPTIASQPLSLRPEACRPAAGGAVHTRGLDFACDIYIW

APLAGTCGVLLLSLVITLYCWLTKKKYSSSVHDPNGEYMFMRAVNTAKKSRLT

DVTLRVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTATKDT

YDALHMQALPPRRAKRGSGATNFSLLKQAGDVEENPGPRAKRNIMALPVTALL

LPLALLLHAARPQVQLQQSGPGLVKPSQTLSLTCAISGDSVSSNSAAWNWIRQS

PSRGLEWLGRTYYRSKWYTDYAVSVKNRITINPDTSKNQFSLQLNSVTPEDTAV

YYCAQEVEPQDAFDIWGQGTMVTVSSGGGGSGGGGSGGGGSDIQMTQSPSSVS

ASVGDKVTITCRASQDVSGWLAWYQQKPGLAPQLLIFGASTLQGEVPSRFSGSG

SGTDFTLTISSLQPEDFATYYCQQAKYFPYTFGRGTKLEIKASATTTPAPRPPTPA

PTIASQPLSLRPEACRPAAGGAVHTRGLDFACDIYIWAPLAGTCGVLLLSLVITL

YCRVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDTYD

ALHMQALPPR

-continued nucleotide sequence of CAR D0147 CD19 CD8H OX40TM OX40 z_CD22 CD8H & TM z

SEQ ID NO: 78

ATGCACTGGGTGCGACAGGCCCCTGGACAAGGGCTTGAGTGGATGGGATTA

ATCAACCCTAGTGGTGGTAGCACAAGCTACGCACAGAAGTTCCAGGGCAGA

GTCACCATGACCAGGGACACGTCCACGAGCACAGTCTACATGGAGCTGAGC

AGCCTGAGATCTGAGGACACGGCCGTGTATTACTGTGCGAGATCGGATCGG

GGAATTACCGCCACGGACGCTTTTGATATCTGGGGCCAAGGGACAATGGTC

ACCGTCTCTTCAGGCGGAGGAGGCTCCGGGGGAGGAGGTTCCGGGGGCGGG

GGTTCCCAGTCTGTGCTGACTCAGCCACCCTCGGTGTCAGTGGCCCCAGGGC

GGATGGCCAAGATTACCTGTGGGGGAAGTGACATTGGAAATAAAAATGTCC

ACTGGTATCAGCAGAAGCCAGGCCAGGCCCCTGTCCTGGTTGTCTATGATGA

TTACGACCGGCCCTCAGGGATCCCTGAGCGATTCTCTGGCTCCAACTCTGGG

GACGCGGCCACCCTGACGATCAGCACGGTCGAAGTCGGGGATGAGGCCGAC

TATTTCTGTCAGGTGTGGGACGGTAGTGGTGATCCTTATTGGATGTTCGGCG

GAGGGACCCAGCTCACCGTTTTAGGTGCGGCCGCAACGACCACTCCAGCAC

CGAGACCGCCAACCCCCGCGCCTACCATCGCAAGTCAACCACTTTCTCTCAG

GCCTGAAGCGTGCCGACCTGCAGCTGGTGGGGCAGTACATACCAGGGGTTT

GGACTTCGCATGTGACGTGGCGGCAATTCTCGGCCTGGGACTTGTCCTTGGT

CTGCTTGGTCCGCTCGCAATACTTCTGGCCTTGTACCTGCTCCGCAGAGACC

AAAGACTTCCGCCCGACGCCCACAAGCCCCCAGGAGGAGGTTCCTTCAGAA

CGCCTATACAAGAAGAACAAGCAGATGCCCACTCTACCCTGGCTAAAATCA

GGGTGAAGTTTAGCCGCTCAGCCGATGCACCGGCCTACCAGCAGGGACAGA

ACCAGCTCTACAACGAGCTCAACCTGGGTCGGCGGGAAGAATATGACGTGC

TGGACAAACGGCGCGGCAGAGATCCGGAGATGGGGGGAAAGCCGAGGAGG

AAGAACCCTCAAGAGGGCCTGTACAACGAACTGCAGAAGGACAAGATGGCG

GAAGCCTACTCCGAGATCGGCATGAAGGGAGAACGCCGGAGAGGGAAGGG

TCATGACGGACTGTACCAGGGCCTGTCAACTGCCACTAAGGACACTTACGAT

GCGCTCCATATGCAAGCTTTGCCCCCGCGGCGCGCGAAACGCGGCAGCGGC

GCGACCAACTTTAGCCTGCTGAAACAGGCGGGCGATGTGGAAGAAAACCCG

GGCCCGCGAGCAAAGAGGAATATTATGGCTCTGCCTGTTACGGCACTGCTCC

TTCCGCTTGCATTGTTGTTGCACGCAGCGCGGCCCCAAGTGCAGCTGCAGCA

GTCCGGTCCTGGACTGGTCAAGCCGTCCCAGACTCTGAGCCTGACTTGCGCA

ATTAGCGGGGACTCAGTCTCGTCCAATTCGGCGGCCTGGAACTGGATCCGGC

AGTCACCATCAAGGGGCCTGGAATGGCTCGGGCGCACTTACTACCGGTCCA

AATGGTATACCGACTACGCCGTGTCCGTGAAGAATCGGATCACCATTAACCC

CGACACCTCGAAGAACCAGTTCTCACTCCAACTGAACAGCGTGACCCCCGA

GGATACCGCGGTGTACTACTGCGCACAAGAAGTGGAACCGCAGGACGCCTT

CGACATTTGGGGACAGGGAACGATGGTCACAGTGTCGTCCGGTGGAGGAGG

TTCCGGAGGCGGTGGATCTGGAGGCGGAGGTTCGGATATCCAGATGACCCA

GAGCCCCTCCTCGGTGTCCGCATCCGTGGGCGATAAGGTCACCATTACCTGT

AGAGCGTCCCAGGACGTGTCCGGATGGCTGGCCTGGTACCAGCAGAAGCCA

GGCTTGGCTCCTCAACTGCTGATCTTCGGCGCCAGCACTCTTCAGGGGGAAG

TGCCATCACGCTTCTCCGGATCCGGTTCCGGCACCGACTTCACCCTGACCAT

CAGCAGCCTCCAGCCTGAGGACTTCGCCACTTACTACTGCCAACAGGCCAAG

TACTTCCCCTATACCTTCGGAAGAGGCACTAAGCTGGAAATCAAGGCTAGCG

CAACCACTACGCCTGCTCCGCGGCCTCCAACGCCCGCGCCCACGATAGCTAG

TCAGCCGTTGTCTCTCCGACCAGAGGCGTGTAGACCGGCCGCTGGCGGAGCC

GTACATACTCGCGGACTCGACTTCGCTTGCGACATCTACATTTGGGCACCCT

TGGCTGGGACCTGTGGGGTGCTGTTGCTGTCCTTGGTTATTACGTTGTACTGC

AGAGTCAAATTTTCCAGGTCCGCAGATGCCCCCGCGTACCAGCAAGGCCAG

AACCAACTTTACAACGAACTGAACCTGGGTCGCCGGGAGGAATATGATGTG

CTGGATAAACGAAGGGGGAGGGACCCTGAGATGGGAGGGAAACCTCGCAG

GAAAAACCCGCAGGAAGGTTTGTACAACGAGTTGCAGAAGGATAAGATGGC

TGAGGCTTACTCTGAAATAGGGATGAAGGGAGAGAGACGGAGAGGAAAAG

GCCATGATGGCCTTTACCAGGGCTTAAGCACAGCAACAAAGGATACTTACG

ACGCTCTTCACATGCAAGCTCTGCCACCACGG amino acid sequence of CAR D0147 CD19 CD8H OX40TM OX40 z_CD22 CD8H & TM 3z

SEQ ID NO: 79

MHWVRQAPGQGLEWMGLINPSGGSTSYAQKFQGRVTMTRDTSTSTVYMELSS

LRSEDTAVYYCARSDRGITATDAFDIWGQGTMVTVSSGGGGSGGGGSGGGGSQ

SVLTQPPSVSVAPGRMAKITCGGSDIGNKNVHWYQQKPGQAPVLVVYDDYDRP

SGIPERFSGSNSGDAATLTISTVEVGDEADYFCQVWDGSGDPYWMFGGGTQLT

VLGAAATTTPAPRPPTPAPTIASQPLSLRPEACRPAAGGAVHTRGLDFACDVAAI

LGLGLVLGLLGPLAILLALYLLRRDQRLPPDAHKPPGGGSFRTPIQEEQADAHST

LAKIRVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTATKDT

YDALHMQALPPRRAKRGSGATNFSLLKQAGDVEENPGPRAKRNIMALPVTALL

LPLALLLHAARPQVQLQQSGPGLVKPSQTLSLTCAISGDSVSSNSAAWNWIRQS

PSRGLEWLGRTYYRSKWYTDYAVSVKNRITINPDTSKNQFSLQLNSVTPEDTAV

YYCAQEVEPQDAFDIWGQGTMVTVSSGGGGSGGGGSGGGGSDIQMTQSPSSVS

ASVGDKVTITCRASQDVSGWLAWYQQKPGLAPQLLIFGASTLQGEVPSRFSGSG

SGTDFTLTISSLQPEDFATYYCQQAKYFPYTFGRGTKLEIKASATTTPAPRPPTPA

PTIASQPLSLRPEACRPAAGGAVHTRGLDFACDIYIWAPLAGTCGVLLLSLVITL

YCRVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDTYD

ALHMQALPPR nucleotide sequence of CAR D0148 CD19 CD8H OX40TM OX40 z_CD22 CD8H & TM ICOS z

SEQ ID NO: 80

ATGCTGCTGCTGGTGACCAGCCTGCTGCTGTGCGAACTGCCGCATCCGGCGT

TTCTGCTGATTCCGGAGGTCCAGCTGGTACAGTCTGGAGCTGAGGTGAAGAA

GCCTGGGGCCTCAGTGAAGGTCTCCTGCAAGGCTTCTGGATACACCTTCACC

AGCTACTATATGCACTGGGTGCGACAGGCCCCTGGACAAGGGCTTGAGTGG

-continued

ATGGGATTAATCAACCCTAGTGGTGGTAGCACAAGCTACGCACAGAAGTTC

CAGGGCAGAGTCACCATGACCAGGGACACGTCCACGAGCACAGTCTACATG

GAGCTGAGCAGCCTGAGATCTGAGGACACGGCCGTGTATTACTGTGCGAGA

TCGGATCGGGGAATTACCGCCACGGACGCTTTTGATATCTGGGGCCAAGGG

ACAATGGTCACCGTCTCTTCAGGCGGAGGAGGCTCCGGGGGAGGAGGTTCC

GGGGGCGGGGGTTCCCAGTCTGTGCTGACTCAGCCACCCTCGGTGTCAGTGG

CCCCAGGGCGGATGGCCAAGATTACCTGTGGGGGAAGTGACATTGGAAATA

AAAATGTCCACTGGTATCAGCAGAAGCCAGGCCAGGCCCCTGTCCTGGTTGT

CTATGATGATTACGACCGGCCCTCAGGGATCCCTGAGCGATTCTCTGGCTCC

AACTCTGGGGACGCGGCCACCCTGACGATCAGCACGGTCGAAGTCGGGGAT

GAGGCCGACTATTTCTGTCAGGTGTGGGACGGTAGTGGTGATCCTTATTGGA

TGTTCGGCGGAGGGACCCAGCTCACCGTTTTAGGTGCGGCCGCAACGACCAC

TCCAGCACCGAGACCGCCAACCCCCGCGCCTACCATCGCAAGTCAACCACTT

TCTCTCAGGCCTGAAGCGTGCCGACCTGCAGCTGGTGGGGCAGTACATACCA

GGGGTTTGGACTTCGCATGTGACGTGGCGGCAATTCTCGGCCTGGGACTTGT

CCTTGGTCTGCTTGGTCCGCTCGCAATACTTCTGGCCTTGTACCTGCTCCGCA

GAGACCAAAGACTTCCGCCCGACGCCCACAAGCCCCCAGGAGGAGGTTCCT

TCAGAACGCCTATACAAGAAGAACAAGCAGATGCCCACTCTACCCTGGCTA

AAATCAGGGTGAAGTTTAGCCGCTCAGCCGATGCACCGGCCTACCAGCAGG

GACAGAACCAGCTCTACAACGAGCTCAACCTGGGTCGGCGGGAAGAATATG

ACGTGCTGGACAAACGGCGCGGCAGAGATCCGGAGATGGGGGGAAAGCCG

AGGAGGAAGAACCCTCAAGAGGGCCTGTACAACGAACTGCAGAAGGACAA

GATGGCGGAAGCCTACTCCGAGATCGGCATGAAGGGAGAACGCCGGAGAG

GGAAGGGTCATGACGGACTGTACCAGGGCCTGTCAACTGCCACTAAGGACA

CTTACGATGCGCTCCATATGCAAGCTTTGCCCCCGCGGCGCGCGAAACGCGG

CAGCGGCGCGACCAACTTTAGCCTGCTGAAACAGGCGGGCGATGTGGAAGA

AAACCCGGGCCCGCGAGCAAAGAGGAATATTATGGCTCTGCCTGTTACGGC

ACTGCTCCTTCCGCTTGCATTGTTGTTGCACGCAGCGCGGCCCCAAGTGCAG

CTGCAGCAGTCCGGTCCTGGACTGGTCAAGCCGTCCCAGACTCTGAGCCTGA

CTTGCGCAATTAGCGGGGACTCAGTCTCGTCCAATTCGGCGGCCTGGAACTG

GATCCGGCAGTCACCATCAAGGGGCCTGGAATGGCTCGGGCGCACTTACTA

CCGGTCCAAATGGTATACCGACTACGCCGTGTCCGTGAAGAATCGGATCACC

ATTAACCCCGACACCTCGAAGAACCAGTTCTCACTCCAACTGAACAGCGTGA

CCCCCGAGGATACCGCGGTGTACTACTGCGCACAAGAAGTGGAACCGCAGG

ACGCCTTCGACATTTGGGGACAGGGAACGATGGTCACAGTGTCGTCCGGTG

GAGGAGGTTCCGGAGGCGGTGGATCTGGAGGCGGAGGTTCGGATATCCAGA

TGACCCAGAGCCCCTCCTCGGTGTCCGCATCCGTGGGCGATAAGGTCACCAT

TACCTGTAGAGCGTCCCAGGACGTGTCCGGATGGCTGGCCTGGTACCAGCAG

AAGCCAGGCTTGGCTCCTCAACTGCTGATCTTCGGCGCCAGCACTCTTCAGG

GGGAAGTGCCATCACGCTTCTCCGGATCCGGTTCCGGCACCGACTTCACCCT

GACCATCAGCAGCCTCCAGCCTGAGGACTTCGCCACTTACTACTGCCAACAG

-continued

GCCAAGTACTTCCCCTATACCTTCGGAAGAGGCACTAAGCTGGAAATCAAG

GCTAGCGCAACCACTACGCCTGCTCCGCGGCCTCCAACGCCCGCGCCCACGA

TAGCTAGTCAGCCGTTGTCTCTCCGACCAGAGGCGTGTAGACCGGCCGCTGG

CGGAGCCGTACATACTCGCGGACTCGACTTCGCTTGCGACATCTACATTTGG

GCACCCTTGGCTGGGACCTGTGGGGTGCTGTTGCTGTCCTTGGTTATTACGTT

GTACTGCTGGCTGACAAAAAAGAAGTATTCATCTAGTGTACATGATCCGAAC

GGTGAATACATGTTCATGCGCGCGGTGAACACGGCCAAGAAGAGCAGACTG

ACCGACGTAACCCTTAGAGTCAAATTTTCCAGGTCCGCAGATGCCCCCGCGT

ACCAGCAAGGCCAGAACCAACTTTACAACGAACTGAACCTGGGTCGCCGGG

AGGAATATGATGTGCTGGATAAACGAAGGGGGAGGGACCCTGAGATGGGA

GGGAAACCTCGCAGGAAAAACCCGCAGGAAGGTTTGTACAACGAGTTGCAG

AAGGATAAGATGGCTGAGGCTTACTCTGAAATAGGGATGAAGGGAGAGAGA

CGGAGAGGAAAAGGCCATGATGGCCTTTACCAGGGCTTGAGCACAGCAACA

AAGGATACTTACGACGCTCTTCACATGCAAGCTCTGCCACCACGG amino acid sequence of CAR D0148 CD19 CD8H OX40TM OX40 z_CD22 CD8H & TM ICOS z

SEQ ID NO: 81

MLLLVTSLLLCELPHPAFLLIPEVQLVQSGAEVKKPGASVKVSCKASGYTFTSYY

MHWVRQAPGQGLEWMGLINPSGGSTSYAQKFQGRVTMTRDTSTSTVYMELSS

LRSEDTAVYYCARSDRGITATDAFDIWGQGTMVTVSSGGGGSGGGGSGGGGSQ

SVLTQPPSVSVAPGRMAKITCGGSDIGNKNVHWYQQKPGQAPVLVVYDDYDRP

SGIPERFSGSNSGDAATLTISTVEVGDEADYFCQVWDGSGDPYWMFGGGTQLT

VLGAAATTTPAPRPPTPAPTIASQPLSLRPEACRPAAGGAVHTRGLDFACDVAAI

LGLGLVLGLLGPLAILLALYLLRRDQRLPPDAHKPPGGGSFRTPIQEEQADAHST

LAKIRVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTATKDT

YDALHMQALPPRRAKRGSGATNFSLLKQAGDVEENPGPRAKRNIMALPVTALL

LPLALLLHAARPQVQLQQSGPGLVKPSQTLSLTCAISGDSVSSNSAAWNWIRQS

PSRGLEWLGRTYYRSKWYTDYAVSVKNRITINPDTSKNQFSLQLNSVTPEDTAV

YYCAQEVEPQDAFDIWGQGTMVTVSSGGGGSGGGGSGGGGSDIQMTQSPSSVS

ASVGDKVTITCRASQDVSGWLAWYQQKPGLAPQLLIFGASTLQGEVPSRFSGSG

SGTDFTLTISSLQPEDFATYYCQQAKYFPYTFGRGTKLEIKASATTTPAPRPPTPA

PTIASQPLSLRPEACRPAAGGAVHTRGLDFACDIYIWAPLAGTCGVLLLSLVITL

YCWLTKKKYSSSVHDPNGEYMFMRAVNTAKKSRLTDVTLRVKFSRSADAPAY

QQGQNQLYNELNLGRREEYDVLDKRRGRDPEMGGKPRRKNPQEGLYNELQKD

KMAEAYSEIGMKGERRRGKGHDGLYQGLSTATKDTYDALHMQALPPR nucleotide sequence of CAR D0149 CD19 CD8H & TM CD27 z_CD22 CD8H & TM ICOS3 z

SEQ ID NO: 82

ATGCACTGGGTGCGACAGGCCCCTGGACAAGGGCTTGAGTGGATGGGATTA

ATCAACCCTAGTGGTGGTAGCACAAGCTACGCACAGAAGTTCCAGGGCAGA

GTCACCATGACCAGGGACACGTCCACGAGCACAGTCTACATGGAGCTGAGC

AGCCTGAGATCTGAGGACACGGCCGTGTATTACTGTGCGAGATCGGATCGG

-continued

GGAATTACCGCCACGGACGCTTTTGATATCTGGGGCCAAGGGACAATGGTC

ACCGTCTCTTCAGGCGGAGGAGGCTCCGGGGGAGGAGGTTCCGGGGGCGGG

GGTTCCCAGTCTGTGCTGACTCAGCCACCCTCGGTGTCAGTGGCCCCAGGGC

GGATGGCCAAGATTACCTGTGGGGGAAGTGACATTGGAAATAAAAATGTCC

ACTGGTATCAGCAGAAGCCAGGCCAGGCCCCTGTCCTGGTTGTCTATGATGA

TTACGACCGGCCCTCAGGGATCCCTGAGCGATTCTCTGGCTCCAACTCTGGG

GACGCGGCCACCCTGACGATCAGCACGGTCGAAGTCGGGGATGAGGCCGAC

TATTTCTGTCAGGTGTGGGACGGTAGTGGTGATCCTTATTGGATGTTCGGCG

GAGGGACCCAGCTCACCGTTTTAGGTGCGGCCGCGACTACCACTCCTGCACC

ACGGCCACCTACCCCAGCCCCCACCATTGCAAGCCAGCCACTTTCACTGCGC

CCCGAAGCGTGTAGACCAGCTGCTGGAGGAGCCGTGCATACCCGAGGGCTG

GACTTCGCCTGTGACATCTACATCTGGGCCCCATTGGCTGGAACTTGCGGCG

TGCTGCTCTTGTCTCTGGTCATTACCCTGTACTGCCAACGGCGCAAATACCGC

TCCAATAAAGGCGAAAGTCCGGTAGAACCCGCAGAACCTTGCCACTACAGT

TGTCCCAGAGAAGAAGAGGGTTCTACAATACCTATTCAAGAGGACTATAGG

AAACCAGAGCCCGCATGTAGTCCCAGAGTGAAGTTCAGCCGCTCAGCCGAT

GCACCGGCCTACCAGCAGGGACAGAACCAGCTCTACAACGAGCTCAACCTG

GGTCGGCGGGAAGAATATGACGTGCTGGACAAACGGCGCGGCAGAGATCCG

GAGATGGGGGGAAAGCCGAGGAGGAAGAACCCTCAAGAGGGCCTGTACAA

CGAACTGCAGAAGGACAAGATGGCGGAAGCCTACTCCGAGATCGGCATGAA

GGGAGAACGCCGGAGAGGGAAGGGTCATGACGGACTGTACCAGGGCCTGTC

AACTGCCACTAAGGACACTTACGATGCGCTCCATATGCAAGCTTTGCCCCCG

CGGCGCGCGAAACGCGGCAGCGGCGCGACCAACTTTAGCCTGCTGAAACAG

GCGGGCGATGTGGAAGAAAACCCGGGCCCGCGAGCAAAGAGGAATATTATG

GCTCTGCCTGTTACGGCACTGCTCCTTCCGCTTGCATTGTTGTTGCACGCAGC

GCGGCCCCAAGTGCAGCTGCAGCAGTCCGGTCCTGGACTGGTCAAGCCGTCC

CAGACTCTGAGCCTGACTTGCGCAATTAGCGGGGACTCAGTCTCGTCCAATT

CGGCGGCCTGGAACTGGATCCGGCAGTCACCATCAAGGGGCCTGGAATGGC

TCGGGCGCACTTACTACCGGTCCAAATGGTATACCGACTACGCCGTGTCCGT

GAAGAATCGGATCACCATTAACCCCGACACCTCGAAGAACCAGTTCTCACTC

CAACTGAACAGCGTGACCCCCGAGGATACCGCGGTGTACTACTGCGCACAA

GAAGTGGAACCGCAGGACGCCTTCGACATTTGGGGACAGGGAACGATGGTC

ACAGTGTCGTCCGGTGGAGGAGGTTCCGGAGGCGGTGGATCTGGAGGCGGA

GGTTCGGATATCCAGATGACCCAGAGCCCCTCCTCGGTGTCCGCATCCGTGG

GCGATAAGGTCACCATTACCTGTAGAGCGTCCCAGGACGTGTCCGGATGGCT

GGCCTGGTACCAGCAGAAGCCAGGCTTGGCTCCTCAACTGCTGATCTTCGGC

GCCAGCACTCTTCAGGGGGAAGTGCCATCACGCTTCTCCGGATCCGGTTCCG

GCACCGACTTCACCCTGACCATCAGCAGCCTCCAGCCTGAGGACTTCGCCAC

TTACTACTGCCAACAGGCCAAGTACTTCCCCTATACCTTCGGAAGAGGCACT

AAGCTGGAAATCAAGGCTAGCGCAACCACTACGCCTGCTCCGCGGCCTCCA

ACGCCCGCGCCCACGATAGCTAGTCAGCCGTTGTCTCTCCGACCAGAGGCGT

GTAGACCGGCCGCTGGCGGAGCCGTACATACTCGCGGACTCGACTTCGCTTG

CGACATCTACATTTGGGCACCCTTGGCTGGGACCTGTGGGGTGCTGTTGCTG

TCCTTGGTTATTACGTTGTACTGCTGGCTGACAAAAAAGAAGTATTCATCTA

GTGTACATGATCCGAACGGTGAATACATGTTCATGCGCGCGGTGAACACGG

CCAAGAAGAGCAGACTGACCGACGTAACCCTTAGAGTCAAATTTTCCAGGT

CCGCAGATGCCCCCGCGTACCAGCAAGGCCAGAACCAACTTTACAACGAAC

TGAACCTGGGTCGCCGGGAGGAATATGATGTGCTGGATAAACGAAGGGGGA

GGGACCCTGAGATGGGAGGGAAACCTCGCAGGAAAAACCCGCAGGAAGGT

TTGTACAACGAGTTGCAGAAGGATAAGATGGCTGAGGCTTACTCTGAAATA

GGGATGAAGGGAGAGAGACGGAGAGGAAAAGGCCATGATGGCCTTTACCA

GGGCTTGAGCACAGCAACAAAGGATACTTACGACGCTCTTCACATGCAAGC

TCTGCCACCACGG amino acid sequence of CAR D0149 CD19 CD8H & TM ICOS z CD22 CD8H & TM ICOS z

SEQ ID NO: 83

MHWVRQAPGQGLEWMGLINPSGGSTSYAQKFQGRVTMTRDTSTSTVYMELSS

LRSEDTAVYYCARSDRGITATDAFDIWGQGTMVTVSSGGGGSGGGGSGGGGS

QSVLTQPPSVSVAPGRMAKITCGGSDIGNKNVHWYQQKPGQAPVLVVYDDYD

RPSGIPERFSGSNSGDAATLTISTVEVGDEADYFCQVWDGSGDPYWMFGGGTQ

LTVLGAAATTTPAPRPPTPAPTIASQPLSLRPEACRPAAGGAVHTRGLDFACDIY

IWAPLAGTCGVLLLSLVITLYCQRRKYRSNKGESPVEPAEPCHYSCPREEEGSTI

PIQEDYRKPEPACSPRVKFSRSADAPAYQQGQNQLYNELNLGRREEYDVLDKR

RGRDPEMGGKPRRKNPQEGLYNELQKDKMAEAYSEIGMKGERRRGKGHDGL

YQGLSTATKDTYDALHMQALPPRRAKRGSGATNFSLLKQAGDVEENPGPRAK

RNIMALPVTALLLPLALLLHAARPQVQLQQSGPGLVKPSQTLSLTCAISGDSVS

SNSAAWNWIRQSPSRGLEWLGRTYYRSKWYTDYAVSVKNRITINPDTSKNQFS

LQLNSVTPEDTAVYYCAQEVEPQDAFDIWGQGTMVTVSSGGGGSGGGGSGGG

GSDIQMTQSPSSVSASVGDKVTITCRASQDVSGWLAWYQQKPGLAPQLLIFGA

STLQGEVPSRFSGSGSGTDFTLTISSLQPEDFATYYCQQAKYFPYTFGRGTKLEI

KASATTTPAPRPPTPAPTIASQPLSLRPEACRPAAGGAVHTRGLDFACDIYIWAP

LAGTCGVLLLSLVITLYCWLTKKKYSSSVHDPNGEYMFMRAVNTAKKSRLTD

VTLRVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATKDT

YDALHMQALPPR nucleotide sequence of D0101 (EF-1a-TSLPR-CD19 (19217_1) CD8 BBz)

SEQ ID NO: 84

ATGCTGCTGCTGGTGACCAGCCTGCTTCTGTGCGAACTGCCGCATCCGGCGTTTC

TGTTGATTCCGCAAGTCACCCTCAAAGAGTCAGGGCCAGGAATCCTCAAGCCCTC

ACAGACTCTGTCTCTTACTTGCTCATTCAGCGGATTCAGCCTTTCCACCTCTGGTA

TGGGCGTGGGGTGGATTAGGCAACCTAGCGGAAAGGGGCTTGAATGGCTGGCCC

ACATCTGGTGGGACGACGACAAGTACTACAACCCCTCACTGAAGTCCCAGCTCA

CTATTTCCAAAGATACTTCCCGGAATCAGGTGTTCCTCAAGATTACCTCTGTCGA

-continued

CACCGCTGATACCGCCACTTACTATTGTTCACGCAGACCGAGAGGTACCATGGAC

GCAATGGACTACTGGGGACAGGGCACCAGCGTGACCGTGTCATCTGGCGGTGGA

GGGTCAGGAGGTGGAGGTAGCGGAGGCGGTGGGTCCGACATTGTCATGACCCAG

GCCGCCAGCTCCCTGAGCGCTTCACTGGGCGACAGGGTGACCATCAGCTGTCGC

GCATCACAAGATATCTCTAAGTATCTTAATTGGTACCAGCAAAAGCCGGATGGA

ACCGTGAAGCTGCTGATCTACTACACCTCACGGCTGCATTCTGGAGTGCCTAGCC

GCTTTAGCGGATCTGGGTCCGGTACTGACTACAGCCTCACCATTAGAAACCTTGA

ACAGGAGGACATCGCAACTTATTTCTGCCAACAGGTCTATACTCTGCCGTGGACC

TTCGGCGGAGGTACCAAACTGGAGATTAAGGGTGGAGGTGGTTCAGGCGGCGGA

GGCTCAGGCGGCGGCGGTAGCGGCGGAGGAGGAAGCGGAGGTGGCGGATCAGA

GGTCCAGCTGGTACAGTCTGGAGCTGAGGTGAAGAAGCCTGGGGCCTCAGTGAA

GGTCTCCTGCAAGGCTTCTGGATACACCTTCACCAGCTACTATATGCACTGGGTG

CGACAGGCCCCTGGACAAGGGCTTGAGTGGATGGGATTAATCAACCCTAGTGGT

GGTAGCACAAGCTACGCACAGAAGTTCCAGGGCAGAGTCACCATGACCAGGGAC

ACGTCCACGAGCACAGTCTACATGGAGCTGAGCAGCCTGAGATCTGAGGACACG

GCCGTGTATTACTGTGCGAGATCGGATCGGGGAATTACCGCCACGGACGCTTTTG

ATATCTGGGGCCAAGGGACAATGGTCACCGTCTCTTCAGGCGGAGGAGGCTCTG

GGGGAGGAGGTTCCGGAGGAGGCGGTTCCCAGTCTGTGCTGACTCAGCCACCCT

CGGTGTCAGTGGCCCCAGGGCGGATGGCCAAGATTACCTGTGGGGGAAGTGACA

TTGGAAATAAAAATGTCCACTGGTATCAGCAGAAGCCAGGCCAGGCCCCTGTCC

TGGTTGTCTATGATGATTACGACCGGCCCTCAGGGATCCCTGAGCGATTCTCTGG

CTCCAACTCTGGGGACGCGGCCACCCTGACGATCAGCACGGTCGAAGTCGGGGA

TGAGGCCGACTATTTCTGTCAGGTGTGGGACGGTAGTGGTGATCCTTATTGGATG

TTCGGCGGAGGGACCCAGCTCACCGTTTTAGGTGCGGCCGCAACGACCACTCCTG

CACCCCGCCCTCCGACTCCGGCCCCAACCATTGCCAGCCAGCCCCTGTCCCTGCG

GCCGGAAGCCTGCAGACCGGCTGCCGGCGGAGCCGTCCATACCCGGGGACTGGA

TTTCGCCTGCGATATCTATATCTGGGCACCACTCGCCGGAACCTGTGGAGTGCTG

CTGCTGTCCCTTGTGATCACCCTGTACTGCAAGCGCGGACGGAAGAAACTCTTGT

ACATCTTCAAGCAGCCGTTCATGCGCCCTGTGCAAACCACCCAAGAAGAGGACG

GGTGCTCCTGCCGGTTCCCGGAAGAGGAAGAGGGCGGCTGCGAACTGCGCGTGA

AGTTTTCCCGGTCCGCCGACGCTCCGGCGTACCAGCAGGGGCAAAACCAGCTGT

ACAACGAACTTAACCTCGGTCGCCGGGAAGAATATGACGTGCTGGACAAGCGGC

GGGGAAGAGATCCCGAGATGGGTGGAAAGCCGCGGCGGAAGAACCCTCAGGAG

GGCTTGTACAACGAGCTGCAAAAGGACAAAATGGCCGAAGCCTACTCCGAGATT

GGCATGAAGGGAGAGCGCAGACGCGGGAAGGGACACGATGGACTGTACCAGGG

ACTGTCAACCGCGACTAAGGACACTTACGACGCCCTGCACATGCAGGCCCTGCC

CCCGCGC amino acid sequence of D0101 (EF-1a-TSLPR-CD19 (19217_1) CD8 BBz)

SEQ ID NO: 85

MLLLVTSLLLCELPHPAFLLIPQVTLKESGPGILKPSQTLSLTCSFSGFSLSTSGMGVG

WIRQPSGKGLEWLAHIWWDDDKYYNPSLKSQLTISKDTSRNQVFLKITSVDTADTAT

-continued

YYCSRRPRGTMDAMDYWGQGTSVTVSSGGGGSGGGGSGGGGSDIVMTQAASSLSA

SLGDRVTISCRASQDISKYLNWYQQKPDGTVKLLIYYTSRLHSGVPSRFSGSGSGTDY

SLTIRNLEQEDIATYFCQQVYTLPWTFGGGTKLEIKGGGGSGGGGSGGGGSGGGGSG

GGGSEVQLVQSGAEVKKPGASVKVSCKASGYTFTSYYMHWVRQAPGQGLEWMGL

INPSGGSTSYAQKFQGRVTMTRDTSTSTVYMELSSLRSEDTAVYYCARSDRGITATD

AFDIWGQGTMVTVSSGGGGSGGGGSGGGGSQSVLTQPPSVSVAPGRMAKITCGGSD

IGNKNVHWYQQKPGQAPVLVVYDDYDRPSGIPERFSGSNSGDAATLTISTVEVGDEA

DYFCQVWDGSGDPYWMFGGGTQLTVLGAAATTTPAPRPPTPAPTIASQPLSLRPEAC

RPAAGGAVHTRGLDFACDIYIWAPLAGTCGVLLLSLVITLYCKRGRKKLLYIFKQPF

MRPVQTTQEEDGCSCRFPEEEEGGCELRVKFSRSADAPAYQQGQNQLYNELNLGRR

EEYDVLDKRRGRDPEMGGKPRRKNPQEGLYNELQKDKMAEAYSEIGMKGERRRGK

GHDGLYQGLSTATKDTYDALHMQALPPR nucleotide sequence of D0102 (EF-1a-CD19 (19217_1)-TSLPR CD8 BBz)

SEQ ID NO: 86

ATGCTGCTGCTGGTGACCAGCCTGCTTCTGTGCGAACTGCCGCATCCGGCGTTTC

TGTTGATTCCGGAGGTCCAGCTGGTACAGTCTGGAGCTGAGGTGAAGAAGCCTG

GGGCCTCAGTGAAGGTCTCCTGCAAGGCTTCTGGATACACCTTCACCAGCTACTA

TATGCACTGGGTGCGACAGGCCCCTGGACAAGGGCTTGAGTGGATGGGATTAAT

CAACCCTAGTGGTGGTAGCACAAGCTACGCACAGAAGTTCCAGGGCAGAGTCAC

CATGACCAGGGACACGTCCACGAGCACAGTCTACATGGAGCTGAGCAGCCTGAG

ATCTGAGGACACGGCCGTGTATTACTGTGCGAGATCGGATCGGGGAATTACCGC

CACGGACGCTTTTGATATCTGGGGCCAAGGGACAATGGTCACCGTCTCTTCAGGC

GGAGGAGGCTCTGGGGGAGGAGGTTCCGGAGGAGGCGGTTCCCAGTCTGTGCTG

ACTCAGCCACCCTCGGTGTCAGTGGCCCCAGGGCGGATGGCCAAGATTACCTGT

GGGGGAAGTGACATTGGAAATAAAAATGTCCACTGGTATCAGCAGAAGCCAGGC

CAGGCCCCTGTCCTGGTTGTCTATGATGATTACGACCGGCCCTCAGGGATCCCTG

AGCGATTCTCTGGCTCCAACTCTGGGGACGCGGCCACCCTGACGATCAGCACGGT

CGAAGTCGGGGATGAGGCCGACTATTTCTGTCAGGTGTGGGACGGTAGTGGTGA

TCCTTATTGGATGTTCGGCGGAGGGACCCAGCTCACCGTTTTAGGTGGTGGAGGT

GGTTCAGGCGGAGGAGGCTCAGGCGGAGGCGGTAGCGGCGGAGGAGGAAGCGG

AGGTGGCGGATCACAAGTCACCCTCAAAGAGTCAGGGCCAGGAATCCTCAAGCC

CTCACAGACTCTGTCTCTTACTTGCTCATTCAGCGGATTCAGCCTTTCCACCTCTG

GTATGGGCGTGGGGTGGATTAGGCAACCTAGCGGAAAGGGGCTTGAATGGCTGG

CCCACATCTGGTGGGACGACGACAAGTACTACAACCCCTCACTGAAGTCCCAGC

TCACTATTTCCAAAGATACTTCCCGGAATCAGGTGTTCCTCAAGATTACCTCTGTC

GACACCGCTGATACCGCCACTTACTATTGTTCACGCAGACCGAGAGGTACCATGG

ACGCAATGGACTACTGGGGACAGGGCACCAGCGTGACCGTGTCATCTGGCGGTG

GAGGGTCAGGAGGTGGAGGTAGCGGAGGCGGTGGGTCCGACATTGTCATGACCC

AGGCCGCCAGCTCCCTGAGCGCTTCACTGGGCGACAGGGTGACCATCAGCTGTC

GCGCATCACAAGATATCTCTAAGTATCTTAATTGGTACCAGCAAAAGCCGGATG

GAACCGTGAAGCTGCTGATCTACTACACCTCACGGCTGCATTCTGGAGTGCCTAG

-continued

CCGCTTTAGCGGATCTGGGTCCGGTACTGACTACAGCCTCACCATTAGAAACCTT

GAACAGGAGGACATCGCAACTTATTTCTGCCAACAGGTCTATACTCTGCCGTGGA

CCTTCGGCGGAGGTACCAAACTGGAGATTAAGGCGGCCGCAACGACCACTCCTG

CACCCCGCCCTCCGACTCCGGCCCCAACCATTGCCAGCCAGCCCCTGTCCCTGCG

GCCGGAAGCCTGCAGACCGGCTGCCGGCGGAGCCGTCCATACCCGGGGACTGGA

TTTCGCCTGCGATATCTATATCTGGGCACCACTCGCCGGAACCTGTGGAGTGCTG

CTGCTGTCCCTTGTGATCACCCTGTACTGCAAGCGCGGACGGAAGAAACTCTTGT

ACATCTTCAAGCAGCCGTTCATGCGCCCTGTGCAAACCACCCAAGAAGAGGACG

GGTGCTCCTGCCGGTTCCCGGAAGAGGAAGAGGGCGGCTGCGAACTGCGCGTGA

AGTTTTCCCGGTCCGCCGACGCTCCGGCGTACCAGCAGGGGCAAAACCAGCTGT

ACAACGAACTTAACCTCGGTCGCCGGGAAGAATATGACGTGCTGGACAAGCGGC

GGGGAAGAGATCCCGAGATGGGTGGAAAGCCGCGGCGGAAGAACCCTCAGGAG

GGCTTGTACAACGAGCTGCAAAAGGACAAAATGGCCGAAGCCTACTCCGAGATT

GGCATGAAGGGAGAGCGCAGACGCGGGAAGGGACACGATGGACTGTACCAGGG

ACTGTCAACCGCGACTAAGGACACTTACGACGCCCTGCACATGCAGGCCCTGCC

CCCGCGC amino acid sequence of D0102 (EF-1a-CD19 (19217_1)-TSLPR CD8 BBz)

SEQ ID NO: 87

MLLLVTSLLLCELPHPAFLLIPEVQLVQSGAEVKKPGASVKVSCKASGYTFTSYYMH

WVRQAPGQGLEWMGLINPSGGSTSYAQKFQGRVTMTRDTSTSTVYMELSSLRSEDT

AVYYCARSDRGITATDAFDIWGQGTMVTVSSGGGGSGGGGSGGGGSQSVLTQPPSV

SVAPGRMAKITCGGSDIGNKNVHWYQQKPGQAPVLVVYDDYDRPSGIPERFSGSNS

GDAATLTISTVEVGDEADYFCQVWDGSGDPYWMFGGGTQLTVLGGGGGSGGGGS

GGGGSGGGGSGGGGSQVTLKESGPGILKPSQTLSLTCSFSGFSLSTSGMGVGWIRQPS

GKGLEWLAHIWWDDDKYYNPSLKSQLTISKDTSRNQVFLKITSVDTADTATYYCSR

RPRGTMDAMDYWGQGTSVTVSSGGGGSGGGGSGGGGSDIVMTQAASSLSASLGDR

VTISCRASQDISKYLNWYQQKPDGTVKLLIYYTSRLHSGVPSRFSGSGSGTDYSLTIR

NLEQEDIATYFCQQVYTLPWTFGGGTKLEIKAAATTTPAPRPPTPAPTIASQPLSLRPE

ACRPAAGGAVHTRGLDFACDIYIWAPLAGTCGVLLLSLVITLYCKRGRKKLLYIFKQ

PFMRPVQTTQEEDGCSCRFPEEEEGGCELRVKFSRSADAPAYQQGQNQLYNELNLG

RREEYDVLDKRRGRDPEMGGKPRRKNPQEGLYNELQKDKMAEAYSEIGMKGERRR

GKGHDGLYQGLSTATKDTYDALHMQALPPR nucleotide sequence of D0103 (EF-1a-TSLPR-CD22 (16P17) CD8 BBz)

SEQ ID NO: 88

ATGCTTCTTTTGGTGACTTCCCTTTTGCTGTGCGAGTTGCCACACCCCGCCTTCCT

GCTTATTCCCCAAGTCACCCTCAAAGAGTCAGGGCCAGGAATCCTCAAGCCCTCA

CAGACTCTGTCTCTTACTTGCTCATTCAGCGGATTCAGCCTTTCCACCTCTGGTAT

GGGCGTGGGGTGGATTAGGCAACCTAGCGGAAAGGGGCTTGAATGGCTGGCCCA

CATCTGGTGGGACGACGACAAGTACTACAACCCCTCACTGAAGTCCCAGCTCACT

ATTTCCAAAGATACTTCCCGGAATCAGGTGTTCCTCAAGATTACCTCTGTCGACA

CCGCTGATACCGCCACTTACTATTGTTCACGCAGACCGAGAGGTACCATGGACGC

AATGGACTACTGGGGACAGGGCACCAGCGTGACCGTGTCATCTGGCGGTGGAGG

-continued

GTCAGGAGGTGGAGGTAGCGGAGGCGGTGGGTCCGACATTGTCATGACCCAGGC

CGCCAGCTCCCTGAGCGCTTCACTGGGCGACAGGGTGACCATCAGCTGTCGCGC

ATCACAAGATATCTCTAAGTATCTTAATTGGTACCAGCAAAAGCCGGATGGAAC

CGTGAAGCTGCTGATCTACTACACCTCACGGCTGCATTCTGGAGTGCCTAGCCGC

TTTAGCGGATCTGGGTCCGGTACTGACTACAGCCTCACCATTAGAAACCTTGAAC

AGGAGGACATCGCAACTTATTTCTGCCAACAGGTCTATACTCTGCCGTGGACCTT

CGGCGGAGGTACCAAACTGGAGATTAAGGGTGGAGGTGGTTCAGGCGGAGGAG

GCTCAGGCGGAGGCGGTAGCGGCGGAGGAGGAAGCGGAGGTGGCGGATCACAG

GTACAGCTTCAACAGAGTGGGCCGGGACTGGTGAAACACTCCCAAACACTTTCT

CTGACGTGCGCTATATCAGGTGACTCTGTTTCATCTAATTCTGCTGCGTGGAACT

GGATTCGACAATCTCCCAGTCGCGGGTTGGAATGGCTGGGACGAACATATTATC

GGTCTAAGTGGTATAACGATTATGCTGTATCTGTTAAATCTCGAATTACGATTAA

TCCTGACACCTCCAAGAACCAATTCTCCCTCCAGTTGAATAGCGTGACTCCCGAG

GACACGGCCGTTTACTATTGCGCCCAGGAAGTTGAACCCCACGATGCATTCGACA

TCTGGGGCCAGGGAACGATGGTCACCGTCAGCAGTGGCGGCGGCGGATCTGGGG

GTGGCGGTTCTGGCGGTGGAGGATCAGACATACAAATGACGCAGAGTCCCTCAA

GTGTGTACGCGAGTGTGGGGGATAAGGTAACTATTACGTGCAGAGCGTCACAGG

ATGTTAGTGGATGGCTTGCCTGGTATCAGCAGAAGCCAGGCCTTGCTCCACAGCT

CCTTATCAGTGGTGCTTCTACACTTCAGGGCGAGGTTCCGAGTAGATTCTCTGGT

TCTGGATCTGGTACTGACTTCACTCTTACAATTTCTTCTTTGCAACCAGAAGACTT

TGCGACTTATTACTGCCAACAGGCCAAATACTTCCCTTATACATTTGGCCAAGGT

ACCAAGTTGGAGATAAAGGCGGCCGCAACGACCACTCCTGCACCCCGCCCTCCG

ACTCCGGCCCCAACCATTGCCAGCCAGCCCCTGTCCCTGCGGCCGGAAGCCTGCA

GACCGGCTGCCGGCGGAGCCGTCCATACCCGGGGACTGGATTTCGCCTGCGATA

TCTATATCTGGGCACCACTCGCCGGAACCTGTGGAGTGCTGCTGCTGTCCCTTGT

GATCACCCTGTACTGCAAGCGCGGACGGAAGAAACTCTTGTACATCTTCAAGCA

GCCGTTCATGCGCCCTGTGCAAACCACCCAAGAAGAGGACGGGTGCTCCTGCCG

GTTCCCGGAAGAGGAAGAGGGCGGCTGCGAACTGCGCGTGAAGTTTTCCCGGTC

CGCCGACGCTCCGGCGTACCAGCAGGGGCAAAACCAGCTGTACAACGAACTTAA

CCTCGGTCGCCGGGAAGAATATGACGTGCTGGACAAGCGGCGGGGAAGAGATCC

CGAGATGGGTGGAAAGCCGCGGCGGAAGAACCCTCAGGAGGGCTTGTACAACG

AGCTGCAAAAGGACAAAATGGCCGAAGCCTACTCCGAGATTGGCATGAAGGGA

GAGCGCAGACGCGGGAAGGGACACGATGGACTGTACCAGGGACTGTCAACCGC

GACTAAGGACACTTACGACGCCCTGCACATGCAGGCCCTGCCCCCGCGC amino acid sequence of D0103 (EF-1a-TSLPR-CD22 (16P17) CD8 BBz)

SEQ ID NO: 89

MLLLVTSLLLCELPHPAFLLIPQVTLKESGPGILKPSQTLSLTCSFSGFSLSTSGMGVG

WIRQPSGKGLEWLAHIWWDDDKYYNPSLKSQLTISKDTSRNQVFLKITSVDTADTA

TYYCSRRPRGTMDAMDYWGQGTSVTVSSGGGGSGGGGSGGGGSDIVMTQAASSLS

ASLGDRVTISCRASQDISKYLNWYQQKPDGTVKLLIYYTSRLHSGVPSRFSGSGSGT

DYSLTIRNLEQEDIATYFCQQVYTLPWTFGGGTKLEIKGGGGSGGGGSGGGGSGGG

-continued

GSGGGGSQVQLQQSGPGLVKHSQTLSLTCAISGDSVSSNSAAWNWIRQSPSRGLEW

LGRTYYRSKWYNDYAVSVKSRITINPDTSKNQFSLQLNSVTPEDTAVYYCAQEVEP

HDAFDIWGQGTMVTVSSGGGGSGGGGSGGGGSDIQMTQSPSSVYASVGDKVTITCR

ASQDVSGWLAWYQQKPGLAPQLLISGASTLQGEVPSRFSGSGSGTDFTLTISSLQPED

FATYYCQQAKYFPYTFGQGTKLEIKAAATTTPAPRPPTPAPTIASQPLSLRPEACRPA

AGGAVHTRGLDFACDIYIWAPLAGTCGVLLLSLVITLYCKRGRKKLLYIFKQPFMRP

VQTTQEEDGCSCRFPEEEEGGCELRVKFSRSADAPAYQQGQNQLYNELNLGRREEY

DVLDKRRGRDPEMGGKPRRKNPQEGLYNELQKDKMAEAYSEIGMKGERRRGKGH

DGLYQGLSTATKDTYDALHMQALPPR nucleotide sequence of D0104 (EF-1a-CD22 (16P17)-
TSLPR CD8 BBz)

SEQ ID NO: 90

ATGCTTCTTTTGGTGACTTCCCTTTTGCTGTGCGAGTTGCCACACCCCGCCTTCCT

GCTTATTCCCCAGGTACAGCTTCAACAGAGTGGGCCGGGACTGGTGAAACACTC

CCAAACACTTTCTCTGACGTGCGCTATATCAGGTGACTCTGTTTCATCTAATTCTG

CTGCGTGGAACTGGATTCGACAATCTCCCAGTCGCGGGTTGGAATGGCTGGGAC

GAACATATTATCGGTCTAAGTGGTATAACGATTATGCTGTATCTGTTAAATCTCG

AATTACGATTAATCCTGACACCTCCAAGAACCAGTTCTCCCTCCAGTTGAACTCA

GTCACACCGGAAGACACTGCGGTCTACTATTGCGCTCAAGAAGTCGAGCCACAT

GATGCATTCGACATCTGGGGCCAGGGAACGATGGTCACCGTCAGCAGTGGCGGC

GGCGGATCTGGGGGTGGCGGTTCTGGCGGTGGAGGATCAGACATACAAATGACG

CAGAGTCCCTCAAGTGTGTACGCGAGTGTGGGGGATAAGGTAACTATTACGTGC

AGAGCGTCACAGGATGTTAGTGGATGGCTTGCCTGGTATCAGCAGAAGCCAGGC

CTTGCTCCACAGCTCCTTATCAGTGGTGCTTCTACACTTCAGGGCGAGGTTCCGA

GTAGATTCTCTGGTTCTGGATCTGGTACTGACTTCACTCTTACAATTTCTTCTTTG

CAACCAGAAGACTTTGCGACTTATTACTGCCAACAGGCCAAATACTTCCCTTATA

CATTTGGCCAAGGTACCAAGTTGGAGATAAAGGGTGGAGGTGGTTCAGGCGGAG

GAGGCTCAGGCGGAGGCGGTAGCGGCGGAGGAGGAAGCGGAGGTGGCGGATCA

CAAGTCACCCTCAAAGAGTCAGGGCCAGGAATCCTCAAGCCCTCACAGACTCTG

TCTCTTACTTGCTCATTCAGCGGATTCAGCCTTTCCACCTCTGGTATGGGCGTGGG

GTGGATTAGGCAACCTAGCGGAAAGGGGCTTGAATGGCTGGCCCACATCTGGTG

GGACGACGACAAGTACTACAACCCCTCACTGAAGTCCCAGCTCACTATTTCCAAA

GATACTTCCCGGAATCAGGTGTTCCTCAAGATTACCTCTGTCGACACCGCTGATA

CCGCCACTTACTATTGTTCACGCAGACCGAGAGGTACCATGGACGCAATGGACT

ACTGGGGACAGGGCACCAGCGTGACCGTGTCATCTGGCGGTGGAGGGTCAGGAG

GTGGAGGTAGCGGAGGCGGTGGGTCCGACATTGTCATGACCCAGGCCGCCAGCT

CCCTGAGCGCTTCACTGGGCGACAGGGTGACCATCAGCTGTCGCGCATCACAAG

ATATCTCTAAGTATCTTAATTGGTACCAGCAAAAGCCGGATGGAACCGTGAAGCT

GCTGATCTACTACACCTCACGGCTGCATTCTGGAGTGCCTAGCCGCTTTAGCGGA

TCTGGGTCCGGTACTGACTACAGCCTCACCATTAGAAACCTTGAACAGGAGGAC

ATCGCAACTTATTTCTGCCAACAGGTCTATACTCTGCCGTGGACCTTCGGCGGAG

GTACCAAACTGGAGATTAAGGCGGCCGCAACGACCACTCCTGCACCCCGCCCTC

-continued

CGACTCCGGCCCCAACCATTGCCAGCCAGCCCCTGTCCCTGCGGCCGGAAGCCTG
CAGACCGGCTGCCGGCGGAGCCGTCCATACCCGGGGACTGGATTTCGCCTGCGA
TATCTATATCTGGGCACCACTCGCCGGAACCTGTGGAGTGCTGCTGCTGTCCCTT
GTGATCACCCTGTACTGCAAGCGCGGACGGAAGAAACTCTTGTACATCTTCAAGC
AGCCGTTCATGCGCCCTGTGCAAACCACCCAAGAAGAGGACGGGTGCTCCTGCC
GGTTCCCGGAAGAGGAAGAGGGCGGCTGCGAACTGCGCGTGAAGTTTTCCCGGT
CCGCCGACGCTCCGGCGTACCAGCAGGGGCAAAACCAGCTGTACAACGAACTTA
ACCTCGGTCGCCGGGAAGAATATGACGTGCTGGACAAGCGGCGGGGAAGAGATC
CCGAGATGGGTGGAAAGCCGCGGCGGAAGAACCCTCAGGAGGGCTTGTACAAC
GAGCTGCAAAAGGACAAAATGGCCGAAGCCTACTCCGAGATTGGCATGAAGGG
AGAGCGCAGACGCGGGAAGGGACACGATGGACTGTACCAGGGACTGTCAACCG
CGACTAAGGACACTTACGACGCCCTGCACATGCAGGCCCTGCCCCCGCGC amino acid sequence of D0104 (EF-1a-CD22 (16P17)-TSLPR CD8 BBz)

SEQ ID NO: 91

MLLLVTSLLLCELPHPAFLLIPQVQLQQSGPGLVKHSQTLSLTCAISGDSVSSNSAAW
NWIRQSPSRGLEWLGRTYYRSKWYNDYAVSVKSRITINPDTSKNQFSLQLNSVTPED
TAVYYCAQEVEPHDAFDIWGQGTMVTVSSGGGGSGGGGSGGGGSDIQMTQSPSSV
YASVGDKVTITCRASQDVSGWLAWYQQKPGLAPQLLISGASTLQGEVPSRFSGSGS
GTDFTLTISSLQPEDFATYYCQQAKYFPYTFGQGTKLEIKGGGGSGGGGSGGGGSGG
GGSGGGGSQVTLKESGPGILKPSQTLSLTCSFSGFSLSTSGMGVGWIRQPSGKGLEW
LAHIWWDDDKYYNPSLKSQLTISKDTSRNQVFLKITSVDTADTATYYCSRRPRGTM
DAMDYWGQGTSVTVSSGGGGSGGGGSGGGGSDIVMTQAASSLSASLGDRVTISCR
ASQDISKYLNWYQQKPDGTVKLLIYYTSRLHSGVPSRFSGSGSGTDYSLTIRNLEQED
IATYFCQQVYTLPWTFGGGTKLEIKAAATTTPAPRPPTPAPTIASQPLSLRPEACRPAA
GGAVHTRGLDFACDIYIWAPLAGTCGVLLLSLVITLYCKRGRKKLLYIFKQPFMRPV
QTTQEEDGCSCRFPEEEEGGCELRVKFSRSADAPAYQQGQNQLYNELNLGRREEYD
VLDKRRGRDPEMGGKPRRKNPQEGLYNELQKDKMAEAYSEIGMKGERRRGKGHD
GLYQGLSTATKDTYDALHMQALPPR nucleotide sequence of D0111 (EF-1a-TSLPR-CD22 (m971) CD8 BBz)

SEQ ID NO: 92

ATGCTTCTTTTGGTGACTTCCCTTTTGCTGTGCGAGTTGCCACACCCCGCCTTCCT
GCTTATTCCCCAAGTCACCCTCAAAGAGTCAGGGCCAGGAATCCTCAAGCCCTCA
CAGACTCTGTCTCTTACTTGCTCATTCAGCGGATTCAGCCTTTCCACCTCTGGTAT
GGGCGTGGGGTGGATTAGGCAACCTAGCGGAAAGGGGCTTGAATGGCTGGCCCA
CATCTGGTGGGACGACGACAAGTACTACAACCCCTCACTGAAGTCCCAGCTCACT
ATTTCCAAAGATACTTCCCGGAATCAGGTGTTCCTCAAGATTACCTCTGTCGACA
CCGCTGATACCGCCACTTACTATTGTTCACGCAGACCGAGAGGTACCATGGACGC
AATGGACTACTGGGGACAGGGCACCAGCGTGACCGTGTCATCTGGCGGTGGAGG
GTCAGGAGGTGGAGGTAGCGGAGGCGGTGGGTCCGACATTGTCATGACCCAGGC
CGCCAGCTCCCTGAGCGCTTCACTGGGCGACAGGGTGACCATCAGCTGTCGCGC
ATCACAAGATATCTCTAAGTATCTTAATTGGTACCAGCAAAAGCCGGATGGAAC

-continued

CGTGAAGCTGCTGATCTACTACACCTCACGGCTGCATTCTGGAGTGCCTAGCCGC

TTTAGCGGATCTGGGTCCGGTACTGACTACAGCCTCACCATTAGAAACCTTGAAC

AGGAGGACATCGCAACTTATTTCTGCCAACAGGTCTATACTCTGCCGTGGACCTT

CGGCGGAGGTACCAAACTGGAGATTAAGGGTGGAGGTGGTTCAGGCGGAGGAG

GCTCAGGCGGAGGCGGTAGCGGCGGAGGAGGAAGCGGAGGTGGCGGATCACAG

GTACAACTTCAACAGAGTGGTCCAGGGCTGGTCAAACCTTCCCAAACCCTTTCCT

TGACTTGTGCGATTAGTGGAGACTCCGTTTCCAGCAATTCTGCCGCCTGGAATTG

GATCCGGCAGTCCCCTAGTCGGGGATTGGAGTGGCTTGGCAGGACGTACTACCG

GAGTAAGTGGTACAACGATTACGCTGTTTCCGTAAAATCTCGCATAACCATTAAT

CCTGACACAAGCAAAAACCAATTTTCTCTTCAGCTTAATTCCGTTACACCAGAGG

ACACCGCGGTCTATTACTGCGCTCGGGAAGTAACCGGCGATTTGGAGGATGCTTT

CGATATTTGGGGACAAGGCACTATGGTAACAGTTAGCAGTGGTGGAGGCGGAAG

TGGCGGAGGAGGTTCTGGTGGTGGTGGAAGTGACATCCAAATGACACAGAGTCC

GTCTTCACTCAGCGCTAGCGTCGGTGATCGCGTAACCATAACGTGCAGGGCAAG

CCAAACGATATGGTCTTATCTTAATTGGTATCAACAGCGCCCAGGCAAGGCACCA

AATCTTCTTATCTATGCAGCGAGCAGTCTCCAGTCCGGCGTCCCGTCCCGCTTCA

GTGGGAGGGGATCCGGTACAGATTTCACTCTGACAATATCCTCCTTGCAAGCAGA

GGACTTCGCTACGTACTACTGCCAACAGTCATACTCTATTCCGCAGACATTTGGA

CAGGGGACCAAACTTGAGATCAAGGCGGCCGCAACGACCACTCCTGCACCCCGC

CCTCCGACTCCGGCCCCAACCATTGCCAGCCAGCCCCTGTCCCTGCGGCCGGAAG

CCTGCAGACCGGCTGCCGGCGGAGCCGTCCATACCCGGGGACTGGATTTCGCCT

GCGATATCTATATCTGGGCACCACTCGCCGGAACCTGTGGAGTGCTGCTGCTGTC

CCTTGTGATCACCCTGTACTGCAAGCGCGGACGGAAGAAACTCTTGTACATCTTC

AAGCAGCCGTTCATGCGCCCTGTGCAAACCACCCAAGAAGAGGACGGGTGCTCC

TGCCGGTTCCCGGAAGAGGAAGAGGGCGGCTGCGAACTGCGCGTGAAGTTTTCC

CGGTCCGCCGACGCTCCGGCGTACCAGCAGGGGCAAAACCAGCTGTACAACGAA

CTTAACCTCGGTCGCCGGGAAGAATATGACGTGCTGGACAAGCGGCGGGGAAGA

GATCCCGAGATGGGTGGAAAGCCGCGGCGGAAGAACCCTCAGGAGGGCTTGTAC

AACGAGCTGCAAAAGGACAAAATGGCCGAAGCCTACTCCGAGATTGGCATGAAG

GGAGAGCGCAGACGCGGGAAGGGACACGATGGACTGTACCAGGGACTGTCAAC

CGCGACTAAGGACACTTACGACGCCCTGCACATGCAGGCCCTGCCCCCGCGC mino acid sequence of D0111 (EF-1a-TSLPR-CD22 (m971) CD8 BBz)

SEQ ID NO: 93

MLLLVTSLLLCELPHPAFLLIPQVTLKESGPGILKPSQTLSLTCSFSGFSLSTSGMGVG

WIRQPSGKGLEWLAHIWWDDDKYYNPSLKSQLTISKDTSRNQVFLKITSVDTADTA

TYYCSRRPRGTMDAMDYWGQGTSVTVSSGGGGSGGGGSGGGGSDIVMTQAASSLS

ASLGDRVTISCRASQDISKYLNWYQQKPDGTVKLLIYYTSRLHSGVPSRFSGSGSGT

DYSLTIRNLEQEDIATYFCQQVYTLPWTFGGGTKLEIKGGGGSGGGGSGGGGSGGG

GSGGGGSQVQLQQSGPGLVKPSQTLSLTCAISGDSVSSNSAAWNWIRQSPSRGLEWL

GRTYYRSKWYNDYAVSVKSRITINPDTSKNQFSLQLNSVTPEDTAVYYCAREVTGD

LEDAFDIWGQGTMVTVSSGGGGSGGGGSGGGGSDIQMTQSPSSLSASVGDRVTITC

-continued

RASQTIWSYLNWYQQRPGKAPNLLIYAASSLQSGVPSRFSGRGSGTDFTLTISSLQAE

DFATYYCQQSYSIPQTFGQGTKLEIKAAATTTPAPRPPTPAPTIASQPLSLRPEACRPA

AGGAVHTRGLDFACDIYIWAPLAGTCGVLLLSLVITLYCKRGRKKLLYIFKQPFMRP

VQTTQEEDGCSCRFPEEEEGGCELRVKFSRSADAPAYQQGQNQLYNELNLGRREEY

DVLDKRRGRDPEMGGKPRRKNPQEGLYNELQKDKMAEAYSEIGMKGERRRGKGH

DGLYQGLSTATKDTYDALHMQALPPR nucleotide sequence of D0112 (EF-1a-CD22 (m971)-
TSLPR CD8 BBz)

SEQ ID NO: 94

ATGCTTCTTTTGGTGACTTCCCTTTTGCTGTGCGAGTTGCCACACCCCGCCTTCCT

GCTTATTCCCCAGGTACAACTTCAACAGAGTGGTCCAGGGCTGGTCAAACCTTCC

CAAACCCTTTCCTTGACTTGTGCGATTAGTGGAGACTCCGTTTCCAGCAATTCTGC

CGCCTGGAATTGGATCCGGCAGTCCCCTAGTCGGGGATTGGAGTGGCTTGGCAG

GACGTACTACCGGAGTAAGTGGTACAACGATTACGCTGTTTCCGTAAAATCTCGC

ATAACCATTAATCCTGACACAAGCAAAAACCAATTTTCTCTTCAGCTTAATTCCG

TTACACCAGAGGACACCGCGGTCTATTACTGCGCTCGGGAAGTAACCGGCGATTT

GGAGGATGCTTTCGATATTTGGGGACAAGGCACTATGGTAACAGTTAGCAGTGG

TGGAGGCGGAAGTGGCGGAGGAGGTTCTGGTGGTGGTGGAAGTGACATCCAAAT

GACACAGAGTCCGTCTTCACTCAGCGCTAGCGTCGGTGATCGCGTAACCATAACG

TGCAGGGCAAGCCAAACGATATGGTCTTATCTTAATTGGTATCAACAGCGCCCAG

GCAAGGCACCAAATCTTCTTATCTATGCAGCGAGCAGTCTCCAGTCCGGCGTCCC

GTCCCGCTTCAGTGGGAGGGGATCCGGTACAGATTTCACTCTGACAATATCCTCC

TTGCAAGCAGAGGACTTCGCTACGTACTACTGCCAACAGTCATACTCTATTCCGC

AGACATTTGGACAGGGGACCAAACTTGAGATCAAGGGTGGAGGTGGTTCAGGCG

GAGGAGGCTCAGGCGGTGGCGGTAGCGGCGGAGGAGGAAGCGGAGGTGGCGGA

TCACAAGTCACCCTCAAAGAGTCAGGGCCAGGAATCCTCAAGCCCTCACAGACT

CTGTCTCTTACTTGCTCATTCAGCGGATTCAGCCTTTCCACCTCTGGTATGGGCGT

GGGGTGGATTAGGCAACCTAGCGGAAAGGGGCTTGAATGGCTGGCCCACATCTG

GTGGGACGACGACAAGTACTACAACCCCTCACTGAAGTCCCAGCTCACTATTTCC

AAAGATACTTCCCGGAATCAGGTGTTCCTCAAGATTACCTCTGTCGACACCGCTG

ATACCGCCACTTACTATTGTTCACGCAGACCGAGAGGTACCATGGACGCAATGG

ACTACTGGGGACAGGGCACCAGCGTGACCGTGTCATCTGGCGGTGGAGGGTCAG

GAGGTGGAGGTAGCGGAGGCGGTGGGTCCGACATTGTCATGACCCAGGCCGCCA

GCTCCCTGAGCGCTTCACTGGGCGACAGGGTGACCATCAGCTGTCGCGCATCACA

AGATATCTCTAAGTATCTTAATTGGTACCAGCAAAAGCCGGATGGAACCGTGAA

GCTGCTGATCTACTACACCTCACGGCTGCATTCTGGAGTGCCTAGCCGCTTTAGC

GGATCTGGGTCCGGTACTGACTACAGCCTCACCATTAGAAACCTTGAACAGGAG

GACATCGCAACTTATTTCTGCCAACAGGTCTATACTCTGCCGTGGACCTTCGGCG

GAGGTACCAAACTGGAGATTAAGGCGGCCGCAACGACCACTCCTGCACCCCGCC

CTCCGACTCCGGCCCCAACCATTGCCAGCCAGCCCCTGTCCCTGCGGCCGGAAGC

CTGCAGACCGGCTGCCGGCGGAGCCGTCCATACCCGGGGACTGGATTTCGCCTG

CGATATCTATATCTGGGCACCACTCGCCGGAACCTGTGGAGTGCTGCTGCTGTCC

-continued

CTTGTGATCACCCTGTACTGCAAGCGCGGACGGAAGAAACTCTTGTACATCTTCA

AGCAGCCGTTCATGCGCCCTGTGCAAACCACCCAAGAAGAGGACGGGTGCTCCT

GCCGGTTCCCGGAAGAGGAAGAGGGCGGCTGCGAACTGCGCGTGAAGTTTTCCC

GGTCCGCCGACGCTCCGGCGTACCAGCAGGGGCAAAACCAGCTGTACAACGAAC

TTAACCTCGGTCGCCGGGAAGAATATGACGTGCTGGACAAGCGGCGGGGAAGAG

ATCCCGAGATGGGTGGAAAGCCGCGGCGGAAGAACCCTCAGGAGGGCTTGTACA

ACGAGCTGCAAAAGGACAAAATGGCCGAAGCCTACTCCGAGATTGGCATGAAGG

GAGAGCGCAGACGCGGGAAGGGACACGATGGACTGTACCAGGGACTGTCAACC

GCGACTAAGGACACTTACGACGCCCTGCACATGCAGGCCCTGCCCCCGCGC amino acid sequence of D0112 (EF-1a-CD22 (m971)-TSLPR CD8 BBz)

SEQ ID NO: 95

MLLLVTSLLLCELPHPAFLLIPQVQLQQSGPGLVKPSQTLSLTCAISGDSVSSNSAAW

NWIRQSPSRGLEWLGRTYYRSKWYNDYAVSVKSRITINPDTSKNQFSLQLNSVTPED

TAVYYCAREVTGDLEDAFDIWGQGTMVTVSSGGGGSGGGGSGGGGSDIQMTQSPS

SLSASVGDRVTITCRASQTIWSYLNWYQQRPGKAPNLLIYAASSLQSGVPSRFSGRGS

GTDFTLTISSLQAEDFATYYCQQSYSIPQTFGQGTKLEIKGGGGSGGGGSGGGGSGG

GGSGGGGSQVTLKESGPGILKPSQTLSLTCSFSGFSLSTSGMGVGWIRQPSGKGLEW

LAHIWWDDDKYYNPSLKSQLTISKDTSRNQVFLKITSVDTADTATYYCSRRPRGTM

DAMDYWGQGTSVTVSSGGGGSGGGGSGGGGSDIVMTQAASSLSASLGDRVTISCR

ASQDISKYLNWYQQKPDGTVKLLIYYTSRLHSGVPSRFSGSGSGTDYSLTIRNLEQED

IATYFCQQVYTLPWTFGGGTKLEIKAAATTTPAPRPPTPAPTIASQPLSLRPEACRPAA

GGAVHTRGLDFACDIYIWAPLAGTCGVLLLSLVITLYCKRGRKKLLYIFKQPFMRPV

QTTQEEDGCSCRFPEEEEGGCELRVKFSRSADAPAYQQGQNQLYNELNLGRREEYD

VLDKRRGRDPEMGGKPRRKNPQEGLYNELQKDKMAEAYSEIGMKGERRRGKGHD

GLYQGLSTATKDTYDALHMQALPPR nucleotide sequence of D0205 (EF-1a-CD19 (FMC63)-TSLPR- CD8 BBz)

SEQ ID NO: 96

ATGTTGCTGTTGGTGACCTCCCTGCTGCTGTGCGAGTTGCCGCACCCCGCCTTCCT

GCTTATTCCGGATATCCAGATGACCCAGACCACCTCCTCGCTGTCCGCATCGCTG

GGTGACAGAGTGACCATTAGCTGCAGGGCCTCCCAAGATATCTCGAAATACCTG

AACTGGTACCAACAGAAGCCTGACGGAACGGTCAAGCTGCTGATCTACCATACT

TCAAGGCTGCACTCCGGTGTCCCGTCCAGATTCTCCGGAAGCGGTAGCGGCACTG

ACTACTCCTTGACCATCAGCAACCTCGAACAGGAAGATATAGCAACTTACTTCTG

CCAGCAGGGAAACACTCTCCCGTACACTTTCGGAGGAGGAACCAAGCTGGAGAT

CACGGGTGGCGGGGGTTCAGGGGGAGGTGGATCCGGAGGAGGGGGTTCCGAGG

TGAAGCTGCAGGAGTCAGGACCTGGCCTCGTCGCCCCTTCCCAGTCGCTGTCGGT

GACTTGCACGGTGTCCGGAGTGAGCCTGCCCGACTATGGAGTGTCCTGGATCCGG

CAGCCCCCAAGAAAGGGCCTCGAGTGGCTCGGAGTGATCTGGGGGTCCGAAACT

ACCTACTACAACTCAGCCCTCAAGAGCAGACTGACCATTATCAAGGACAACTCC

AAGTCACAGGTCTTTCTGAAGATGAACAGCCTCCAGACAGATGATACCGCCATCT

ACTATTGTGCCAAGCATTACTACTACGGGGGATCCTACGCCATGGATTACTGGGG

GCAGGGCACTTCGGTGACTGTGTCGTCCGGTGGTGGAGGGTCGGGTGGAGGAGG

-continued

ATCAGGTGGAGGCGGATCCGGCGGAGGTGGTTCGGGAGGCGGAGGCTCCCAGGT

GACCCTCAAGGAGAGCGGGCCTGGGATCTTGAAGCCGTCCCAGACCCTGTCGCT

GACCTGTTCCTTCTCGGGATTTTCCCTGTCGACCTCGGGAATGGGAGTGGGATGG

ATCAGACAGCCTTCCGGGAAGGGCCTCGAATGGCTGGCCCATATTTGGTGGGAT

GATGACAAATACTACAACCCGTCACTCAAGTCCCAGCTGACTATCTCAAAAGAC

ACCTCCCGGAACCAGGTGTTTCTCAAGATTACCAGCGTGGACACCGCCGACACTG

CCACCTACTACTGCTCTAGGAGGCCCAGAGGGACCATGGATGCCATGGACTACT

GGGGTCAGGGCACTAGCGTGACCGTGAGCTCCGGTGGAGGGGGCTCCGGAGGCG

GCGGGTCCGGTGGGGGGGGCTCCGATATCGTGATGACTCAGGCCGCCAGCAGCC

TGTCCGCCTCCCTCGGGGACCGCGTGACCATTTCCTGTCGCGCGAGCCAGGATAT

CTCTAAGTACCTGAATTGGTATCAACAAAAGCCTGACGGCACTGTGAAGCTGCTG

ATCTACTATACATCCAGGCTCCACTCCGGCGTGCCCAGCCGGTTCTCCGGATCCG

GCTCCGGCACCGACTACTCGCTTACTATCCGGAACCTTGAGCAGGAAGATATCGC

CACCTACTTCTGTCAACAGGTCTACACCCTGCCATGGACCTTCGGCGGAGGAACT

AAACTGGAGATCAAAGCGGCCGCAACGACCACTCCTGCACCCCGCCCTCCGACT

CCGGCCCCAACCATTGCCAGCCAGCCCCTGTCCCTGCGGCCGGAAGCCTGCAGA

CCGGCTGCCGGCGGAGCCGTCCATACCCGGGGACTGGATTTCGCCTGCGATATCT

ATATCTGGGCACCACTCGCCGGAACCTGTGGAGTGCTGCTGCTGTCCCTTGTGAT

CACCCTGTACTGCAAGCGCGGACGGAAGAAACTCTTGTACATCTTCAAGCAGCC

GTTCATGCGCCCTGTGCAAACCACCCAAGAAGAGGACGGGTGCTCCTGCCGGTT

CCCGGAAGAGGAAGAGGGCGGCTGCGAACTGCGCGTGAAGTTTTCCCGGTCCGC

CGACGCTCCGGCGTACCAGCAGGGGCAAAACCAGCTGTACAACGAACTTAACCT

CGGTCGCCGGGAAGAATATGACGTGCTGGACAAGCGGCGGGGAAGAGATCCCG

AGATGGGTGGAAAGCCGCGGCGGAAGAACCCTCAGGAGGGCTTGTACAACGAG

CTGCAAAAGGACAAAATGGCCGAAGCCTACTCCGAGATTGGCATGAAGGGAGA

GCGCAGACGCGGGAAGGGACACGATGGACTGTACCAGGGACTGTCAACCGCGA

CTAAGGACACTTACGACGCCCTGCACATGCAGGCCCTGCCCCCGCGC amino acid sequence of D0205 (EF-1a-CD19 (FMC63)-TSLPR-CD8 BBz)

SEQ ID NO: 97

MLLLVTSLLLCELPHPAFLLIPDIQMTQTTSSLSASLGDRVTISCRASQDISKYLNWYQ

QKPDGTVKLLIYHTSRLHSGVPSRFSGSGSGTDYSLTISNLEQEDIATYFCQQGNTLP

YTFGGGTKLEITGGGGSGGGGSGGGGSEVKLQESGPGLVAPSQSLSVTCTVSGVSLP

DYGVSWIRQPPRKGLEWLGVIWGSETTYYNSALKSRLTIIKDNSKSQVFLKMNSLQT

DDTAIYYCAKHYYYGGSYAMDYWGQGTSVTVSSGGGGSGGGGSGGGGSGGGGSG

GGGSQVTLKESGPGILKPSQTLSLTCSFSGFSLSTSGMGVGWIRQPSGKGLEWLAHI

WWDDDKYYNPSLKSQLTISKDTSRNQVFLKITSVDTADTATYYCSRRPRGTMDAM

DYWGQGTSVTVSSGGGGSGGGGSGGGGSDIVMTQAASSLSASLGDRVTISCRASQD

ISKYLNWYQQKPDGTVKLLIYYTSRLHSGVPSRFSGSGSGTDYSLTIRNLEQEDIATY

FCQQVYTLPWTFGGGTKLEIKAAATTTPAPRPPTPAPTIASQPLSLRPEACRPAAGGA

VHTRGLDFACDIYIWAPLAGTCGVLLLSLVITLYCKRGRKKLLYIFKQPFMRPVQTT

QEEDGCSCRFPEEEEGGCELRVKFSRSADAPAYQQGQNQLYNELNLGRREEYDVLD

-continued

KRRGRDPEMGGKPRRKNPQEGLYNELQKDKMAEAYSEIGMKGERRRGKGHDGLY

QGLSTATKDTYDALHMQALPPR nucleotide sequence of D0206 (EF-1a-TSLPR-CD19 (FMC63)-CD8 BBz)

SEQ ID NO: 98

ATGTTGCTGTTGGTGACCTCCCTGCTGCTGTGCGAGTTGCCGCACCCCGCCTTCCT

GCTTATTCCGCAGGTGACCCTCAAGGAGAGCGGGCCTGGGATCTTGAAGCCGTC

CCAGACCCTGTCGCTGACCTGTTCCTTCTCGGGATTTTCCCTGTCGACCTCGGGAA

TGGGAGTGGGATGGATCAGACAGCCTTCCGGGAAGGGCCTCGAATGGCTGGCCC

ATATTTGGTGGGATGATGACAAATACTACAACCCGTCACTCAAGTCCCAGCTGAC

TATCTCAAAAGACACCTCCCGGAACCAGGTGTTTCTCAAGATTACCAGCGTGGAC

ACCGCCGACACTGCCACCTACTACTGCTCTAGGAGGCCCAGAGGGACCATGGAT

GCCATGGACTACTGGGGTCAGGGCACTAGCGTGACCGTGAGCTCCGGTGGAGGG

GGCTCCGGAGGCGGCGGGTCCGGTGGGGGGGGCTCCGATATCGTGATGACTCAG

GCCGCCAGCAGCCTGTCCGCCTCCCTCGGGGACCGCGTGACCATTTCCTGTCGCG

CGAGCCAGGATATCTCTAAGTACCTGAATTGGTATCAACAAAAGCCTGACGGCA

CTGTGAAGCTGCTGATCTACTATACATCCAGGCTCCACTCCGGCGTGCCCAGCCG

GTTCTCCGGATCCGGCTCCGGCACCGACTACTCGCTTACTATCCGGAACCTTGAG

CAGGAAGATATCGCCACCTACTTCTGTCAACAGGTCTACACCCTGCCATGGACCT

TCGGCGGAGGAACTAAACTGGAGATCAAAGGTGGTGGAGGGTCGGGTGGAGGA

GGATCAGGTGGAGGCGGATCCGGCGGAGGTGGTTCGGGAGGCGGAGGCTCCGAT

ATCCAGATGACCCAGACCACCTCCTCGCTGTCCGCATCGCTGGGTGACAGAGTGA

CCATTAGCTGCAGGGCCTCCCAAGATATCTCGAAATACCTGAACTGGTACCAACA

GAAGCCTGACGGAACGGTCAAGCTGCTGATCTACCATACTTCAAGGCTGCACTCC

GGTGTCCCGTCCAGATTCTCCGGAAGCGGTAGCGGCACTGACTACTCCTTGACCA

TCAGCAACCTCGAACAGGAAGATATAGCAACTTACTTCTGCCAGCAGGGAAACA

CTCTCCCGTACACTTTCGGAGGAGGAACCAAGCTGGAGATCACGGGTGGCGGGG

GTTCAGGGGGAGGTGGATCCGGAGGAGGGGGTTCCGAGGTGAAGCTGCAGGAG

TCAGGACCTGGCCTCGTCGCCCCTTCCCAGTCGCTGTCGGTGACTTGCACGGTGT

CCGGAGTGAGCCTGCCCGACTATGGAGTGTCCTGGATCCGGCAGCCCCCAAGAA

AGGGCCTCGAGTGGCTCGGAGTGATCTGGGGGTCCGAAACTACCTACTACAACT

CAGCCCTCAAGAGCAGACTGACCATTATCAAGGACAACTCCAAGTCACAGGTCT

TTCTGAAGATGAACAGCCTCCAGACAGATGATACCGCCATCTACTATTGTGCCAA

GCATTACTACTACGGGGGATCCTACGCCATGGATTACTGGGGGCAGGGCACTTC

GGTGACTGTGTCGTCCGCGGCCGCAACGACCACTCCTGCACCCCGCCCTCCGACT

CCGGCCCCAACCATTGCCAGCCAGCCCCTGTCCCTGCGGCCGGAAGCCTGCAGA

CCGGCTGCCGGCGGAGCCGTCCATACCCGGGGACTGGATTTCGCCTGCGATATCT

ATATCTGGGCACCACTCGCCGGAACCTGTGGAGTGCTGCTGCTGTCCCTTGTGAT

CACCCTGTACTGCAAGCGCGGACGGAAGAAACTCTTGTACATCTTCAAGCAGCC

GTTCATGCGCCCTGTGCAAACCACCCAAGAAGAGGACGGGTGCTCCTGCCGGTT

CCCGGAAGAGGAAGAGGGCGGCTGCGAACTGCGCGTGAAGTTTTCCCGGTCCGC

CGACGCTCCGGCGTACCAGCAGGGGCAAAACCAGCTGTACAACGAACTTAACCT

-continued

CGGTCGCCGGGAAGAATATGACGTGCTGGACAAGCGGCGGGGAAGAGATCCCG

AGATGGGTGGAAAGCCGCGGCGGAAGAACCCTCAGGAGGGCTTGTACAACGAG

CTGCAAAAGGACAAAATGGCCGAAGCCTACTCCGAGATTGGCATGAAGGGAGA

GCGCAGACGCGGGAAGGGACACGATGGACTGTACCAGGGACTGTCAACCGCGA

CTAAGGACACTTACGACGCCCTGCACATGCAGGCCCTGCCCCCGCGC amino acid sequence of D0206 (EF-1a-TSLPR-CD19 (FMC63)-CD8 BBz)

SEQ ID NO: 99

MLLLVTSLLLCELPHPAFLLIPQVTLKESGPGILKPSQTLSLTCSFSGFSLSTSGMGVG

WIRQPSGKGLEWLAHIWWDDDKYYNPSLKSQLTISKDTSRNQVFLKITSVDTADTAT

YYCSRRPRGTMDAMDYWGQGTSVTVSSGGGGSGGGGSGGGGSDIVMTQAASSLSA

SLGDRVTISCRASQDISKYLNWYQQKPDGTVKLLIYYTSRLHSGVPSRFSGSGSGTDY

SLTIRNLEQEDIATYFCQQVYTLPWTFGGGTKLEIKGGGGSGGGGSGGGGSGGGGSG

GGGSDIQMTQTTSSLSASLGDRVTISCRASQDISKYLNWYQQKPDGTVKLLIYHTSRL

HSGVPSRFSGSGSGTDYSLTISNLEQEDIATYFCQQGNTLPYTFGGGTKLEITGGGGS

GGGGSGGGGSEVKLQESGPGLVAPSQSLSVTCTVSGVSLPDYGVSWIRQPPRKGLE

WLGVIWGSETTYYNSALKSRLTIIKDNSKSQVFLKMNSLQTDDTAIYYCAKHYYYG

GSYAMDYWGQGTSVTVSSAAATTTPAPRPPTPAPTIASQPLSLRPEACRPAAGGAVH

TRGLDFACDIYIWAPLAGTCGVLLLSLVITLYCKRGRKKLLYIFKQPFMRPVQTTQEE

DGCSCRFPEEEEGGCELRVKFSRSADAPAYQQGQNQLYNELNLGRREEYDVLDKRR

GRDPEMGGKPRRKNPQEGLYNELQKDKMAEAYSEIGMKGERRRGKGHDGLYQGLS

TATKDTYDALHMQALPPR nucleotide sequence of LTG2282 (EF-1a-TSLPR (3G11) CD8 BBz)

SEQ ID NO: 100

ATGGCACTGCCCGTGACCGCCCTGCTTCTGCCGCTTGCACTTCTGCTGCACGCCG

CTAGGCCCCAAGTCACCCTCAAAGAGTCAGGGCCAGGAATCCTCAAGCCCTCAC

AGACTCTGTCTCTTACTTGCTCATTCAGCGGATTCAGCCTTTCCACCTCTGGTATG

GGCGTGGGGTGGATTAGGCAACCTAGCGGAAAGGGGCTTGAATGGCTGGCCCAC

ATCTGGTGGGACGACGACAAGTACTACAACCCCTCACTGAAGTCCCAGCTCACT

ATTTCCAAAGATACTTCCCGGAATCAGGTGTTCCTCAAGATTACCTCTGTCGACA

CCGCTGATACCGCCACTTACTATTGTTCACGCAGACCGAGAGGTACCATGGACGC

AATGGACTACTGGGGACAGGGCACCAGCGTGACCGTGTCATCTGGCGGTGGAGG

GTCAGGAGGTGGAGGTAGCGGAGGCGGTGGGTCCGACATTGTCATGACCCAGGC

CGCCAGCAGCCTGAGCGCTTCACTGGGCGACAGGGTGACCATCAGCTGTCGCGC

ATCACAAGATATCTCTAAGTATCTTAATTGGTACCAGCAAAAGCCGGATGGAAC

CGTGAAGCTGCTGATCTACTACACCTCACGGCTGCATTCTGGAGTGCCTAGCCGC

TTTAGCGGATCTGGGTCCGGTACTGACTACAGCCTCACCATTAGAAACCTTGAAC

AGGAGGACATCGCAACTTATTTCTGCCAACAGGTCTATACTCTGCCGTGGACCTT

CGGCGGAGGTACCAAACTGGAGATTAAGGCGGCCGCAACTACCACCCCTGCCCC

TCGGCCGCCGACTCCGGCCCCAACCATCGCAAGCCAACCCCTCTCCTTGCGCCCC

GAAGCTTGCCGCCCGGCCGCGGGTGGAGCCGTGCATACCCGGGGGCTGGACTTT

GCCTGCGATATCTACATTTGGGCCCCGCTGGCCGGCACTTGCGGCGTGCTCCTGC

-continued

TGTCGCTGGTCATCACCCTTTACTGCAAGAGGGGCCGGAAGAAGCTGCTTTACAT

CTTCAAGCAGCCGTTCATGCGGCCCGTGCAGACGACTCAGGAAGAGGACGGATG

CTCGTGCAGATTCCCTGAGGAGGAAGAGGGGGGATGCGAACTGCGCGTCAAGTT

CTCACGGTCCGCCGACGCCCCCGCATATCAACAGGGCCAGAATCAGCTCTACAA

CGAGCTGAACCTGGGAAGGAGAGAGGAGTACGACGTGCTGGACAAGCGACGCG

GACGCGACCCGGAGATGGGGGGGAAACCACGGCGGAAAAACCCTCAGGAAGGA

CTGTACAACGAACTCCAGAAAGACAAGATGGCGGAAGCCTACTCAGAAATCGGG

ATGAAGGGAGAGCGGAGGAGGGGAAAGGGTCACGACGGGCTGTACCAGGGACT

GAGCACCGCCACTAAGGATACCTACGATGCCTTGCATATGCAAGCACTCCCACCC

CGGTCTAGAGCTAAACGCTCTGGGTCTGGTGAAGGACGAGGTAGCCTTCTTACGT

GCGGAGACGTGGAGGAAAACCCAGGACCCATGCTGCTGCTTGTTACAAGCCTTT

TGCTCTGCGAACTCCCCCATCCAGCTTTTCTCCTGATTCCAAGGAAGGTTTGCAAT

GGAATCGGTATAGGGGAGTTTAAGGATTCACTTAGCATAAACGCTACTAATATTA

AACACTTCAAAAACTGTACGAGTATAAGTGGAGATCTTCACATTTTGCCGGTTGC

ATTCCGAGGCGATTCATTCACCCACACGCCACCGCTTGACCCACAAGAATTGGAT

ATTCTTAAAACCGTTAAAGAAATAACGGGGTTTTTGCTCATTCAAGCGTGGCCAG

AAAATCGCACTGACCTCCATGCTTTCGAGAACCTGGAGATTATAAGAGGACGAA

CTAAGCAGCATGGTCAATTCTCCCTTGCTGTGGTCAGCCTGAACATCACCAGTCT

TGGTTTGCGGTCCCTCAAGGAAATTTCAGATGGAGATGTCATCATAAGCGGCAAC

AAGAATTTGTGCTATGCAAATACCATAAACTGGAAAAAACTGTTTGGCACTTCCG

GCCAGAAAACCAAGATTATTTCAAATCGGGGTGAGAACAGCTGCAAAGCCACCG

GCCAGGTTTGTCATGCCTTGTGCTCTCCGGAAGGCTGTTGGGGGCCAGAACCCAG

GGACTGCGTCAGTTGCAGAAACGTCTCAAGAGGCCGCGAATGCGTTGACAAGTG

TAACCTCCTTGAGGGTGAGCCACGAGAGTTTGTTGAGAACAGCGAGTGTATACA

ATGTCACCCTGAATGTTTGCCCCAGGCTATGAATATAACCTGCACAGGCCGCGGG

CCTGATAACTGCATCCAGTGTGCTCATTACATAGATGGACCTCACTGTGTGAAAA

CCTGCCCGGCCGGAGTTATGGGAGAAAACAACACTCTGGTGTGGAAATACGCTG

ATGCAGGCCACGTGTGCCACCTTTGTCACCCGAATTGTACATATGGGTGTACCGG

TCCTGGACTTGAAGGTTGCCCTACCAATGGCCCTAAAATACCCAGTATCGCAACT

GGCATGGTAGGCGCTCTTCTCTTGCTCTTGGTAGTTGCTCTCGGCATAGGTCTTTT

TATGTGAC amino acid sequence of LTG2282 (EF-1a-TSLPR (3G11) CD8 BBz)

SEQ ID NO: 101

MALPVTALLLPLALLLHAARPQVTLKESGPGILKPSQTLSLTCSFSGFSLSTSGMGVG

WIRQPSGKGLEWLAHIWWDDDKYYNPSLKSQLTISKDTSRNQVFLKITSVDTADTAT

YYCSRRPRGTMDAMDYWGQGTSVTVSSGGGGSGGGGSGGGGSDIVMTQAASSLSA

SLGDRVTISCRASQDISKYLNWYQQKPDGTVKLLIYYTSRLHSGVPSRFSGSGSGTDY

SLTIRNLEQEDIATYFCQQVYTLPWTFGGGTKLEIKAAATTTPAPRPPTPAPTIASQPL

SLRPEACRPAAGGAVHTRGLDFACDIYIWAPLAGTCGVLLLSLVITLYCKRGRKKLL

YIFKQPFMRPVQTTQEEDGCSCRFPEEEEGGCELRVKFSRSADAPAYQQGQNQLYNE

LNLGRREEYDVLDKRRGRDPEMGGKPRRKNPQEGLYNELQKDKMAEAYSEIGMKG

-continued

ERRRGKGHDGLYQGLSTATKDTYDALHMQALPPRSRAKRSGSGEGRGSLLTCGDVE

ENPGPMLLLVTSLLLCELPHPAFLLIPRKVCNGIGIGEFKDSLSINATNIKHFKNCTSIS

GDLHILPVAFRGDSFTHTPPLDPQELDILKTVKEITGFLLIQAWPENRTDLHAFENLEII

RGRTKQHGQFSLAVVSLNITSLGLRSLKEISDGDVIISGNKNLCYANTINWKKLFGTS

GQKTKIISNRGENSCKATGQVCHALCSPEGCWGPEPRDCVSCRNVSRGRECVDKCN

LLEGEPREFVENSECIQCHPECLPQAMNITCTGRGPDNCIQCAHYIDGPHCVKTCPAG

VMGENNTLVWKYADAGHVCHLCHPNCTYGCTGPGLEGCPTNGPKIPSIATGMVGA

LLLLLVVALGIGLFM

---

What is claimed is:

1. A method of treating a B-cell hematological cancer in a human subject in need thereof, the method comprising administering to the human subject a pharmaceutical composition comprising an effective amount of a population of autologous T cells, wherein the autologous T cells comprise a nucleic acid sequence that encodes a CD19-TSLPR tandem chimeric antigen receptor (CAR) or a CD22-TSLPR tandem CAR, wherein the CD19-TSLPR tandem CAR or the CD22-TSLPR tandem CAR comprises the amino acid sequence comprising SEQ ID NO: 87, 91, or 95, thereby treating the B-cell hematological cancer of the human subject.

2. The method of claim 1, wherein the CD19-TSLPR tandem CAR or the CD22-TSLPR tandem CAR is encoded by a nucleotide sequence comprising SEQ ID NO. 86, 90, or 94, or a sequence with 85%, 90%, 95%, 96%, 97%, 98% or 99% identity thereof.

3. The method of claim 1, wherein the B-cell hematological cancer is leukemia, lymphoma or multiple myeloma.

4. The method of claim 3, wherein the leukemia is chronic lymphocytic leukemia (CLL), acute lymphocytic leukemia (ALL), or chronic myelogenous leukemia (CML).

5. The method of claim 3, wherein the lymphoma is mantle cell lymphoma, non-Hodgkin's lymphoma or Hodgkin's lymphoma.

* * * * *

SEQUENCE LISTING

<160> NUMBER OF SEQ ID NOS: 101

<210> SEQ ID NO 1
<211> LENGTH: 2292
<212> TYPE: DNA
<213> ORGANISM: Artificial Sequence
<220> FEATURE:
<223> OTHER INFORMATION: LTG2681 D0023 Leader-CD22 VH-(GGGGS)-3 CD22 VL (GGGGS)-5 CD19 VH (GGGGS)-3 CD19 VL CD8 hinge+TM-4-1BB- CD3z (Construct CAR 2219)

<400> SEQUENCE: 1

```
atgctcttgc tcgtgacttc tttgcttttg tgcgaacttc cgcacccagc cttccttttg     60

atacctcagg tacagcttca acaaagcgga ccgggacttg ttaagcattc ccaaaccctt    120

tctctcacgt gtgcaattag cggcgatagt gtatcctcta attctgcggc ctggaactgg    180

atacgacaat caccaagccg gggactcgag tggttgggcc gaacctacta tcggtccaaa    240

tggtataatg actacgcagt atccgtgaaa tctcgcatta cgatcaatcc agacacctcc    300

aaaaatcaat tttctctgca gttgaatagc gtgactcccg aggacacggc cgtttactat    360

tgcgcccagg aagttgaacc ccacgatgca tttgatattt ggggccaggg aaccatggtg    420

acagtgagta gtgggggtgg aggatctgga ggaggcggta gcggcggggg cggcagtgat    480

atccagatga cgcagtcacc ttccagcgtg tatgcgagtg tgggggacaa ggtcaccata    540

acctgtcgcg ctagccaaga tgtcagcggg tggctggctt ggtaccagca gaaaccaggt    600

ttggctcctc agcttttgat ctcaggagcg agcacgcttc agggtgaggt cccaagtcgc    660

tttagtggct ctggctccgg gacagacttc acgttgacga tcagcagttt gcagcctgag    720

gatttcgcga cctactactg ccagcaagcg aaatattttc cgtacacttt cggtcagggg    780

accaaattgg agatcaaagg tgggggtggt tcaggcggcg gaggctcagg cggcggcggt    840

agcggaggag gcggaagcgg gggtggcgga tcagaagtgc aactcgttca gagtggcgcg    900

gaggttaaga aacccggtgc atctgtaaag gttagctgta aggcatcagg atacactttt    960

accagctatt acatgcattg ggtgagacag gctcccggtc aggggctcga atggatgggg   1020

ttgatcaacc cgagtggtgg ttcaacatct tacgcccaga agtttcaggg ccgagtaaca   1080

atgactcggg acacgtctac ctcaactgtg tatatggagc tttccagcct gcgctcagag   1140

gatacagcag tctattactg cgcacggtca gacagaggta taacggccac tgatgcgttc   1200

gatatctggg gacaagggac tatggtaact gtgtcttccg gaggaggagg tagtggaggg   1260

ggaggaagcg gtgggggggg ctcacagtcc gttttgactc agccaccaag cgtctcagtc   1320

gcaccggggc gaatggcgaa aattacttgc ggcgggagcg acataggcaa caagaatgtg   1380
```

```
cattggtacc aacagaaacc aggtcaagca cctgttctcg tggtgtatga tgactacgat   1440

cgcccaagcg ggatcccgga gcggttctct ggatcaaatt ctggtgatgc agccactctg   1500

acaatatcaa cggtggaagt cggtgacgag gctgattact tctgccaagt atggatggc    1560

agcggagatc cctactggat gtttggagga ggtactcaac tgacagttct gggcgcggcc   1620

gcaacgacca ctcctgcacc ccgccctccg actccggccc caaccattgc cagccagccc   1680

ctgtccctgc ggccggaagc ctgcagaccg gctgccggcg gagccgtcca tacccgggga   1740

ctggatttcg cctgcgatat ctatatctgg gcaccactcg ccggaacctg tggagtgctg   1800

ctgctgtccc ttgtgatcac cctgtactgc aagcgcggac ggaagaaact cttgtacatc   1860

ttcaagcagc cgttcatgcg ccctgtgcaa accacccaag aagaggacgg gtgctcctgc   1920

cggttcccgg aagaggaaga gggcggctgc gaactgcgcg tgaagttttc ccggtccgcc   1980

gacgctccgg cgtaccagca ggggcaaaac cagctgtaca acgaacttaa cctcggtcgc   2040

cgggaagaat atgacgtgct ggacaagcgg cggggaagag atcccgagat gggtggaaag   2100

ccgcggcgga agaaccctca ggagggcttg tacaacgagc tgcaaaagga caaaatggcc   2160

gaagcctact ccgagattgg catgaaggga gagcgcagac gcgggaaggg acacgatgga   2220

ctgtaccagg gactgtcaac cgcgactaag gacacttacg acgccctgca catgcaggcc   2280

ctgcccccgc gc                                                       2292
```

```
<210> SEQ ID NO 2
<211> LENGTH: 764
<212> TYPE: PRT
<213> ORGANISM: Artificial Sequence
<220> FEATURE:
<223> OTHER INFORMATION: LTG2681 D0023 Leader-CD22 VH-(GGGGS)-3 CD22 VL
      (GGGGS)-5 CD19 VH (GGGGS)-3 CD19 VL CD8 hinge+TM-4-1BB- CD3z
      (Construct CAR 2219)

<400> SEQUENCE: 2

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys His Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro His
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Asp
145                 150                 155                 160

Ile Gln Met Thr Gln Ser Pro Ser Ser Val Tyr Ala Ser Val Gly Asp
                165                 170                 175

Lys Val Thr Ile Thr Cys Arg Ala Ser Gln Asp Val Ser Gly Trp Leu
            180                 185                 190
```

```
Ala Trp Tyr Gln Gln Lys Pro Gly Leu Ala Pro Gln Leu Leu Ile Ser
        195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Gly Gly Gly Gly Ser Gly
            260                 265                 270

Gly Gly Gly Ser Gly Gly Gly Gly Ser Gly Gly Gly Gly Ser Gly Gly
        275                 280                 285

Gly Gly Ser Glu Val Gln Leu Val Gln Ser Gly Ala Glu Val Lys Lys
    290                 295                 300

Pro Gly Ala Ser Val Lys Val Ser Cys Lys Ala Ser Gly Tyr Thr Phe
305                 310                 315                 320

Thr Ser Tyr Tyr Met His Trp Val Arg Gln Ala Pro Gly Gln Gly Leu
                325                 330                 335

Glu Trp Met Gly Leu Ile Asn Pro Ser Gly Gly Ser Thr Ser Tyr Ala
            340                 345                 350

Gln Lys Phe Gln Gly Arg Val Thr Met Thr Arg Asp Thr Ser Thr Ser
        355                 360                 365

Thr Val Tyr Met Glu Leu Ser Ser Leu Arg Ser Glu Asp Thr Ala Val
    370                 375                 380

Tyr Tyr Cys Ala Arg Ser Asp Arg Gly Ile Thr Ala Thr Asp Ala Phe
385                 390                 395                 400

Asp Ile Trp Gly Gln Gly Thr Met Val Thr Val Ser Ser Gly Gly Gly
                405                 410                 415

Gly Ser Gly Gly Gly Gly Ser Gly Gly Gly Gly Ser Gln Ser Val Leu
            420                 425                 430

Thr Gln Pro Pro Ser Val Ser Val Ala Pro Gly Arg Met Ala Lys Ile
        435                 440                 445

Thr Cys Gly Gly Ser Asp Ile Gly Asn Lys Asn Val His Trp Tyr Gln
    450                 455                 460

Gln Lys Pro Gly Gln Ala Pro Val Leu Val Val Tyr Asp Asp Tyr Asp
465                 470                 475                 480

Arg Pro Ser Gly Ile Pro Glu Arg Phe Ser Gly Ser Asn Ser Gly Asp
                485                 490                 495

Ala Ala Thr Leu Thr Ile Ser Thr Val Glu Val Gly Asp Glu Ala Asp
            500                 505                 510

Tyr Phe Cys Gln Val Trp Asp Gly Ser Gly Asp Pro Tyr Trp Met Phe
        515                 520                 525

Gly Gly Gly Thr Gln Leu Thr Val Leu Gly Ala Ala Ala Thr Thr Thr
    530                 535                 540

Pro Ala Pro Arg Pro Pro Thr Pro Ala Pro Thr Ile Ala Ser Gln Pro
545                 550                 555                 560

Leu Ser Leu Arg Pro Glu Ala Cys Arg Pro Ala Ala Gly Gly Ala Val
                565                 570                 575

His Thr Arg Gly Leu Asp Phe Ala Cys Asp Ile Tyr Ile Trp Ala Pro
            580                 585                 590

Leu Ala Gly Thr Cys Gly Val Leu Leu Leu Ser Leu Val Ile Thr Leu
        595                 600                 605
```

```
Tyr Cys Lys Arg Gly Arg Lys Lys Leu Leu Tyr Ile Phe Lys Gln Pro
    610                 615                 620

Phe Met Arg Pro Val Gln Thr Thr Gln Glu Glu Asp Gly Cys Ser Cys
625                 630                 635                 640

Arg Phe Pro Glu Glu Glu Glu Gly Gly Cys Glu Leu Arg Val Lys Phe
                645                 650                 655

Ser Arg Ser Ala Asp Ala Pro Ala Tyr Gln Gln Gly Gln Asn Gln Leu
            660                 665                 670

Tyr Asn Glu Leu Asn Leu Gly Arg Arg Glu Glu Tyr Asp Val Leu Asp
        675                 680                 685

Lys Arg Arg Gly Arg Asp Pro Glu Met Gly Gly Lys Pro Arg Arg Lys
    690                 695                 700

Asn Pro Gln Glu Gly Leu Tyr Asn Glu Leu Gln Lys Asp Lys Met Ala
705                 710                 715                 720

Glu Ala Tyr Ser Glu Ile Gly Met Lys Gly Glu Arg Arg Arg Gly Lys
                725                 730                 735

Gly His Asp Gly Leu Tyr Gln Gly Leu Ser Thr Ala Thr Lys Asp Thr
            740                 745                 750

Tyr Asp Ala Leu His Met Gln Ala Leu Pro Pro Arg
        755                 760
```

```
<210> SEQ ID NO 3
<211> LENGTH: 2292
<212> TYPE: DNA
<213> ORGANISM: Artificial Sequence
<220> FEATURE:
<223> OTHER INFORMATION: LTG2791 D0024 Leader-CD19 VH (GGGGS)3 - CD19
      VL -(GGGGS)5 -CD22 VH (GGGGS)3 - CD22 VH CD8 hinge+TM-4-1BB- CD3z
      (Construct CAR 1922)

<400> SEQUENCE: 3

atgttgcttc tggttacttc ccttcttctt tgcgagcttc cacacccagc attcctgctc     60

attccggagg tgcaactcgt ccaatccggg gccgaagtta agaagccggg agcatctgtt    120

aaagtatcct gtaaggccag tgggtatact ttcacctcat attatatgca ctgggtgagg    180

caggctccag gccaagggtt ggagtggatg ggactgataa acccatctgg gggatcaact    240

tcttatgcgc aaaagttcca aggtcgggtc actatgacaa gggacacatc caccagcact    300

gtttatatgg aactgagcag cctgagatct gaggataccg cagtatatta ctgtgcacgc    360

agtgatagag gcataacggc gactgacgcc ttcgacattt ggggccaagg gacaatggtc    420

acggtttcaa gtggaggtgg agggtctggt ggcggggggt ctggtggtgg aggcagtcag    480

agcgtcctga cccagccgcc tagcgtcagt gtggcccccg gccgcatggc caagataacg    540

tgtggcggaa gcgatattgg gaataagaac gtccactggt atcagcagaa gccagggcag    600

gctcccgtcc tcgtagtata cgacgattat gatcggccca gtggaatccc cgagagattt    660

agcgggagta actctgggga tgcagcgaca cttactatct ccactgttga agtaggagac    720

gaggctgact atttttgtca ggtttgggac ggatccggag atccttattg gatgtttggc    780

ggaggtactc aattgaccgt gcttggaggt ggcggaggga gcgggggtgg gggctcaggg    840

ggaggtgggt caggcggggg cggaagtggt ggcgggggtt cccaagtcca actccagcag    900

tcaggacctg gactggtaaa acactctcaa accctgtctc tcacgtgtgc catatctggc    960

gatagtgtat cttcaaactc tgctgcatgg aactggatca ggcaaagtcc atcccgcggc   1020

cttgagtggc tcggtcgaac ctattaccga agcaaatggt acaacgatta tgcggtttca   1080

gtcaagtcaa gaattacgat caaccctgat acgagtaaga accagtttag tttgcaattg   1140
```

```
aacagtgtaa ctcccgagga cacggcggtg tactattgtg cgcaagaagt cgaaccgcat   1200

gatgcgttcg atatctgggg gcagggcaca atggtgaccg tatcttctgg cggcggcggc   1260

tctggaggag gaggaagcgg cggagggga tctgacatac aaatgacaca atccccaagt   1320

tcagtatatg ctagcgtcgg ggataaagtg acaattactt gtagggcttc tcaagacgta   1380

agtggctggt tggcgtggta ccagcaaaag ccgggtctcg cccctcaact ccttatcagc   1440

ggagcttcaa ctcttcaggg agaggtccca agtcgattct caggctctgg ctccgggaca   1500

gatttcacct tgacaattag ttcactgcaa cccgaggatt tcgcaactta ctactgtcaa   1560

caggccaagt acttcccgta tacgtttggt caaggcacaa aactggagat taaggcggcc   1620

gcaacgacca ctcctgcacc ccgccctccg actccggccc caaccattgc cagccagccc   1680

ctgtccctgc ggccggaagc ctgcagaccg gctgccggcg gagccgtcca tacccgggga   1740

ctggatttcg cctgcgatat ctatatctgg gcaccactcg ccggaacctg tggagtgctg   1800

ctgctgtccc ttgtgatcac cctgtactgc aagcgcggac ggaagaaact cttgtacatc   1860

ttcaagcagc cgttcatgcg ccctgtgcaa accacccaag aagaggacgg gtgctcctgc   1920

cggttcccgg aagaggaaga gggcggctgc gaactgcgcg tgaagttttc ccggtccgcc   1980

gacgctccgg cgtaccagca ggggcaaaac cagctgtaca acgaacttaa cctcggtcgc   2040

cgggaagaat atgacgtgct ggacaagcgg cggggaagag atcccgagat gggtggaaag   2100

ccgcggcgga agaaccctca ggagggcttg tacaacgagc tgcaaaagga caaaatggcc   2160

gaagcctact ccgagattgg catgaaggga gagcgcagac gcgggaaggg acacgatgga   2220

ctgtaccagg gactgtcaac cgcgactaag gacacttacg acgccctgca catgcaggcc   2280

ctgcccccgc gc                                                         2292
```

<210> SEQ ID NO 4
<211> LENGTH: 764
<212> TYPE: PRT
<213> ORGANISM: Artificial Sequence
<220> FEATURE:
<223> OTHER INFORMATION: LTG2791 D0024 Leader-CD19 VH (GGGGS)3 - CD19 VL -(GGGGS)5 -CD22 VH (GGGGS)3 - CD22 VH CD8 hinge+TM-4-1BB- CD3z (Construct CAR 1922)

<400> SEQUENCE: 4

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Ser Tyr Tyr Met His Trp Val Arg Gln Ala Pro Gly
    50                  55                  60

Gln Gly Leu Glu Trp Met Gly Leu Ile Asn Pro Ser Gly Gly Ser Thr
65                  70                  75                  80

Ser Tyr Ala Gln Lys Phe Gln Gly Arg Val Thr Met Thr Arg Asp Thr
                85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Ser Asp Arg Gly Ile Thr Ala Thr
        115                 120                 125

Asp Ala Phe Asp Ile Trp Gly Gln Gly Thr Met Val Thr Val Ser Ser
    130                 135                 140
```

```
Gly Gly Gly Gly Ser Gly Gly Gly Gly Ser Gly Gly Gly Gly Ser Gln
145                 150                 155                 160

Ser Val Leu Thr Gln Pro Pro Ser Val Ser Val Ala Pro Gly Arg Met
                165                 170                 175

Ala Lys Ile Thr Cys Gly Gly Ser Asp Ile Gly Asn Lys Asn Val His
            180                 185                 190

Trp Tyr Gln Gln Lys Pro Gly Gln Ala Pro Val Leu Val Val Tyr Asp
        195                 200                 205

Asp Tyr Asp Arg Pro Ser Gly Ile Pro Glu Arg Phe Ser Gly Ser Asn
    210                 215                 220

Ser Gly Asp Ala Ala Thr Leu Thr Ile Ser Thr Val Glu Val Gly Asp
225                 230                 235                 240

Glu Ala Asp Tyr Phe Cys Gln Val Trp Asp Gly Ser Gly Asp Pro Tyr
                245                 250                 255

Trp Met Phe Gly Gly Gly Thr Gln Leu Thr Val Leu Gly Gly Gly Gly
            260                 265                 270

Gly Ser Gly Gly Gly Gly Ser Gly Gly Gly Gly Ser Gly Gly Gly Gly
        275                 280                 285

Ser Gly Gly Gly Gly Ser Gln Val Gln Leu Gln Gln Ser Gly Pro Gly
    290                 295                 300

Leu Val Lys His Ser Gln Thr Leu Ser Leu Thr Cys Ala Ile Ser Gly
305                 310                 315                 320

Asp Ser Val Ser Ser Asn Ser Ala Ala Trp Asn Trp Ile Arg Gln Ser
                325                 330                 335

Pro Ser Arg Gly Leu Glu Trp Leu Gly Arg Thr Tyr Tyr Arg Ser Lys
            340                 345                 350

Trp Tyr Asn Asp Tyr Ala Val Ser Val Lys Ser Arg Ile Thr Ile Asn
        355                 360                 365

Pro Asp Thr Ser Lys Asn Gln Phe Ser Leu Gln Leu Asn Ser Val Thr
    370                 375                 380

Pro Glu Asp Thr Ala Val Tyr Tyr Cys Ala Gln Glu Val Glu Pro His
385                 390                 395                 400

Asp Ala Phe Asp Ile Trp Gly Gln Gly Thr Met Val Thr Val Ser Ser
                405                 410                 415

Gly Gly Gly Gly Ser Gly Gly Gly Gly Ser Gly Gly Gly Gly Ser Asp
            420                 425                 430

Ile Gln Met Thr Gln Ser Pro Ser Ser Val Tyr Ala Ser Val Gly Asp
        435                 440                 445

Lys Val Thr Ile Thr Cys Arg Ala Ser Gln Asp Val Ser Gly Trp Leu
    450                 455                 460

Ala Trp Tyr Gln Gln Lys Pro Gly Leu Ala Pro Gln Leu Leu Ile Ser
465                 470                 475                 480

Gly Ala Ser Thr Leu Gln Gly Glu Val Pro Ser Arg Phe Ser Gly Ser
                485                 490                 495

Gly Ser Gly Thr Asp Phe Thr Leu Thr Ile Ser Ser Leu Gln Pro Glu
            500                 505                 510

Asp Phe Ala Thr Tyr Tyr Cys Gln Gln Ala Lys Tyr Phe Pro Tyr Thr
        515                 520                 525

Phe Gly Gln Gly Thr Lys Leu Glu Ile Lys Ala Ala Ala Thr Thr Thr
    530                 535                 540

Pro Ala Pro Arg Pro Pro Thr Pro Ala Pro Thr Ile Ala Ser Gln Pro
545                 550                 555                 560
```

```
Leu Ser Leu Arg Pro Glu Ala Cys Arg Pro Ala Ala Gly Gly Ala Val
                565                 570                 575

His Thr Arg Gly Leu Asp Phe Ala Cys Asp Ile Tyr Ile Trp Ala Pro
            580                 585                 590

Leu Ala Gly Thr Cys Gly Val Leu Leu Leu Ser Leu Val Ile Thr Leu
        595                 600                 605

Tyr Cys Lys Arg Gly Arg Lys Lys Leu Leu Tyr Ile Phe Lys Gln Pro
    610                 615                 620

Phe Met Arg Pro Val Gln Thr Thr Gln Glu Glu Asp Gly Cys Ser Cys
625                 630                 635                 640

Arg Phe Pro Glu Glu Glu Glu Gly Gly Cys Glu Leu Arg Val Lys Phe
                645                 650                 655

Ser Arg Ser Ala Asp Ala Pro Ala Tyr Gln Gln Gly Gln Asn Gln Leu
            660                 665                 670

Tyr Asn Glu Leu Asn Leu Gly Arg Arg Glu Glu Tyr Asp Val Leu Asp
        675                 680                 685

Lys Arg Arg Gly Arg Asp Pro Glu Met Gly Gly Lys Pro Arg Arg Lys
    690                 695                 700

Asn Pro Gln Glu Gly Leu Tyr Asn Glu Leu Gln Lys Asp Lys Met Ala
705                 710                 715                 720

Glu Ala Tyr Ser Glu Ile Gly Met Lys Gly Glu Arg Arg Arg Gly Lys
                725                 730                 735

Gly His Asp Gly Leu Tyr Gln Gly Leu Ser Thr Ala Thr Lys Asp Thr
            740                 745                 750

Tyr Asp Ala Leu His Met Gln Ala Leu Pro Pro Arg
        755                 760


<210> SEQ ID NO 5
<211> LENGTH: 1485
<212> TYPE: DNA
<213> ORGANISM: Artificial Sequence
<220> FEATURE:
<223> OTHER INFORMATION: CAR19 LTG2065 (M19217-1-CD8 TM-4-1BB zeta)

<400> SEQUENCE: 5

atgctgctgc tggtgaccag cctgctgctg tgcgaactgc cgcatccggc gtttctgctg      60

attccggagg tccagctggt acagtctgga gctgaggtga agaagcctgg ggcctcagtg     120

aaggtctcct gcaaggcttc tggatacacc ttcaccagct actatatgca ctgggtgcga     180

caggcccctg gacaagggct tgagtggatg ggattaatca accctagtgg tggtagcaca     240

agctacgcac agaagttcca gggcagagtc accatgacca gggacacgtc cacgagcaca     300

gtctacatgg agctgagcag cctgagatct gaggacacgg ccgtgtatta ctgtgcgaga     360

tcggatcggg gaattaccgc cacggacgct tttgatatct ggggccaagg gacaatggtc     420

accgtctctt caggcggagg aggctccggg ggaggaggtt ccgggggcgg gggttcccag     480

tctgtgctga ctcagccacc ctcggtgtca gtggccccag ggcggatggc caagattacc     540

tgtgggggaa gtgacattgg aaataaaaat gtccactggt atcagcagaa gccaggccag     600

gcccctgtcc tggttgtcta tgatgattac gaccggccct cagggatccc tgagcgattc     660

tctggctcca actctgggga cgcggccacc ctgacgatca gcacggtcga agtcggggat     720

gaggccgact atttctgtca ggtgtgggac ggtagtggtg atccttattg gatgttcggc     780

ggagggaccc agctcaccgt tttaggtgcg gccgcaacta ccacccctgc ccctcggccg     840

ccgactccgg ccccaaccat cgcaagccaa cccctctcct tgcgccccga agcttgccgc     900
```

```
ccggccgcgg gtggagccgt gcatacccgg gggctggact ttgcctgcga tatctacatt    960

tgggccccgc tggccggcac ttgcggcgtg ctcctgctgt cgctggtcat caccctttac   1020

tgcaagaggg gccggaagaa gctgctttac atcttcaagc agccgttcat gcggcccgtg   1080

cagacgactc aggaagagga cggatgctcg tgcagattcc ctgaggagga agaggggga    1140

tgcgaactgc gcgtcaagtt ctcacggtcc gccgacgccc ccgcatatca acagggccag   1200

aatcagctct acaacgagct gaacctggga aggagagagg agtacgacgt gctggacaag   1260

cgacgcggac gcgacccgga gatggggggg aaaccacggc ggaaaaaccc tcaggaagga   1320

ctgtacaacg aactccagaa agacaagatg gcggaagcct actcagaaat cgggatgaag   1380

ggagagcgga ggaggggaaa gggtcacgac gggctgtacc agggactgag caccgccact   1440

aaggatacct acgatgcctt gcatatgcaa gcactcccac cccgg                   1485
```

<210> SEQ ID NO 6
<211> LENGTH: 495
<212> TYPE: PRT
<213> ORGANISM: Artificial Sequence
<220> FEATURE:
<223> OTHER INFORMATION: CAR19 LTG2065 (M19217-1-CD8 TM-4-1BB zeta)

<400> SEQUENCE: 6

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Ser Tyr Tyr Met His Trp Val Arg Gln Ala Pro Gly
    50                  55                  60

Gln Gly Leu Glu Trp Met Gly Leu Ile Asn Pro Ser Gly Gly Ser Thr
65                  70                  75                  80

Ser Tyr Ala Gln Lys Phe Gln Gly Arg Val Thr Met Thr Arg Asp Thr
                85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Ser Asp Arg Gly Ile Thr Ala Thr
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Gln
145                 150                 155                 160

Ser Val Leu Thr Gln Pro Pro Ser Val Ser Val Ala Pro Gly Arg Met
                165                 170                 175

Ala Lys Ile Thr Cys Gly Gly Ser Asp Ile Gly Asn Lys Asn Val His
            180                 185                 190

Trp Tyr Gln Gln Lys Pro Gly Gln Ala Pro Val Leu Val Val Tyr Asp
        195                 200                 205

Asp Tyr Asp Arg Pro Ser Gly Ile Pro Glu Arg Phe Ser Gly Ser Asn
    210                 215                 220

Ser Gly Asp Ala Ala Thr Leu Thr Ile Ser Thr Val Glu Val Gly Asp
225                 230                 235                 240

Glu Ala Asp Tyr Phe Cys Gln Val Trp Asp Gly Ser Gly Asp Pro Tyr
                245                 250                 255

Trp Met Phe Gly Gly Gly Thr Gln Leu Thr Val Leu Gly Ala Ala Ala
```

```
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495


<210> SEQ ID NO 7
<211> LENGTH: 1470
<212> TYPE: DNA
<213> ORGANISM: Artificial Sequence
<220> FEATURE:
<223> OTHER INFORMATION: mouse scFv CAR19 LTG1538

<400> SEQUENCE: 7

atgcttctcc tggtcacctc cctgctcctc tgcgaactgc ctcaccctgc cttccttctg     60

attcctgaca ttcagatgac tcagaccacc tcttccttgt ccgcgtcact gggagacaga    120

gtgaccatct cgtgtcgcgc aagccaggat atctccaagt acctgaactg gtaccaacag    180

aagcccgacg ggactgtgaa gctgctgatc taccacacct cacgcctgca cagcggagtg    240

ccaagcagat tctccggctc cggctcggga accgattact cgcttaccat tagcaacctc    300

gagcaggagg acatcgctac ctacttctgc cagcaaggaa ataccctgcc ctacaccttc    360

ggcggaggaa ccaaattgga aatcaccggc ggaggaggct ccgggggagg aggttccggg    420

ggcgggggtt ccgaagtgaa gctccaggag tccggccccg gcctggtggc gccgtcgcaa    480

tcactctctg tgacctgtac cgtgtcggga gtgtccctgc ctgattacgg cgtgagctgg    540

attcggcagc cgccgcggaa gggcctggaa tggctgggtg tcatctgggg atccgagact    600

acctactaca actcggccct gaagtcccgc ctgactatca tcaaagacaa ctcgaagtcc    660

caggtctttc tgaagatgaa ctccctgcaa actgacgaca ccgccatcta ttactgtgct    720

aagcactact actacggtgg aagctatgct atggactact gggggcaagg cacttcggtg    780
```

```
actgtgtcaa gcgcggccgc aactaccacc cctgcccctc ggccgccgac tccggcccca    840

accatcgcaa gccaacccct ctccttgcgc cccgaagctt gccgcccggc cgcgggtgga    900

gccgtgcata cccgggggct ggactttgcc tgcgatatct acatttgggc cccgctggcc    960

ggcacttgcg gcgtgctcct gctgtcgctg gtcatcaccc tttactgcaa gaggggccgg   1020

aagaagctgc tttacatctt caagcagccg ttcatgcggc ccgtgcagac gactcaggaa   1080

gaggacggat gctcgtgcag attccctgag gaggaagagg ggggatgcga actgcgcgtc   1140

aagttctcac ggtccgccga cgcccccgca tatcaacagg gccagaatca gctctacaac   1200

gagctgaacc tgggaaggag agaggagtac gacgtgctgg acaagcgacg cggacgcgac   1260

ccggagatgg gggggaaacc acggcggaaa aaccctcagg aaggactgta caacgaactc   1320

cagaaagaca agatggcgga agcctactca gaaatcggga tgaagggaga gcggaggagg   1380

ggaaagggtc acgacgggct gtaccaggga ctgagcaccg ccactaagga tacctacgat   1440

gccttgcata tgcaagcact cccaccccgg                                    1470
```

<210> SEQ ID NO 8
<211> LENGTH: 489
<212> TYPE: PRT
<213> ORGANISM: Artificial Sequence
<220> FEATURE:
<223> OTHER INFORMATION: mouse scFv CAR19 LTG1538

<400> SEQUENCE: 8

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Gly Ser Gly Gly Gly Gly Ser
    130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
    210                 215                 220

Lys Met Asn Ser Leu Gln Thr Asp Asp Thr Ala Ile Tyr Tyr Cys Ala
225                 230                 235                 240
```

```
Lys His Tyr Tyr Tyr Gly Gly Ser Tyr Ala Met Asp Tyr Trp Gly Gln
                245                 250                 255

Gly Thr Ser Val Thr Val Ser Ser Ala Ala Ala Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro
                485
```

<210> SEQ ID NO 9
<211> LENGTH: 1476
<212> TYPE: DNA
<213> ORGANISM: Artificial Sequence
<220> FEATURE:
<223> OTHER INFORMATION: CAR22 LTG2209

<400> SEQUENCE: 9

```
atgcttcttt tggtgacttc ccttttgctg tgcgagttgc cacaccccgc cttcctgctt      60

attccccagg tacagcttca acagagtggg ccgggactgg tgaaacactc ccaaacactt     120

tctctgacgt gcgctatatc aggtgactct gtttcatcta attctgctgc gtggaactgg     180

attcgacaat ctcccagtcg cgggttggaa tggctgggac gaacatatta tcggtctaag     240

tggtataacg attatgctgt atctgttaaa tctcgaatta cgattaatcc tgacacctcc     300

aagaaccagt tctccctcca gttgaactca gtcacaccgg aagacactgc ggtctactat     360

tgcgctcaag aagtcgagcc acatgatgca ttcgacatct ggggccaggg aacgatggtc     420

accgtcagca gtggcggcgg cggatctggg ggtggcggtt ctggcggtgg aggatcagac     480

atacaaatga cgcagagtcc ctcaagtgtg tacgcgagtg tgggggataa ggtaactatt     540

acgtgcagag cgtcacagga tgttagtgga tggcttgcct ggtatcagca gaagccaggc     600
```

-continued

```
cttgctccac agctccttat cagtggtgct tctacacttc agggcgaggt tccgagtaga    660

ttctctggtt ctggatctgg tactgacttc actcttacaa tttcttcttt gcaaccagaa    720

gactttgcga cttattactg ccaacaggcc aaatacttcc cttatacatt tggccaaggt    780

accaagttgg agataaaggc ggccgcaact accacccctg cccctcggcc gccgactccg    840

gccccaacca tcgcaagcca acccctctcc ttgcgccccg aagcttgccg cccggccgcg    900

ggtggagccg tgcatacccg ggggctggac tttgcctgcg atatctacat ttgggccccg    960

ctggccggca cttgcggcgt gctcctgctg tcgctggtca tcacccttta ctgcaagagg   1020

ggccggaaga agctgcttta catcttcaag cagccgttca tgcggcccgt gcagacgact   1080

caggaagagg acggatgctc gtgcagattc cctgaggagg aagagggggg atgcgaactg   1140

cgcgtcaagt tctcacggtc cgccgacgcc cccgcatatc aacagggcca gaatcagctc   1200

tacaacgagc tgaacctggg aaggagagag gagtacgacg tgctggacaa gcgacgcgga   1260

cgcgacccgg agatgggggg gaaaccacgg cggaaaaacc ctcaggaagg actgtacaac   1320

gaactccaga aagacaagat ggcggaagcc tactcagaaa tcgggatgaa gggagagcgg   1380

aggaggggaa agggtcacga cgggctgtac cagggactga gcaccgccac taaggatacc   1440

tacgatgcct tgcatatgca agcactccca ccccgg                             1476
```

```
<210> SEQ ID NO 10
<211> LENGTH: 492
<212> TYPE: PRT
<213> ORGANISM: Artificial Sequence
<220> FEATURE:
<223> OTHER INFORMATION: CAR22 LTG2209

<400> SEQUENCE: 10

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys His Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro His
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Asp
145                 150                 155                 160

Ile Gln Met Thr Gln Ser Pro Ser Ser Val Tyr Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
        195                 200                 205
```

```
Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490


<210> SEQ ID NO 11
<211> LENGTH: 66
<212> TYPE: DNA
<213> ORGANISM: Artificial Sequence
<220> FEATURE:
<223> OTHER INFORMATION: leader/signal peptide sequence (LP)

<400> SEQUENCE: 11

atgctgctgc tggtgaccag cctgctgctg tgcgaactgc cgcatccggc gtttctgctg      60

attccg                                                                 66


<210> SEQ ID NO 12
<211> LENGTH: 22
<212> TYPE: PRT
<213> ORGANISM: Artificial Sequence
<220> FEATURE:
<223> OTHER INFORMATION: leader/signal peptide sequence (LP)

<400> SEQUENCE: 12

Met Leu Leu Leu Val Thr Ser Leu Leu Leu Cys Glu Leu Pro His Pro
```

```
1               5                   10                  15

Ala Phe Leu Leu Ile Pro
            20

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23
```

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35
<211> LENGTH: 66
<212> TYPE: DNA
<213> ORGANISM: Artificial Sequence
<220> FEATURE:
<223> OTHER INFORMATION: CD8 transmembrane domain

<400> SEQUENCE: 35

```
atttgggccc cgctggccgg cacttgcggc gtgctcctgc tgtcgctggt catcaccctt     60

tactgc                                                                66
```

<210> SEQ ID NO 36
<211> LENGTH: 22
<212> TYPE: PRT
<213> ORGANISM: Artificial Sequence
<220> FEATURE:
<223> OTHER INFORMATION: CD8 transmembrane domain

<400> SEQUENCE: 36

```
Ile Trp Ala Pro Leu Ala Gly Thr Cys Gly Val Leu Leu Leu Ser Leu
1               5                   10                  15

Val Ile Thr Leu Tyr Cys
            20
```

<210> SEQ ID NO 37
<211> LENGTH: 141
<212> TYPE: DNA
<213> ORGANISM: Artificial Sequence
<220> FEATURE:
<223> OTHER INFORMATION: CD8 hinge domain

<400> SEQUENCE: 37

```
actaccaccc ctgcccctcg gccgccgact ccggccccaa ccatcgcaag ccaacccctc     60

tccttgcgcc ccgaagcttg ccgcccggcc gcgggtggag ccgtgcatac ccgggggctg    120

gactttgcct gcgatatcta c                                              141
```

<210> SEQ ID NO 38
<211> LENGTH: 47
<212> TYPE: PRT
<213> ORGANISM: Artificial Sequence
<220> FEATURE:
<223> OTHER INFORMATION: CD8 hinge domain

<400> SEQUENCE: 38

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45
```

<210> SEQ ID NO 39
<211> LENGTH: 69
<212> TYPE: PRT
<213> ORGANISM: Artificial Sequence
<220> FEATURE:
<223> OTHER INFORMATION: hinge and  transmembrane region of CD8.alpha

<400> SEQUENCE: 39

```
Thr Thr Thr Pro Ala Pro Arg Pro Pro Thr Pro Ala Pro Thr Ile Ala
1               5                   10                  15
```

```
Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65


<210> SEQ ID NO 40
<211> LENGTH: 126
<212> TYPE: DNA
<213> ORGANISM: Artificial Sequence
<220> FEATURE:
<223> OTHER INFORMATION: signaling domain of 4-1BB

<400> SEQUENCE: 40

aagaggggcc ggaagaagct gctttacatc ttcaagcagc cgttcatgcg gcccgtgcag     60

acgactcagg aagaggacgg atgctcgtgc agattccctg aggaggaaga gggggggatgc    120

gaactg                                                                126


<210> SEQ ID NO 41
<211> LENGTH: 42
<212> TYPE: PRT
<213> ORGANISM: Artificial Sequence
<220> FEATURE:
<223> OTHER INFORMATION: signaling domain of 4-1BB

<400> SEQUENCE: 41

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 42
<211> LENGTH: 336
<212> TYPE: DNA
<213> ORGANISM: Artificial Sequence
<220> FEATURE:
<223> OTHER INFORMATION: Signaling domain of CD3-zeta

<400> SEQUENCE: 42

cgcgtcaagt tctcacggtc cgccgacgcc cccgcatatc aacagggcca gaatcagctc     60

tacaacgagc tgaacctggg aaggagagag gagtacgacg tgctggacaa gcgacgcgga    120

cgcgacccgg agatgggggg gaaaccacgg cggaaaaacc ctcaggaagg actgtacaac    180

gaactccaga aagacaagat ggcggaagcc tactcagaaa tcgggatgaa gggagagcgg    240

aggaggggaa agggtcacga cgggctgtac cagggactga gcaccgccac taaggatacc    300

tacgatgcct tgcatatgca agcactccca ccccgg                              336


<210> SEQ ID NO 43
<211> LENGTH: 112
<212> TYPE: PRT
<213> ORGANISM: Artificial Sequence
<220> FEATURE:
<223> OTHER INFORMATION: Signaling domain of CD3-zeta

<400> SEQUENCE: 43
```

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 44
<211> LENGTH: 726
<212> TYPE: DNA
<213> ORGANISM: Artificial Sequence
<220> FEATURE:
<223> OTHER INFORMATION: ScFv CD19 (FMC63)

<400> SEQUENCE: 44

gacattcaga tgactcagac cacctcttcc ttgtccgcgt cactgggaga cagagtgacc     60

atctcgtgtc gcgcaagcca ggatatctcc aagtacctga actggtacca acagaagccc    120

gacgggactg tgaagctgct gatctaccac acctcacgcc tgcacagcgg agtgccaagc    180

agattctccg gctccggctc gggaaccgat tactcgctta ccattagcaa cctcgagcag    240

gaggacatcg ctacctactt ctgccagcaa ggaaataccc tgccctacac cttcggcgga    300

ggaaccaaat tggaaatcac cggcggagga ggctccgggg gaggaggttc cgggggcggg    360

ggttccgaag tgaagctcca ggagtccggc cccggcctgg tggcgccgtc gcaatcactc    420

tctgtgacct gtaccgtgtc gggagtgtcc ctgcctgatt acggcgtgag ctggattcgg    480

cagccgccgc ggaagggcct ggaatggctg ggtgtcatct ggggatccga gactacctac    540

tacaactcgg ccctgaagtc ccgcctgact atcatcaaag acaactcgaa gtcccaggtc    600

tttctgaaga tgaactccct gcaaactgac gacaccgcca tctattactg tgctaagcac    660

tactactacg gtggaagcta tgctatggac tactgggggc aaggcacttc ggtgactgtg    720

tcaagc                                                               726


<210> SEQ ID NO 45
<211> LENGTH: 242
<212> TYPE: PRT
<213> ORGANISM: Artificial Sequence
<220> FEATURE:
<223> OTHER INFORMATION: ScFv CD19 (FMC63)

<400> SEQUENCE: 45

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60
```

```
Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser


<210> SEQ ID NO 46
<211> LENGTH: 1491
<212> TYPE: DNA
<213> ORGANISM: Artificial Sequence
<220> FEATURE:
<223> OTHER INFORMATION: anti-CD33 CAR (LTG1936)

<400> SEQUENCE: 46

atgctgctgc tggtgaccag cctgctgctg tgcgaactgc cgcatccggc gtttctgctg      60

attccgcagg tgcagctggt gcaatctggg gcagaggtga aaaagcccgg ggagtctctg     120

aggatctcct gtaagggttc tggattcagt tttcccacct actggatcgg ctgggtgcgc     180

cagatgcccg ggaaaggcct ggagtggatg gggatcatct atcctggtga ctctgatacc     240

agatacagcc cgtccttcca aggccaggtc accatctcag ccgacaagtc catcagcacc     300

gcctacctgc agtggagcag cctgaaggcc tcggacaccg ccatgtatta ctgtgcgaga     360

ctagttggag atggctacaa tacgggggct tttgatatct ggggccaagg gacaatggtc     420

accgtctctt caggaggtgg cgggtctggt ggtggcggta gcggtggtgg cggatccgat     480

attgtgatga cccacactcc actctctctg tccgtcaccc ctggacagcc ggcctccatc     540

tcctgcaagt ctagtcagag cctcctgcat agtaatggaa agacctattt gtattggtac     600

ctgcagaagc caggccagcc tccacagctc ctgatctatg gagcttccaa ccggttctct     660

ggagtgccag acaggttcag tggcagcggg tcagggacag atttcacact gaaaatcagc     720

cgggtggagg ctgaggatgt tggggtttat tactgcatgc aaagtataca gcttcctatc     780

accttcggcc aagggacacg actggagatt aaagcggccg caactaccac ccctgcccct     840

cggccgccga ctccggcccc aaccatcgca agccaacccc tctccttgcg ccccgaagct     900

tgccgcccgg ccgcgggtgg agccgtgcat acccgggggc tggactttgc ctgcgatatc     960

tacatttggg ccccgctggc cggcacttgc ggcgtgctcc tgctgtcgct ggtcatcacc    1020
```

-continued

```
ctttactgca agaggggccg gaagaagctg ctttacatct tcaagcagcc gttcatgcgg   1080

cccgtgcaga cgactcagga agaggacgga tgctcgtgca gattccctga ggaggaagag   1140

gggggatgcg aactgcgcgt caagttctca cggtccgccg acgcccccgc atatcaacag   1200

ggccagaatc agctctacaa cgagctgaac ctgggaagga gagaggagta cgacgtgctg   1260

gacaagcgac gcggacgcga cccggagatg ggggggaaac cacggcggaa aaaccctcag   1320

gaaggactgt acaacgaact ccagaaagac aagatggcgg aagcctactc agaaatcggg   1380

atgaagggag agcggaggag gggaaagggt cacgacgggc tgtaccaggg actgagcacc   1440

gccactaagg atacctacga tgccttgcat atgcaagcac tcccaccccg g            1491


<210> SEQ ID NO 47
<211> LENGTH: 496
<212> TYPE: PRT
<213> ORGANISM: Artificial Sequence
<220> FEATURE:
<223> OTHER INFORMATION: anti-CD33 CAR (LTG1936)

<400> SEQUENCE: 47

Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
            20                  25                  30

Val Lys Lys Pro Gly Glu Ser Leu Arg Ile Ser Cys Lys Gly Ser Gly
        35                  40                  45

Phe Ser Phe Pro Thr Tyr Trp Ile Gly Trp Val Arg Gln Met Pro Gly
    50                  55                  60

Lys Gly Leu Glu Trp Met Gly Ile Ile Tyr Pro Gly Asp Ser Asp Thr
65                  70                  75                  80

Arg Tyr Ser Pro Ser Phe Gln Gly Gln Val Thr Ile Ser Ala Asp Lys
                85                  90                  95

Ser Ile Ser Thr Ala Tyr Leu Gln Trp Ser Ser Leu Lys Ala Ser Asp
            100                 105                 110

Thr Ala Met Tyr Tyr Cys Ala Arg Leu Val Gly Asp Gly Tyr Asn Thr
        115                 120                 125

Gly Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Asp
145                 150                 155                 160

Ile Val Met Thr His Thr Pro Leu Ser Leu Ser Val Thr Pro Gly Gln
                165                 170                 175

Pro Ala Ser Ile Ser Cys Lys Ser Ser Gln Ser Leu Leu His Ser Asn
            180                 185                 190

Gly Lys Thr Tyr Leu Tyr Trp Tyr Leu Gln Lys Pro Gly Gln Pro Pro
        195                 200                 205

Gln Leu Leu Ile Tyr Gly Ala Ser Asn Arg Phe Ser Gly Val Pro Asp
    210                 215                 220

Arg Phe Ser Gly Ser Gly Ser Gly Thr Asp Phe Thr Leu Lys Ile Ser
225                 230                 235                 240

Arg Val Glu Ala Glu Asp Val Gly Val Tyr Tyr Cys Met Gln Ser Ile
                245                 250                 255

Gln Leu Pro Ile Thr Phe Gly Gln Gly Thr Arg Leu Glu Ile Lys Ala
            260                 265                 270

Ala Ala Thr Thr Thr Pro Ala Pro Arg Pro Pro Thr Pro Ala Pro Thr
        275                 280                 285
```

```
Ile Ala Ser Gln Pro Leu Ser Leu Arg Pro Glu Ala Cys Arg Pro Ala
    290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Lys Arg Gly Arg Lys Lys Leu Leu Tyr
            340                 345                 350

Ile Phe Lys Gln Pro Phe Met Arg Pro Val Gln Thr Thr Gln Glu Glu
        355                 360                 365

Asp Gly Cys Ser Cys Arg Phe Pro Glu Glu Glu Glu Gly Gly Cys Glu
    370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495
```

<210> SEQ ID NO 48
<211> LENGTH: 1476
<212> TYPE: DNA
<213> ORGANISM: Artificial Sequence
<220> FEATURE:
<223> OTHER INFORMATION: anti-mesothelin CAR (LTG1904)

<400> SEQUENCE: 48

```
atgctgctgc tggtgaccag cctgctgctg tgcgaactgc cgcatccggc gtttctgctg      60

attccggagg tccagctggt acagtctggg ggaggcttgg tacagcctgg ggggtccctg     120

agactctcct gtgcagcctc tggattcacc tttgatgatt atgccatgca ctgggtccgg     180

caagctccag ggaagggcct ggagtgggtc tcaggtatta gttggaatag tggtagcata     240

ggctatgcgg actctgtgaa gggccgattc accatctcca gagacaacgc caagaactcc     300

ctgtatctgc aaatgaacag tctgagagct gaggacacgg ccttgtatta ctgtgcaaaa     360

gatttatcgt cagtggctgg accctttaac tactggggcc agggcaccct ggtcaccgtc     420

tcctcaggag gtggcgggtc tggtggaggc ggtagcggcg gtggcggatc ctcttctgag     480

ctgactcagg accctgctgt gtctgtggcc ttgggacaga cagtcaggat cacatgccaa     540

ggagacagcc tcagaagcta ttatgcaagc tggtaccagc agaagccagg acaggcccct     600

gtacttgtca tctatggtaa aaacaaccgg ccctcaggga tcccagaccg attctctggc     660

tccagctcag gaaacacagc ttccttgacc atcactgggg ctcaggcgga ggatgaggct     720

gactattact gtaactcccg ggacagcagt ggtaaccatc tggtattcgg cggaggcacc     780

cagctgaccg tcctcggtgc ggccgcaact accacccctg cccctcggcc gccgactccg     840

gccccaacca tcgcaagcca acccctctcc ttgcgccccg aagcttgccg cccggccgcg     900
```

```
ggtggagccg tgcatacccg gggctggac tttgcctgcg atatctacat ttgggccccg    960

ctggccggca cttgcggcgt gctcctgctg tcgctggtca tcaccctta ctgcaagagg   1020

ggccggaaga agctgcttta catcttcaag cagccgttca tgcggcccgt gcagacgact   1080

caggaagagg acggatgctc gtgcagattc cctgaggagg aagaggggg atgcgaactg   1140

cgcgtcaagt tctcacggtc cgccgacgcc cccgcatatc aacagggcca gaatcagctc   1200

tacaacgagc tgaacctggg aaggagagag gagtacgacg tgctggacaa gcgacgcgga   1260

cgcgacccgg agatgggggg gaaaccacgg cggaaaaacc ctcaggaagg actgtacaac   1320

gaactccaga aagacaagat ggcggaagcc tactcagaaa tcgggatgaa gggagagcgg   1380

aggaggggaa agggtcacga cgggctgtac cagggactga gcaccgccac taaggatacc   1440

tacgatgcct tgcatatgca agcactccca ccccgg                             1476
```

<210> SEQ ID NO 49
<211> LENGTH: 492
<212> TYPE: PRT
<213> ORGANISM: Artificial Sequence
<220> FEATURE:
<223> OTHER INFORMATION: anti-mesothelin CAR (LTG1904)

<400> SEQUENCE: 49

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Gly Gly
            20                  25                  30

Leu Val Gln Pro Gly Gly Ser Leu Arg Leu Ser Cys Ala Ala Ser Gly
        35                  40                  45

Phe Thr Phe Asp Asp Tyr Ala Met His Trp Val Arg Gln Ala Pro Gly
    50                  55                  60

Lys Gly Leu Glu Trp Val Ser Gly Ile Ser Trp Asn Ser Gly Ser Ile
65                  70                  75                  80

Gly Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Leu Tyr Tyr Cys Ala Lys Asp Leu Ser Ser Val Ala Gly Pro
        115                 120                 125

Phe Asn Tyr Trp Gly Gln Gly Thr Leu Val Thr Val Ser Ser Gly Gly
    130                 135                 140

Gly Gly Ser Gly Gly Gly Gly Ser Gly Gly Gly Gly Ser Ser Ser Glu
145                 150                 155                 160

Leu Thr Gln Asp Pro Ala Val Ser Val Ala Leu Gly Gln Thr Val Arg
                165                 170                 175

Ile Thr Cys Gln Gly Asp Ser Leu Arg Ser Tyr Tyr Ala Ser Trp Tyr
            180                 185                 190

Gln Gln Lys Pro Gly Gln Ala Pro Val Leu Val Ile Tyr Gly Lys Asn
        195                 200                 205

Asn Arg Pro Ser Gly Ile Pro Asp Arg Phe Ser Gly Ser Ser Ser Gly
    210                 215                 220

Asn Thr Ala Ser Leu Thr Ile Thr Gly Ala Gln Ala Glu Asp Glu Ala
225                 230                 235                 240

Asp Tyr Tyr Cys Asn Ser Arg Asp Ser Ser Gly Asn His Leu Val Phe
                245                 250                 255
```

```
Gly Gly Gly Thr Gln Leu Thr Val Leu Gly Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490
```

<210> SEQ ID NO 50
<211> LENGTH: 366
<212> TYPE: DNA
<213> ORGANISM: Artificial Sequence
<220> FEATURE:
<223> OTHER INFORMATION: heavy chain scFv 16P17

<400> SEQUENCE: 50

```
caggtacagc ttcaacagag tggccgggga ctggtgaaac actcccaaac actttctctg     60

acgtgcgcta tatcaggtga ctctgtttca tctaattctg ctgcgtggaa ctggattcga    120

caatctccca gtcgcgggtt ggaatggctg ggacgaacat attatcggtc taagtggtat    180

aacgattatg ctgtatctgt taaatctcga attacgatta atcctgacac ctccaagaac    240

cagttctccc tccagttgaa ctcagtcaca ccggaagaca ctgcggtcta ctattgcgct    300

caagaagtcg agccacatga tgcattcgac atctggggcc agggaacgat ggtcaccgtc    360

agcagt                                                               366
```

<210> SEQ ID NO 51
<211> LENGTH: 122
<212> TYPE: PRT
<213> ORGANISM: Artificial Sequence
<220> FEATURE:
<223> OTHER INFORMATION: heavy chain scFv 16P17

<400> SEQUENCE: 51

```
Gln Val Gln Leu Gln Gln Ser Gly Pro Gly Leu Val Lys His Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Gln Glu Val Glu Pro His Asp Ala Phe Asp Ile Trp
            100                 105                 110

Gly Gln Gly Thr Met Val Thr Val Ser Ser
        115                 120


<210> SEQ ID NO 52
<211> LENGTH: 321
<212> TYPE: DNA
<213> ORGANISM: Artificial Sequence
<220> FEATURE:
<223> OTHER INFORMATION: light chain scFv 16P17

<400> SEQUENCE: 52

gacatacaaa tgacgcagag tccctcaagt gtgtacgcga gtgtggggga taaggtaact      60

attacgtgca gagcgtcaca ggatgttagt ggatggcttg cctggtatca gcagaagcca     120

ggccttgctc cacagctcct tatcagtggt gcttctacac ttcagggcga ggttccgagt     180

agattctctg gttctggatc tggtactgac ttcactctta caatttcttc tttgcaacca     240

gaagactttg cgacttatta ctgccaacag gccaaatact tcccttatac atttggccaa     300

ggtaccaagt tggagataaa g                                               321


<210> SEQ ID NO 53
<211> LENGTH: 107
<212> TYPE: PRT
<213> ORGANISM: Artificial Sequence
<220> FEATURE:
<223> OTHER INFORMATION: light chain scFv 16P17

<400> SEQUENCE: 53

Asp Ile Gln Met Thr Gln Ser Pro Ser Ser Val Tyr Ala Ser Val Gly
1               5                   10                  15

Asp Lys Val Thr Ile Thr Cys Arg Ala Ser Gln Asp Val Ser Gly Trp
            20                  25                  30

Leu Ala Trp Tyr Gln Gln Lys Pro Gly Leu Ala Pro Gln Leu Leu Ile
        35                  40                  45

Ser Gly Ala Ser Thr Leu Gln Gly Glu Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Lys Tyr Phe Pro Tyr
                85                  90                  95

Thr Phe Gly Gln Gly Thr Lys Leu Glu Ile Lys
            100                 105


<210> SEQ ID NO 54
```

<211> LENGTH: 366
<212> TYPE: DNA
<213> ORGANISM: Artificial Sequence
<220> FEATURE:
<223> OTHER INFORMATION: heavy chain scFv M19217-1

<400> SEQUENCE: 54

```
gaggtccagc tggtacagtc tggagctgag gtgaagaagc ctggggcctc agtgaaggtc     60

tcctgcaagg cttctggata caccttcacc agctactata tgcactgggt gcgacaggcc    120

cctggacaag ggcttgagtg gatgggatta atcaacccta gtggtggtag cacaagctac    180

gcacagaagt tccagggcag agtcaccatg accagggaca cgtccacgag cacagtctac    240

atggagctga gcagcctgag atctgaggac acggccgtgt attactgtgc gagatcggat    300

cggggaatta ccgccacgga cgcttttgat atctggggcc aagggacaat ggtcaccgtc    360

tcttca                                                               366
```

<210> SEQ ID NO 55
<211> LENGTH: 122
<212> TYPE: PRT
<213> ORGANISM: Artificial Sequence
<220> FEATURE:
<223> OTHER INFORMATION: heavy chain scFv M19217-1

<400> SEQUENCE: 55

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Leu Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Asp Arg Gly Ile Thr Ala Thr Asp Ala Phe Asp Ile Trp
            100                 105                 110

Gly Gln Gly Thr Met Val Thr Val Ser Ser
        115                 120
```

<210> SEQ ID NO 56
<211> LENGTH: 330
<212> TYPE: DNA
<213> ORGANISM: Artificial Sequence
<220> FEATURE:
<223> OTHER INFORMATION: light chain scFv M19217-1

<400> SEQUENCE: 56

```
cagtctgtgc tgactcagcc accctcggtg tcagtggccc cagggcggat ggccaagatt     60

acctgtgggg gaagtgacat tggaaataaa aatgtccact ggtatcagca gaagccaggc    120

caggcccctg tcctggttgt ctatgatgat tacgaccggc cctcagggat ccctgagcga    180

ttctctggct ccaactctgg ggacgcggcc accctgacga tcagcacggt cgaagtcggg    240

gatgaggccg actatttctg tcaggtgtgg gacggtagtg gtgatcctta ttggatgttc    300

ggcggaggga cccagctcac cgttttaggt                                     330
```

<210> SEQ ID NO 57
<211> LENGTH: 110
<212> TYPE: PRT
<213> ORGANISM: Artificial Sequence
<220> FEATURE:
<223> OTHER INFORMATION: light chain scFv M19217-1

<400> SEQUENCE: 57

```
Gln Ser Val Leu Thr Gln Pro Pro Ser Val Ser Val Ala Pro Gly Arg
1               5                   10                  15

Met Ala Lys Ile Thr Cys Gly Gly Ser Asp Ile Gly Asn Lys Asn Val
            20                  25                  30

His Trp Tyr Gln Gln Lys Pro Gly Gln Ala Pro Val Leu Val Val Tyr
        35                  40                  45

Asp Asp Tyr Asp Arg Pro Ser Gly Ile Pro Glu Arg Phe Ser Gly Ser
    50                  55                  60

Asn Ser Gly Asp Ala Ala Thr Leu Thr Ile Ser Thr Val Glu Val Gly
65                  70                  75                  80

Asp Glu Ala Asp Tyr Phe Cys Gln Val Trp Asp Gly Ser Gly Asp Pro
                85                  90                  95

Tyr Trp Met Phe Gly Gly Gly Thr Gln Leu Thr Val Leu Gly
            100                 105                 110
```

<210> SEQ ID NO 58
<211> LENGTH: 1482
<212> TYPE: DNA
<213> ORGANISM: Artificial Sequence
<220> FEATURE:
<223> OTHER INFORMATION: CAR22 LTG2200 (M971-CD8TM-4-1BB-zeta)

<400> SEQUENCE: 58

```
atgcttcttt tggtgacttc ccttttgctg tgcgagttgc cacaccccgc cttcctgctt     60

attccccagg tacagctcca gcagagtggc ccagggctcg tgaagccaag ccagacgctg    120

tccctgactt gtgcaatttc aggggattca gtttcatcaa atagcgcggc gtggaattgg    180

attcgacaat ctccttcccg agggttggaa tggcttggac gaacatatta cagatccaaa    240

tggtataacg actatgcggt atcagtaaag tcaagaataa ccattaaccc cgacacaagc    300

aagaaccaat tctctttgca gcttaactct gtcacgccag aagacacggc agtctattat    360

tgcgctcgcg aggtaacggg tgacctggaa gacgcttttg acatttgggg gcagggtacg    420

atggtgacag tcagttcagg gggcggtggg agtgggggag gggtagcgg gggggaggg    480

tcagacattc agatgaccca gtccccttca tccttgtctg cctccgtcgg tgacagggtg    540

acaataacat gcagagcaag ccaaacaatc tggagctatc tcaactggta ccagcagcga    600

ccaggaaaag cgccaaacct gctgatttac gctgcttcct ccctccaatc aggcgtgcct    660

agtagattta gcggtagggg ctccggcacc gattttacgc tcactataag ctctcttcaa    720

gcagaagatt ttgcgactta ttactgccag cagtcctata gtatacctca gactttcgga    780

cagggtacca agttggagat taaggcggcc gcaactacca cccctgcccc tcggccgccg    840

actccggccc caaccatcgc aagccaaccc ctctccttgc gccccgaagc ttgccgcccg    900

gccgcgggtg gagccgtgca tacccggggg ctggactttg cctgcgatat ctacatttgg    960

gccccgctgg ccggcacttg cggcgtgctc ctgctgtcgc tggtcatcac cctttactgc   1020

aagaggggcc ggaagaagct gctttacatc ttcaagcagc cgttcatgcg gcccgtgcag   1080

acgactcagg aagaggacgg atgctcgtgc agattccctg aggaggaaga gggggggatgc   1140

gaactgcgcg tcaagttctc acggtccgcc gacgcccccg catatcaaca gggccagaat   1200
```

```
cagctctaca acgagctgaa cctgggaagg agagaggagt acgacgtgct ggacaagcga   1260

cgcggacgcg acccggagat gggggggaaa ccacggcgga aaaaccctca ggaaggactg   1320

tacaacgaac tccagaaaga caagatggcg gaagcctact cagaaatcgg gatgaaggga   1380

gagcggagga ggggaaaggg tcacgacggg ctgtaccagg gactgagcac cgccactaag   1440

gatacctacg atgccttgca tatgcaagca ctcccacccc gg                      1482
```

<210> SEQ ID NO 59
<211> LENGTH: 494
<212> TYPE: PRT
<213> ORGANISM: Artificial Sequence
<220> FEATURE:
<223> OTHER INFORMATION: CAR22 LTG2200 (M971-CD8TM-4-1BB-zeta)

<400> SEQUENCE: 59

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Glu Val Thr Gly Asp
        115                 120                 125

Leu Glu Asp Ala Phe Asp Ile Trp Gly Gln Gly Thr Met Val Thr Val
    130                 135                 140

Ser Ser Gly Gly Gly Gly Ser Gly Gly Gly Gly Ser Gly Gly Gly Gly
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Arg Ala Ser Gln Thr Ile Trp Ser
            180                 185                 190

Tyr Leu Asn Trp Tyr Gln Gln Arg Pro Gly Lys Ala Pro Asn Leu Leu
        195                 200                 205

Ile Tyr Ala Ala Ser Ser Leu Gln Ser Gly Val Pro Ser Arg Phe Ser
    210                 215                 220

Gly Arg Gly Ser Gly Thr Asp Phe Thr Leu Thr Ile Ser Ser Leu Gln
225                 230                 235                 240

Ala Glu Asp Phe Ala Thr Tyr Tyr Cys Gln Gln Ser Tyr Ser Ile Pro
                245                 250                 255

Gln Thr Phe Gly Gln Gly Thr Lys Leu Glu Ile Lys Ala Ala Ala Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
```

```
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490


<210> SEQ ID NO 60
<211> LENGTH: 2292
<212> TYPE: DNA
<213> ORGANISM: Artificial Sequence
<220> FEATURE:
<223> OTHER INFORMATION: CAR LTG2737 (CD22-19 CD8 BBz)

<400> SEQUENCE: 60

atgctcttgc tcgtgacttc tttgcttttg tgcgaacttc cgcacccagc cttccttttg      60

atacctcagg tacagcttca acaaagcgga ccgggacttg ttaagcattc ccaaaccctt     120

tctctcacgt gtgcaattag cggcgatagt gtatcctcta attctgcggc ctggaactgg     180

atacgacaat caccaagccg gggactcgag tggttgggcc gaacctacta tcggtccaaa     240

tggtataatg actacgcagt atccgtgaaa tctcgcatta cgatcaatcc agacacctcc     300

aaaaatcaat tttctctgca gttgaatagc gtgactcccg aggacacggc cgtttactat     360

tgcgcccagg aagttgaacc ccacgatgca tttgatattt ggggccaggg aaccatggtg     420

acagtgagta gtgggggtgg aggatctgga ggaggcggta gcggcggggg cggcagtgat     480

atccagatga cgcagtcacc ttccagcgtg tatgcgagtg tgggggacaa ggtcaccata     540

acctgtcgcg ctagccaaga tgtcagcggg tggctggctt ggtaccagca gaaaccaggt     600

ttggctcctc agcttttgat ctcaggagcg agcacgcttc agggtgaggt cccaagtcgc     660

tttagtggct ctggctccgg gacagacttc acgttgacga tcagcagttt gcagcctgag     720

gatttcgcga cctactactg ccagcaagcg aaatattttc cgtacacttt cggtcagggg     780

accaaattgg agatcaaagg tgggggtggt tcaggcggcg gaggctcagg cggcggcggt     840

agcggaggag gcggaagcgg gggtggcgga tcagaagtgc aactcgttca gagtggcgcg     900

gaggttaaga aacccggtgc atctgtaaag gttagctgta aggcatcagg atacactttt     960

accagctatt acatgcattg ggtgagacag gctcccggtc aggggctcga atggatgggg    1020
```

```
ttgatcaacc cgagtggtgg ttcaacatct tacgcccaga agtttcaggg ccgagtaaca   1080

atgactcggg acacgtctac ctcaactgtg tatatggagc tttccagcct gcgctcagag   1140

gatacagcag tctattactg cgcacggtca gacagaggta taacggccac tgatgcgttc   1200

gatatctggg gacaagggac tatggtaact gtgtcttccg gaggaggagg tagtggaggg   1260

ggaggaagcg gtgggggggg ctcacagtcc gttttgactc agccaccaag cgtctcagtc   1320

gcaccggggc gaatggcgaa aattacttgc ggcgggagcg acataggcaa caagaatgtg   1380

cattggtacc aacagaaacc aggtcaagca cctgttctcg tggtgtatga tgactacgat   1440

cgcccaagcg ggatcccgga gcggttctct ggatcaaatt ctggtgatgc agccactctg   1500

acaatatcaa cggtggaagt cggtgacgag gctgattact tctgccaagt atgggatggc   1560

agcggagatc cctactggat gtttggagga ggtactcaac tgacagttct gggcgcggcc   1620

gcaacgacca ctcctgcacc ccgccctccg actccggccc caaccattgc cagccagccc   1680

ctgtccctgc ggccggaagc ctgcagaccg gctgccggcg gagccgtcca tacccgggga   1740

ctggatttcg cctgcgatat ctatatctgg gcaccactcg ccggaacctg tggagtgctg   1800

ctgctgtccc ttgtgatcac cctgtactgc aagcgcggac ggaagaaact cttgtacatc   1860

ttcaagcagc cgttcatgcg ccctgtgcaa accacccaag aagaggacgg gtgctcctgc   1920

cggttcccgg aagaggaaga gggcggctgc gaactgcgcg tgaagttttc ccggtccgcc   1980

gacgctccgg cgtaccagca ggggcaaaac cagctgtaca acgaacttaa cctcggtcgc   2040

cgggaagaat atgacgtgct ggacaagcgg cggggaagag atcccgagat gggtggaaag   2100

ccgcggcgga agaaccctca ggagggcttg tacaacgagc tgcaaaagga caaaatggcc   2160

gaagcctact ccgagattgg catgaaggga gagcgcagac gcgggaaggg acacgatgga   2220

ctgtaccagg gactgtcaac cgcgactaag gacacttacg acgccctgca catgcaggcc   2280

ctgcccccgc gc                                                        2292
```

```
<210> SEQ ID NO 61
<211> LENGTH: 764
<212> TYPE: PRT
<213> ORGANISM: Artificial Sequence
<220> FEATURE:
<223> OTHER INFORMATION: CAR LTG2737 (CD22-19 CD8 BBz)

<400> SEQUENCE: 61

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys His Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro His
        115                 120                 125

Asp Ala Phe Asp Ile Trp Gly Gln Gly Thr Met Val Thr Val Ser Ser
```

```
    130                 135                 140

Gly Gly Gly Gly Ser Gly Gly Gly Gly Ser Gly Gly Gly Gly Ser Asp
145                 150                 155                 160

Ile Gln Met Thr Gln Ser Pro Ser Ser Val Tyr Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
        195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Gly Gly Gly Gly Ser Gly
            260                 265                 270

Gly Gly Gly Ser Gly Gly Gly Gly Ser Gly Gly Gly Gly Ser Gly Gly
        275                 280                 285

Gly Gly Ser Glu Val Gln Leu Val Gln Ser Gly Ala Glu Val Lys Lys
    290                 295                 300

Pro Gly Ala Ser Val Lys Val Ser Cys Lys Ala Ser Gly Tyr Thr Phe
305                 310                 315                 320

Thr Ser Tyr Tyr Met His Trp Val Arg Gln Ala Pro Gly Gln Gly Leu
                325                 330                 335

Glu Trp Met Gly Leu Ile Asn Pro Ser Gly Gly Ser Thr Ser Tyr Ala
            340                 345                 350

Gln Lys Phe Gln Gly Arg Val Thr Met Thr Arg Asp Thr Ser Thr Ser
        355                 360                 365

Thr Val Tyr Met Glu Leu Ser Ser Leu Arg Ser Glu Asp Thr Ala Val
    370                 375                 380

Tyr Tyr Cys Ala Arg Ser Asp Arg Gly Ile Thr Ala Thr Asp Ala Phe
385                 390                 395                 400

Asp Ile Trp Gly Gln Gly Thr Met Val Thr Val Ser Ser Gly Gly Gly
                405                 410                 415

Gly Ser Gly Gly Gly Gly Ser Gly Gly Gly Gly Ser Gln Ser Val Leu
            420                 425                 430

Thr Gln Pro Pro Ser Val Ser Val Ala Pro Gly Arg Met Ala Lys Ile
        435                 440                 445

Thr Cys Gly Gly Ser Asp Ile Gly Asn Lys Asn Val His Trp Tyr Gln
    450                 455                 460

Gln Lys Pro Gly Gln Ala Pro Val Leu Val Val Tyr Asp Asp Tyr Asp
465                 470                 475                 480

Arg Pro Ser Gly Ile Pro Glu Arg Phe Ser Gly Ser Asn Ser Gly Asp
                485                 490                 495

Ala Ala Thr Leu Thr Ile Ser Thr Val Glu Val Gly Asp Glu Ala Asp
            500                 505                 510

Tyr Phe Cys Gln Val Trp Asp Gly Ser Gly Asp Pro Tyr Trp Met Phe
        515                 520                 525

Gly Gly Gly Thr Gln Leu Thr Val Leu Gly Ala Ala Ala Thr Thr Thr
    530                 535                 540

Pro Ala Pro Arg Pro Pro Thr Pro Ala Pro Thr Ile Ala Ser Gln Pro
545                 550                 555                 560
```

```
Leu Ser Leu Arg Pro Glu Ala Cys Arg Pro Ala Ala Gly Gly Ala Val
                565                 570                 575

His Thr Arg Gly Leu Asp Phe Ala Cys Asp Ile Tyr Ile Trp Ala Pro
            580                 585                 590

Leu Ala Gly Thr Cys Gly Val Leu Leu Leu Ser Leu Val Ile Thr Leu
        595                 600                 605

Tyr Cys Lys Arg Gly Arg Lys Lys Leu Leu Tyr Ile Phe Lys Gln Pro
    610                 615                 620

Phe Met Arg Pro Val Gln Thr Thr Gln Glu Glu Asp Gly Cys Ser Cys
625                 630                 635                 640

Arg Phe Pro Glu Glu Glu Glu Gly Gly Cys Glu Leu Arg Val Lys Phe
                645                 650                 655

Ser Arg Ser Ala Asp Ala Pro Ala Tyr Gln Gln Gly Gln Asn Gln Leu
            660                 665                 670

Tyr Asn Glu Leu Asn Leu Gly Arg Arg Glu Glu Tyr Asp Val Leu Asp
        675                 680                 685

Lys Arg Arg Gly Arg Asp Pro Glu Met Gly Gly Lys Pro Arg Arg Lys
    690                 695                 700

Asn Pro Gln Glu Gly Leu Tyr Asn Glu Leu Gln Lys Asp Lys Met Ala
705                 710                 715                 720

Glu Ala Tyr Ser Glu Ile Gly Met Lys Gly Glu Arg Arg Arg Gly Lys
                725                 730                 735

Gly His Asp Gly Leu Tyr Gln Gly Leu Ser Thr Ala Thr Lys Asp Thr
            740                 745                 750

Tyr Asp Ala Leu His Met Gln Ala Leu Pro Pro Arg
        755                 760
```

<210> SEQ ID NO 62
<211> LENGTH: 2289
<212> TYPE: DNA
<213> ORGANISM: Artificial Sequence
<220> FEATURE:
<223> OTHER INFORMATION: CAR D0135 CD22-19 CD8 CD28z

<400> SEQUENCE: 62

```
atgctcttgc tcgtgacttc tttgcttttg tgcgaacttc cgcacccagc cttccttttg     60

atacctcagg tacagcttca acaaagcgga ccgggacttg ttaagcattc ccaaaccctt    120

tctctcacgt gtgcaattag cggcgatagt gtatcctcta attctgcggc ctggaactgg    180

atacgacaat caccaagccg gggactcgag tggttgggcc gaacctacta tcggtccaaa    240

tggtataatg actacgcagt atccgtgaaa tctcgcatta cgatcaatcc agacacctcc    300

aaaaatcaat tttctctgca gttgaatagc gtgactcccg aggacacggc cgtttactat    360

tgcgcccagg aagttgaacc ccacgatgca tttgatattt ggggccaggg aaccatggtg    420

acagtgagta gtgggggtgg aggatctgga ggaggcggta gcggcggggg cggcagtgat    480

atccagatga cgcagtcacc ttccagcgtg tatgcgagtg tgggggacaa ggtcaccata    540

acctgtcgcg ctagccaaga tgtcagcggg tggctggctt ggtaccagca gaaaccaggt    600

ttggctcctc agcttttgat ctcaggagcg agcacgcttc agggtgaggt cccaagtcgc    660

tttagtggct ctggctccgg gacagacttc acgttgacga tcagcagttt gcagcctgag    720

gatttcgcga cctactactg ccagcaagcg aaatattttc cgtacacttt cggtcagggg    780

accaaattgg agatcaaagg tgggggtggt tcaggcggcg gaggctcagg cggcggcggt    840

agcggaggag gcggaagcgg gggtggcgga tcagaagtgc aactcgttca gagtggcgcg    900
```

```
gaggttaaga aacccggtgc atctgtaaag gttagctgta aggcatcagg atacactttt    960
accagctatt acatgcattg ggtgagacag gctcccggtc aggggctcga atggatgggg   1020
ttgatcaacc cgagtggtgg ttcaacatct tacgcccaga agtttcaggg ccgagtaaca   1080
atgactcggg acacgtctac ctcaactgtg tatatggagc tttccagcct gcgctcagag   1140
gatacagcag tctattactg cgcacggtca gacagaggta taacggccac tgatgcgttc   1200
gatatctggg gacaagggac tatggtaact gtgtcttccg gaggaggagg tagtggaggg   1260
ggaggaagcg gtgggggggg ctcacagtcc gttttgactc agccaccaag cgtctcagtc   1320
gcaccggggc gaatggcgaa aattacttgc ggcgggagcg acataggcaa caagaatgtg   1380
cattggtacc aacagaaacc aggtcaagca cctgttctcg tggtgtatga tgactacgat   1440
cgcccaagcg ggatcccgga gcggttctct ggatcaaatt ctggtgatgc agccactctg   1500
acaatatcaa cggtggaagt cggtgacgag gctgattact tctgccaagt atgggatggc   1560
agcggagatc cctactggat gtttggagga ggtactcaac tgacagttct gggcgcggcc   1620
gcgactacca ctcctgcacc acggccacct accccagccc ccaccattgc aagccagcca   1680
ctttcactgc gccccgaagc gtgtagacca gctgctggag gagccgtgca tacccgaggg   1740
ctggacttcg cctgtgacat ctacatctgg gccccattgg ctggaacttg cggcgtgctg   1800
ctcttgtctc tggtcattac cctgtactgc cggtcgaaga ggtccagact cttgcactcc   1860
gactacatga acatgactcc tagaaggccc ggacccacta gaaagcacta ccagccgtac   1920
gcccctcctc gggatttcgc cgcataccgg tccagagtga agttcagccg ctcagccgat   1980
gcaccggcct accagcaggg acagaaccag ctctacaacg agctcaacct gggtcggcgg   2040
gaagaatatg acgtgctgga caaacggcgc ggcagagatc cggagatggg gggaaagccg   2100
aggaggaaga accctcaaga gggcctgtac aacgaactgc agaaggacaa gatggcggaa   2160
gcctactccg agatcggcat gaagggagaa cgccggagag ggaagggtca tgacggactg   2220
taccagggcc tgtcaactgc cactaaggac acttacgatg cgctccatat gcaagctttg   2280
cccccgcgg                                                           2289
```

```
<210> SEQ ID NO 63
<211> LENGTH: 763
<212> TYPE: PRT
<213> ORGANISM: Artificial Sequence
<220> FEATURE:
<223> OTHER INFORMATION: CAR D0135 CD22-19 CD8 CD28z

<400> SEQUENCE: 63

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys His Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110
```

```
Pro Glu Asp Thr Ala Val Tyr Tyr Cys Ala Gln Glu Val Glu Pro His
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Asp
145                 150                 155                 160

Ile Gln Met Thr Gln Ser Pro Ser Ser Val Tyr Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
        195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Gly Gly Gly Gly Ser Gly
            260                 265                 270

Gly Gly Gly Ser Gly Gly Gly Gly Ser Gly Gly Gly Gly Ser Gly Gly
        275                 280                 285

Gly Gly Ser Glu Val Gln Leu Val Gln Ser Gly Ala Glu Val Lys Lys
    290                 295                 300

Pro Gly Ala Ser Val Lys Val Ser Cys Lys Ala Ser Gly Tyr Thr Phe
305                 310                 315                 320

Thr Ser Tyr Tyr Met His Trp Val Arg Gln Ala Pro Gly Gln Gly Leu
                325                 330                 335

Glu Trp Met Gly Leu Ile Asn Pro Ser Gly Gly Ser Thr Ser Tyr Ala
            340                 345                 350

Gln Lys Phe Gln Gly Arg Val Thr Met Thr Arg Asp Thr Ser Thr Ser
        355                 360                 365

Thr Val Tyr Met Glu Leu Ser Ser Leu Arg Ser Glu Asp Thr Ala Val
    370                 375                 380

Tyr Tyr Cys Ala Arg Ser Asp Arg Gly Ile Thr Ala Thr Asp Ala Phe
385                 390                 395                 400

Asp Ile Trp Gly Gln Gly Thr Met Val Thr Val Ser Ser Gly Gly Gly
                405                 410                 415

Gly Ser Gly Gly Gly Gly Ser Gly Gly Gly Gly Ser Gln Ser Val Leu
            420                 425                 430

Thr Gln Pro Pro Ser Val Ser Val Ala Pro Gly Arg Met Ala Lys Ile
        435                 440                 445

Thr Cys Gly Gly Ser Asp Ile Gly Asn Lys Asn Val His Trp Tyr Gln
    450                 455                 460

Gln Lys Pro Gly Gln Ala Pro Val Leu Val Val Tyr Asp Asp Tyr Asp
465                 470                 475                 480

Arg Pro Ser Gly Ile Pro Glu Arg Phe Ser Gly Ser Asn Ser Gly Asp
                485                 490                 495

Ala Ala Thr Leu Thr Ile Ser Thr Val Glu Val Gly Asp Glu Ala Asp
            500                 505                 510

Tyr Phe Cys Gln Val Trp Asp Gly Ser Gly Asp Pro Tyr Trp Met Phe
        515                 520                 525
```

```
Gly Gly Gly Thr Gln Leu Thr Val Leu Gly Ala Ala Ala Thr Thr Thr
    530                 535                 540

Pro Ala Pro Arg Pro Pro Thr Pro Ala Pro Thr Ile Ala Ser Gln Pro
545                 550                 555                 560

Leu Ser Leu Arg Pro Glu Ala Cys Arg Pro Ala Ala Gly Gly Ala Val
                565                 570                 575

His Thr Arg Gly Leu Asp Phe Ala Cys Asp Ile Tyr Ile Trp Ala Pro
            580                 585                 590

Leu Ala Gly Thr Cys Gly Val Leu Leu Leu Ser Leu Val Ile Thr Leu
        595                 600                 605

Tyr Cys Arg Ser Lys Arg Ser Arg Leu Leu His Ser Asp Tyr Met Asn
    610                 615                 620

Met Thr Pro Arg Arg Pro Gly Pro Thr Arg Lys His Tyr Gln Pro Tyr
625                 630                 635                 640

Ala Pro Pro Arg Asp Phe Ala Ala Tyr Arg Ser Arg Val Lys Phe Ser
                645                 650                 655

Arg Ser Ala Asp Ala Pro Ala Tyr Gln Gln Gly Gln Asn Gln Leu Tyr
            660                 665                 670

Asn Glu Leu Asn Leu Gly Arg Arg Glu Glu Tyr Asp Val Leu Asp Lys
        675                 680                 685

Arg Arg Gly Arg Asp Pro Glu Met Gly Gly Lys Pro Arg Arg Lys Asn
    690                 695                 700

Pro Gln Glu Gly Leu Tyr Asn Glu Leu Gln Lys Asp Lys Met Ala Glu
705                 710                 715                 720

Ala Tyr Ser Glu Ile Gly Met Lys Gly Glu Arg Arg Arg Gly Lys Gly
                725                 730                 735

His Asp Gly Leu Tyr Gln Gly Leu Ser Thr Ala Thr Lys Asp Thr Tyr
            740                 745                 750

Asp Ala Leu His Met Gln Ala Leu Pro Pro Arg
        755                 760
```

<210> SEQ ID NO 64
<211> LENGTH: 2277
<212> TYPE: DNA
<213> ORGANISM: Artificial Sequence
<220> FEATURE:
<223> OTHER INFORMATION: CAR D0136 CD22-19 CD8 ICOSz DNA

<400> SEQUENCE: 64

```
atgctcttgc tcgtgacttc tttgcttttg tgcgaacttc cgcacccagc cttccttttg     60

atacctcagg tacagcttca acaaagcgga ccgggacttg ttaagcattc ccaaaccctt    120

tctctcacgt gtgcaattag cggcgatagt gtatcctcta attctgcggc ctggaactgg    180

atacgacaat caccaagccg gggactcgag tggttgggcc gaacctacta tcggtccaaa    240

tggtataatg actacgcagt atccgtgaaa tctcgcatta cgatcaatcc agacacctcc    300

aaaaatcaat tttctctgca gttgaatagc gtgactcccg aggacacggc cgtttactat    360

tgcgcccagg aagttgaacc ccacgatgca tttgatattt ggggccaggg aaccatggtg    420

acagtgagta gtgggggtgg aggatctgga ggaggcggta gcggcggggg cggcagtgat    480

atccagatga cgcagtcacc ttccagcgtg tatgcgagtg tgggggacaa ggtcaccata    540

acctgtcgcg ctagccaaga tgtcagcggg tggctggctt ggtaccagca gaaaccaggt    600

ttggctcctc agcttttgat ctcaggagcg agcacgcttc agggtgaggt cccaagtcgc    660

tttagtggct ctggctccgg gacagacttc acgttgacga tcagcagttt gcagcctgag    720
```

```
gatttcgcga cctactactg ccagcaagcg aaatattttc cgtacacttt cggtcagggg    780

accaaattgg agatcaaagg tgggggtggt tcaggcggcg gaggctcagg cggcggcggt    840

agcggaggag gcggaagcgg gggtggcgga tcagaagtgc aactcgttca gagtggcgcg    900

gaggttaaga aacccggtgc atctgtaaag gttagctgta aggcatcagg atacactttt    960

accagctatt acatgcattg ggtgagacag gctcccggtc aggggctcga atggatgggg   1020

ttgatcaacc cgagtggtgg ttcaacatct tacgcccaga agtttcaggg ccgagtaaca   1080

atgactcggg acacgtctac ctcaactgtg tatatggagc tttccagcct gcgctcagag   1140

gatacagcag tctattactg cgcacggtca gacagaggta taacggccac tgatgcgttc   1200

gatatctggg gacaagggac tatggtaact gtgtcttccg gaggaggagg tagtggaggg   1260

ggaggaagcg gtgggggggg ctcacagtcc gttttgactc agccaccaag cgtctcagtc   1320

gcaccggggc gaatggcgaa aattacttgc ggcgggagcg acataggcaa caagaatgtg   1380

cattggtacc aacagaaacc aggtcaagca cctgttctcg tggtgtatga tgactacgat   1440

cgcccaagcg ggatcccgga gcggttctct ggatcaaatt ctggtgatgc agccactctg   1500

acaatatcaa cggtggaagt cggtgacgag gctgattact tctgccaagt atgggatggc   1560

agcggagatc cctactggat gtttggagga ggtactcaac tgacagttct gggcgcggcc   1620

gcgactacca ctcctgcacc acggccacct accccagccc ccaccattgc aagccagcca   1680

ctttcactgc gccccgaagc gtgtagacca gctgctggag gagccgtgca tacccgaggg   1740

ctggacttcg cctgtgacat ctacatctgg gccccattgg ctggaacttg cggcgtgctg   1800

ctcttgtctc tggtcattac cctgtactgc tggctgacaa aaaagaagta ttcatctagt   1860

gtacatgatc cgaacggtga atacatgttc atgcgcgcgg tgaacacggc caagaagagc   1920

agactgaccg acgtaaccct tagagtgaag ttcagccgct cagccgatgc accggcctac   1980

cagcagggac agaaccagct ctacaacgag ctcaacctgg gtcggcggga agaatatgac   2040

gtgctggaca aacggcgcgg cagagatccg gagatggggg gaaagccgag gaggaagaac   2100

cctcaagagg gcctgtacaa cgaactgcag aaggacaaga tggcggaagc ctactccgag   2160

atcggcatga agggagaacg ccggagaggg aagggtcatg acggactgta ccagggcctg   2220

tcaactgcca ctaaggacac ttacgatgcg ctccatatgc aagctttgcc cccgcgg      2277
```

<210> SEQ ID NO 65
<211> LENGTH: 759
<212> TYPE: PRT
<213> ORGANISM: Artificial Sequence
<220> FEATURE:
<223> OTHER INFORMATION: CAR D0136 CD22-19 CD8 ICOSz DNA

<400> SEQUENCE: 65

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys His Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95
```

```
Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro His
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Asp
145                 150                 155                 160

Ile Gln Met Thr Gln Ser Pro Ser Ser Val Tyr Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
        195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Gly Gly Gly Gly Ser Gly
            260                 265                 270

Gly Gly Gly Ser Gly Gly Gly Gly Ser Gly Gly Gly Gly Ser Gly Gly
        275                 280                 285

Gly Gly Ser Glu Val Gln Leu Val Gln Ser Gly Ala Glu Val Lys Lys
    290                 295                 300

Pro Gly Ala Ser Val Lys Val Ser Cys Lys Ala Ser Gly Tyr Thr Phe
305                 310                 315                 320

Thr Ser Tyr Tyr Met His Trp Val Arg Gln Ala Pro Gly Gln Gly Leu
                325                 330                 335

Glu Trp Met Gly Leu Ile Asn Pro Ser Gly Gly Ser Thr Ser Tyr Ala
            340                 345                 350

Gln Lys Phe Gln Gly Arg Val Thr Met Thr Arg Asp Thr Ser Thr Ser
        355                 360                 365

Thr Val Tyr Met Glu Leu Ser Ser Leu Arg Ser Glu Asp Thr Ala Val
    370                 375                 380

Tyr Tyr Cys Ala Arg Ser Asp Arg Gly Ile Thr Ala Thr Asp Ala Phe
385                 390                 395                 400

Asp Ile Trp Gly Gln Gly Thr Met Val Thr Val Ser Ser Gly Gly Gly
                405                 410                 415

Gly Ser Gly Gly Gly Gly Ser Gly Gly Gly Gly Ser Gln Ser Val Leu
            420                 425                 430

Thr Gln Pro Pro Ser Val Ser Val Ala Pro Gly Arg Met Ala Lys Ile
        435                 440                 445

Thr Cys Gly Gly Ser Asp Ile Gly Asn Lys Asn Val His Trp Tyr Gln
    450                 455                 460

Gln Lys Pro Gly Gln Ala Pro Val Leu Val Val Tyr Asp Asp Tyr Asp
465                 470                 475                 480

Arg Pro Ser Gly Ile Pro Glu Arg Phe Ser Gly Ser Asn Ser Gly Asp
                485                 490                 495

Ala Ala Thr Leu Thr Ile Ser Thr Val Glu Val Gly Asp Glu Ala Asp
            500                 505                 510
```

```
Tyr Phe Cys Gln Val Trp Asp Gly Ser Gly Asp Pro Tyr Trp Met Phe
        515                 520                 525

Gly Gly Gly Thr Gln Leu Thr Val Leu Gly Ala Ala Ala Thr Thr Thr
    530                 535                 540

Pro Ala Pro Arg Pro Pro Thr Pro Ala Pro Thr Ile Ala Ser Gln Pro
545                 550                 555                 560

Leu Ser Leu Arg Pro Glu Ala Cys Arg Pro Ala Ala Gly Gly Ala Val
                565                 570                 575

His Thr Arg Gly Leu Asp Phe Ala Cys Asp Ile Tyr Ile Trp Ala Pro
            580                 585                 590

Leu Ala Gly Thr Cys Gly Val Leu Leu Leu Ser Leu Val Ile Thr Leu
        595                 600                 605

Tyr Cys Trp Leu Thr Lys Lys Lys Tyr Ser Ser Ser Val His Asp Pro
    610                 615                 620

Asn Gly Glu Tyr Met Phe Met Arg Ala Val Asn Thr Ala Lys Lys Ser
625                 630                 635                 640

Arg Leu Thr Asp Val Thr Leu Arg Val Lys Phe Ser Arg Ser Ala Asp
                645                 650                 655

Ala Pro Ala Tyr Gln Gln Gly Gln Asn Gln Leu Tyr Asn Glu Leu Asn
            660                 665                 670

Leu Gly Arg Arg Glu Glu Tyr Asp Val Leu Asp Lys Arg Arg Gly Arg
        675                 680                 685

Asp Pro Glu Met Gly Gly Lys Pro Arg Arg Lys Asn Pro Gln Glu Gly
    690                 695                 700

Leu Tyr Asn Glu Leu Gln Lys Asp Lys Met Ala Glu Ala Tyr Ser Glu
705                 710                 715                 720

Ile Gly Met Lys Gly Glu Arg Arg Arg Gly Lys Gly His Asp Gly Leu
                725                 730                 735

Tyr Gln Gly Leu Ser Thr Ala Thr Lys Asp Thr Tyr Asp Ala Leu His
            740                 745                 750

Met Gln Ala Leu Pro Pro Arg
        755
```

<210> SEQ ID NO 66
<211> LENGTH: 2283
<212> TYPE: DNA
<213> ORGANISM: Artificial Sequence
<220> FEATURE:
<223> OTHER INFORMATION: CAR D0137 CD22-19 CD8 OX40TM OX40z

<400> SEQUENCE: 66

```
atgctcttgc tcgtgacttc tttgcttttg tgcgaacttc cgcacccagc cttccttttg     60

atacctcagg tacagcttca acaaagcgga ccgggacttg ttaagcattc ccaaaccctt    120

tctctcacgt gtgcaattag cggcgatagt gtatcctcta attctgcggc ctggaactgg    180

atacgacaat caccaagccg gggactcgag tggttgggcc gaacctacta tcggtccaaa    240

tggtataatg actacgcagt atccgtgaaa tctcgcatta cgatcaatcc agacacctcc    300

aaaaatcaat tttctctgca gttgaatagc gtgactcccg aggacacggc cgtttactat    360

tgcgcccagg aagttgaacc ccacgatgca tttgatattt ggggccaggg aaccatggtg    420

acagtgagta gtgggggtgg aggatctgga ggaggcggta gcggcggggg cggcagtgat    480

atccagatga cgcagtcacc ttccagcgtg tatgcgagtg tgggggacaa ggtcaccata    540

acctgtcgcg ctagccaaga tgtcagcggg tggctggctt ggtaccagca gaaaccaggt    600

ttggctcctc agcttttgat ctcaggagcg agcacgcttc agggtgaggt cccaagtcgc    660
```

```
tttagtggct ctggctccgg gacagacttc acgttgacga tcagcagttt gcagcctgag    720

gatttcgcga cctactactg ccagcaagcg aaatattttc cgtacacttt cggtcagggg    780

accaaattgg agatcaaagg tgggggtggt tcaggcggcg gaggctcagg cggcggcggt    840

agcggaggag gcggaagcgg gggtggcgga tcagaagtgc aactcgttca gagtggcgcg    900

gaggttaaga aacccggtgc atctgtaaag gttagctgta aggcatcagg atacactttt    960

accagctatt acatgcattg ggtgagacag gctcccggtc aggggctcga atggatgggg   1020

ttgatcaacc cgagtggtgg ttcaacatct tacgcccaga agtttcaggg ccgagtaaca   1080

atgactcggg acacgtctac ctcaactgtg tatatggagc tttccagcct gcgctcagag   1140

gatacagcag tctattactg cgcacggtca gacagaggta taacggccac tgatgcgttc   1200

gatatctggg gacaagggac tatggtaact gtgtcttccg gaggaggagg tagtggaggg   1260

ggaggaagcg gtgggggggg ctcacagtcc gttttgactc agccaccaag cgtctcagtc   1320

gcaccggggc gaatggcgaa aattacttgc ggcgggagcg acataggcaa caagaatgtg   1380

cattggtacc aacagaaacc aggtcaagca cctgttctcg tggtgtatga tgactacgat   1440

cgcccaagcg ggatcccgga gcggttctct ggatcaaatt ctggtgatgc agccactctg   1500

acaatatcaa cggtggaagt cggtgacgag gctgattact tctgccaagt atgggatggc   1560

agcggagatc cctactggat gtttggagga ggtactcaac tgacagttct gggcgcggcc   1620

gcaacgacca ctccagcacc gagaccgcca acccccgcgc ctaccatcgc aagtcaacca   1680

ctttctctca ggcctgaagc gtgccgacct gcagctggtg gggcagtaca taccaggggt   1740

ttggacttcg catgtgacgt ggcggcaatt ctcggcctgg gacttgtcct tggtctgctt   1800

ggtccgctcg caatacttct ggccttgtac ctgctccgca gagaccaaag acttccgccc   1860

gacgcccaca agccccccagg aggaggttcc ttcagaacgc ctatacaaga agaacaagca   1920

gatgcccact ctaccctggc taaaatcagg gtgaagttta gccggtcagc tgatgcacct   1980

gcatatcagc agggacagaa ccagctgtac aatgagctga acctcggacg aagagaggag   2040

tacgacgtgt tggacaaaag acgaggtaga gaccccgaga tgggcggcaa gccgagaaga   2100

aaaaacccac aagaagggct ttataatgag cttcagaaag ataagatggc agaggcctac   2160

agtgagattg gcatgaaggg cgaaagaagg aggggcaaag gacacgacgg tctctaccaa   2220

ggcctcagca cggctaccaa agatacgtat gacgcattgc atatgcaggc attgccgccc   2280

cgc                                                                 2283
```

```
<210> SEQ ID NO 67
<211> LENGTH: 760
<212> TYPE: PRT
<213> ORGANISM: Artificial Sequence
<220> FEATURE:
<223> OTHER INFORMATION: CAR D0137 CD22-19 CD8 OX40TM OX40z

<400> SEQUENCE: 67

Leu Leu Leu Val Thr Ser Leu Leu Leu Cys Glu Leu Pro His Pro Ala
1               5                   10                  15

Phe Leu Leu Ile Pro Gln Val Gln Leu Gln Gln Ser Gly Pro Gly Leu
            20                  25                  30

Val Lys His Ser Gln Thr Leu Ser Leu Thr Cys Ala Ile Ser Gly Asp
        35                  40                  45

Ser Val Ser Ser Asn Ser Ala Ala Trp Asn Trp Ile Arg Gln Ser Pro
    50                  55                  60
```

```
Ser Arg Gly Leu Glu Trp Leu Gly Arg Thr Tyr Tyr Arg Ser Lys Trp
65                  70                  75                  80

Tyr Asn Asp Tyr Ala Val Ser Val Lys Ser Arg Ile Thr Ile Asn Pro
                85                  90                  95

Asp Thr Ser Lys Asn Gln Phe Ser Leu Gln Leu Asn Ser Val Thr Pro
            100                 105                 110

Glu Asp Thr Ala Val Tyr Tyr Cys Ala Gln Glu Val Glu Pro His Asp
        115                 120                 125

Ala Phe Asp Ile Trp Gly Gln Gly Thr Met Val Thr Val Ser Ser Gly
    130                 135                 140

Gly Gly Gly Ser Gly Gly Gly Gly Ser Gly Gly Gly Gly Ser Asp Ile
145                 150                 155                 160

Gln Met Thr Gln Ser Pro Ser Ser Val Tyr Ala Ser Val Gly Asp Lys
                165                 170                 175

Val Thr Ile Thr Cys Arg Ala Ser Gln Asp Val Ser Gly Trp Leu Ala
            180                 185                 190

Trp Tyr Gln Gln Lys Pro Gly Leu Ala Pro Gln Leu Leu Ile Ser Gly
        195                 200                 205

Ala Ser Thr Leu Gln Gly Glu Val Pro Ser Arg Phe Ser Gly Ser Gly
    210                 215                 220

Ser Gly Thr Asp Phe Thr Leu Thr Ile Ser Ser Leu Gln Pro Glu Asp
225                 230                 235                 240

Phe Ala Thr Tyr Tyr Cys Gln Gln Ala Lys Tyr Phe Pro Tyr Thr Phe
                245                 250                 255

Gly Gln Gly Thr Lys Leu Glu Ile Lys Gly Gly Gly Gly Ser Gly Gly
            260                 265                 270

Gly Gly Ser Gly Gly Gly Gly Ser Gly Gly Gly Gly Ser Gly Gly Gly
        275                 280                 285

Gly Ser Glu Val Gln Leu Val Gln Ser Gly Ala Glu Val Lys Lys Pro
    290                 295                 300

Gly Ala Ser Val Lys Val Ser Cys Lys Ala Ser Gly Tyr Thr Phe Thr
305                 310                 315                 320

Ser Tyr Tyr Met His Trp Val Arg Gln Ala Pro Gly Gln Gly Leu Glu
                325                 330                 335

Trp Met Gly Leu Ile Asn Pro Ser Gly Gly Ser Thr Ser Tyr Ala Gln
            340                 345                 350

Lys Phe Gln Gly Arg Val Thr Met Thr Arg Asp Thr Ser Thr Ser Thr
        355                 360                 365

Val Tyr Met Glu Leu Ser Ser Leu Arg Ser Glu Asp Thr Ala Val Tyr
    370                 375                 380

Tyr Cys Ala Arg Ser Asp Arg Gly Ile Thr Ala Thr Asp Ala Phe Asp
385                 390                 395                 400

Ile Trp Gly Gln Gly Thr Met Val Thr Val Ser Ser Gly Gly Gly Gly
                405                 410                 415

Ser Gly Gly Gly Gly Ser Gly Gly Gly Gly Ser Gln Ser Val Leu Thr
            420                 425                 430

Gln Pro Pro Ser Val Ser Val Ala Pro Gly Arg Met Ala Lys Ile Thr
        435                 440                 445

Cys Gly Gly Ser Asp Ile Gly Asn Lys Asn Val His Trp Tyr Gln Gln
    450                 455                 460

Lys Pro Gly Gln Ala Pro Val Leu Val Val Tyr Asp Asp Tyr Asp Arg
465                 470                 475                 480

Pro Ser Gly Ile Pro Glu Arg Phe Ser Gly Ser Asn Ser Gly Asp Ala
```

```
                485                 490                 495

Ala Thr Leu Thr Ile Ser Thr Val Glu Val Gly Asp Glu Ala Asp Tyr
            500                 505                 510

Phe Cys Gln Val Trp Asp Gly Ser Gly Asp Pro Tyr Trp Met Phe Gly
        515                 520                 525

Gly Gly Thr Gln Leu Thr Val Leu Gly Ala Ala Ala Thr Thr Thr Pro
    530                 535                 540

Ala Pro Arg Pro Pro Thr Pro Ala Pro Thr Ile Ala Ser Gln Pro Leu
545                 550                 555                 560

Ser Leu Arg Pro Glu Ala Cys Arg Pro Ala Ala Gly Gly Ala Val His
                565                 570                 575

Thr Arg Gly Leu Asp Phe Ala Cys Asp Val Ala Ala Ile Leu Gly Leu
            580                 585                 590

Gly Leu Val Leu Gly Leu Leu Gly Pro Leu Ala Ile Leu Leu Ala Leu
        595                 600                 605

Tyr Leu Leu Arg Arg Asp Gln Arg Leu Pro Pro Asp Ala His Lys Pro
    610                 615                 620

Pro Gly Gly Gly Ser Phe Arg Thr Pro Ile Gln Glu Glu Gln Ala Asp
625                 630                 635                 640

Ala His Ser Thr Leu Ala Lys Ile Arg Val Lys Phe Ser Arg Ser Ala
                645                 650                 655

Asp Ala Pro Ala Tyr Gln Gln Gly Gln Asn Gln Leu Tyr Asn Glu Leu
            660                 665                 670

Asn Leu Gly Arg Arg Glu Glu Tyr Asp Val Leu Asp Lys Arg Arg Gly
        675                 680                 685

Arg Asp Pro Glu Met Gly Gly Lys Pro Arg Arg Lys Asn Pro Gln Glu
    690                 695                 700

Gly Leu Tyr Asn Glu Leu Gln Lys Asp Lys Met Ala Glu Ala Tyr Ser
705                 710                 715                 720

Glu Ile Gly Met Lys Gly Glu Arg Arg Arg Gly Lys Gly His Asp Gly
                725                 730                 735

Leu Tyr Gln Gly Leu Ser Thr Ala Thr Lys Asp Thr Tyr Asp Ala Leu
            740                 745                 750

His Met Gln Ala Leu Pro Pro Arg
        755                 760
```

<210> SEQ ID NO 68
<211> LENGTH: 2310
<212> TYPE: DNA
<213> ORGANISM: Artificial Sequence
<220> FEATURE:
<223> OTHER INFORMATION: CAR D0138 CD22-19 CD8 CD27z

<400> SEQUENCE: 68

```
atgctcttgc tcgtgacttc tttgcttttg tgcgaacttc cgcacccagc cttccttttg      60

atacctcagg tacagcttca acaaagcgga ccgggacttg ttaagcattc ccaaaccctt     120

tctctcacgt gtgcaattag cggcgatagt gtatcctcta attctgcggc ctggaactgg     180

atacgacaat caccaagccg gggactcgag tggttgggcc gaacctacta tcggtccaaa     240

tggtataatg actacgcagt atccgtgaaa tctcgcatta cgatcaatcc agacacctcc     300

aaaaatcaat tttctctgca gttgaatagc gtgactcccg aggacacggc cgtttactat     360

tgcgcccagg aagttgaacc ccacgatgca tttgatattt ggggccaggg aaccatggtg     420

acagtgagta gtgggggtgg aggatctgga ggaggcggta gcggcggggg cggcagtgat     480
```

```
atccagatga cgcagtcacc ttccagcgtg tatgcgagtg tgggggacaa ggtcaccata    540
acctgtcgcg ctagccaaga tgtcagcggg tggctggctt ggtaccagca gaaaccaggt    600
ttggctcctc agcttttgat ctcaggagcg agcacgcttc agggtgaggt cccaagtcgc    660
tttagtggct ctggctccgg gacagacttc acgttgacga tcagcagttt gcagcctgag    720
gatttcgcga cctactactg ccagcaagcg aaatattttc cgtacacttt cggtcagggg    780
accaaattgg agatcaaagg tgggggtggt tcaggcggcg gaggctcagg cggcggcggt    840
agcggaggag gcggaagcgg gggtggcgga tcagaagtgc aactcgttca gagtggcgcg    900
gaggttaaga aacccggtgc atctgtaaag gttagctgta aggcatcagg atacactttt    960
accagctatt acatgcattg ggtgagacag gctcccggtc aggggctcga atggatgggg   1020
ttgatcaacc cgagtggtgg ttcaacatct tacgcccaga agtttcaggg ccgagtaaca   1080
atgactcggg acacgtctac ctcaactgtg tatatggagc tttccagcct gcgctcagag   1140
gatacagcag tctattactg cgcacggtca gacagaggta taacggccac tgatgcgttc   1200
gatatctggg gacaagggac tatggtaact gtgtcttccg gaggaggagg tagtggaggg   1260
ggaggaagcg gtgggggggg ctcacagtcc gttttgactc agccaccaag cgtctcagtc   1320
gcaccggggc gaatggcgaa aattacttgc ggcgggagcg acataggcaa caagaatgtg   1380
cattggtacc aacagaaacc aggtcaagca cctgttctcg tggtgtatga tgactacgat   1440
cgcccaagcg ggatcccgga gcggttctct ggatcaaatt ctggtgatgc agccactctg   1500
acaatatcaa cggtggaagt cggtgacgag gctgattact tctgccaagt atgggatggc   1560
agcggagatc cctactggat gtttggagga ggtactcaac tgacagttct gggcgcggcc   1620
gcgactacca ctcctgcacc acggccacct accccagccc ccaccattgc aagccagcca   1680
ctttcactgc gccccgaagc gtgtagacca gctgctggag gagccgtgca tacccgaggg   1740
ctggacttcg cctgtgacat ctacatctgg gccccattgg ctggaacttg cggcgtgctg   1800
ctcttgtctc tggtcattac cctgtactgc caacggcgca aataccgctc caataaaggc   1860
gaaagtccgg tagaacccgc agaaccttgc cactacagtt gtcccagaga agaagagggt   1920
tctacaatac ctattcaaga ggactatagg aaaccagagc ccgcatgtag tcccagagtg   1980
aagttcagcc gctcagccga tgcaccggcc taccagcagg gacagaacca gctctacaac   2040
gagctcaacc tgggtcggcg ggaagaatat gacgtgctgg acaaacggcg cggcagagat   2100
ccggagatgg ggggaaagcc gaggaggaag aaccctcaag agggcctgta caacgaactg   2160
cagaaggaca agatggcgga agcctactcc gagatcggca tgaagggaga acgccggaga   2220
gggaagggtc atgacggact gtaccagggc ctgtcaactg ccactaagga cacttacgat   2280
gcgctccata tgcaagcttt gcccccgcgg                                     2310
```

<210> SEQ ID NO 69
<211> LENGTH: 769
<212> TYPE: PRT
<213> ORGANISM: Artificial Sequence
<220> FEATURE:
<223> OTHER INFORMATION: CAR D0138 CD22-19 CD8 CD27z

<400> SEQUENCE: 69

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys His Ser Gln Thr Leu Ser Leu Thr Cys Ala Ile Ser Gly
```

```
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro His
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Asp
145                 150                 155                 160

Ile Gln Met Thr Gln Ser Pro Ser Ser Val Tyr Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
        195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Gly Gly Gly Gly Ser Gly
            260                 265                 270

Gly Gly Gly Ser Gly Gly Gly Gly Ser Gly Gly Gly Gly Ser Gly Gly
        275                 280                 285

Gly Gly Ser Glu Val Gln Leu Val Gln Ser Gly Ala Glu Val Lys Lys
    290                 295                 300

Pro Gly Ala Ser Val Lys Val Ser Cys Lys Ala Ser Gly Tyr Thr Phe
305                 310                 315                 320

Thr Ser Tyr Tyr Met His Trp Val Arg Gln Ala Pro Gly Gln Gly Leu
                325                 330                 335

Glu Trp Met Gly Leu Ile Asn Pro Ser Gly Gly Ser Thr Ser Tyr Ala
            340                 345                 350

Gln Lys Phe Gln Gly Arg Val Thr Met Thr Arg Asp Thr Ser Thr Ser
        355                 360                 365

Thr Val Tyr Met Glu Leu Ser Ser Leu Arg Ser Glu Asp Thr Ala Val
    370                 375                 380

Tyr Tyr Cys Ala Arg Ser Asp Arg Gly Ile Thr Ala Thr Asp Ala Phe
385                 390                 395                 400

Asp Ile Trp Gly Gln Gly Thr Met Val Thr Val Ser Ser Gly Gly Gly
                405                 410                 415

Gly Ser Gly Gly Gly Gly Ser Gly Gly Gly Gly Ser Gln Ser Val Leu
            420                 425                 430

Thr Gln Pro Pro Ser Val Ser Val Ala Pro Gly Arg Met Ala Lys Ile
        435                 440                 445

Thr Cys Gly Gly Ser Asp Ile Gly Asn Lys Asn Val His Trp Tyr Gln
    450                 455                 460
```

```
Gln Lys Pro Gly Gln Ala Pro Val Leu Val Val Tyr Asp Asp Tyr Asp
465                 470                 475                 480

Arg Pro Ser Gly Ile Pro Glu Arg Phe Ser Gly Ser Asn Ser Gly Asp
                485                 490                 495

Ala Ala Thr Leu Thr Ile Ser Thr Val Glu Val Gly Asp Glu Ala Asp
            500                 505                 510

Tyr Phe Cys Gln Val Trp Asp Gly Ser Gly Asp Pro Tyr Trp Met Phe
        515                 520                 525

Gly Gly Gly Thr Gln Leu Thr Val Leu Gly Ala Ala Ala Thr Thr Thr
    530                 535                 540

Pro Ala Pro Arg Pro Pro Thr Pro Ala Pro Thr Ile Ala Ser Gln Pro
545                 550                 555                 560

Leu Ser Leu Arg Pro Glu Ala Cys Arg Pro Ala Ala Gly Gly Ala Val
                565                 570                 575

His Thr Arg Gly Leu Asp Phe Ala Cys Asp Ile Tyr Ile Trp Ala Pro
            580                 585                 590

Leu Ala Gly Thr Cys Gly Val Leu Leu Leu Ser Leu Val Ile Thr Leu
        595                 600                 605

Tyr Cys Gln Arg Arg Lys Tyr Arg Ser Asn Lys Gly Glu Ser Pro Val
    610                 615                 620

Glu Pro Ala Glu Pro Cys His Tyr Ser Cys Pro Arg Glu Glu Glu Gly
625                 630                 635                 640

Ser Thr Ile Pro Ile Gln Glu Asp Tyr Arg Lys Pro Glu Pro Ala Cys
                645                 650                 655

Ser Pro Arg Val Lys Phe Ser Arg Ser Ala Asp Ala Pro Ala Tyr Gln
            660                 665                 670

Gln Gly Gln Asn Gln Leu Tyr Asn Glu Leu Asn Leu Gly Arg Arg Glu
        675                 680                 685

Glu Tyr Asp Val Leu Asp Lys Arg Arg Gly Arg Asp Pro Glu Met Gly
    690                 695                 700

Gly Lys Pro Arg Arg Lys Asn Pro Gln Glu Gly Leu Tyr Asn Glu Leu
705                 710                 715                 720

Gln Lys Asp Lys Met Ala Glu Ala Tyr Ser Glu Ile Gly Met Lys Gly
                725                 730                 735

Glu Arg Arg Arg Gly Lys Gly His Asp Gly Leu Tyr Gln Gly Leu Ser
            740                 745                 750

Thr Ala Thr Lys Asp Thr Tyr Asp Ala Leu His Met Gln Ala Leu Pro
        755                 760                 765

Pro
```

<210> SEQ ID NO 70
<211> LENGTH: 2280
<212> TYPE: DNA
<213> ORGANISM: Artificial Sequence
<220> FEATURE:
<223> OTHER INFORMATION: CAR D0139 CD22-19 CD28 CD28z

<400> SEQUENCE: 70

```
atgctcttgc tcgtgacttc tttgcttttg tgcgaacttc cgcacccagc cttccttttg     60

atacctcagg tacagcttca acaaagcgga ccgggacttg ttaagcattc ccaaaccctt    120

tctctcacgt gtgcaattag cggcgatagt gtatcctcta attctgcggc ctggaactgg    180

atacgacaat caccaagccg gggactcgag tggttgggcc gaacctacta tcggtccaaa    240

tggtataatg actacgcagt atccgtgaaa tctcgcatta cgatcaatcc agacacctcc    300
```

```
aaaaatcaat tttctctgca gttgaatagc gtgactcccg aggacacggc cgtttactat    360

tgcgcccagg aagttgaacc ccacgatgca tttgatattt ggggccaggg aaccatggtg    420

acagtgagta gtgggggtgg aggatctgga ggaggcggta gcggcggggg cggcagtgat    480

atccagatga cgcagtcacc ttccagcgtg tatgcgagtg tgggggacaa ggtcaccata    540

acctgtcgcg ctagccaaga tgtcagcggg tggctggctt ggtaccagca gaaaccaggt    600

ttggctcctc agcttttgat ctcaggagcg agcacgcttc agggtgaggt cccaagtcgc    660

tttagtggct ctggctccgg gacagacttc acgttgacga tcagcagttt gcagcctgag    720

gatttcgcga cctactactg ccagcaagcg aaatattttc cgtacacttt cggtcagggg    780

accaaattgg agatcaaagg tgggggtggt tcaggcggcg gaggctcagg cggcggcggt    840

agcggaggag gcggaagcgg gggtggcgga tcagaagtgc aactcgttca gagtggcgcg    900

gaggttaaga aacccggtgc atctgtaaag gttagctgta aggcatcagg atacactttt    960

accagctatt acatgcattg ggtgagacag gctcccggtc aggggctcga atggatgggg   1020

ttgatcaacc cgagtggtgg ttcaacatct tacgcccaga agtttcaggg ccgagtaaca   1080

atgactcggg acacgtctac ctcaactgtg tatatggagc tttccagcct gcgctcagag   1140

gatacagcag tctattactg cgcacggtca gacagaggta taacggccac tgatgcgttc   1200

gatatctggg gacaagggac tatggtaact gtgtcttccg gaggaggagg tagtggaggg   1260

ggaggaagcg gtgggggggg ctcacagtcc gttttgactc agccaccaag cgtctcagtc   1320

gcaccggggc gaatggcgaa aattacttgc ggcgggagcg acataggcaa caagaatgtg   1380

cattggtacc aacagaaacc aggtcaagca cctgttctcg tggtgtatga tgactacgat   1440

cgcccaagcg ggatcccgga gcggttctct ggatcaaatt ctggtgatgc agccactctg   1500

acaatatcaa cggtggaagt cggtgacgag gctgattact tctgccaagt atgggatggc   1560

agcggagatc cctactggat gtttggagga ggtactcaac tgacagttct gggcgcggcc   1620

gcaatcgaag tgatgtatcc acctccgtac ctcgataacg agaaatcaaa tggaacgatc   1680

attcatgtga aagggaaaca tctgtgccca agcccattgt tcccaggtcc gtcaaaacca   1740

ttctgggtgc ttgtcgttgt tgggggtgta ctcgcatgtt attctttgct ggtgactgtg   1800

gcgtttatca tcttctgggt aaggagtaaa cgcagccgcc tgctgcattc agactacatg   1860

aacatgaccc cacggcggcc cggcccaacg cgcaaacact accaacctta cgccccaccg   1920

cgagactttg ccgcctacag atcccgcgtg aagttttccc ggtccgccga cgctccggcg   1980

taccagcagg ggcaaaacca gctgtacaac gaacttaacc tcggtcgccg ggaagaatat   2040

gacgtgctgg acaagcggcg gggaagagat cccgagatgg gtggaaagcc gcggcggaag   2100

aaccctcagg agggcttgta caacgagctg caaaaggaca aaatggccga agcctactcc   2160

gagattggca tgaagggaga gcgcagacgc gggaagggac acgatggact gtaccaggga   2220

ctgtcaaccg cgactaagga cacttacgac gccctgcaca tgcaggccct gccccgcgc    2280
```

<210> SEQ ID NO 71
<211> LENGTH: 760
<212> TYPE: PRT
<213> ORGANISM: Artificial Sequence
<220> FEATURE:
<223> OTHER INFORMATION: CAR D0139 CD22-19 CD28 CD28z

<400> SEQUENCE: 71

```
Met Leu Leu Leu Val Thr Ser Leu Leu Leu Cys Glu Leu Pro His Pro
1               5                   10                  15
```

```
Ala Phe Leu Leu Ile Pro Gln Val Gln Leu Gln Gln Ser Gly Pro Gly
            20                  25                  30

Leu Val Lys His Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro His
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Asp
145                 150                 155                 160

Ile Gln Met Thr Gln Ser Pro Ser Ser Val Tyr Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
        195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Gly Gly Gly Gly Ser Gly
            260                 265                 270

Gly Gly Gly Ser Gly Gly Gly Gly Ser Gly Gly Gly Gly Ser Gly Gly
        275                 280                 285

Gly Gly Ser Glu Val Gln Leu Val Gln Ser Gly Ala Glu Val Lys Lys
    290                 295                 300

Pro Gly Ala Ser Val Lys Val Ser Cys Lys Ala Ser Gly Tyr Thr Phe
305                 310                 315                 320

Thr Ser Tyr Tyr Met His Trp Val Arg Gln Ala Pro Gly Gln Gly Leu
                325                 330                 335

Glu Trp Met Gly Leu Ile Asn Pro Ser Gly Gly Ser Thr Ser Tyr Ala
            340                 345                 350

Gln Lys Phe Gln Gly Arg Val Thr Met Thr Arg Asp Thr Ser Thr Ser
        355                 360                 365

Thr Val Tyr Met Glu Leu Ser Ser Leu Arg Ser Glu Asp Thr Ala Val
    370                 375                 380

Tyr Tyr Cys Ala Arg Ser Asp Arg Gly Ile Thr Ala Thr Asp Ala Phe
385                 390                 395                 400

Asp Ile Trp Gly Gln Gly Thr Met Val Thr Val Ser Ser Gly Gly Gly
                405                 410                 415

Gly Ser Gly Gly Gly Gly Ser Gly Gly Gly Gly Ser Gln Ser Val Leu
            420                 425                 430
```

```
Thr Gln Pro Pro Ser Val Ser Val Ala Pro Gly Arg Met Ala Lys Ile
        435                 440                 445

Thr Cys Gly Gly Ser Asp Ile Gly Asn Lys Asn Val His Trp Tyr Gln
    450                 455                 460

Gln Lys Pro Gly Gln Ala Pro Val Leu Val Val Tyr Asp Asp Tyr Asp
465                 470                 475                 480

Arg Pro Ser Gly Ile Pro Glu Arg Phe Ser Gly Ser Asn Ser Gly Asp
                485                 490                 495

Ala Ala Thr Leu Thr Ile Ser Thr Val Glu Val Gly Asp Glu Ala Asp
            500                 505                 510

Tyr Phe Cys Gln Val Trp Asp Gly Ser Gly Asp Pro Tyr Trp Met Phe
        515                 520                 525

Gly Gly Gly Thr Gln Leu Thr Val Leu Gly Ala Ala Ala Ile Glu Val
    530                 535                 540

Met Tyr Pro Pro Pro Tyr Leu Asp Asn Glu Lys Ser Asn Gly Thr Ile
545                 550                 555                 560

Ile His Val Lys Gly Lys His Leu Cys Pro Ser Pro Leu Phe Pro Gly
                565                 570                 575

Pro Ser Lys Pro Phe Trp Val Leu Val Val Val Gly Gly Val Leu Ala
            580                 585                 590

Cys Tyr Ser Leu Leu Val Thr Val Ala Phe Ile Ile Phe Trp Val Arg
        595                 600                 605

Ser Lys Arg Ser Arg Leu Leu His Ser Asp Tyr Met Asn Met Thr Pro
    610                 615                 620

Arg Arg Pro Gly Pro Thr Arg Lys His Tyr Gln Pro Tyr Ala Pro Pro
625                 630                 635                 640

Arg Asp Phe Ala Ala Tyr Arg Ser Arg Val Lys Phe Ser Arg Ser Ala
                645                 650                 655

Asp Ala Pro Ala Tyr Gln Gln Gly Gln Asn Gln Leu Tyr Asn Glu Leu
            660                 665                 670

Asn Leu Gly Arg Arg Glu Glu Tyr Asp Val Leu Asp Lys Arg Arg Gly
        675                 680                 685

Arg Asp Pro Glu Met Gly Gly Lys Pro Arg Arg Lys Asn Pro Gln Glu
    690                 695                 700

Gly Leu Tyr Asn Glu Leu Gln Lys Asp Lys Met Ala Glu Ala Tyr Ser
705                 710                 715                 720

Glu Ile Gly Met Lys Gly Glu Arg Arg Arg Gly Lys Gly His Asp Gly
                725                 730                 735

Leu Tyr Gln Gly Leu Ser Thr Ala Thr Lys Asp Thr Tyr Asp Ala Leu
            740                 745                 750

His Met Gln Ala Leu Pro Pro Arg
        755                 760
```

<210> SEQ ID NO 72
<211> LENGTH: 2292
<212> TYPE: DNA
<213> ORGANISM: Artificial Sequence
<220> FEATURE:
<223> OTHER INFORMATION: CAR D0145 CD22-19 CD8 OX40z

<400> SEQUENCE: 72

```
atgctcttgc tcgtgacttc tttgcttttg tgcgaacttc cgcacccagc cttccttttg      60

atacctcagg tacagcttca acaaagcgga ccgggacttg ttaagcattc ccaaaccctt     120

tctctcacgt gtgcaattag cggcgatagt gtatcctcta attctgcggc ctggaactgg     180
```

-continued

```
atacgacaat caccaagccg gggactcgag tggttgggcc gaacctacta tcggtccaaa    240
tggtataatg actacgcagt atccgtgaaa tctcgcatta cgatcaatcc agacacctcc    300
aaaaatcaat ttctctgca gttgaatagc gtgactcccg aggacacggc cgtttactat     360
tgcgcccagg aagttgaacc ccacgatgca tttgatattt ggggccaggg aaccatggtg    420
acagtgagta gtgggggtgg aggatctgga ggaggcggta gcggcggggg cggcagtgat    480
atccagatga cgcagtcacc ttccagcgtg tatgcgagtg tgggggacaa ggtcaccata    540
acctgtcgcg ctagccaaga tgtcagcggg tggctggctt ggtaccagca gaaaccaggt    600
ttggctcctc agcttttgat ctcaggagcg agcacgcttc agggtgaggt cccaagtcgc    660
tttagtggct ctggctccgg gacagacttc acgttgacga tcagcagttt gcagcctgag    720
gatttcgcga cctactactg ccagcaagcg aaatattttc cgtacacttt cggtcagggg    780
accaaattgg agatcaaagg tgggggtggt tcaggcggcg gaggctcagg cggcggcggt    840
agcggaggag gcggaagcgg gggtggcgga tcagaagtgc aactcgttca gagtggcgcg    900
gaggttaaga aacccggtgc atctgtaaag gttagctgta aggcatcagg atacactttt    960
accagctatt acatgcattg ggtgagacag gctcccggtc aggggctcga atggatgggg   1020
ttgatcaacc cgagtggtgg ttcaacatct tacgcccaga agtttcaggg ccgagtaaca   1080
atgactcggg acacgtctac ctcaactgtg tatatggagc tttccagcct gcgctcagag   1140
gatacagcag tctattactg cgcacggtca gacagaggta taacggccac tgatgcgttc   1200
gatatctggg gacaagggac tatggtaact gtgtcttccg gaggaggagg tagtggaggg   1260
ggaggaagcg gtgggggggg ctcacagtcc gttttgactc agccaccaag cgtctcagtc   1320
gcaccggggc gaatggcgaa aattacttgc ggcgggagcg acataggcaa caagaatgtg   1380
cattggtacc aacagaaacc aggtcaagca cctgttctcg tggtgtatga tgactacgat   1440
cgcccaagcg ggatcccgga gcggttctct ggatcaaatt ctggtgatgc agccactctg   1500
acaatatcaa cggtggaagt cggtgacgag gctgattact tctgccaagt atgggatggc   1560
agcggagatc cctactggat gtttggagga ggtactcaac tgacagttct gggcgcggcc   1620
gcaacaacca ctccagcacc tagaccgcca acacctgcac ctaccatcgc aagtcaacca   1680
ctttctctca ggcctgaagc gtgccgacct gcagctggtg gggcagtaca taccaggggt   1740
ttggacttcg catgtgacat ctacatctgg gccccattgg ctggaacttg cggcgtgctg   1800
ctcttgtctc tggtcattac cctgtactgc gccttgtacc tgctccgcag agaccaaaga   1860
cttccgcccg acgcccacaa gcccccagga ggaggttcct tcagaacgcc tatacaagaa   1920
gaacaagcag atgcccactc taccctggct aaaatcaggg tgaagtttag ccggtcagct   1980
gatgcacctg catatcagca gggacagaac cagctgtaca atgagctgaa cctcggacga   2040
agagaggagt acgacgtgtt ggacaaaaga cgaggtagag accccgagat gggcggcaag   2100
ccgagaagaa aaaacccaca agaagggctt tataatgagc ttcagaaaga taagatggca   2160
gaggcctaca gtgagattgg catgaagggc gaaagaagga ggggcaaagg acacgacggt   2220
ctctaccaag gcctcagcac ggctaccaaa gatacgtatg acgcattgca tatgcaggca   2280
ttgccgcccc gc                                                       2292
```

<210> SEQ ID NO 73
<211> LENGTH: 764
<212> TYPE: PRT
<213> ORGANISM: Artificial Sequence
<220> FEATURE:
<223> OTHER INFORMATION: CAR D0145 CD22-19 CD8 OX40z

<400> SEQUENCE: 73

Met Leu Leu Leu Val Thr Ser Leu Leu Leu Cys Glu Leu Pro His Pro
1 5 10 15

Ala Phe Leu Leu Ile Pro Gln Val Gln Leu Gln Gln Ser Gly Pro Gly
20 25 30

Leu Val Lys His Ser Gln Thr Leu Ser Leu Thr Cys Ala Ile Ser Gly
35 40 45

Asp Ser Val Ser Ser Asn Ser Ala Ala Trp Asn Trp Ile Arg Gln Ser
50 55 60

Pro Ser Arg Gly Leu Glu Trp Leu Gly Arg Thr Tyr Tyr Arg Ser Lys
65 70 75 80

Trp Tyr Asn Asp Tyr Ala Val Ser Val Lys Ser Arg Ile Thr Ile Asn
85 90 95

Pro Asp Thr Ser Lys Asn Gln Phe Ser Leu Gln Leu Asn Ser Val Thr
100 105 110

Pro Glu Asp Thr Ala Val Tyr Tyr Cys Ala Gln Glu Val Glu Pro His
115 120 125

Asp Ala Phe Asp Ile Trp Gly Gln Gly Thr Met Val Thr Val Ser Ser
130 135 140

Gly Gly Gly Gly Ser Gly Gly Gly Gly Ser Gly Gly Gly Gly Ser Asp
145 150 155 160

Ile Gln Met Thr Gln Ser Pro Ser Ser Val Tyr Ala Ser Val Gly Asp
165 170 175

Lys Val Thr Ile Thr Cys Arg Ala Ser Gln Asp Val Ser Gly Trp Leu
180 185 190

Ala Trp Tyr Gln Gln Lys Pro Gly Leu Ala Pro Gln Leu Leu Ile Ser
195 200 205

Gly Ala Ser Thr Leu Gln Gly Glu Val Pro Ser Arg Phe Ser Gly Ser
210 215 220

Gly Ser Gly Thr Asp Phe Thr Leu Thr Ile Ser Ser Leu Gln Pro Glu
225 230 235 240

Asp Phe Ala Thr Tyr Tyr Cys Gln Gln Ala Lys Tyr Phe Pro Tyr Thr
245 250 255

Phe Gly Gln Gly Thr Lys Leu Glu Ile Lys Gly Gly Gly Gly Ser Gly
260 265 270

Gly Gly Gly Ser Gly Gly Gly Gly Ser Gly Gly Gly Gly Ser Gly Gly
275 280 285

Gly Gly Ser Glu Val Gln Leu Val Gln Ser Gly Ala Glu Val Lys Lys
290 295 300

Pro Gly Ala Ser Val Lys Val Ser Cys Lys Ala Ser Gly Tyr Thr Phe
305 310 315 320

Thr Ser Tyr Tyr Met His Trp Val Arg Gln Ala Pro Gly Gln Gly Leu
325 330 335

Glu Trp Met Gly Leu Ile Asn Pro Ser Gly Gly Ser Thr Ser Tyr Ala
340 345 350

Gln Lys Phe Gln Gly Arg Val Thr Met Thr Arg Asp Thr Ser Thr Ser
355 360 365

Thr Val Tyr Met Glu Leu Ser Ser Leu Arg Ser Glu Asp Thr Ala Val
370 375 380

Tyr Tyr Cys Ala Arg Ser Asp Arg Gly Ile Thr Ala Thr Asp Ala Phe
385 390 395 400

Asp Ile Trp Gly Gln Gly Thr Met Val Thr Val Ser Ser Gly Gly Gly

```
                405                 410                 415

Gly Ser Gly Gly Gly Gly Ser Gly Gly Gly Gly Ser Gln Ser Val Leu
            420                 425                 430

Thr Gln Pro Pro Ser Val Ser Val Ala Pro Gly Arg Met Ala Lys Ile
        435                 440                 445

Thr Cys Gly Gly Ser Asp Ile Gly Asn Lys Asn Val His Trp Tyr Gln
    450                 455                 460

Gln Lys Pro Gly Gln Ala Pro Val Leu Val Val Tyr Asp Asp Tyr Asp
465                 470                 475                 480

Arg Pro Ser Gly Ile Pro Glu Arg Phe Ser Gly Ser Asn Ser Gly Asp
                485                 490                 495

Ala Ala Thr Leu Thr Ile Ser Thr Val Glu Val Gly Asp Glu Ala Asp
            500                 505                 510

Tyr Phe Cys Gln Val Trp Asp Gly Ser Gly Asp Pro Tyr Trp Met Phe
        515                 520                 525

Gly Gly Gly Thr Gln Leu Thr Val Leu Gly Ala Ala Ala Thr Thr Thr
    530                 535                 540

Pro Ala Pro Arg Pro Pro Thr Pro Ala Pro Thr Ile Ala Ser Gln Pro
545                 550                 555                 560

Leu Ser Leu Arg Pro Glu Ala Cys Arg Pro Ala Ala Gly Gly Ala Val
                565                 570                 575

His Thr Arg Gly Leu Asp Phe Ala Cys Asp Ile Tyr Ile Trp Ala Pro
            580                 585                 590

Leu Ala Gly Thr Cys Gly Val Leu Leu Leu Ser Leu Val Ile Thr Leu
        595                 600                 605

Tyr Cys Ala Leu Tyr Leu Leu Arg Arg Asp Gln Arg Leu Pro Pro Asp
    610                 615                 620

Ala His Lys Pro Pro Gly Gly Gly Ser Phe Arg Thr Pro Ile Gln Glu
625                 630                 635                 640

Glu Gln Ala Asp Ala His Ser Thr Leu Ala Lys Ile Arg Val Lys Phe
                645                 650                 655

Ser Arg Ser Ala Asp Ala Pro Ala Tyr Gln Gln Gly Gln Asn Gln Leu
            660                 665                 670

Tyr Asn Glu Leu Asn Leu Gly Arg Arg Glu Glu Tyr Asp Val Leu Asp
        675                 680                 685

Lys Arg Arg Gly Arg Asp Pro Glu Met Gly Gly Lys Pro Arg Arg Lys
    690                 695                 700

Asn Pro Gln Glu Gly Leu Tyr Asn Glu Leu Gln Lys Asp Lys Met Ala
705                 710                 715                 720

Glu Ala Tyr Ser Glu Ile Gly Met Lys Gly Glu Arg Arg Arg Gly Lys
                725                 730                 735

Gly His Asp Gly Leu Tyr Gln Gly Leu Ser Thr Ala Thr Lys Asp Thr
            740                 745                 750

Tyr Asp Ala Leu His Met Gln Ala Leu Pro Pro Arg
        755                 760
```

<210> SEQ ID NO 74
<211> LENGTH: 2406
<212> TYPE: DNA
<213> ORGANISM: Artificial Sequence
<220> FEATURE:
<223> OTHER INFORMATION: D0140 CD22-19 CD28 CD28 BBz

<400> SEQUENCE: 74

```
atgctcttgc tcgtgacttc tttgcttttg tgcgaacttc cgcacccagc cttccttttg     60
```

```
atacctcagg tacagcttca acaaagcgga ccgggacttg ttaagcattc ccaaaccctt    120
tctctcacgt gtgcaattag cggcgatagt gtatcctcta attctgcggc ctggaactgg    180
atacgacaat caccaagccg gggactcgag tggttgggcc gaacctacta tcggtccaaa    240
tggtataatg actacgcagt atccgtgaaa tctcgcatta cgatcaatcc agacacctcc    300
aaaaatcaat tttctctgca gttgaatagc gtgactcccg aggacacggc cgtttactat    360
tgcgcccagg aagttgaacc ccacgatgca tttgatattt ggggccaggg aaccatggtg    420
acagtgagta gtgggggtgg aggatctgga ggaggcggta gcggcggggg cggcagtgat    480
atccagatga cgcagtcacc ttccagcgtg tatgcgagtg tgggggacaa ggtcaccata    540
acctgtcgcg ctagccaaga tgtcagcggg tggctggctt ggtaccagca gaaaccaggt    600
ttggctcctc agcttttgat ctcaggagcg agcacgcttc agggtgaggt cccaagtcgc    660
tttagtggct ctggctccgg gacagacttc acgttgacga tcagcagttt gcagcctgag    720
gatttcgcga cctactactg ccagcaagcg aaatattttc cgtacacttt cggtcagggg    780
accaaattgg agatcaaagg tgggggtggt tcaggcggcg gaggctcagg cggcggcggt    840
agcggaggag gcggaagcgg gggtggcgga tcagaagtgc aactcgttca gagtggcgcg    900
gaggttaaga aacccggtgc atctgtaaag gttagctgta aggcatcagg atacactttt    960
accagctatt acatgcattg ggtgagacag gctcccggtc aggggctcga atggatgggg   1020
ttgatcaacc cgagtggtgg ttcaacatct tacgcccaga agtttcaggg ccgagtaaca   1080
atgactcggg acacgtctac ctcaactgtg tatatggagc tttccagcct gcgctcagag   1140
gatacagcag tctattactg cgcacggtca gacagaggta taacggccac tgatgcgttc   1200
gatatctggg gacaagggac tatggtaact gtgtcttccg gaggaggagg tagtggaggg   1260
ggaggaagcg gtgggggggg ctcacagtcc gttttgactc agccaccaag cgtctcagtc   1320
gcaccggggc gaatggcgaa aattacttgc ggcgggagcg acataggcaa caagaatgtg   1380
cattggtacc aacagaaacc aggtcaagca cctgttctcg tggtgtatga tgactacgat   1440
cgcccaagcg ggatcccgga gcggttctct ggatcaaatt ctggtgatgc agccactctg   1500
acaatatcaa cggtggaagt cggtgacgag gctgattact tctgccaagt atgggatggc   1560
agcggagatc cctactggat gtttggagga ggtactcaac tgacagttct gggcgcggcc   1620
gcaatcgaag tgatgtatcc acctccgtac ctcgataacg agaaatcaaa tggaacgatc   1680
attcatgtga aagggaaaca tctgtgccca agcccattgt tcccaggtcc gtcaaaacca   1740
ttctgggtgc ttgtcgttgt tgggggtgta ctcgcatgtt attctttgct ggtgactgtg   1800
gcgtttatca tcttctgggt aaggagtaaa cgcagccgcc tgctgcattc agactacatg   1860
aacatgaccc cacggcggcc cggcccaacg cgcaaacact accaacctta cgccccaccg   1920
cgagactttg ccgcctacag atccaagcgc ggacggaaga aactcttgta catcttcaag   1980
cagccgttca tgcgccctgt gcaaaccacc caagaagagg acgggtgctc ctgccggttc   2040
ccggaagagg aagagggcgg ctgcgaactg cgcgtgaagt tttcccggtc cgccgacgct   2100
ccggcgtacc agcaggggca aaaccagctg tacaacgaac ttaacctcgg tcgccgggaa   2160
gaatatgacg tgctggacaa gcggcgggga agagatcccg agatgggtgg aaagccgcgg   2220
cggaagaacc ctcaggaggg cttgtacaac gagctgcaaa aggacaaaat ggccgaagcc   2280
tactccgaga ttggcatgaa gggagagcgc agacgcggga agggacacga tggactgtac   2340
cagggactgt caaccgcgac taaggacact tacgacgccc tgcacatgca ggccctgccc   2400
```

```
ccgcgc                                                                  2406


<210> SEQ ID NO 75
<211> LENGTH: 802
<212> TYPE: PRT
<213> ORGANISM: Artificial Sequence
<220> FEATURE:
<223> OTHER INFORMATION: D0140 CD22-19 CD28 CD28 BBz

<400> SEQUENCE: 75

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys His Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro His
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Asp
145                 150                 155                 160

Ile Gln Met Thr Gln Ser Pro Ser Ser Val Tyr Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
        195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Gly Gly Gly Gly Ser Gly
            260                 265                 270

Gly Gly Gly Ser Gly Gly Gly Gly Ser Gly Gly Gly Gly Ser Gly Gly
        275                 280                 285

Gly Gly Ser Glu Val Gln Leu Val Gln Ser Gly Ala Glu Val Lys Lys
    290                 295                 300

Pro Gly Ala Ser Val Lys Val Ser Cys Lys Ala Ser Gly Tyr Thr Phe
305                 310                 315                 320

Thr Ser Tyr Tyr Met His Trp Val Arg Gln Ala Pro Gly Gln Gly Leu
                325                 330                 335

Glu Trp Met Gly Leu Ile Asn Pro Ser Gly Gly Ser Thr Ser Tyr Ala
            340                 345                 350

Gln Lys Phe Gln Gly Arg Val Thr Met Thr Arg Asp Thr Ser Thr Ser
```

```
        355                 360                 365

Thr Val Tyr Met Glu Leu Ser Ser Leu Arg Ser Glu Asp Thr Ala Val
    370                 375                 380

Tyr Tyr Cys Ala Arg Ser Asp Arg Gly Ile Thr Ala Thr Asp Ala Phe
385                 390                 395                 400

Asp Ile Trp Gly Gln Gly Thr Met Val Thr Val Ser Ser Gly Gly Gly
                405                 410                 415

Gly Ser Gly Gly Gly Gly Ser Gly Gly Gly Gly Ser Gln Ser Val Leu
            420                 425                 430

Thr Gln Pro Pro Ser Val Ser Val Ala Pro Gly Arg Met Ala Lys Ile
        435                 440                 445

Thr Cys Gly Gly Ser Asp Ile Gly Asn Lys Asn Val His Trp Tyr Gln
    450                 455                 460

Gln Lys Pro Gly Gln Ala Pro Val Leu Val Val Tyr Asp Asp Tyr Asp
465                 470                 475                 480

Arg Pro Ser Gly Ile Pro Glu Arg Phe Ser Gly Ser Asn Ser Gly Asp
                485                 490                 495

Ala Ala Thr Leu Thr Ile Ser Thr Val Glu Val Gly Asp Glu Ala Asp
            500                 505                 510

Tyr Phe Cys Gln Val Trp Asp Gly Ser Gly Asp Pro Tyr Trp Met Phe
        515                 520                 525

Gly Gly Gly Thr Gln Leu Thr Val Leu Gly Ala Ala Ala Ile Glu Val
    530                 535                 540

Met Tyr Pro Pro Pro Tyr Leu Asp Asn Glu Lys Ser Asn Gly Thr Ile
545                 550                 555                 560

Ile His Val Lys Gly Lys His Leu Cys Pro Ser Pro Leu Phe Pro Gly
                565                 570                 575

Pro Ser Lys Pro Phe Trp Val Leu Val Val Val Gly Gly Val Leu Ala
            580                 585                 590

Cys Tyr Ser Leu Leu Val Thr Val Ala Phe Ile Ile Phe Trp Val Arg
        595                 600                 605

Ser Lys Arg Ser Arg Leu Leu His Ser Asp Tyr Met Asn Met Thr Pro
    610                 615                 620

Arg Arg Pro Gly Pro Thr Arg Lys His Tyr Gln Pro Tyr Ala Pro Pro
625                 630                 635                 640

Arg Asp Phe Ala Ala Tyr Arg Ser Lys Arg Gly Arg Lys Lys Leu Leu
                645                 650                 655

Tyr Ile Phe Lys Gln Pro Phe Met Arg Pro Val Gln Thr Thr Gln Glu
            660                 665                 670

Glu Asp Gly Cys Ser Cys Arg Phe Pro Glu Glu Glu Glu Gly Gly Cys
        675                 680                 685

Glu Leu Arg Val Lys Phe Ser Arg Ser Ala Asp Ala Pro Ala Tyr Gln
    690                 695                 700

Gln Gly Gln Asn Gln Leu Tyr Asn Glu Leu Asn Leu Gly Arg Arg Glu
705                 710                 715                 720

Glu Tyr Asp Val Leu Asp Lys Arg Arg Gly Arg Asp Pro Glu Met Gly
                725                 730                 735

Gly Lys Pro Arg Arg Lys Asn Pro Gln Glu Gly Leu Tyr Asn Glu Leu
            740                 745                 750

Gln Lys Asp Lys Met Ala Glu Ala Tyr Ser Glu Ile Gly Met Lys Gly
        755                 760                 765

Glu Arg Arg Arg Gly Lys Gly His Asp Gly Leu Tyr Gln Gly Leu Ser
    770                 775                 780
```

Thr Ala Thr Lys Asp Thr Tyr Asp Ala Leu His Met Gln Ala Leu Pro
785 790 795 800

Pro Arg

<210> SEQ ID NO 76
<211> LENGTH: 2913
<212> TYPE: DNA
<213> ORGANISM: Artificial Sequence
<220> FEATURE:
<223> OTHER INFORMATION: CAR D0146 CD19 CD8H&TM ICOS z_CD22 CD8H&TM 3z

<400> SEQUENCE: 76
atgctgctgc tggtgaccag cctgctgctg tgcgaactgc cgcatccggc gtttctgctg 60
attccggagg tccagctggt acagtctgga gctgaggtga agaagcctgg ggcctcagtg 120
aaggtctcct gcaaggcttc tggatacacc ttcaccagct actatatgca ctgggtgcga 180
caggcccctg gacaagggct tgagtggatg ggattaatca accctagtgg tggtagcaca 240
agctacgcac agaagttcca gggcagagtc accatgacca gggacacgtc cacgagcaca 300
gtctacatgg agctgagcag cctgagatct gaggacacgg ccgtgtatta ctgtgcgaga 360
tcggatcggg gaattaccgc cacggacgct tttgatatct ggggccaagg gacaatggtc 420
accgtctctt caggcggagg aggctccggg ggaggaggtt ccgggggcgg gggttcccag 480
tctgtgctga ctcagccacc ctcggtgtca gtggccccag ggcggatggc caagattacc 540
tgtgggggaa gtgacattgg aaataaaaat gtccactggt atcagcagaa gccaggccag 600
gcccctgtcc tggttgtcta tgatgattac gaccggccct cagggatccc tgagcgattc 660
tctggctcca actctgggga cgcggccacc ctgacgatca gcacggtcga agtcggggat 720
gaggccgact atttctgtca ggtgtgggac ggtagtggtg atccttattg gatgttcggc 780
ggagggaccc agctcaccgt tttaggtgcg gccgcaacga ccactcctgc accacggcca 840
cctaccccag cccccaccat tgcaagccag ccactttcac tgcgccccga agcgtgtaga 900
ccagctgctg gaggagccgt gcatacccga gggctggact tcgcctgtga catctacatc 960
tgggccccat tggctggaac ttgcggcgtg ctgctcttgt ctctggtcat taccctgtac 1020
tgctggctga caaaaaagaa gtattcatct agtgtacatg atccgaacgg tgaatacatg 1080
ttcatgcgcg cggtgaacac ggccaagaag agcagactga ccgacgtaac ccttagagtg 1140
aagtttagcc gctcagccga tgcaccggcc taccagcagg gacagaacca gctctacaac 1200
gagctcaacc tgggtcggcg ggaagaatat gacgtgctgg acaaacggcg cggcagagat 1260
ccggagatgg ggggaaagcc gaggaggaag aaccctcaag agggcctgta caacgaactg 1320
cagaaggaca agatggcgga agcctactcc gagatcggca tgaagggaga acgccggaga 1380
gggaagggtc atgacggact gtaccagggc ctgtcaactg ccactaagga cacttacgat 1440
gcgctccata tgcaagcttt gcccccgcgg cgcgcgaaac gcggcagcgg cgcgaccaac 1500
tttagcctgc tgaaacaggc gggcgatgtg gaagaaaacc cgggcccgcg agcaaagagg 1560
aatattatgg ctctgcctgt tacggcactg ctccttccgc ttgcattgtt gttgcacgca 1620
gcgcggcccc aagtgcagct gcagcagtcc ggtcctggac tggtcaagcc gtcccagact 1680
ctgagcctga cttgcgcaat tagcggggac tcagtctcgt ccaattcggc ggcctggaac 1740
tggatccggc agtcaccatc aaggggcctg gaatggctcg ggcgcactta ctaccggtcc 1800
aaatggtata ccgactacgc cgtgtccgtg aagaatcgga tcaccattaa ccccgacacc 1860
tcgaagaacc agttctcact ccaactgaac agcgtgaccc ccgaggatac cgcggtgtac 1920

```
tactgcgcac aagaagtgga accgcaggac gccttcgaca tttggggaca gggaacgatg   1980

gtcacagtgt cgtccggtgg aggaggttcc ggaggcggtg gatctggagg cggaggttcg   2040

gatatccaga tgacccagag cccctcctcg gtgtccgcat ccgtgggcga taaggtcacc   2100

attacctgta gagcgtccca ggacgtgtcc ggatggctgg cctggtacca gcagaagcca   2160

ggcttggctc ctcaactgct gatcttcggc gccagcactc ttcaggggga agtgccatca   2220

cgcttctccg gatccggttc cggcaccgac ttcaccctga ccatcagcag cctccagcct   2280

gaggacttcg ccacttacta ctgccaacag gccaagtact tcccctatac cttcggaaga   2340

ggcactaagc tggaaatcaa ggctagcgca accactacgc ctgctccgcg gcctccaacg   2400

cccgcgccca cgatagctag tcagccgttg tctctccgac cagaggcgtg tagaccggcc   2460

gctggcggag ccgtacatac tcgcggactc gacttcgctt gcgacatcta catttgggca   2520

cccttggctg ggacctgtgg ggtgctgttg ctgtccttgg ttattacgtt gtactgcaga   2580

gtcaaatttt ccaggtccgc agatgccccc gcgtaccagc aaggccagaa ccaactttac   2640

aacgaactga acctgggtcg ccgggaggaa tatgatgtgc tggataaacg aagggggagg   2700

gaccctgaga tgggagggaa acctcgcagg aaaaacccgc aggaaggttt gtacaacgag   2760

ttgcagaagg ataagatggc tgaggcttac tctgaaatag ggatgaaggg agagagacgg   2820

agaggaaaag gccatgatgg cctttaccag ggcttaagca cagcaacaaa ggatacttac   2880

gacgctcttc acatgcaagc tctgccacca cgg                                2913
```

```
<210> SEQ ID NO 77
<211> LENGTH: 971
<212> TYPE: PRT
<213> ORGANISM: Artificial Sequence
<220> FEATURE:
<223> OTHER INFORMATION: CAR D0146 CD19 CD8H&TM ICOS z_CD22 CD8H&TMz

<400> SEQUENCE: 77

Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Ser Tyr Tyr Met His Trp Val Arg Gln Ala Pro Gly
    50                  55                  60

Gln Gly Leu Glu Trp Met Gly Leu Ile Asn Pro Ser Gly Gly Ser Thr
65                  70                  75                  80

Ser Tyr Ala Gln Lys Phe Gln Gly Arg Val Thr Met Thr Arg Asp Thr
                85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Ser Asp Arg Gly Ile Thr Ala Thr
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Gln
145                 150                 155                 160

Ser Val Leu Thr Gln Pro Pro Ser Val Ser Val Ala Pro Gly Arg Met
                165                 170                 175

Ala Lys Ile Thr Cys Gly Gly Ser Asp Ile Gly Asn Lys Asn Val His
```

```
            180                 185                 190

Trp Tyr Gln Gln Lys Pro Gly Gln Ala Pro Val Leu Val Val Tyr Asp
        195                 200                 205

Asp Tyr Asp Arg Pro Ser Gly Ile Pro Glu Arg Phe Ser Gly Ser Asn
    210                 215                 220

Ser Gly Asp Ala Ala Thr Leu Thr Ile Ser Thr Val Glu Val Gly Asp
225                 230                 235                 240

Glu Ala Asp Tyr Phe Cys Gln Val Trp Asp Gly Ser Gly Asp Pro Tyr
                245                 250                 255

Trp Met Phe Gly Gly Gly Thr Gln Leu Thr Val Leu Gly Ala Ala Ala
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Trp Leu Thr Lys Lys Lys Tyr Ser Ser Ser Val
            340                 345                 350

His Asp Pro Asn Gly Glu Tyr Met Phe Met Arg Ala Val Asn Thr Ala
        355                 360                 365

Lys Lys Ser Arg Leu Thr Asp Val Thr Leu Arg Val Lys Phe Ser Arg
    370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg Arg Ala Lys Arg Gly Ser
                485                 490                 495

Gly Ala Thr Asn Phe Ser Leu Leu Lys Gln Ala Gly Asp Val Glu Glu
            500                 505                 510

Asn Pro Gly Pro Arg Ala Lys Arg Asn Ile Met Ala Leu Pro Val Thr
        515                 520                 525

Ala Leu Leu Leu Pro Leu Ala Leu Leu Leu His Ala Ala Arg Pro Gln
    530                 535                 540

Val Gln Leu Gln Gln Ser Gly Pro Gly Leu Val Lys Pro Ser Gln Thr
545                 550                 555                 560

Leu Ser Leu Thr Cys Ala Ile Ser Gly Asp Ser Val Ser Ser Asn Ser
                565                 570                 575

Ala Ala Trp Asn Trp Ile Arg Gln Ser Pro Ser Arg Gly Leu Glu Trp
            580                 585                 590

Leu Gly Arg Thr Tyr Tyr Arg Ser Lys Trp Tyr Thr Asp Tyr Ala Val
        595                 600                 605
```

```
Ser Val Lys Asn Arg Ile Thr Ile Asn Pro Asp Thr Ser Lys Asn Gln
    610                 615                 620

Phe Ser Leu Gln Leu Asn Ser Val Thr Pro Glu Asp Thr Ala Val Tyr
625                 630                 635                 640

Tyr Cys Ala Gln Glu Val Glu Pro Gln Asp Ala Phe Asp Ile Trp Gly
                645                 650                 655

Gln Gly Thr Met Val Thr Val Ser Ser Gly Gly Gly Gly Ser Gly Gly
            660                 665                 670

Gly Gly Ser Gly Gly Gly Gly Ser Asp Ile Gln Met Thr Gln Ser Pro
        675                 680                 685

Ser Ser Val Ser Ala Ser Val Gly Asp Lys Val Thr Ile Thr Cys Arg
    690                 695                 700

Ala Ser Gln Asp Val Ser Gly Trp Leu Ala Trp Tyr Gln Gln Lys Pro
705                 710                 715                 720

Gly Leu Ala Pro Gln Leu Leu Ile Phe Gly Ala Ser Thr Leu Gln Gly
                725                 730                 735

Glu Val Pro Ser Arg Phe Ser Gly Ser Gly Ser Gly Thr Asp Phe Thr
            740                 745                 750

Leu Thr Ile Ser Ser Leu Gln Pro Glu Asp Phe Ala Thr Tyr Tyr Cys
        755                 760                 765

Gln Gln Ala Lys Tyr Phe Pro Tyr Thr Phe Gly Arg Gly Thr Lys Leu
    770                 775                 780

Glu Ile Lys Ala Ser Ala Thr Thr Thr Pro Ala Pro Arg Pro Pro Thr
785                 790                 795                 800

Pro Ala Pro Thr Ile Ala Ser Gln Pro Leu Ser Leu Arg Pro Glu Ala
                805                 810                 815

Cys Arg Pro Ala Ala Gly Gly Ala Val His Thr Arg Gly Leu Asp Phe
            820                 825                 830

Ala Cys Asp Ile Tyr Ile Trp Ala Pro Leu Ala Gly Thr Cys Gly Val
        835                 840                 845

Leu Leu Leu Ser Leu Val Ile Thr Leu Tyr Cys Arg Val Lys Phe Ser
    850                 855                 860

Arg Ser Ala Asp Ala Pro Ala Tyr Gln Gln Gly Gln Asn Gln Leu Tyr
865                 870                 875                 880

Asn Glu Leu Asn Leu Gly Arg Arg Glu Glu Tyr Asp Val Leu Asp Lys
                885                 890                 895

Arg Arg Gly Arg Asp Pro Glu Met Gly Gly Lys Pro Arg Arg Lys Asn
            900                 905                 910

Pro Gln Glu Gly Leu Tyr Asn Glu Leu Gln Lys Asp Lys Met Ala Glu
        915                 920                 925

Ala Tyr Ser Glu Ile Gly Met Lys Gly Glu Arg Arg Arg Gly Lys Gly
    930                 935                 940

His Asp Gly Leu Tyr Gln Gly Leu Ser Thr Ala Thr Lys Asp Thr Tyr
945                 950                 955                 960

Asp Ala Leu His Met Gln Ala Leu Pro Pro Arg
                965                 970
```

```
<210> SEQ ID NO 78
<211> LENGTH: 2754
<212> TYPE: DNA
<213> ORGANISM: Artificial Sequence
<220> FEATURE:
<223> OTHER INFORMATION: CAR D0147 CD19 CD8H OX40TM OX40 z_CD22 CD8H&TM
      z
```

<400> SEQUENCE: 78

```
atgcactggg tgcgacaggc ccctggacaa gggcttgagt ggatgggatt aatcaaccct     60
agtggtggta gcacaagcta cgcacagaag ttccagggca gagtcaccat gaccagggac    120
acgtccacga gcacagtcta catggagctg agcagcctga gatctgagga cacggccgtg    180
tattactgtg cgagatcgga tcggggaatt accgccacgg acgcttttga tatctggggc    240
caagggacaa tggtcaccgt ctcttcaggc ggaggaggct ccgggggagg aggttccggg    300
ggcgggggtt cccagtctgt gctgactcag ccaccctcgg tgtcagtggc cccagggcgg    360
atggccaaga ttacctgtgg gggaagtgac attggaaata aaaatgtcca ctggtatcag    420
cagaagccag gccaggcccc tgtcctggtt gtctatgatg attacgaccg gccctcaggg    480
atccctgagc gattctctgg ctccaactct ggggacgcgg ccaccctgac gatcagcacg    540
gtcgaagtcg gggatgaggc cgactatttc tgtcaggtgt gggacggtag tggtgatcct    600
tattggatgt tcggcggagg gacccagctc accgttttag gtgcggccgc aacgaccact    660
ccagcaccga gaccgccaac cccgcgcct accatcgcaa gtcaaccact ttctctcagg    720
cctgaagcgt gccgacctgc agctggtggg gcagtacata ccaggggttt ggacttcgca    780
tgtgacgtgg cggcaattct cggcctggga cttgtccttg gtctgcttgg tccgctcgca    840
atacttctgg ccttgtacct gctccgcaga gaccaaagac ttccgcccga cgcccacaag    900
cccccaggag gaggttcctt cagaacgcct atacaagaag aacaagcaga tgcccactct    960
accctggcta aaatcagggt gaagtttagc cgctcagccg atgcaccggc ctaccagcag   1020
ggacagaacc agctctacaa cgagctcaac ctgggtcggc gggaagaata tgacgtgctg   1080
gacaaacggc gcggcagaga tccggagatg gggggaaagc cgaggaggaa gaaccctcaa   1140
gagggcctgt acaacgaact gcagaaggac aagatggcgg aagcctactc cgagatcggc   1200
atgaagggag aacgccggag agggaagggt catgacggac tgtaccaggg cctgtcaact   1260
gccactaagg acacttacga tgcgctccat atgcaagctt tgcccccgcg gcgcgcgaaa   1320
cgcggcagcg gcgcgaccaa ctttagcctg ctgaaacagg cgggcgatgt ggaagaaaac   1380
ccgggcccgc gagcaaagag gaatattatg gctctgcctg ttacggcact gctccttccg   1440
cttgcattgt tgttgcacgc agcgcggccc caagtgcagc tgcagcagtc cggtcctgga   1500
ctggtcaagc cgtcccagac tctgagcctg acttgcgcaa ttagcgggga ctcagtctcg   1560
tccaattcgg cggcctggaa ctggatccgg cagtcaccat caaggggcct ggaatggctc   1620
gggcgcactt actaccggtc caaatggtat accgactacg ccgtgtccgt gaagaatcgg   1680
atcaccatta accccgacac ctcgaagaac cagttctcac tccaactgaa cagcgtgacc   1740
cccgaggata ccgcggtgta ctactgcgca caagaagtgg aaccgcagga cgccttcgac   1800
atttggggac agggaacgat ggtcacagtg tcgtccggtg gaggaggttc cggaggcggt   1860
ggatctggag gcggaggttc ggatatccag atgacccaga gcccctcctc ggtgtccgca   1920
tccgtgggcg ataaggtcac cattacctgt agagcgtccc aggacgtgtc cggatggctg   1980
gcctggtacc agcagaagcc aggcttggct cctcaactgc tgatcttcgg cgccagcact   2040
cttcaggggg aagtgccatc acgcttctcc ggatccggtt ccggcaccga cttcaccctg   2100
accatcagca gcctccagcc tgaggacttc gccacttact actgccaaca ggccaagtac   2160
ttcccctata ccttcggaag aggcactaag ctggaaatca aggctagcgc aaccactacg   2220
cctgctccgc ggcctccaac gcccgcgccc acgatagcta gtcagccgtt gtctctccga   2280
ccagaggcgt gtagaccggc cgctggcgga gccgtacata ctcgcggact cgacttcgct   2340
```

```
tgcgacatct acatttgggc acccttggct gggacctgtg ggtgctgtt gctgtccttg   2400

gttattacgt tgtactgcag agtcaaattt tccaggtccg cagatgcccc cgcgtaccag   2460

caaggccaga accaacttta caacgaactg aacctgggtc gccgggagga atatgatgtg   2520

ctggataaac gaagggggag ggaccctgag atgggaggga aacctcgcag gaaaaacccg   2580

caggaaggtt tgtacaacga gttgcagaag gataagatgg ctgaggctta ctctgaaata   2640

gggatgaagg gagagagacg gagaggaaaa ggccatgatg gcctttacca gggcttaagc   2700

acagcaacaa aggatactta cgacgctctt cacatgcaag ctctgccacc acgg         2754


<210> SEQ ID NO 79
<211> LENGTH: 918
<212> TYPE: PRT
<213> ORGANISM: Artificial Sequence
<220> FEATURE:
<223> OTHER INFORMATION: CAR D0147 CD19 CD8H OX40TM OX40 z_CD22 CD8H&TM
      z

<400> SEQUENCE: 79

Met His Trp Val Arg Gln Ala Pro Gly Gln Gly Leu Glu Trp Met Gly
1               5                   10                  15

Leu Ile Asn Pro Ser Gly Gly Ser Thr Ser Tyr Ala Gln Lys Phe Gln
            20                  25                  30

Gly Arg Val Thr Met Thr Arg Asp Thr Ser Thr Ser Thr Val Tyr Met
        35                  40                  45

Glu Leu Ser Ser Leu Arg Ser Glu Asp Thr Ala Val Tyr Tyr Cys Ala
    50                  55                  60

Arg Ser Asp Arg Gly Ile Thr Ala Thr Asp Ala Phe Asp Ile Trp Gly
65                  70                  75                  80

Gln Gly Thr Met Val Thr Val Ser Ser Gly Gly Gly Gly Ser Gly Gly
                85                  90                  95

Gly Gly Ser Gly Gly Gly Gly Ser Gln Ser Val Leu Thr Gln Pro Pro
            100                 105                 110

Ser Val Ser Val Ala Pro Gly Arg Met Ala Lys Ile Thr Cys Gly Gly
        115                 120                 125

Ser Asp Ile Gly Asn Lys Asn Val His Trp Tyr Gln Gln Lys Pro Gly
    130                 135                 140

Gln Ala Pro Val Leu Val Val Tyr Asp Asp Tyr Asp Arg Pro Ser Gly
145                 150                 155                 160

Ile Pro Glu Arg Phe Ser Gly Ser Asn Ser Gly Asp Ala Ala Thr Leu
                165                 170                 175

Thr Ile Ser Thr Val Glu Val Gly Asp Glu Ala Asp Tyr Phe Cys Gln
            180                 185                 190

Val Trp Asp Gly Ser Gly Asp Pro Tyr Trp Met Phe Gly Gly Gly Thr
        195                 200                 205

Gln Leu Thr Val Leu Gly Ala Ala Ala Thr Thr Thr Pro Ala Pro Arg
    210                 215                 220

Pro Pro Thr Pro Ala Pro Thr Ile Ala Ser Gln Pro Leu Ser Leu Arg
225                 230                 235                 240

Pro Glu Ala Cys Arg Pro Ala Ala Gly Gly Ala Val His Thr Arg Gly
                245                 250                 255

Leu Asp Phe Ala Cys Asp Val Ala Ala Ile Leu Gly Leu Gly Leu Val
            260                 265                 270

Leu Gly Leu Leu Gly Pro Leu Ala Ile Leu Leu Ala Leu Tyr Leu Leu
        275                 280                 285
```

```
Arg Arg Asp Gln Arg Leu Pro Pro Asp Ala His Lys Pro Pro Gly Gly
    290                 295                 300

Gly Ser Phe Arg Thr Pro Ile Gln Glu Glu Gln Ala Asp Ala His Ser
305                 310                 315                 320

Thr Leu Ala Lys Ile Arg Val Lys Phe Ser Arg Ser Ala Asp Ala Pro
                325                 330                 335

Ala Tyr Gln Gln Gly Gln Asn Gln Leu Tyr Asn Glu Leu Asn Leu Gly
            340                 345                 350

Arg Arg Glu Glu Tyr Asp Val Leu Asp Lys Arg Arg Gly Arg Asp Pro
        355                 360                 365

Glu Met Gly Gly Lys Pro Arg Arg Lys Asn Pro Gln Glu Gly Leu Tyr
    370                 375                 380

Asn Glu Leu Gln Lys Asp Lys Met Ala Glu Ala Tyr Ser Glu Ile Gly
385                 390                 395                 400

Met Lys Gly Glu Arg Arg Arg Gly Lys Gly His Asp Gly Leu Tyr Gln
                405                 410                 415

Gly Leu Ser Thr Ala Thr Lys Asp Thr Tyr Asp Ala Leu His Met Gln
            420                 425                 430

Ala Leu Pro Pro Arg Arg Ala Lys Arg Gly Ser Gly Ala Thr Asn Phe
        435                 440                 445

Ser Leu Leu Lys Gln Ala Gly Asp Val Glu Glu Asn Pro Gly Pro Arg
    450                 455                 460

Ala Lys Arg Asn Ile Met Ala Leu Pro Val Thr Ala Leu Leu Leu Pro
465                 470                 475                 480

Leu Ala Leu Leu Leu His Ala Ala Arg Pro Gln Val Gln Leu Gln Gln
                485                 490                 495

Ser Gly Pro Gly Leu Val Lys Pro Ser Gln Thr Leu Ser Leu Thr Cys
            500                 505                 510

Ala Ile Ser Gly Asp Ser Val Ser Ser Asn Ser Ala Ala Trp Asn Trp
        515                 520                 525

Ile Arg Gln Ser Pro Ser Arg Gly Leu Glu Trp Leu Gly Arg Thr Tyr
    530                 535                 540

Tyr Arg Ser Lys Trp Tyr Thr Asp Tyr Ala Val Ser Val Lys Asn Arg
545                 550                 555                 560

Ile Thr Ile Asn Pro Asp Thr Ser Lys Asn Gln Phe Ser Leu Gln Leu
                565                 570                 575

Asn Ser Val Thr Pro Glu Asp Thr Ala Val Tyr Tyr Cys Ala Gln Glu
            580                 585                 590

Val Glu Pro Gln Asp Ala Phe Asp Ile Trp Gly Gln Gly Thr Met Val
        595                 600                 605

Thr Val Ser Ser Gly Gly Gly Gly Ser Gly Gly Gly Gly Ser Gly Gly
    610                 615                 620

Gly Gly Ser Asp Ile Gln Met Thr Gln Ser Pro Ser Ser Val Ser Ala
625                 630                 635                 640

Ser Val Gly Asp Lys Val Thr Ile Thr Cys Arg Ala Ser Gln Asp Val
                645                 650                 655

Ser Gly Trp Leu Ala Trp Tyr Gln Gln Lys Pro Gly Leu Ala Pro Gln
            660                 665                 670

Leu Leu Ile Phe Gly Ala Ser Thr Leu Gln Gly Glu Val Pro Ser Arg
        675                 680                 685

Phe Ser Gly Ser Gly Ser Gly Thr Asp Phe Thr Leu Thr Ile Ser Ser
    690                 695                 700
```

Leu Gln Pro Glu Asp Phe Ala Thr Tyr Tyr Cys Gln Gln Ala Lys Tyr
705 710 715 720

Phe Pro Tyr Thr Phe Gly Arg Gly Thr Lys Leu Glu Ile Lys Ala Ser
725 730 735

Ala Thr Thr Thr Pro Ala Pro Arg Pro Pro Thr Pro Ala Pro Thr Ile
740 745 750

Ala Ser Gln Pro Leu Ser Leu Arg Pro Glu Ala Cys Arg Pro Ala Ala
755 760 765

Gly Gly Ala Val His Thr Arg Gly Leu Asp Phe Ala Cys Asp Ile Tyr
770 775 780

Ile Trp Ala Pro Leu Ala Gly Thr Cys Gly Val Leu Leu Leu Ser Leu
785 790 795 800

Val Ile Thr Leu Tyr Cys Arg Val Lys Phe Ser Arg Ser Ala Asp Ala
805 810 815

Pro Ala Tyr Gln Gln Gly Gln Asn Gln Leu Tyr Asn Glu Leu Asn Leu
820 825 830

Gly Arg Arg Glu Glu Tyr Asp Val Leu Asp Lys Arg Arg Gly Arg Asp
835 840 845

Pro Glu Met Gly Gly Lys Pro Arg Arg Lys Asn Pro Gln Glu Gly Leu
850 855 860

Tyr Asn Glu Leu Gln Lys Asp Lys Met Ala Glu Ala Tyr Ser Glu Ile
865 870 875 880

Gly Met Lys Gly Glu Arg Arg Arg Gly Lys Gly His Asp Gly Leu Tyr
885 890 895

Gln Gly Leu Ser Thr Ala Thr Lys Asp Thr Tyr Asp Ala Leu His Met
900 905 910

Gln Ala Leu Pro Pro Arg
915

<210> SEQ ID NO 80
<211> LENGTH: 3030
<212> TYPE: DNA
<213> ORGANISM: Artificial Sequence
<220> FEATURE:
<223> OTHER INFORMATION: CAR D0148 CD19 CD8H OX40TM OX40 z_CD22 CD8H&TM ICOS z

<400> SEQUENCE: 80
atgctgctgc tggtgaccag cctgctgctg tgcgaactgc cgcatccggc gtttctgctg 60
attccggagg tccagctggt acagtctgga gctgaggtga agaagcctgg ggcctcagtg 120
aaggtctcct gcaaggcttc tggatacacc ttcaccagct actatatgca ctgggtgcga 180
caggcccctg gacaagggct tgagtggatg ggattaatca accctagtgg tggtagcaca 240
agctacgcac agaagttcca gggcagagtc accatgacca gggacacgtc cacgagcaca 300
gtctacatgg agctgagcag cctgagatct gaggacacgg ccgtgtatta ctgtgcgaga 360
tcggatcggg gaattaccgc cacggacgct tttgatatct ggggccaagg gacaatggtc 420
accgtctctt caggcggagg aggctccggg ggaggaggtt ccgggggcgg gggttcccag 480
tctgtgctga ctcagccacc ctcggtgtca gtggccccag ggcggatggc caagattacc 540
tgtgggggaa gtgacattgg aaataaaaat gtccactggt atcagcagaa gccaggccag 600
gcccctgtcc tggttgtcta tgatgattac gaccggccct cagggatccc tgagcgattc 660
tctggctcca actctgggga cgcggccacc ctgacgatca gcacggtcga agtcggggat 720
gaggccgact atttctgtca ggtgtgggac ggtagtggtg atccttattg gatgttcggc 780

```
ggagggaccc agctcaccgt tttaggtgcg gccgcaacga ccactccagc accgagaccg    840
ccaaccccg cgcctaccat cgcaagtcaa ccactttctc tcaggcctga agcgtgccga     900
cctgcagctg gtggggcagt acataccagg ggtttggact tcgcatgtga cgtggcggca    960
attctcggcc tgggacttgt ccttggtctg cttggtccgc tcgcaatact tctggccttg   1020
tacctgctcc gcagagacca aagacttccg cccgacgccc acaagccccc aggaggaggt   1080
tccttcagaa cgcctataca agaagaacaa gcagatgccc actctaccct ggctaaaatc   1140
agggtgaagt ttagccgctc agccgatgca ccggcctacc agcagggaca gaaccagctc   1200
tacaacgagc tcaacctggg tcggcgggaa gaatatgacg tgctggacaa acggcgcggc   1260
agagatccgg agatgggggg aaagccgagg aggaagaacc ctcaagaggg cctgtacaac   1320
gaactgcaga aggacaagat ggcggaagcc tactccgaga tcggcatgaa gggagaacgc   1380
cggagaggga agggtcatga cggactgtac cagggcctgt caactgccac taaggacact   1440
tacgatgcgc tccatatgca agctttgccc ccgcggcgcg cgaaacgcgg cagcggcgcg   1500
accaacttta gcctgctgaa acaggcgggc gatgtggaag aaaacccggg cccgcgagca   1560
aagaggaata ttatggctct gcctgttacg gcactgctcc ttccgcttgc attgttgttg   1620
cacgcagcgc ggccccaagt gcagctgcag cagtccggtc ctggactggt caagccgtcc   1680
cagactctga gcctgacttg cgcaattagc ggggactcag tctcgtccaa ttcggcggcc   1740
tggaactgga tccggcagtc accatcaagg ggcctggaat ggctcgggcg cacttactac   1800
cggtccaaat ggtataccga ctacgccgtg tccgtgaaga atcggatcac cattaacccc   1860
gacacctcga agaaccagtt ctcactccaa ctgaacagcg tgacccccga ggataccgcg   1920
gtgtactact gcgcacaaga agtggaaccg caggacgcct tcgacatttg ggacacagga   1980
acgatggtca cagtgtcgtc cggtggagga ggttccggag gcggtggatc tggaggcgga   2040
ggttcggata tccagatgac ccagagcccc tcctcggtgt ccgcatccgt gggcgataag   2100
gtcaccatta cctgtagagc gtcccaggac gtgtccggat ggctggcctg gtaccagcag   2160
aagccaggct tggctcctca actgctgatc ttcggcgcca gcactcttca gggggaagtg   2220
ccatcacgct tctccggatc cggttccggc accgacttca ccctgaccat cagcagcctc   2280
cagcctgagg acttcgccac ttactactgc caacaggcca agtacttccc ctataccttc   2340
ggaagaggca ctaagctgga aatcaaggct agcgcaacca ctacgcctgc tccgcggcct   2400
ccaacgcccg cgcccacgat agctagtcag ccgttgtctc tccgaccaga ggcgtgtaga   2460
ccggccgctg gcggagccgt acatactcgc ggactcgact tcgcttgcga catctacatt   2520
tgggcaccct tggctgggac ctgtggggtg ctgttgctgt ccttggttat tacgttgtac   2580
tgctggctga caaaaaagaa gtattcatct agtgtacatg atccgaacgg tgaatacatg   2640
ttcatgcgcg cggtgaacac ggccaagaag agcagactga ccgacgtaac ccttagagtc   2700
aaattttcca ggtccgcaga tgcccccgcg taccagcaag gccagaacca actttacaac   2760
gaactgaacc tgggtcgccg ggaggaatat gatgtgctgg ataaacgaag gggggaggac   2820
cctgagatgg gagggaaacc tcgcaggaaa aacccgcagg aaggtttgta caacgagttg   2880
cagaaggata agatggctga ggcttactct gaaataggga tgaagggaga gagacggaga   2940
ggaaaaggcc atgatggcct ttaccagggc ttgagcacag caacaaagga tacttacgac   3000
gctcttcaca tgcaagctct gccaccacgg                                    3030
```

<210> SEQ ID NO 81
<211> LENGTH: 1010

<212> TYPE: PRT
<213> ORGANISM: Artificial Sequence
<220> FEATURE:
<223> OTHER INFORMATION: CAR D0148 CD19 CD8H OX40TM OX40 z_CD22 CD8H&TM ICOS z

<400> SEQUENCE: 81

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Ser Tyr Tyr Met His Trp Val Arg Gln Ala Pro Gly
    50                  55                  60

Gln Gly Leu Glu Trp Met Gly Leu Ile Asn Pro Ser Gly Gly Ser Thr
65                  70                  75                  80

Ser Tyr Ala Gln Lys Phe Gln Gly Arg Val Thr Met Thr Arg Asp Thr
                85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Ser Asp Arg Gly Ile Thr Ala Thr
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Gln
145                 150                 155                 160

Ser Val Leu Thr Gln Pro Pro Ser Val Ser Val Ala Pro Gly Arg Met
                165                 170                 175

Ala Lys Ile Thr Cys Gly Gly Ser Asp Ile Gly Asn Lys Asn Val His
            180                 185                 190

Trp Tyr Gln Gln Lys Pro Gly Gln Ala Pro Val Leu Val Val Tyr Asp
        195                 200                 205

Asp Tyr Asp Arg Pro Ser Gly Ile Pro Glu Arg Phe Ser Gly Ser Asn
    210                 215                 220

Ser Gly Asp Ala Ala Thr Leu Thr Ile Ser Thr Val Glu Val Gly Asp
225                 230                 235                 240

Glu Ala Asp Tyr Phe Cys Gln Val Trp Asp Gly Ser Gly Asp Pro Tyr
                245                 250                 255

Trp Met Phe Gly Gly Gly Thr Gln Leu Thr Val Leu Gly Ala Ala Ala
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Val Ala Ala
305                 310                 315                 320

Ile Leu Gly Leu Gly Leu Val Leu Gly Leu Leu Gly Pro Leu Ala Ile
                325                 330                 335

Leu Leu Ala Leu Tyr Leu Leu Arg Arg Asp Gln Arg Leu Pro Pro Asp
            340                 345                 350

Ala His Lys Pro Pro Gly Gly Gly Ser Phe Arg Thr Pro Ile Gln Glu
        355                 360                 365

Glu Gln Ala Asp Ala His Ser Thr Leu Ala Lys Ile Arg Val Lys Phe
    370                 375                 380
```

```
Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg Arg Ala Lys Arg
                485                 490                 495

Gly Ser Gly Ala Thr Asn Phe Ser Leu Leu Lys Gln Ala Gly Asp Val
            500                 505                 510

Glu Glu Asn Pro Gly Pro Arg Ala Lys Arg Asn Ile Met Ala Leu Pro
        515                 520                 525

Val Thr Ala Leu Leu Leu Pro Leu Ala Leu Leu Leu His Ala Ala Arg
    530                 535                 540

Pro Gln Val Gln Leu Gln Gln Ser Gly Pro Gly Leu Val Lys Pro Ser
545                 550                 555                 560

Gln Thr Leu Ser Leu Thr Cys Ala Ile Ser Gly Asp Ser Val Ser Ser
                565                 570                 575

Asn Ser Ala Ala Trp Asn Trp Ile Arg Gln Ser Pro Ser Arg Gly Leu
            580                 585                 590

Glu Trp Leu Gly Arg Thr Tyr Tyr Arg Ser Lys Trp Tyr Thr Asp Tyr
        595                 600                 605

Ala Val Ser Val Lys Asn Arg Ile Thr Ile Asn Pro Asp Thr Ser Lys
    610                 615                 620

Asn Gln Phe Ser Leu Gln Leu Asn Ser Val Thr Pro Glu Asp Thr Ala
625                 630                 635                 640

Val Tyr Tyr Cys Ala Gln Glu Val Glu Pro Gln Asp Ala Phe Asp Ile
                645                 650                 655

Trp Gly Gln Gly Thr Met Val Thr Val Ser Ser Gly Gly Gly Gly Ser
            660                 665                 670

Gly Gly Gly Gly Ser Gly Gly Gly Gly Ser Asp Ile Gln Met Thr Gln
        675                 680                 685

Ser Pro Ser Ser Val Ser Ala Ser Val Gly Asp Lys Val Thr Ile Thr
    690                 695                 700

Cys Arg Ala Ser Gln Asp Val Ser Gly Trp Leu Ala Trp Tyr Gln Gln
705                 710                 715                 720

Lys Pro Gly Leu Ala Pro Gln Leu Leu Ile Phe Gly Ala Ser Thr Leu
                725                 730                 735

Gln Gly Glu Val Pro Ser Arg Phe Ser Gly Ser Gly Ser Gly Thr Asp
            740                 745                 750

Phe Thr Leu Thr Ile Ser Ser Leu Gln Pro Glu Asp Phe Ala Thr Tyr
        755                 760                 765

Tyr Cys Gln Gln Ala Lys Tyr Phe Pro Tyr Thr Phe Gly Arg Gly Thr
    770                 775                 780

Lys Leu Glu Ile Lys Ala Ser Ala Thr Thr Thr Pro Ala Pro Arg Pro
785                 790                 795                 800
```

```
Pro Thr Pro Ala Pro Thr Ile Ala Ser Gln Pro Leu Ser Leu Arg Pro
                805                 810                 815

Glu Ala Cys Arg Pro Ala Ala Gly Gly Ala Val His Thr Arg Gly Leu
            820                 825                 830

Asp Phe Ala Cys Asp Ile Tyr Ile Trp Ala Pro Leu Ala Gly Thr Cys
        835                 840                 845

Gly Val Leu Leu Leu Ser Leu Val Ile Thr Leu Tyr Cys Trp Leu Thr
    850                 855                 860

Lys Lys Lys Tyr Ser Ser Ser Val His Asp Pro Asn Gly Glu Tyr Met
865                 870                 875                 880

Phe Met Arg Ala Val Asn Thr Ala Lys Lys Ser Arg Leu Thr Asp Val
                885                 890                 895

Thr Leu Arg Val Lys Phe Ser Arg Ser Ala Asp Ala Pro Ala Tyr Gln
            900                 905                 910

Gln Gly Gln Asn Gln Leu Tyr Asn Glu Leu Asn Leu Gly Arg Arg Glu
        915                 920                 925

Glu Tyr Asp Val Leu Asp Lys Arg Arg Gly Arg Asp Pro Glu Met Gly
    930                 935                 940

Gly Lys Pro Arg Arg Lys Asn Pro Gln Glu Gly Leu Tyr Asn Glu Leu
945                 950                 955                 960

Gln Lys Asp Lys Met Ala Glu Ala Tyr Ser Glu Ile Gly Met Lys Gly
                965                 970                 975

Glu Arg Arg Arg Gly Lys Gly His Asp Gly Leu Tyr Gln Gly Leu Ser
            980                 985                 990

Thr Ala Thr Lys Asp Thr Tyr Asp  Ala Leu His Met Gln  Ala Leu Pro
        995                 1000                 1005

Pro Arg
    1010
```

<210> SEQ ID NO 82
<211> LENGTH: 2892
<212> TYPE: DNA
<213> ORGANISM: Artificial Sequence
<220> FEATURE:
<223> OTHER INFORMATION: CAR D0149 CD19 CD8H&TM CD27 z_CD22 CD8H&TM ICOS3 z

<400> SEQUENCE: 82

```
atgcactggg tgcgacaggc ccctggacaa gggcttgagt ggatgggatt aatcaaccct     60

agtggtggta gcacaagcta cgcacagaag ttccagggca gagtcaccat gaccagggac    120

acgtccacga gcacagtcta catggagctg agcagcctga gatctgagga cacggccgtg    180

tattactgtg cgagatcgga tcggggaatt accgccacgg acgcttttga tatctggggc    240

caagggacaa tggtcaccgt ctcttcaggc ggaggaggct ccgggggagg aggttccggg    300

ggcgggggtt cccagtctgt gctgactcag ccaccctcgg tgtcagtggc cccagggcgg    360

atggccaaga ttacctgtgg gggaagtgac attggaaata aaaatgtcca ctggtatcag    420

cagaagccag gccaggcccc tgtcctggtt gtctatgatg attacgaccg gccctcaggg    480

atccctgagc gattctctgg ctccaactct ggggacgcgg ccaccctgac gatcagcacg    540

gtcgaagtcg gggatgaggc cgactatttc tgtcaggtgt gggacggtag tggtgatcct    600

tattggatgt tcggcggagg gacccagctc accgttttag gtgcggccgc gactaccact    660

cctgcaccac ggccacctac cccagccccc accattgcaa gccagccact ttcactgcgc    720

cccgaagcgt gtagaccagc tgctggagga gccgtgcata cccgagggct ggacttcgcc    780
```

```
tgtgacatct acatctgggc cccattggct ggaacttgcg gcgtgctgct cttgtctctg    840

gtcattaccc tgtactgcca acggcgcaaa taccgctcca ataaaggcga aagtccggta    900

gaacccgcag aaccttgcca ctacagttgt cccagagaag aagagggttc tacaatacct    960

attcaagagg actataggaa accagagccc gcatgtagtc ccagagtgaa gttcagccgc   1020

tcagccgatg caccggccta ccagcaggga cagaaccagc tctacaacga gctcaacctg   1080

ggtcggcggg aagaatatga cgtgctggac aaacggcgcg gcagagatcc ggagatgggg   1140

ggaaagccga ggaggaagaa ccctcaagag ggcctgtaca acgaactgca gaaggacaag   1200

atggcggaag cctactccga gatcggcatg aagggagaac gccggagagg gaagggtcat   1260

gacggactgt accagggcct gtcaactgcc actaaggaca cttacgatgc gctccatatg   1320

caagctttgc ccccgcggcg cgcgaaacgc ggcagcggcg cgaccaactt tagcctgctg   1380

aaacaggcgg gcgatgtgga agaaaacccg ggcccgcgag caaagaggaa tattatggct   1440

ctgcctgtta cggcactgct ccttccgctt gcattgttgt tgcacgcagc gcggccccaa   1500

gtgcagctgc agcagtccgg tcctggactg gtcaagccgt cccagactct gagcctgact   1560

tgcgcaatta gcggggactc agtctcgtcc aattcggcgg cctggaactg gatccggcag   1620

tcaccatcaa ggggcctgga atggctcggg cgcacttact accggtccaa atggtatacc   1680

gactacgccg tgtccgtgaa gaatcggatc accattaacc ccgacacctc gaagaaccag   1740

ttctcactcc aactgaacag cgtgaccccc gaggataccg cggtgtacta ctgcgcacaa   1800

gaagtggaac cgcaggacgc cttcgacatt tggggacagg gaacgatggt cacagtgtcg   1860

tccggtggag gaggttccgg aggcggtgga tctggaggcg gaggttcgga tatccagatg   1920

acccagagcc cctcctcggt gtccgcatcc gtgggcgata aggtcaccat tacctgtaga   1980

gcgtcccagg acgtgtccgg atggctggcc tggtaccagc agaagccagg cttggctcct   2040

caactgctga tcttcggcgc cagcactctt caggggggaag tgccatcacg cttctccgga   2100

tccggttccg gcaccgactt caccctgacc atcagcagcc tccagcctga ggacttcgcc   2160

acttactact gccaacaggc caagtacttc ccctatacct tcggaagagg cactaagctg   2220

gaaatcaagg ctagcgcaac cactacgcct gctccgcggc ctccaacgcc cgcgcccacg   2280

atagctagtc agccgttgtc tctccgacca gaggcgtgta gaccggccgc tggcggagcc   2340

gtacatactc gcggactcga cttcgcttgc gacatctaca tttgggcacc cttggctggg   2400

acctgtgggg tgctgttgct gtccttggtt attacgttgt actgctggct gacaaaaaag   2460

aagtattcat ctagtgtaca tgatccgaac ggtgaataca tgttcatgcg cgcggtgaac   2520

acggccaaga agagcagact gaccgacgta acccttagag tcaaattttc caggtccgca   2580

gatgcccccg cgtaccagca aggccagaac caactttaca acgaactgaa cctgggtcgc   2640

cgggaggaat atgatgtgct ggataaacga agggggaggg accctgagat gggagggaaa   2700

cctcgcagga aaaacccgca ggaaggtttg tacaacgagt tgcagaagga taagatggct   2760

gaggcttact ctgaaatagg gatgaaggga gagagacgga gaggaaaagg ccatgatggc   2820

ctttaccagg gcttgagcac agcaacaaag gatacttacg acgctcttca catgcaagct   2880

ctgccaccac gg                                                       2892
```

```
<210> SEQ ID NO 83
<211> LENGTH: 964
<212> TYPE: PRT
<213> ORGANISM: Artificial Sequence
<220> FEATURE:
<223> OTHER INFORMATION: CAR D0149 CD19 CD8H&TM CD27 z_CD22 CD8H&TM
```

ICOS3 z

<400> SEQUENCE: 83

```
Met His Trp Val Arg Gln Ala Pro Gly Gln Gly Leu Glu Trp Met Gly
1               5                   10                  15

Leu Ile Asn Pro Ser Gly Gly Ser Thr Ser Tyr Ala Gln Lys Phe Gln
            20                  25                  30

Gly Arg Val Thr Met Thr Arg Asp Thr Ser Thr Ser Thr Val Tyr Met
        35                  40                  45

Glu Leu Ser Ser Leu Arg Ser Glu Asp Thr Ala Val Tyr Tyr Cys Ala
    50                  55                  60

Arg Ser Asp Arg Gly Ile Thr Ala Thr Asp Ala Phe Asp Ile Trp Gly
65                  70                  75                  80

Gln Gly Thr Met Val Thr Val Ser Ser Gly Gly Gly Gly Ser Gly Gly
                85                  90                  95

Gly Gly Ser Gly Gly Gly Gly Ser Gln Ser Val Leu Thr Gln Pro Pro
            100                 105                 110

Ser Val Ser Val Ala Pro Gly Arg Met Ala Lys Ile Thr Cys Gly Gly
        115                 120                 125

Ser Asp Ile Gly Asn Lys Asn Val His Trp Tyr Gln Gln Lys Pro Gly
    130                 135                 140

Gln Ala Pro Val Leu Val Val Tyr Asp Asp Tyr Asp Arg Pro Ser Gly
145                 150                 155                 160

Ile Pro Glu Arg Phe Ser Gly Ser Asn Ser Gly Asp Ala Ala Thr Leu
                165                 170                 175

Thr Ile Ser Thr Val Glu Val Gly Asp Glu Ala Asp Tyr Phe Cys Gln
            180                 185                 190

Val Trp Asp Gly Ser Gly Asp Pro Tyr Trp Met Phe Gly Gly Gly Thr
        195                 200                 205

Gln Leu Thr Val Leu Gly Ala Ala Ala Thr Thr Thr Pro Ala Pro Arg
    210                 215                 220

Pro Pro Thr Pro Ala Pro Thr Ile Ala Ser Gln Pro Leu Ser Leu Arg
225                 230                 235                 240

Pro Glu Ala Cys Arg Pro Ala Ala Gly Gly Ala Val His Thr Arg Gly
                245                 250                 255

Leu Asp Phe Ala Cys Asp Ile Tyr Ile Trp Ala Pro Leu Ala Gly Thr
            260                 265                 270

Cys Gly Val Leu Leu Leu Ser Leu Val Ile Thr Leu Tyr Cys Gln Arg
        275                 280                 285

Arg Lys Tyr Arg Ser Asn Lys Gly Glu Ser Pro Val Glu Pro Ala Glu
    290                 295                 300

Pro Cys His Tyr Ser Cys Pro Arg Glu Glu Glu Gly Ser Thr Ile Pro
305                 310                 315                 320

Ile Gln Glu Asp Tyr Arg Lys Pro Glu Pro Ala Cys Ser Pro Arg Val
                325                 330                 335

Lys Phe Ser Arg Ser Ala Asp Ala Pro Ala Tyr Gln Gln Gly Gln Asn
            340                 345                 350

Gln Leu Tyr Asn Glu Leu Asn Leu Gly Arg Arg Glu Glu Tyr Asp Val
        355                 360                 365

Leu Asp Lys Arg Arg Gly Arg Asp Pro Glu Met Gly Gly Lys Pro Arg
    370                 375                 380

Arg Lys Asn Pro Gln Glu Gly Leu Tyr Asn Glu Leu Gln Lys Asp Lys
385                 390                 395                 400
```

```
Met Ala Glu Ala Tyr Ser Glu Ile Gly Met Lys Gly Glu Arg Arg Arg
                405                 410                 415

Gly Lys Gly His Asp Gly Leu Tyr Gln Gly Leu Ser Thr Ala Thr Lys
            420                 425                 430

Asp Thr Tyr Asp Ala Leu His Met Gln Ala Leu Pro Pro Arg Arg Ala
        435                 440                 445

Lys Arg Gly Ser Gly Ala Thr Asn Phe Ser Leu Leu Lys Gln Ala Gly
    450                 455                 460

Asp Val Glu Glu Asn Pro Gly Pro Arg Ala Lys Arg Asn Ile Met Ala
465                 470                 475                 480

Leu Pro Val Thr Ala Leu Leu Leu Pro Leu Ala Leu Leu Leu His Ala
                485                 490                 495

Ala Arg Pro Gln Val Gln Leu Gln Gln Ser Gly Pro Gly Leu Val Lys
            500                 505                 510

Pro Ser Gln Thr Leu Ser Leu Thr Cys Ala Ile Ser Gly Asp Ser Val
        515                 520                 525

Ser Ser Asn Ser Ala Ala Trp Asn Trp Ile Arg Gln Ser Pro Ser Arg
    530                 535                 540

Gly Leu Glu Trp Leu Gly Arg Thr Tyr Tyr Arg Ser Lys Trp Tyr Thr
545                 550                 555                 560

Asp Tyr Ala Val Ser Val Lys Asn Arg Ile Thr Ile Asn Pro Asp Thr
                565                 570                 575

Ser Lys Asn Gln Phe Ser Leu Gln Leu Asn Ser Val Thr Pro Glu Asp
            580                 585                 590

Thr Ala Val Tyr Tyr Cys Ala Gln Glu Val Glu Pro Gln Asp Ala Phe
        595                 600                 605

Asp Ile Trp Gly Gln Gly Thr Met Val Thr Val Ser Ser Gly Gly Gly
    610                 615                 620

Gly Ser Gly Gly Gly Gly Ser Gly Gly Gly Gly Ser Asp Ile Gln Met
625                 630                 635                 640

Thr Gln Ser Pro Ser Ser Val Ser Ala Ser Val Gly Asp Lys Val Thr
                645                 650                 655

Ile Thr Cys Arg Ala Ser Gln Asp Val Ser Gly Trp Leu Ala Trp Tyr
            660                 665                 670

Gln Gln Lys Pro Gly Leu Ala Pro Gln Leu Leu Ile Phe Gly Ala Ser
        675                 680                 685

Thr Leu Gln Gly Glu Val Pro Ser Arg Phe Ser Gly Ser Gly Ser Gly
    690                 695                 700

Thr Asp Phe Thr Leu Thr Ile Ser Ser Leu Gln Pro Glu Asp Phe Ala
705                 710                 715                 720

Thr Tyr Tyr Cys Gln Gln Ala Lys Tyr Phe Pro Tyr Thr Phe Gly Arg
                725                 730                 735

Gly Thr Lys Leu Glu Ile Lys Ala Ser Ala Thr Thr Thr Pro Ala Pro
            740                 745                 750

Arg Pro Pro Thr Pro Ala Pro Thr Ile Ala Ser Gln Pro Leu Ser Leu
        755                 760                 765

Arg Pro Glu Ala Cys Arg Pro Ala Ala Gly Gly Ala Val His Thr Arg
    770                 775                 780

Gly Leu Asp Phe Ala Cys Asp Ile Tyr Ile Trp Ala Pro Leu Ala Gly
785                 790                 795                 800

Thr Cys Gly Val Leu Leu Leu Ser Leu Val Ile Thr Leu Tyr Cys Trp
                805                 810                 815

Leu Thr Lys Lys Lys Tyr Ser Ser Ser Val His Asp Pro Asn Gly Glu
```

```
            820                 825                 830

Tyr Met Phe Met Arg Ala Val Asn Thr Ala Lys Lys Ser Arg Leu Thr
        835                 840                 845

Asp Val Thr Leu Arg Val Lys Phe Ser Arg Ser Ala Asp Ala Pro Ala
    850                 855                 860

Tyr Gln Gln Gly Gln Asn Gln Leu Tyr Asn Glu Leu Asn Leu Gly Arg
865                 870                 875                 880

Arg Glu Glu Tyr Asp Val Leu Asp Lys Arg Arg Gly Arg Asp Pro Glu
                885                 890                 895

Met Gly Gly Lys Pro Arg Arg Lys Asn Pro Gln Glu Gly Leu Tyr Asn
            900                 905                 910

Glu Leu Gln Lys Asp Lys Met Ala Glu Ala Tyr Ser Glu Ile Gly Met
        915                 920                 925

Lys Gly Glu Arg Arg Arg Gly Lys Gly His Asp Gly Leu Tyr Gln Gly
    930                 935                 940

Leu Ser Thr Ala Thr Lys Asp Thr Tyr Asp Ala Leu His Met Gln Ala
945                 950                 955                 960

Leu Pro Pro Arg
```

<210> SEQ ID NO 84
<211> LENGTH: 2289
<212> TYPE: DNA
<213> ORGANISM: Artificial Sequence
<220> FEATURE:
<223> OTHER INFORMATION: D0101 (EF-1a-TSLPR-CD19 (19217_1) CD8 BBz)

<400> SEQUENCE: 84

```
atgctgctgc tggtgaccag cctgcttctg tgcgaactgc cgcatccggc gtttctgttg     60

attccgcaag tcaccctcaa agagtcaggg ccaggaatcc tcaagccctc acagactctg    120

tctcttactt gctcattcag cggattcagc ctttccacct ctggtatggg cgtggggtgg    180

attaggcaac ctagcggaaa ggggcttgaa tggctggccc acatctggtg ggacgacgac    240

aagtactaca acccctcact gaagtcccag ctcactattt ccaaagatac ttcccggaat    300

caggtgttcc tcaagattac ctctgtcgac accgctgata ccgccactta ctattgttca    360

cgcagaccga gaggtaccat ggacgcaatg gactactggg gacagggcac cagcgtgacc    420

gtgtcatctg gcggtggagg gtcaggaggt ggaggtagcg gaggcggtgg gtccgacatt    480

gtcatgaccc aggccgccag ctccctgagc gcttcactgg gcgacagggt gaccatcagc    540

tgtcgcgcat cacaagatat ctctaagtat cttaattggt accagcaaaa gccggatgga    600

accgtgaagc tgctgatcta ctacacctca cggctgcatt ctggagtgcc tagccgcttt    660

agcggatctg ggtccggtac tgactacagc ctcaccatta gaaaccttga acaggaggac    720

atcgcaactt atttctgcca acaggtctat actctgccgt ggaccttcgg cggaggtacc    780

aaactggaga ttaagggtgg aggtggttca ggcggcggag gctcaggcgg cggcggtagc    840

ggcggaggag gaagcggagg tggcggatca gaggtccagc tggtacagtc tggagctgag    900

gtgaagaagc ctggggcctc agtgaaggtc tcctgcaagg cttctggata caccttcacc    960

agctactata tgcactgggt gcgacaggcc cctggacaag ggcttgagtg gatgggatta   1020

atcaacccta gtggtggtag cacaagctac gcacagaagt tccagggcag agtcaccatg   1080

accagggaca cgtccacgag cacagtctac atggagctga gcagcctgag atctgaggac   1140

acggccgtgt attactgtgc gagatcggat cggggaatta ccgccacgga cgcttttgat   1200

atctggggcc aagggacaat ggtcaccgtc tcttcaggcg gaggaggctc tgggggagga   1260
```

```
ggttccggag gaggcggttc ccagtctgtg ctgactcagc caccctcggt gtcagtggcc   1320

ccagggcgga tggccaagat tacctgtggg ggaagtgaca ttggaaataa aaatgtccac   1380

tggtatcagc agaagccagg ccaggcccct gtcctggttg tctatgatga ttacgaccgg   1440

ccctcaggga tccctgagcg attctctggc tccaactctg ggacgcggc caccctgacg    1500

atcagcacgg tcgaagtcgg ggatgaggcc gactatttct gtcaggtgtg ggacggtagt   1560

ggtgatcctt attggatgtt cggcggaggg acccagctca ccgttttagg tgcggccgca   1620

acgaccactc ctgcaccccg ccctccgact ccggccccaa ccattgccag ccagcccctg   1680

tccctgcggc cggaagcctg cagaccggct gccggcggag ccgtccatac ccggggactg   1740

gatttcgcct gcgatatcta tatctgggca ccactcgccg gaacctgtgg agtgctgctg   1800

ctgtcccttg tgatcaccct gtactgcaag cgcggacgga agaaactctt gtacatcttc   1860

aagcagccgt tcatgcgccc tgtgcaaacc acccaagaag aggacgggtg ctcctgccgg   1920

ttcccggaag aggaagaggg cggctgcgaa ctgcgcgtga agttttcccg gtccgccgac   1980

gctccggcgt accagcaggg gcaaaaccag ctgtacaacg aacttaacct cggtcgccgg   2040

gaagaatatg acgtgctgga caagcggcgg ggaagagatc ccgagatggg tggaaagccg   2100

cggcggaaga accctcagga gggcttgtac aacgagctgc aaaaggacaa aatggccgaa   2160

gcctactccg agattggcat gaagggagag cgcagacgcg ggaagggaca cgatggactg   2220

taccaggac tgtcaaccgc gactaaggac acttacgacg ccctgcacat gcaggccctg    2280

cccccgcgc                                                           2289
```

<210> SEQ ID NO 85
<211> LENGTH: 763
<212> TYPE: PRT
<213> ORGANISM: Artificial Sequence
<220> FEATURE:
<223> OTHER INFORMATION: D0101 (EF-1a-TSLPR-CD19 (19217_1) CD8 BBz)

<400> SEQUENCE: 85

```
Met Leu Leu Leu Val Thr Ser Leu Leu Leu Cys Glu Leu Pro His Pro
1               5                   10                  15

Ala Phe Leu Leu Ile Pro Gln Val Thr Leu Lys Glu Ser Gly Pro Gly
            20                  25                  30

Ile Leu Lys Pro Ser Gln Thr Leu Ser Leu Thr Cys Ser Phe Ser Gly
        35                  40                  45

Phe Ser Leu Ser Thr Ser Gly Met Gly Val Gly Trp Ile Arg Gln Pro
    50                  55                  60

Ser Gly Lys Gly Leu Glu Trp Leu Ala His Ile Trp Trp Asp Asp Asp
65                  70                  75                  80

Lys Tyr Tyr Asn Pro Ser Leu Lys Ser Gln Leu Thr Ile Ser Lys Asp
                85                  90                  95

Thr Ser Arg Asn Gln Val Phe Leu Lys Ile Thr Ser Val Asp Thr Ala
            100                 105                 110

Asp Thr Ala Thr Tyr Tyr Cys Ser Arg Arg Pro Arg Gly Thr Met Asp
        115                 120                 125

Ala Met Asp Tyr Trp Gly Gln Gly Thr Ser Val Thr Val Ser Ser Gly
    130                 135                 140

Gly Gly Gly Ser Gly Gly Gly Gly Ser Gly Gly Gly Gly Ser Asp Ile
145                 150                 155                 160

Val Met Thr Gln Ala Ala Ser Ser Leu Ser Ala Ser Leu Gly Asp Arg
                165                 170                 175
```

```
Val Thr Ile Ser Cys Arg Ala Ser Gln Asp Ile Ser Lys Tyr Leu Asn
            180                 185                 190

Trp Tyr Gln Gln Lys Pro Asp Gly Thr Val Lys Leu Leu Ile Tyr Tyr
        195                 200                 205

Thr Ser Arg Leu His Ser Gly Val Pro Ser Arg Phe Ser Gly Ser Gly
    210                 215                 220

Ser Gly Thr Asp Tyr Ser Leu Thr Ile Arg Asn Leu Glu Gln Glu Asp
225                 230                 235                 240

Ile Ala Thr Tyr Phe Cys Gln Gln Val Tyr Thr Leu Pro Trp Thr Phe
                245                 250                 255

Gly Gly Gly Thr Lys Leu Glu Ile Lys Gly Gly Gly Gly Ser Gly Gly
            260                 265                 270

Gly Gly Ser Gly Gly Gly Gly Ser Gly Gly Gly Gly Ser Gly Gly Gly
        275                 280                 285

Gly Ser Glu Val Gln Leu Val Gln Ser Gly Ala Glu Val Lys Lys Pro
    290                 295                 300

Gly Ala Ser Val Lys Val Ser Cys Lys Ala Ser Gly Tyr Thr Phe Thr
305                 310                 315                 320

Ser Tyr Tyr Met His Trp Val Arg Gln Ala Pro Gly Gln Gly Leu Glu
                325                 330                 335

Trp Met Gly Leu Ile Asn Pro Ser Gly Gly Ser Thr Ser Tyr Ala Gln
            340                 345                 350

Lys Phe Gln Gly Arg Val Thr Met Thr Arg Asp Thr Ser Thr Ser Thr
        355                 360                 365

Val Tyr Met Glu Leu Ser Ser Leu Arg Ser Glu Asp Thr Ala Val Tyr
    370                 375                 380

Tyr Cys Ala Arg Ser Asp Arg Gly Ile Thr Ala Thr Asp Ala Phe Asp
385                 390                 395                 400

Ile Trp Gly Gln Gly Thr Met Val Thr Val Ser Ser Gly Gly Gly Gly
                405                 410                 415

Ser Gly Gly Gly Gly Ser Gly Gly Gly Gly Ser Gln Ser Val Leu Thr
            420                 425                 430

Gln Pro Pro Ser Val Ser Val Ala Pro Gly Arg Met Ala Lys Ile Thr
        435                 440                 445

Cys Gly Gly Ser Asp Ile Gly Asn Lys Asn Val His Trp Tyr Gln Gln
    450                 455                 460

Lys Pro Gly Gln Ala Pro Val Leu Val Val Tyr Asp Asp Tyr Asp Arg
465                 470                 475                 480

Pro Ser Gly Ile Pro Glu Arg Phe Ser Gly Ser Asn Ser Gly Asp Ala
                485                 490                 495

Ala Thr Leu Thr Ile Ser Thr Val Glu Val Gly Asp Glu Ala Asp Tyr
            500                 505                 510

Phe Cys Gln Val Trp Asp Gly Ser Gly Asp Pro Tyr Trp Met Phe Gly
        515                 520                 525

Gly Gly Thr Gln Leu Thr Val Leu Gly Ala Ala Ala Thr Thr Thr Pro
    530                 535                 540

Ala Pro Arg Pro Pro Thr Pro Ala Pro Thr Ile Ala Ser Gln Pro Leu
545                 550                 555                 560

Ser Leu Arg Pro Glu Ala Cys Arg Pro Ala Ala Gly Gly Ala Val His
                565                 570                 575

Thr Arg Gly Leu Asp Phe Ala Cys Asp Ile Tyr Ile Trp Ala Pro Leu
            580                 585                 590
```

```
Ala Gly Thr Cys Gly Val Leu Leu Leu Ser Leu Val Ile Thr Leu Tyr
        595                 600                 605

Cys Lys Arg Gly Arg Lys Lys Leu Leu Tyr Ile Phe Lys Gln Pro Phe
    610                 615                 620

Met Arg Pro Val Gln Thr Thr Gln Glu Glu Asp Gly Cys Ser Cys Arg
625                 630                 635                 640

Phe Pro Glu Glu Glu Glu Gly Gly Cys Glu Leu Arg Val Lys Phe Ser
                645                 650                 655

Arg Ser Ala Asp Ala Pro Ala Tyr Gln Gln Gly Gln Asn Gln Leu Tyr
            660                 665                 670

Asn Glu Leu Asn Leu Gly Arg Arg Glu Glu Tyr Asp Val Leu Asp Lys
        675                 680                 685

Arg Arg Gly Arg Asp Pro Glu Met Gly Gly Lys Pro Arg Arg Lys Asn
    690                 695                 700

Pro Gln Glu Gly Leu Tyr Asn Glu Leu Gln Lys Asp Lys Met Ala Glu
705                 710                 715                 720

Ala Tyr Ser Glu Ile Gly Met Lys Gly Glu Arg Arg Arg Gly Lys Gly
                725                 730                 735

His Asp Gly Leu Tyr Gln Gly Leu Ser Thr Ala Thr Lys Asp Thr Tyr
            740                 745                 750

Asp Ala Leu His Met Gln Ala Leu Pro Pro Arg
        755                 760
```

<210> SEQ ID NO 86
<211> LENGTH: 2289
<212> TYPE: DNA
<213> ORGANISM: Artificial Sequence
<220> FEATURE:
<223> OTHER INFORMATION: D0102 (EF-1a-CD19 (19217_1)-TSLPR CD8 BBz)

<400> SEQUENCE: 86

```
atgctgctgc tggtgaccag cctgcttctg tgcgaactgc cgcatccggc gtttctgttg     60

attccggagg tccagctggt acagtctgga gctgaggtga agaagcctgg ggcctcagtg    120

aaggtctcct gcaaggcttc tggatacacc ttcaccagct actatatgca ctgggtgcga    180

caggcccctg gacaagggct tgagtggatg ggattaatca accctagtgg tggtagcaca    240

agctacgcac agaagttcca gggcagagtc accatgacca gggacacgtc cacgagcaca    300

gtctacatgg agctgagcag cctgagatct gaggacacgg ccgtgtatta ctgtgcgaga    360

tcggatcggg gaattaccgc cacggacgct tttgatatct ggggccaagg gacaatggtc    420

accgtctctt caggcggagg aggctctggg ggaggaggtt ccggaggagg cggttcccag    480

tctgtgctga ctcagccacc ctcggtgtca gtggccccag ggcggatggc caagattacc    540

tgtgggggaa gtgacattgg aaataaaaat gtccactggt atcagcagaa gccaggccag    600

gcccctgtcc tggttgtcta tgatgattac gaccggccct cagggatccc tgagcgattc    660

tctggctcca actctgggga cgcggccacc ctgacgatca gcacggtcga agtcggggat    720

gaggccgact atttctgtca ggtgtgggac ggtagtggtg atccttattg gatgttcggc    780

ggagggaccc agctcaccgt tttaggtggt ggaggtggtt caggcggagg aggctcaggc    840

ggaggcggta gcggcggagg aggaagcgga ggtggcggat cacaagtcac cctcaaagag    900

tcagggccag gaatcctcaa gccctcacag actctgtctc ttacttgctc attcagcgga    960

ttcagccttt ccacctctgg tatgggcgtg ggtggatta ggcaacctag cggaaagggg   1020

cttgaatggc tggcccacat ctggtgggac gacgacaagt actacaaccc ctcactgaag   1080
```

```
tcccagctca ctatttccaa agatacttcc cggaatcagg tgttcctcaa gattacctct   1140

gtcgacaccg ctgataccgc cacttactat tgttcacgca gaccgagagg taccatggac   1200

gcaatggact actggggaca gggcaccagc gtgaccgtgt catctggcgg tggagggtca   1260

ggaggtggag gtagcggagg cggtgggtcc gacattgtca tgacccaggc cgccagctcc   1320

ctgagcgctt cactgggcga cagggtgacc atcagctgtc gcgcatcaca agatatctct   1380

aagtatctta attggtacca gcaaaagccg gatggaaccg tgaagctgct gatctactac   1440

acctcacggc tgcattctgg agtgcctagc cgctttagcg gatctgggtc cggtactgac   1500

tacagcctca ccattagaaa ccttgaacag gaggacatcg caacttattt ctgccaacag   1560

gtctatactc tgccgtggac cttcggcgga ggtaccaaac tggagattaa ggcggccgca   1620

acgaccactc ctgcaccccg ccctccgact ccggccccaa ccattgccag ccagcccctg   1680

tccctgcggc cggaagcctg cagaccggct gccggcggag ccgtccatac ccggggactg   1740

gatttcgcct gcgatatcta tatctgggca ccactcgccg gaacctgtgg agtgctgctg   1800

ctgtcccttg tgatcaccct gtactgcaag cgcggacgga agaaactctt gtacatcttc   1860

aagcagccgt tcatgcgccc tgtgcaaacc acccaagaag aggacgggtg ctcctgccgg   1920

ttcccggaag aggaagaggg cggctgcgaa ctgcgcgtga agttttcccg gtccgccgac   1980

gctccggcgt accagcaggg gcaaaaccag ctgtacaacg aacttaacct cggtcgccgg   2040

gaagaatatg acgtgctgga caagcggcgg ggaagagatc ccgagatggg tggaaagccg   2100

cggcggaaga accctcagga gggcttgtac aacgagctgc aaaaggacaa aatggccgaa   2160

gcctactccg agattggcat gaagggagag cgcagacgcg ggaagggaca cgatggactg   2220

taccagggac tgtcaaccgc gactaaggac acttacgacg ccctgcacat gcaggccctg   2280

cccccgcgc                                                            2289
```

<210> SEQ ID NO 87
<211> LENGTH: 763
<212> TYPE: PRT
<213> ORGANISM: Artificial Sequence
<220> FEATURE:
<223> OTHER INFORMATION: D0102 (EF-1a-CD19 (19217_1)-TSLPR CD8 BBz)

<400> SEQUENCE: 87

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Ser Tyr Tyr Met His Trp Val Arg Gln Ala Pro Gly
    50                  55                  60

Gln Gly Leu Glu Trp Met Gly Leu Ile Asn Pro Ser Gly Gly Ser Thr
65                  70                  75                  80

Ser Tyr Ala Gln Lys Phe Gln Gly Arg Val Thr Met Thr Arg Asp Thr
                85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Ser Asp Arg Gly Ile Thr Ala Thr
        115                 120                 125

Asp Ala Phe Asp Ile Trp Gly Gln Gly Thr Met Val Thr Val Ser Ser
    130                 135                 140
```

-continued

```
Gly Gly Gly Gly Ser Gly Gly Gly Gly Ser Gly Gly Gly Gly Ser Gln
145                 150                 155                 160

Ser Val Leu Thr Gln Pro Pro Ser Val Ser Val Ala Pro Gly Arg Met
                165                 170                 175

Ala Lys Ile Thr Cys Gly Gly Ser Asp Ile Gly Asn Lys Asn Val His
            180                 185                 190

Trp Tyr Gln Gln Lys Pro Gly Gln Ala Pro Val Leu Val Val Tyr Asp
        195                 200                 205

Asp Tyr Asp Arg Pro Ser Gly Ile Pro Glu Arg Phe Ser Gly Ser Asn
    210                 215                 220

Ser Gly Asp Ala Ala Thr Leu Thr Ile Ser Thr Val Glu Val Gly Asp
225                 230                 235                 240

Glu Ala Asp Tyr Phe Cys Gln Val Trp Asp Gly Ser Gly Asp Pro Tyr
                245                 250                 255

Trp Met Phe Gly Gly Gly Thr Gln Leu Thr Val Leu Gly Gly Gly Gly
            260                 265                 270

Gly Ser Gly Gly Gly Gly Ser Gly Gly Gly Gly Ser Gly Gly Gly Gly
        275                 280                 285

Ser Gly Gly Gly Gly Ser Gln Val Thr Leu Lys Glu Ser Gly Pro Gly
    290                 295                 300

Ile Leu Lys Pro Ser Gln Thr Leu Ser Leu Thr Cys Ser Phe Ser Gly
305                 310                 315                 320

Phe Ser Leu Ser Thr Ser Gly Met Gly Val Gly Trp Ile Arg Gln Pro
                325                 330                 335

Ser Gly Lys Gly Leu Glu Trp Leu Ala His Ile Trp Trp Asp Asp Asp
            340                 345                 350

Lys Tyr Tyr Asn Pro Ser Leu Lys Ser Gln Leu Thr Ile Ser Lys Asp
        355                 360                 365

Thr Ser Arg Asn Gln Val Phe Leu Lys Ile Thr Ser Val Asp Thr Ala
    370                 375                 380

Asp Thr Ala Thr Tyr Tyr Cys Ser Arg Arg Pro Arg Gly Thr Met Asp
385                 390                 395                 400

Ala Met Asp Tyr Trp Gly Gln Gly Thr Ser Val Thr Val Ser Ser Gly
                405                 410                 415

Gly Gly Gly Ser Gly Gly Gly Gly Ser Gly Gly Gly Gly Ser Asp Ile
            420                 425                 430

Val Met Thr Gln Ala Ala Ser Ser Leu Ser Ala Ser Leu Gly Asp Arg
        435                 440                 445

Val Thr Ile Ser Cys Arg Ala Ser Gln Asp Ile Ser Lys Tyr Leu Asn
    450                 455                 460

Trp Tyr Gln Gln Lys Pro Asp Gly Thr Val Lys Leu Leu Ile Tyr Tyr
465                 470                 475                 480

Thr Ser Arg Leu His Ser Gly Val Pro Ser Arg Phe Ser Gly Ser Gly
                485                 490                 495

Ser Gly Thr Asp Tyr Ser Leu Thr Ile Arg Asn Leu Glu Gln Glu Asp
            500                 505                 510

Ile Ala Thr Tyr Phe Cys Gln Gln Val Tyr Thr Leu Pro Trp Thr Phe
        515                 520                 525

Gly Gly Gly Thr Lys Leu Glu Ile Lys Ala Ala Ala Thr Thr Thr Pro
    530                 535                 540

Ala Pro Arg Pro Pro Thr Pro Ala Pro Thr Ile Ala Ser Gln Pro Leu
545                 550                 555                 560

Ser Leu Arg Pro Glu Ala Cys Arg Pro Ala Ala Gly Gly Ala Val His
```

```
                565                 570                 575

Thr Arg Gly Leu Asp Phe Ala Cys Asp Ile Tyr Ile Trp Ala Pro Leu
            580                 585                 590

Ala Gly Thr Cys Gly Val Leu Leu Leu Ser Leu Val Ile Thr Leu Tyr
        595                 600                 605

Cys Lys Arg Gly Arg Lys Lys Leu Leu Tyr Ile Phe Lys Gln Pro Phe
    610                 615                 620

Met Arg Pro Val Gln Thr Thr Gln Glu Glu Asp Gly Cys Ser Cys Arg
625                 630                 635                 640

Phe Pro Glu Glu Glu Glu Gly Gly Cys Glu Leu Arg Val Lys Phe Ser
                645                 650                 655

Arg Ser Ala Asp Ala Pro Ala Tyr Gln Gln Gly Gln Asn Gln Leu Tyr
            660                 665                 670

Asn Glu Leu Asn Leu Gly Arg Arg Glu Glu Tyr Asp Val Leu Asp Lys
        675                 680                 685

Arg Arg Gly Arg Asp Pro Glu Met Gly Gly Lys Pro Arg Arg Lys Asn
    690                 695                 700

Pro Gln Glu Gly Leu Tyr Asn Glu Leu Gln Lys Asp Lys Met Ala Glu
705                 710                 715                 720

Ala Tyr Ser Glu Ile Gly Met Lys Gly Glu Arg Arg Arg Gly Lys Gly
                725                 730                 735

His Asp Gly Leu Tyr Gln Gly Leu Ser Thr Ala Thr Lys Asp Thr Tyr
            740                 745                 750

Asp Ala Leu His Met Gln Ala Leu Pro Pro Arg
        755                 760


<210> SEQ ID NO 88
<211> LENGTH: 2280
<212> TYPE: DNA
<213> ORGANISM: Artificial Sequence
<220> FEATURE:
<223> OTHER INFORMATION: D0103 (EF-1a-TSLPR-CD22 (16P17) CD8 BBz)

<400> SEQUENCE: 88

atgcttcttt tggtgacttc ccttttgctg tgcgagttgc cacaccccgc cttcctgctt     60

attccccaag tcaccctcaa agagtcaggg ccaggaatcc tcaagccctc acagactctg    120

tctcttactt gctcattcag cggattcagc ctttccacct ctggtatggg cgtggggtgg    180

attaggcaac ctagcggaaa ggggcttgaa tggctggccc acatctggtg ggacgacgac    240

aagtactaca acccctcact gaagtcccag ctcactattt ccaaagatac ttcccggaat    300

caggtgttcc tcaagattac ctctgtcgac accgctgata ccgccactta ctattgttca    360

cgcagaccga gaggtaccat ggacgcaatg gactactggg gacagggcac cagcgtgacc    420

gtgtcatctg gcggtggagg gtcaggaggt ggaggtagcg gaggcggtgg gtccgacatt    480

gtcatgaccc aggccgccag ctccctgagc gcttcactgg gcgacagggt gaccatcagc    540

tgtcgcgcat cacaagatat ctctaagtat cttaattggt accagcaaaa gccggatgga    600

accgtgaagc tgctgatcta ctacacctca cggctgcatt ctggagtgcc tagccgcttt    660

agcggatctg ggtccggtac tgactacagc ctcaccatta gaaaccttga acaggaggac    720

atcgcaactt atttctgcca acaggtctat actctgccgt ggaccttcgg cggaggtacc    780

aaactggaga ttaagggtgg aggtggttca ggcggaggag gctcaggcgg aggcggtagc    840

ggcggaggag gaagcggagg tggcggatca caggtacagc ttcaacagag tgggccggga    900

ctggtgaaac actcccaaac actttctctg acgtgcgcta tatcaggtga ctctgtttca    960
```

```
tctaattctg ctgcgtggaa ctggattcga caatctccca gtcgcgggtt ggaatggctg   1020

ggacgaacat attatcggtc taagtggtat aacgattatg ctgtatctgt taaatctcga   1080

attacgatta atcctgacac ctccaagaac caattctccc tccagttgaa tagcgtgact   1140

cccgaggaca cggccgttta ctattgcgcc caggaagttg aaccccacga tgcattcgac   1200

atctggggcc agggaacgat ggtcaccgtc agcagtggcg gcggcggatc tgggggtggc   1260

ggttctggcg gtggaggatc agacatacaa atgacgcaga gtccctcaag tgtgtacgcg   1320

agtgtggggg ataaggtaac tattacgtgc agagcgtcac aggatgttag tggatggctt   1380

gcctggtatc agcagaagcc aggccttgct ccacagctcc ttatcagtgg tgcttctaca   1440

cttcagggcg aggttccgag tagattctct ggttctggat ctggtactga cttcactctt   1500

acaatttctt ctttgcaacc agaagacttt gcgacttatt actgccaaca ggccaaatac   1560

ttcccttata catttggcca aggtaccaag ttggagataa aggcggccgc aacgaccact   1620

cctgcacccc gccctccgac tccggcccca accattgcca gccagcccct gtccctgcgg   1680

ccggaagcct gcagaccggc tgccggcgga gccgtccata cccggggact ggatttcgcc   1740

tgcgatatct atatctgggc accactcgcc ggaacctgtg gagtgctgct gctgtccctt   1800

gtgatcaccc tgtactgcaa gcgcggacgg aagaaactct tgtacatctt caagcagccg   1860

ttcatgcgcc ctgtgcaaac cacccaagaa gaggacgggt gctcctgccg gttcccggaa   1920

gaggaagagg gcggctgcga actgcgcgtg aagttttccc ggtccgccga cgctccggcg   1980

taccagcagg ggcaaaacca gctgtacaac gaacttaacc tcggtcgccg ggaagaatat   2040

gacgtgctgg acaagcggcg gggaagagat cccgagatgg gtggaaagcc gcggcggaag   2100

aaccctcagg agggcttgta caacgagctg caaaaggaca aaatggccga agcctactcc   2160

gagattggca tgaagggaga gcgcagacgc gggaagggac acgatggact gtaccaggga   2220

ctgtcaaccg cgactaagga cacttacgac gccctgcaca tgcaggccct gcccccgcgc   2280
```

```
<210> SEQ ID NO 89
<211> LENGTH: 760
<212> TYPE: PRT
<213> ORGANISM: Artificial Sequence
<220> FEATURE:
<223> OTHER INFORMATION: D0103 (EF-1a-TSLPR-CD22 (16P17) CD8 BBz)

<400> SEQUENCE: 89

Met Leu Leu Leu Val Thr Ser Leu Leu Leu Cys Glu Leu Pro His Pro
1               5                   10                  15

Ala Phe Leu Leu Ile Pro Gln Val Thr Leu Lys Glu Ser Gly Pro Gly
            20                  25                  30

Ile Leu Lys Pro Ser Gln Thr Leu Ser Leu Thr Cys Ser Phe Ser Gly
        35                  40                  45

Phe Ser Leu Ser Thr Ser Gly Met Gly Val Gly Trp Ile Arg Gln Pro
    50                  55                  60

Ser Gly Lys Gly Leu Glu Trp Leu Ala His Ile Trp Trp Asp Asp Asp
65                  70                  75                  80

Lys Tyr Tyr Asn Pro Ser Leu Lys Ser Gln Leu Thr Ile Ser Lys Asp
                85                  90                  95

Thr Ser Arg Asn Gln Val Phe Leu Lys Ile Thr Ser Val Asp Thr Ala
            100                 105                 110

Asp Thr Ala Thr Tyr Tyr Cys Ser Arg Arg Pro Arg Gly Thr Met Asp
        115                 120                 125
```

```
Ala Met Asp Tyr Trp Gly Gln Gly Thr Ser Val Thr Val Ser Ser Gly
    130                 135                 140

Gly Gly Gly Ser Gly Gly Gly Gly Ser Gly Gly Gly Gly Ser Asp Ile
145                 150                 155                 160

Val Met Thr Gln Ala Ala Ser Ser Leu Ser Ala Ser Leu Gly Asp Arg
                165                 170                 175

Val Thr Ile Ser Cys Arg Ala Ser Gln Asp Ile Ser Lys Tyr Leu Asn
            180                 185                 190

Trp Tyr Gln Gln Lys Pro Asp Gly Thr Val Lys Leu Leu Ile Tyr Tyr
        195                 200                 205

Thr Ser Arg Leu His Ser Gly Val Pro Ser Arg Phe Ser Gly Ser Gly
    210                 215                 220

Ser Gly Thr Asp Tyr Ser Leu Thr Ile Arg Asn Leu Glu Gln Glu Asp
225                 230                 235                 240

Ile Ala Thr Tyr Phe Cys Gln Gln Val Tyr Thr Leu Pro Trp Thr Phe
                245                 250                 255

Gly Gly Gly Thr Lys Leu Glu Ile Lys Gly Gly Gly Gly Ser Gly Gly
            260                 265                 270

Gly Gly Ser Gly Gly Gly Gly Ser Gly Gly Gly Gly Ser Gly Gly Gly
        275                 280                 285

Gly Ser Gln Val Gln Leu Gln Gln Ser Gly Pro Gly Leu Val Lys His
    290                 295                 300

Ser Gln Thr Leu Ser Leu Thr Cys Ala Ile Ser Gly Asp Ser Val Ser
305                 310                 315                 320

Ser Asn Ser Ala Ala Trp Asn Trp Ile Arg Gln Ser Pro Ser Arg Gly
                325                 330                 335

Leu Glu Trp Leu Gly Arg Thr Tyr Tyr Arg Ser Lys Trp Tyr Asn Asp
            340                 345                 350

Tyr Ala Val Ser Val Lys Ser Arg Ile Thr Ile Asn Pro Asp Thr Ser
        355                 360                 365

Lys Asn Gln Phe Ser Leu Gln Leu Asn Ser Val Thr Pro Glu Asp Thr
    370                 375                 380

Ala Val Tyr Tyr Cys Ala Gln Glu Val Glu Pro His Asp Ala Phe Asp
385                 390                 395                 400

Ile Trp Gly Gln Gly Thr Met Val Thr Val Ser Ser Gly Gly Gly Gly
                405                 410                 415

Ser Gly Gly Gly Gly Ser Gly Gly Gly Gly Ser Asp Ile Gln Met Thr
            420                 425                 430

Gln Ser Pro Ser Ser Val Tyr Ala Ser Val Gly Asp Lys Val Thr Ile
        435                 440                 445

Thr Cys Arg Ala Ser Gln Asp Val Ser Gly Trp Leu Ala Trp Tyr Gln
    450                 455                 460

Gln Lys Pro Gly Leu Ala Pro Gln Leu Leu Ile Ser Gly Ala Ser Thr
465                 470                 475                 480

Leu Gln Gly Glu Val Pro Ser Arg Phe Ser Gly Ser Gly Ser Gly Thr
                485                 490                 495

Asp Phe Thr Leu Thr Ile Ser Ser Leu Gln Pro Glu Asp Phe Ala Thr
            500                 505                 510

Tyr Tyr Cys Gln Gln Ala Lys Tyr Phe Pro Tyr Thr Phe Gly Gln Gly
        515                 520                 525

Thr Lys Leu Glu Ile Lys Ala Ala Ala Thr Thr Thr Pro Ala Pro Arg
    530                 535                 540

Pro Pro Thr Pro Ala Pro Thr Ile Ala Ser Gln Pro Leu Ser Leu Arg
```

```
545                 550                 555                 560

Pro Glu Ala Cys Arg Pro Ala Ala Gly Gly Ala Val His Thr Arg Gly
                565                 570                 575

Leu Asp Phe Ala Cys Asp Ile Tyr Ile Trp Ala Pro Leu Ala Gly Thr
            580                 585                 590

Cys Gly Val Leu Leu Leu Ser Leu Val Ile Thr Leu Tyr Cys Lys Arg
        595                 600                 605

Gly Arg Lys Lys Leu Leu Tyr Ile Phe Lys Gln Pro Phe Met Arg Pro
    610                 615                 620

Val Gln Thr Thr Gln Glu Glu Asp Gly Cys Ser Cys Arg Phe Pro Glu
625                 630                 635                 640

Glu Glu Glu Gly Gly Cys Glu Leu Arg Val Lys Phe Ser Arg Ser Ala
                645                 650                 655

Asp Ala Pro Ala Tyr Gln Gln Gly Gln Asn Gln Leu Tyr Asn Glu Leu
            660                 665                 670

Asn Leu Gly Arg Arg Glu Glu Tyr Asp Val Leu Asp Lys Arg Arg Gly
        675                 680                 685

Arg Asp Pro Glu Met Gly Gly Lys Pro Arg Arg Lys Asn Pro Gln Glu
    690                 695                 700

Gly Leu Tyr Asn Glu Leu Gln Lys Asp Lys Met Ala Glu Ala Tyr Ser
705                 710                 715                 720

Glu Ile Gly Met Lys Gly Glu Arg Arg Arg Gly Lys Gly His Asp Gly
                725                 730                 735

Leu Tyr Gln Gly Leu Ser Thr Ala Thr Lys Asp Thr Tyr Asp Ala Leu
            740                 745                 750

His Met Gln Ala Leu Pro Pro Arg
        755                 760
```

<210> SEQ ID NO 90
<211> LENGTH: 2280
<212> TYPE: DNA
<213> ORGANISM: Artificial Sequence
<220> FEATURE:
<223> OTHER INFORMATION: D0104 (EF-1a-CD22 (16P17)-TSLPR CD8 BBz)

<400> SEQUENCE: 90

```
atgcttcttt tggtgacttc ccttttgctg tgcgagttgc cacaccccgc cttcctgctt     60

attccccagg tacagcttca acagagtggg ccgggactgg tgaaacactc ccaaacactt    120

tctctgacgt gcgctatatc aggtgactct gtttcatcta attctgctgc gtggaactgg    180

attcgacaat ctcccagtcg cgggttggaa tggctgggac gaacatatta tcggtctaag    240

tggtataacg attatgctgt atctgttaaa tctcgaatta cgattaatcc tgacacctcc    300

aagaaccagt tctccctcca gttgaactca gtcacaccgg aagacactgc ggtctactat    360

tgcgctcaag aagtcgagcc acatgatgca ttcgacatct ggggccaggg aacgatggtc    420

accgtcagca gtggcggcgg cggatctggg ggtggcggtt ctggcggtgg aggatcagac    480

atacaaatga cgcagagtcc ctcaagtgtg tacgcgagtg tgggggataa ggtaactatt    540

acgtgcagag cgtcacagga tgttagtgga tggcttgcct ggtatcagca gaagccaggc    600

cttgctccac agctccttat cagtggtgct tctacacttc agggcgaggt tccgagtaga    660

ttctctggtt ctggatctgg tactgacttc actcttacaa tttcttcttt gcaaccagaa    720

gactttgcga cttattactg ccaacaggcc aaatacttcc cttatacatt tggccaaggt    780

accaagttgg agataaaggg tggaggtggt tcaggcggag gaggctcagg cggaggcggt    840
```

```
agcggcggag gaggaagcgg aggtggcgga tcacaagtca ccctcaaaga gtcagggcca    900

ggaatcctca agccctcaca gactctgtct cttacttgct cattcagcgg attcagcctt    960

tccacctctg gtatgggcgt ggggtggatt aggcaaccta gcggaaaggg gcttgaatgg   1020

ctggcccaca tctggtggga cgacgacaag tactacaacc cctcactgaa gtcccagctc   1080

actatttcca aagatacttc ccggaatcag gtgttcctca agattacctc tgtcgacacc   1140

gctgataccg ccacttacta ttgttcacgc agaccgagag gtaccatgga cgcaatggac   1200

tactggggac agggcaccag cgtgaccgtg tcatctggcg gtggagggtc aggaggtgga   1260

ggtagcggag gcggtgggtc cgacattgtc atgacccagg ccgccagctc cctgagcgct   1320

tcactgggcg acagggtgac catcagctgt cgcgcatcac aagatatctc taagtatctt   1380

aattggtacc agcaaaagcc ggatggaacc gtgaagctgc tgatctacta cacctcacgg   1440

ctgcattctg gagtgcctag ccgctttagc ggatctgggt ccggtactga ctacagcctc   1500

accattagaa accttgaaca ggaggacatc gcaacttatt tctgccaaca ggtctatact   1560

ctgccgtgga ccttcggcgg aggtaccaaa ctggagatta aggcggccgc aacgaccact   1620

cctgcacccc gccctccgac tccggcccca accattgcca gccagcccct gtccctgcgg   1680

ccggaagcct gcagaccggc tgccggcgga gccgtccata cccggggact ggatttcgcc   1740

tgcgatatct atatctgggc accactcgcc ggaacctgtg gagtgctgct gctgtccctt   1800

gtgatcaccc tgtactgcaa gcgcggacgg aagaaactct tgtacatctt caagcagccg   1860

ttcatgcgcc ctgtgcaaac cacccaagaa gaggacgggt gctcctgccg gttcccggaa   1920

gaggaagagg gcggctgcga actgcgcgtg aagttttccc ggtccgccga cgctccggcg   1980

taccagcagg ggcaaaacca gctgtacaac gaacttaacc tcggtcgccg ggaagaatat   2040

gacgtgctgg acaagcggcg gggaagagat cccgagatgg gtggaaagcc gcggcggaag   2100

aaccctcagg agggcttgta caacgagctg caaaaggaca aaatggccga agcctactcc   2160

gagattggca tgaagggaga gcgcagacgc gggaagggac acgatggact gtaccaggga   2220

ctgtcaaccg cgactaagga cacttacgac gccctgcaca tgcaggccct gcccccgcgc   2280
```

```
<210> SEQ ID NO 91
<211> LENGTH: 760
<212> TYPE: PRT
<213> ORGANISM: Artificial Sequence
<220> FEATURE:
<223> OTHER INFORMATION: D0104 (EF-1a-CD22 (16P17)-TSLPR CD8 BBz)

<400> SEQUENCE: 91

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys His Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110
```

```
Pro Glu Asp Thr Ala Val Tyr Tyr Cys Ala Gln Glu Val Glu Pro His
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Asp
145                 150                 155                 160

Ile Gln Met Thr Gln Ser Pro Ser Ser Val Tyr Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
        195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Gly Gly Gly Gly Ser Gly
            260                 265                 270

Gly Gly Gly Ser Gly Gly Gly Gly Ser Gly Gly Gly Gly Ser Gly Gly
        275                 280                 285

Gly Gly Ser Gln Val Thr Leu Lys Glu Ser Gly Pro Gly Ile Leu Lys
    290                 295                 300

Pro Ser Gln Thr Leu Ser Leu Thr Cys Ser Phe Ser Gly Phe Ser Leu
305                 310                 315                 320

Ser Thr Ser Gly Met Gly Val Gly Trp Ile Arg Gln Pro Ser Gly Lys
                325                 330                 335

Gly Leu Glu Trp Leu Ala His Ile Trp Trp Asp Asp Asp Lys Tyr Tyr
            340                 345                 350

Asn Pro Ser Leu Lys Ser Gln Leu Thr Ile Ser Lys Asp Thr Ser Arg
        355                 360                 365

Asn Gln Val Phe Leu Lys Ile Thr Ser Val Asp Thr Ala Asp Thr Ala
    370                 375                 380

Thr Tyr Tyr Cys Ser Arg Arg Pro Arg Gly Thr Met Asp Ala Met Asp
385                 390                 395                 400

Tyr Trp Gly Gln Gly Thr Ser Val Thr Val Ser Ser Gly Gly Gly Gly
                405                 410                 415

Ser Gly Gly Gly Gly Ser Gly Gly Gly Gly Ser Asp Ile Val Met Thr
            420                 425                 430

Gln Ala Ala Ser Ser Leu Ser Ala Ser Leu Gly Asp Arg Val Thr Ile
        435                 440                 445

Ser Cys Arg Ala Ser Gln Asp Ile Ser Lys Tyr Leu Asn Trp Tyr Gln
    450                 455                 460

Gln Lys Pro Asp Gly Thr Val Lys Leu Leu Ile Tyr Tyr Thr Ser Arg
465                 470                 475                 480

Leu His Ser Gly Val Pro Ser Arg Phe Ser Gly Ser Gly Ser Gly Thr
                485                 490                 495

Asp Tyr Ser Leu Thr Ile Arg Asn Leu Glu Gln Glu Asp Ile Ala Thr
            500                 505                 510

Tyr Phe Cys Gln Gln Val Tyr Thr Leu Pro Trp Thr Phe Gly Gly Gly
        515                 520                 525

Thr Lys Leu Glu Ile Lys Ala Ala Ala Thr Thr Thr Pro Ala Pro Arg
```

```
    530                 535                 540

Pro Pro Thr Pro Ala Pro Thr Ile Ala Ser Gln Pro Leu Ser Leu Arg
545                 550                 555                 560

Pro Glu Ala Cys Arg Pro Ala Ala Gly Gly Ala Val His Thr Arg Gly
                565                 570                 575

Leu Asp Phe Ala Cys Asp Ile Tyr Ile Trp Ala Pro Leu Ala Gly Thr
            580                 585                 590

Cys Gly Val Leu Leu Leu Ser Leu Val Ile Thr Leu Tyr Cys Lys Arg
        595                 600                 605

Gly Arg Lys Lys Leu Leu Tyr Ile Phe Lys Gln Pro Phe Met Arg Pro
    610                 615                 620

Val Gln Thr Thr Gln Glu Glu Asp Gly Cys Ser Cys Arg Phe Pro Glu
625                 630                 635                 640

Glu Glu Glu Gly Gly Cys Glu Leu Arg Val Lys Phe Ser Arg Ser Ala
                645                 650                 655

Asp Ala Pro Ala Tyr Gln Gln Gly Gln Asn Gln Leu Tyr Asn Glu Leu
            660                 665                 670

Asn Leu Gly Arg Arg Glu Glu Tyr Asp Val Leu Asp Lys Arg Arg Gly
        675                 680                 685

Arg Asp Pro Glu Met Gly Gly Lys Pro Arg Arg Lys Asn Pro Gln Glu
    690                 695                 700

Gly Leu Tyr Asn Glu Leu Gln Lys Asp Lys Met Ala Glu Ala Tyr Ser
705                 710                 715                 720

Glu Ile Gly Met Lys Gly Glu Arg Arg Arg Gly Lys Gly His Asp Gly
                725                 730                 735

Leu Tyr Gln Gly Leu Ser Thr Ala Thr Lys Asp Thr Tyr Asp Ala Leu
            740                 745                 750

His Met Gln Ala Leu Pro Pro Arg
        755                 760


<210> SEQ ID NO 92
<211> LENGTH: 2286
<212> TYPE: DNA
<213> ORGANISM: Artificial Sequence
<220> FEATURE:
<223> OTHER INFORMATION: D0111 (EF-1a-TSLPR-CD22 (m971) CD8 BBz)

<400> SEQUENCE: 92

atgcttcttt tggtgacttc ccttttgctg tgcgagttgc cacaccccgc cttcctgctt     60

attccccaag tcaccctcaa agagtcaggg ccaggaatcc tcaagccctc acagactctg    120

tctcttactt gctcattcag cggattcagc ctttccacct ctggtatggg cgtggggtgg    180

attaggcaac ctagcggaaa ggggcttgaa tggctggccc acatctggtg ggacgacgac    240

aagtactaca acccctcact gaagtcccag ctcactattt ccaaagatac ttcccggaat    300

caggtgttcc tcaagattac ctctgtcgac accgctgata ccgccactta ctattgttca    360

cgcagaccga gaggtaccat ggacgcaatg gactactggg gacagggcac cagcgtgacc    420

gtgtcatctg gcggtggagg gtcaggaggt ggaggtagcg gaggcggtgg gtccgacatt    480

gtcatgaccc aggccgccag ctccctgagc gcttcactgg gcgacagggt gaccatcagc    540

tgtcgcgcat cacaagatat ctctaagtat cttaattggt accagcaaaa gccggatgga    600

accgtgaagc tgctgatcta ctacacctca cggctgcatt ctggagtgcc tagccgcttt    660

agcggatctg ggtccggtac tgactacagc ctcaccatta gaaaccttga acaggaggac    720

atcgcaactt atttctgcca acaggtctat actctgccgt ggaccttcgg cggaggtacc    780
```

```
aaactggaga ttaagggtgg aggtggttca ggcggaggag gctcaggcgg aggcggtagc    840

ggcggaggag gaagcggagg tggcggatca caggtacaac ttcaacagag tggtccaggg    900

ctggtcaaac cttcccaaac cctttccttg acttgtgcga ttagtggaga ctccgtttcc    960

agcaattctg ccgcctggaa ttggatccgg cagtccccta gtcggggatt ggagtggctt   1020

ggcaggacgt actaccggag taagtggtac aacgattacg ctgtttccgt aaaatctcgc   1080

ataaccatta atcctgacac aagcaaaaac caattttctc ttcagcttaa ttccgttaca   1140

ccagaggaca ccgcggtcta ttactgcgct cgggaagtaa ccggcgattt ggaggatgct   1200

ttcgatattt ggggacaagg cactatggta acagttagca gtggtggagg cggaagtggc   1260

ggaggaggtt ctggtggtgg tggaagtgac atccaaatga cacagagtcc gtcttcactc   1320

agcgctagcg tcggtgatcg cgtaaccata acgtgcaggg caagccaaac gatatggtct   1380

tatcttaatt ggtatcaaca gcgcccaggc aaggcaccaa atcttcttat ctatgcagcg   1440

agcagtctcc agtccggcgt cccgtcccgc ttcagtggga ggggatccgg tacagatttc   1500

actctgacaa tatcctcctt gcaagcagag gacttcgcta cgtactactg ccaacagtca   1560

tactctattc cgcagacatt tggacagggg accaaacttg agatcaaggc ggccgcaacg   1620

accactcctg caccccgccc tccgactccg gccccaacca ttgccagcca gcccctgtcc   1680

ctgcggccgg aagcctgcag accggctgcc ggcggagccg tccatacccg gggactggat   1740

ttcgcctgcg atatctatat ctgggcacca ctcgccggaa cctgtggagt gctgctgctg   1800

tcccttgtga tcaccctgta ctgcaagcgc ggacggaaga aactcttgta catcttcaag   1860

cagccgttca tgcgccctgt gcaaaccacc caagaagagg acgggtgctc ctgccggttc   1920

ccggaagagg aagagggcgg ctgcgaactg cgcgtgaagt tttcccggtc cgccgacgct   1980

ccggcgtacc agcaggggca aaaccagctg tacaacgaac ttaacctcgg tcgccgggaa   2040

gaatatgacg tgctggacaa gcggcgggga agagatcccg agatgggtgg aaagccgcgg   2100

cggaagaacc ctcaggaggg cttgtacaac gagctgcaaa aggacaaaat ggccgaagcc   2160

tactccgaga ttggcatgaa gggagagcgc agacgcggga agggacacga tggactgtac   2220

cagggactgt caaccgcgac taaggacact tacgacgccc tgcacatgca ggccctgccc   2280

ccgcgc                                                              2286
```

<210> SEQ ID NO 93
<211> LENGTH: 762
<212> TYPE: PRT
<213> ORGANISM: Artificial Sequence
<220> FEATURE:
<223> OTHER INFORMATION: D0111 (EF-1a-TSLPR-CD22 (m971) CD8 BBz)

<400> SEQUENCE: 93

```
Met Leu Leu Leu Val Thr Ser Leu Leu Leu Cys Glu Leu Pro His Pro
1               5                   10                  15

Ala Phe Leu Leu Ile Pro Gln Val Thr Leu Lys Glu Ser Gly Pro Gly
            20                  25                  30

Ile Leu Lys Pro Ser Gln Thr Leu Ser Leu Thr Cys Ser Phe Ser Gly
        35                  40                  45

Phe Ser Leu Ser Thr Ser Gly Met Gly Val Gly Trp Ile Arg Gln Pro
    50                  55                  60

Ser Gly Lys Gly Leu Glu Trp Leu Ala His Ile Trp Trp Asp Asp Asp
65                  70                  75                  80

Lys Tyr Tyr Asn Pro Ser Leu Lys Ser Gln Leu Thr Ile Ser Lys Asp
```

```
                85                  90                  95

Thr Ser Arg Asn Gln Val Phe Leu Lys Ile Thr Ser Val Asp Thr Ala
            100                 105                 110

Asp Thr Ala Thr Tyr Tyr Cys Ser Arg Arg Pro Arg Gly Thr Met Asp
        115                 120                 125

Ala Met Asp Tyr Trp Gly Gln Gly Thr Ser Val Thr Val Ser Ser Gly
    130                 135                 140

Gly Gly Gly Ser Gly Gly Gly Gly Ser Gly Gly Gly Gly Ser Asp Ile
145                 150                 155                 160

Val Met Thr Gln Ala Ala Ser Ser Leu Ser Ala Ser Leu Gly Asp Arg
                165                 170                 175

Val Thr Ile Ser Cys Arg Ala Ser Gln Asp Ile Ser Lys Tyr Leu Asn
            180                 185                 190

Trp Tyr Gln Gln Lys Pro Asp Gly Thr Val Lys Leu Leu Ile Tyr Tyr
        195                 200                 205

Thr Ser Arg Leu His Ser Gly Val Pro Ser Arg Phe Ser Gly Ser Gly
    210                 215                 220

Ser Gly Thr Asp Tyr Ser Leu Thr Ile Arg Asn Leu Glu Gln Glu Asp
225                 230                 235                 240

Ile Ala Thr Tyr Phe Cys Gln Gln Val Tyr Thr Leu Pro Trp Thr Phe
                245                 250                 255

Gly Gly Gly Thr Lys Leu Glu Ile Lys Gly Gly Gly Gly Ser Gly Gly
            260                 265                 270

Gly Gly Ser Gly Gly Gly Gly Ser Gly Gly Gly Gly Ser Gly Gly Gly
        275                 280                 285

Gly Ser Gln Val Gln Leu Gln Gln Ser Gly Pro Gly Leu Val Lys Pro
    290                 295                 300

Ser Gln Thr Leu Ser Leu Thr Cys Ala Ile Ser Gly Asp Ser Val Ser
305                 310                 315                 320

Ser Asn Ser Ala Ala Trp Asn Trp Ile Arg Gln Ser Pro Ser Arg Gly
                325                 330                 335

Leu Glu Trp Leu Gly Arg Thr Tyr Tyr Arg Ser Lys Trp Tyr Asn Asp
            340                 345                 350

Tyr Ala Val Ser Val Lys Ser Arg Ile Thr Ile Asn Pro Asp Thr Ser
        355                 360                 365

Lys Asn Gln Phe Ser Leu Gln Leu Asn Ser Val Thr Pro Glu Asp Thr
    370                 375                 380

Ala Val Tyr Tyr Cys Ala Arg Glu Val Thr Gly Asp Leu Glu Asp Ala
385                 390                 395                 400

Phe Asp Ile Trp Gly Gln Gly Thr Met Val Thr Val Ser Ser Gly Gly
                405                 410                 415

Gly Gly Ser Gly Gly Gly Gly Ser Gly Gly Gly Gly Ser Asp Ile Gln
            420                 425                 430

Met Thr Gln Ser Pro Ser Ser Leu Ser Ala Ser Val Gly Asp Arg Val
        435                 440                 445

Thr Ile Thr Cys Arg Ala Ser Gln Thr Ile Trp Ser Tyr Leu Asn Trp
    450                 455                 460

Tyr Gln Gln Arg Pro Gly Lys Ala Pro Asn Leu Leu Ile Tyr Ala Ala
465                 470                 475                 480

Ser Ser Leu Gln Ser Gly Val Pro Ser Arg Phe Ser Gly Arg Gly Ser
                485                 490                 495

Gly Thr Asp Phe Thr Leu Thr Ile Ser Ser Leu Gln Ala Glu Asp Phe
            500                 505                 510
```

```
Ala Thr Tyr Tyr Cys Gln Gln Ser Tyr Ser Ile Pro Gln Thr Phe Gly
        515                 520                 525

Gln Gly Thr Lys Leu Glu Ile Lys Ala Ala Ala Thr Thr Thr Pro Ala
    530                 535                 540

Pro Arg Pro Pro Thr Pro Ala Pro Thr Ile Ala Ser Gln Pro Leu Ser
545                 550                 555                 560

Leu Arg Pro Glu Ala Cys Arg Pro Ala Ala Gly Gly Ala Val His Thr
                565                 570                 575

Arg Gly Leu Asp Phe Ala Cys Asp Ile Tyr Ile Trp Ala Pro Leu Ala
            580                 585                 590

Gly Thr Cys Gly Val Leu Leu Leu Ser Leu Val Ile Thr Leu Tyr Cys
        595                 600                 605

Lys Arg Gly Arg Lys Lys Leu Leu Tyr Ile Phe Lys Gln Pro Phe Met
    610                 615                 620

Arg Pro Val Gln Thr Thr Gln Glu Glu Asp Gly Cys Ser Cys Arg Phe
625                 630                 635                 640

Pro Glu Glu Glu Glu Gly Gly Cys Glu Leu Arg Val Lys Phe Ser Arg
                645                 650                 655

Ser Ala Asp Ala Pro Ala Tyr Gln Gln Gly Gln Asn Gln Leu Tyr Asn
            660                 665                 670

Glu Leu Asn Leu Gly Arg Arg Glu Glu Tyr Asp Val Leu Asp Lys Arg
        675                 680                 685

Arg Gly Arg Asp Pro Glu Met Gly Gly Lys Pro Arg Arg Lys Asn Pro
    690                 695                 700

Gln Glu Gly Leu Tyr Asn Glu Leu Gln Lys Asp Lys Met Ala Glu Ala
705                 710                 715                 720

Tyr Ser Glu Ile Gly Met Lys Gly Glu Arg Arg Arg Gly Lys Gly His
                725                 730                 735

Asp Gly Leu Tyr Gln Gly Leu Ser Thr Ala Thr Lys Asp Thr Tyr Asp
            740                 745                 750

Ala Leu His Met Gln Ala Leu Pro Pro Arg
        755                 760
```

<210> SEQ ID NO 94
<211> LENGTH: 2286
<212> TYPE: DNA
<213> ORGANISM: Artificial Sequence
<220> FEATURE:
<223> OTHER INFORMATION: D0112 (EF-1a-CD22 (m971)-TSLPR CD8 BBz)

<400> SEQUENCE: 94

```
atgcttcttt tggtgacttc ccttttgctg tgcgagttgc cacaccccgc cttcctgctt      60

attccccagg tacaacttca acagagtggt ccagggctgg tcaaaccttc ccaaaccctt     120

tccttgactt gtgcgattag tggagactcc gtttccagca attctgccgc ctggaattgg     180

atccggcagt cccctagtcg ggattggag tggcttggca ggacgtacta ccggagtaag      240

tggtacaacg attacgctgt ttccgtaaaa tctcgcataa ccattaatcc tgacacaagc     300

aaaaaccaat tttctcttca gcttaattcc gttacaccag aggacaccgc ggtctattac     360

tgcgctcggg aagtaaccgg cgatttggag gatgctttcg atatttgggg acaaggcact     420

atggtaacag ttagcagtgg tggaggcgga agtggcggag gaggttctgg tggtggtgga     480

agtgacatcc aaatgacaca gagtccgtct tcactcagcg ctagcgtcgg tgatcgcgta     540

accataacgt gcagggcaag ccaaacgata tggtcttatc ttaattggta tcaacagcgc     600
```

```
ccaggcaagg caccaaatct tcttatctat gcagcgagca gtctccagtc cggcgtcccg    660
tcccgcttca gtgggagggg atccggtaca gatttcactc tgacaatatc ctccttgcaa    720
gcagaggact tcgctacgta ctactgccaa cagtcatact ctattccgca gacatttgga    780
caggggacca aacttgagat caagggtgga ggtggttcag gcggaggagg ctcaggcggt    840
ggcggtagcg gcggaggagg aagcggaggt ggcggatcac aagtcaccct caaagagtca    900
gggccaggaa tcctcaagcc ctcacagact ctgtctctta cttgctcatt cagcggattc    960
agcctttcca cctctggtat gggcgtgggg tggattaggc aacctagcgg aaaggggctt   1020
gaatggctgg cccacatctg gtgggacgac gacaagtact acaacccctc actgaagtcc   1080
cagctcacta tttccaaaga tacttcccgg aatcaggtgt tcctcaagat tacctctgtc   1140
gacaccgctg ataccgccac ttactattgt tcacgcagac cgagaggtac catggacgca   1200
atggactact ggggacaggg caccagcgtg accgtgtcat ctggcggtgg agggtcagga   1260
ggtggaggta gcggaggcgg tgggtccgac attgtcatga cccaggccgc cagctccctg   1320
agcgcttcac tgggcgacag ggtgaccatc agctgtcgcg catcacaaga tatctctaag   1380
tatcttaatt ggtaccagca aaagccggat ggaaccgtga agctgctgat ctactacacc   1440
tcacggctgc attctggagt gcctagccgc tttagcggat ctgggtccgg tactgactac   1500
agcctcacca ttagaaacct tgaacaggag gacatcgcaa cttatttctg ccaacaggtc   1560
tatactctgc cgtggacctt cggcggaggt accaaactgg agattaaggc ggccgcaacg   1620
accactcctg caccccgccc tccgactccg gccccaacca ttgccagcca gcccctgtcc   1680
ctgcggccgg aagcctgcag accggctgcc ggcggagccg tccatacccg gggactggat   1740
ttcgcctgcg atatctatat ctgggcacca ctcgccggaa cctgtggagt gctgctgctg   1800
tcccttgtga tcaccctgta ctgcaagcgc ggacggaaga aactcttgta catcttcaag   1860
cagccgttca tgcgccctgt gcaaaccacc caagaagagg acgggtgctc ctgccggttc   1920
ccggaagagg aagagggcgg ctgcgaactg cgcgtgaagt tttcccggtc cgccgacgct   1980
ccggcgtacc agcaggggca aaaccagctg tacaacgaac ttaacctcgg tcgccgggaa   2040
gaatatgacg tgctggacaa gcggcgggga agagatcccg agatgggtgg aaagccgcgg   2100
cggaagaacc ctcaggaggg cttgtacaac gagctgcaaa aggacaaaat ggccgaagcc   2160
tactccgaga ttggcatgaa gggagagcgc agacgcggga agggacacga tggactgtac   2220
cagggactgt caaccgcgac taaggacact tacgacgccc tgcacatgca ggccctgccc   2280
ccgcgc                                                              2286
```

<210> SEQ ID NO 95
<211> LENGTH: 762
<212> TYPE: PRT
<213> ORGANISM: Artificial Sequence
<220> FEATURE:
<223> OTHER INFORMATION: D0112 (EF-1a-CD22 (m971)-TSLPR CD8 BBz)

<400> SEQUENCE: 95

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60
```

```
Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Glu Val Thr Gly Asp
        115                 120                 125

Leu Glu Asp Ala Phe Asp Ile Trp Gly Gln Gly Thr Met Val Thr Val
    130                 135                 140

Ser Ser Gly Gly Gly Gly Ser Gly Gly Gly Gly Ser Gly Gly Gly Gly
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Arg Ala Ser Gln Thr Ile Trp Ser
            180                 185                 190

Tyr Leu Asn Trp Tyr Gln Gln Arg Pro Gly Lys Ala Pro Asn Leu Leu
        195                 200                 205

Ile Tyr Ala Ala Ser Ser Leu Gln Ser Gly Val Pro Ser Arg Phe Ser
    210                 215                 220

Gly Arg Gly Ser Gly Thr Asp Phe Thr Leu Thr Ile Ser Ser Leu Gln
225                 230                 235                 240

Ala Glu Asp Phe Ala Thr Tyr Tyr Cys Gln Gln Ser Tyr Ser Ile Pro
                245                 250                 255

Gln Thr Phe Gly Gln Gly Thr Lys Leu Glu Ile Lys Gly Gly Gly Gly
            260                 265                 270

Ser Gly Gly Gly Gly Ser Gly Gly Gly Gly Ser Gly Gly Gly Gly Ser
        275                 280                 285

Gly Gly Gly Gly Ser Gln Val Thr Leu Lys Glu Ser Gly Pro Gly Ile
    290                 295                 300

Leu Lys Pro Ser Gln Thr Leu Ser Leu Thr Cys Ser Phe Ser Gly Phe
305                 310                 315                 320

Ser Leu Ser Thr Ser Gly Met Gly Val Gly Trp Ile Arg Gln Pro Ser
                325                 330                 335

Gly Lys Gly Leu Glu Trp Leu Ala His Ile Trp Trp Asp Asp Asp Lys
            340                 345                 350

Tyr Tyr Asn Pro Ser Leu Lys Ser Gln Leu Thr Ile Ser Lys Asp Thr
        355                 360                 365

Ser Arg Asn Gln Val Phe Leu Lys Ile Thr Ser Val Asp Thr Ala Asp
    370                 375                 380

Thr Ala Thr Tyr Tyr Cys Ser Arg Arg Pro Arg Gly Thr Met Asp Ala
385                 390                 395                 400

Met Asp Tyr Trp Gly Gln Gly Thr Ser Val Thr Val Ser Ser Gly Gly
                405                 410                 415

Gly Gly Ser Gly Gly Gly Gly Ser Gly Gly Gly Gly Ser Asp Ile Val
            420                 425                 430

Met Thr Gln Ala Ala Ser Ser Leu Ser Ala Ser Leu Gly Asp Arg Val
        435                 440                 445

Thr Ile Ser Cys Arg Ala Ser Gln Asp Ile Ser Lys Tyr Leu Asn Trp
    450                 455                 460

Tyr Gln Gln Lys Pro Asp Gly Thr Val Lys Leu Leu Ile Tyr Tyr Thr
465                 470                 475                 480
```

```
Ser Arg Leu His Ser Gly Val Pro Ser Arg Phe Ser Gly Ser Gly Ser
                485                 490                 495

Gly Thr Asp Tyr Ser Leu Thr Ile Arg Asn Leu Glu Gln Glu Asp Ile
            500                 505                 510

Ala Thr Tyr Phe Cys Gln Gln Val Tyr Thr Leu Pro Trp Thr Phe Gly
        515                 520                 525

Gly Gly Thr Lys Leu Glu Ile Lys Ala Ala Ala Thr Thr Thr Pro Ala
    530                 535                 540

Pro Arg Pro Pro Thr Pro Ala Pro Thr Ile Ala Ser Gln Pro Leu Ser
545                 550                 555                 560

Leu Arg Pro Glu Ala Cys Arg Pro Ala Ala Gly Gly Ala Val His Thr
                565                 570                 575

Arg Gly Leu Asp Phe Ala Cys Asp Ile Tyr Ile Trp Ala Pro Leu Ala
            580                 585                 590

Gly Thr Cys Gly Val Leu Leu Leu Ser Leu Val Ile Thr Leu Tyr Cys
        595                 600                 605

Lys Arg Gly Arg Lys Lys Leu Leu Tyr Ile Phe Lys Gln Pro Phe Met
    610                 615                 620

Arg Pro Val Gln Thr Thr Gln Glu Glu Asp Gly Cys Ser Cys Arg Phe
625                 630                 635                 640

Pro Glu Glu Glu Glu Gly Gly Cys Glu Leu Arg Val Lys Phe Ser Arg
                645                 650                 655

Ser Ala Asp Ala Pro Ala Tyr Gln Gln Gly Gln Asn Gln Leu Tyr Asn
            660                 665                 670

Glu Leu Asn Leu Gly Arg Arg Glu Glu Tyr Asp Val Leu Asp Lys Arg
        675                 680                 685

Arg Gly Arg Asp Pro Glu Met Gly Gly Lys Pro Arg Arg Lys Asn Pro
    690                 695                 700

Gln Glu Gly Leu Tyr Asn Glu Leu Gln Lys Asp Lys Met Ala Glu Ala
705                 710                 715                 720

Tyr Ser Glu Ile Gly Met Lys Gly Glu Arg Arg Arg Gly Lys Gly His
                725                 730                 735

Asp Gly Leu Tyr Gln Gly Leu Ser Thr Ala Thr Lys Asp Thr Tyr Asp
            740                 745                 750

Ala Leu His Met Gln Ala Leu Pro Pro Arg
        755                 760


<210> SEQ ID NO 96
<211> LENGTH: 2274
<212> TYPE: DNA
<213> ORGANISM: Artificial Sequence
<220> FEATURE:
<223> OTHER INFORMATION: D0205 (EF-1a-CD19 (FMC63)-TSLPR- CD8 BBz)

<400> SEQUENCE: 96

atgttgctgt tggtgacctc cctgctgctg tgcgagttgc cgcaccccgc cttcctgctt      60

attccggata tccagatgac ccagaccacc tcctcgctgt ccgcatcgct gggtgacaga     120

gtgaccatta gctgcagggc ctcccaagat atctcgaaat acctgaactg gtaccaacag     180

aagcctgacg gaacggtcaa gctgctgatc taccatactt caaggctgca ctccggtgtc     240

ccgtccagat tctccggaag cggtagcggc actgactact ccttgaccat cagcaacctc     300

gaacaggaag atatagcaac ttacttctgc cagcagggaa acactctccc gtacactttc     360

ggaggaggaa ccaagctgga gatcacgggt ggcgggggtt cagggggagg tggatccgga     420

ggagggggtt ccgaggtgaa gctgcaggag tcaggacctg gcctcgtcgc cccttcccag     480
```

```
tcgctgtcgg tgacttgcac ggtgtccgga gtgagcctgc ccgactatgg agtgtcctgg    540
atccggcagc cccaagaaa gggcctcgag tggctcggag tgatctgggg gtccgaaact    600
acctactaca actcagccct caagagcaga ctgaccatta tcaaggacaa ctccaagtca    660
caggtctttc tgaagatgaa cagcctccag acagatgata ccgccatcta ctattgtgcc    720
aagcattact actacggggg atcctacgcc atggattact gggggcaggg cacttcggtg    780
actgtgtcgt ccggtggtgg agggtcgggt ggaggaggat caggtggagg cggatccggc    840
ggaggtggtt cgggaggcgg aggctcccag gtgaccctca aggagagcgg gcctgggatc    900
ttgaagccgt cccagaccct gtcgctgacc tgttccttct cgggattttc cctgtcgacc    960
tcgggaatgg gagtgggatg gatcagacag ccttccggga agggcctcga atggctggcc   1020
catatttggt gggatgatga caaatactac aacccgtcac tcaagtccca gctgactatc   1080
tcaaaagaca cctcccggaa ccaggtgttt ctcaagatta ccagcgtgga caccgccgac   1140
actgccacct actactgctc taggaggccc agagggacca tggatgccat ggactactgg   1200
ggtcagggca ctagcgtgac cgtgagctcc ggtggagggg gctccggagg cggcgggtcc   1260
ggtggggggg gctccgatat cgtgatgact caggccgcca gcagcctgtc cgcctccctc   1320
ggggaccgcg tgaccatttc ctgtcgcgcg agccaggata tctctaagta cctgaattgg   1380
tatcaacaaa agcctgacgg cactgtgaag ctgctgatct actatacatc caggctccac   1440
tccggcgtgc ccagccggtt ctccggatcc ggctccggca ccgactactc gcttactatc   1500
cggaaccttg agcaggaaga tatcgccacc tacttctgtc aacaggtcta caccctgcca   1560
tggaccttcg gcggaggaac taaactggag atcaaagcgg ccgcaacgac cactcctgca   1620
ccccgccctc cgactccggc cccaaccatt gccagccagc ccctgtccct gcggccggaa   1680
gcctgcagac cggctgccgg cggagccgtc catacccggg gactggattt cgcctgcgat   1740
atctatatct gggcaccact cgccggaacc tgtggagtgc tgctgctgtc ccttgtgatc   1800
accctgtact gcaagcgcgg acggaagaaa ctcttgtaca tcttcaagca gccgttcatg   1860
cgccctgtgc aaaccaccca agaagaggac gggtgctcct gccggttccc ggaagaggaa   1920
gagggcggct gcgaactgcg cgtgaagttt tcccggtccg ccgacgctcc ggcgtaccag   1980
caggggcaaa accagctgta caacgaactt aacctcggtc gccgggaaga atatgacgtg   2040
ctggacaagc ggcggggaag agatcccgag atgggtggaa agccgcggcg gaagaaccct   2100
caggagggct tgtacaacga gctgcaaaag gacaaaatgg ccgaagccta ctccgagatt   2160
ggcatgaagg gagagcgcag acgcgggaag ggacacgatg gactgtacca gggactgtca   2220
accgcgacta aggacactta cgacgccctg cacatgcagg ccctgccccc gcgc         2274
```

<210> SEQ ID NO 97
<211> LENGTH: 758
<212> TYPE: PRT
<213> ORGANISM: Artificial Sequence
<220> FEATURE:
<223> OTHER INFORMATION: D0205 (EF-1a-CD19 (FMC63)-TSLPR- CD8 BBz)

<400> SEQUENCE: 97

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45
```

```
Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Gly Ser Gly Gly Gly Gly Ser
    130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
    210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Ser Val Thr Val Ser Ser Gly Gly Gly Gly Ser Gly Gly Gly
            260                 265                 270

Gly Ser Gly Gly Gly Gly Ser Gly Gly Gly Gly Ser Gly Gly Gly Gly
        275                 280                 285

Ser Gln Val Thr Leu Lys Glu Ser Gly Pro Gly Ile Leu Lys Pro Ser
    290                 295                 300

Gln Thr Leu Ser Leu Thr Cys Ser Phe Ser Gly Phe Ser Leu Ser Thr
305                 310                 315                 320

Ser Gly Met Gly Val Gly Trp Ile Arg Gln Pro Ser Gly Lys Gly Leu
                325                 330                 335

Glu Trp Leu Ala His Ile Trp Trp Asp Asp Asp Lys Tyr Tyr Asn Pro
            340                 345                 350

Ser Leu Lys Ser Gln Leu Thr Ile Ser Lys Asp Thr Ser Arg Asn Gln
        355                 360                 365

Val Phe Leu Lys Ile Thr Ser Val Asp Thr Ala Asp Thr Ala Thr Tyr
    370                 375                 380

Tyr Cys Ser Arg Arg Pro Arg Gly Thr Met Asp Ala Met Asp Tyr Trp
385                 390                 395                 400

Gly Gln Gly Thr Ser Val Thr Val Ser Ser Gly Gly Gly Gly Ser Gly
                405                 410                 415

Gly Gly Gly Ser Gly Gly Gly Gly Ser Asp Ile Val Met Thr Gln Ala
            420                 425                 430

Ala Ser Ser Leu Ser Ala Ser Leu Gly Asp Arg Val Thr Ile Ser Cys
        435                 440                 445

Arg Ala Ser Gln Asp Ile Ser Lys Tyr Leu Asn Trp Tyr Gln Gln Lys
    450                 455                 460
```

```
Pro Asp Gly Thr Val Lys Leu Leu Ile Tyr Tyr Thr Ser Arg Leu His
465                 470                 475                 480

Ser Gly Val Pro Ser Arg Phe Ser Gly Ser Gly Ser Gly Thr Asp Tyr
                485                 490                 495

Ser Leu Thr Ile Arg Asn Leu Glu Gln Glu Asp Ile Ala Thr Tyr Phe
            500                 505                 510

Cys Gln Gln Val Tyr Thr Leu Pro Trp Thr Phe Gly Gly Gly Thr Lys
        515                 520                 525

Leu Glu Ile Lys Ala Ala Ala Thr Thr Thr Pro Ala Pro Arg Pro Pro
    530                 535                 540

Thr Pro Ala Pro Thr Ile Ala Ser Gln Pro Leu Ser Leu Arg Pro Glu
545                 550                 555                 560

Ala Cys Arg Pro Ala Ala Gly Gly Ala Val His Thr Arg Gly Leu Asp
                565                 570                 575

Phe Ala Cys Asp Ile Tyr Ile Trp Ala Pro Leu Ala Gly Thr Cys Gly
            580                 585                 590

Val Leu Leu Leu Ser Leu Val Ile Thr Leu Tyr Cys Lys Arg Gly Arg
        595                 600                 605

Lys Lys Leu Leu Tyr Ile Phe Lys Gln Pro Phe Met Arg Pro Val Gln
    610                 615                 620

Thr Thr Gln Glu Glu Asp Gly Cys Ser Cys Arg Phe Pro Glu Glu Glu
625                 630                 635                 640

Glu Gly Gly Cys Glu Leu Arg Val Lys Phe Ser Arg Ser Ala Asp Ala
                645                 650                 655

Pro Ala Tyr Gln Gln Gly Gln Asn Gln Leu Tyr Asn Glu Leu Asn Leu
            660                 665                 670

Gly Arg Arg Glu Glu Tyr Asp Val Leu Asp Lys Arg Arg Gly Arg Asp
        675                 680                 685

Pro Glu Met Gly Gly Lys Pro Arg Arg Lys Asn Pro Gln Glu Gly Leu
    690                 695                 700

Tyr Asn Glu Leu Gln Lys Asp Lys Met Ala Glu Ala Tyr Ser Glu Ile
705                 710                 715                 720

Gly Met Lys Gly Glu Arg Arg Arg Gly Lys Gly His Asp Gly Leu Tyr
                725                 730                 735

Gln Gly Leu Ser Thr Ala Thr Lys Asp Thr Tyr Asp Ala Leu His Met
            740                 745                 750

Gln Ala Leu Pro Pro Arg
        755
```

<210> SEQ ID NO 98
<211> LENGTH: 2274
<212> TYPE: DNA
<213> ORGANISM: Artificial Sequence
<220> FEATURE:
<223> OTHER INFORMATION: D0206 (EF-1a-TSLPR-CD19 (FMC63)- CD8 BBz)

<400> SEQUENCE: 98

```
atgttgctgt tggtgacctc cctgctgctg tgcgagttgc cgcaccccgc cttcctgctt      60

attccgcagg tgaccctcaa ggagagcggg cctgggatct tgaagccgtc ccagaccctg     120

tcgctgacct gttccttctc gggattttcc ctgtcgacct cgggaatggg agtgggatgg     180

atcagacagc cttccgggaa gggcctcgaa tggctggccc atatttggtg ggatgatgac     240

aaatactaca acccgtcact caagtcccag ctgactatct caaaagacac ctcccggaac     300

caggtgtttc tcaagattac cagcgtggac accgccgaca ctgccaccta ctactgctct     360
```

```
aggaggccca gagggaccat ggatgccatg gactactggg gtcagggcac tagcgtgacc    420

gtgagctccg gtggaggggg ctccggaggc ggcgggtccg gtgggggggg ctccgatatc    480

gtgatgactc aggccgccag cagcctgtcc gcctccctcg ggaccgcgt gaccatttcc    540

tgtcgcgcga gccaggatat ctctaagtac ctgaattggt atcaacaaaa gcctgacggc    600

actgtgaagc tgctgatcta ctatacatcc aggctccact ccggcgtgcc cagccggttc    660

tccggatccg gctccggcac cgactactcg cttactatcc ggaaccttga gcaggaagat    720

atcgccacct acttctgtca acaggtctac accctgccat ggaccttcgg cggaggaact    780

aaactggaga tcaaaggtgg tggagggtcg ggtggaggag gatcaggtgg aggcggatcc    840

ggcggaggtg gttcgggagg cggaggctcc gatatccaga tgacccagac cacctcctcg    900

ctgtccgcat cgctgggtga cagagtgacc attagctgca gggcctccca agatatctcg    960

aaatacctga actggtacca acagaagcct gacggaacgg tcaagctgct gatctaccat   1020

acttcaaggc tgcactccgg tgtcccgtcc agattctccg gaagcggtag cggcactgac   1080

tactccttga ccatcagcaa cctcgaacag gaagatatag caacttactt ctgccagcag   1140

ggaaacactc tcccgtacac tttcggagga ggaaccaagc tggagatcac gggtggcggg   1200

ggttcagggg gaggtggatc cggaggaggg ggttccgagg tgaagctgca ggagtcagga   1260

cctggcctcg tcgccccttc ccagtcgctg tcggtgactt gcacggtgtc cggagtgagc   1320

ctgcccgact atggagtgtc ctggatccgg cagcccccaa gaaagggcct cgagtggctc   1380

ggagtgatct gggggtccga aactacctac tacaactcag ccctcaagag cagactgacc   1440

attatcaagg acaactccaa gtcacaggtc tttctgaaga tgaacagcct ccagacagat   1500

gataccgcca tctactattg tgccaagcat tactactacg gggatcccta cgccatggat   1560

tactgggggc agggcacttc ggtgactgtg tcgtccgcgg ccgcaacgac cactcctgca   1620

ccccgccctc cgactccggc cccaaccatt gccagccagc ccctgtccct gcggccggaa   1680

gcctgcagac cggctgccgg cggagccgtc catacccggg gactggattt cgcctgcgat   1740

atctatatct gggcaccact cgccggaacc tgtggagtgc tgctgctgtc ccttgtgatc   1800

accctgtact gcaagcgcgg acggaagaaa ctcttgtaca tcttcaagca gccgttcatg   1860

cgccctgtgc aaaccaccca agaagaggac gggtgctcct gccggttccc ggaagaggaa   1920

gagggcggct gcgaactgcg cgtgaagttt tcccggtccg ccgacgctcc ggcgtaccag   1980

caggggcaaa accagctgta caacgaactt aacctcggtc gccgggaaga atatgacgtg   2040

ctggacaagc ggcggggaag agatcccgag atgggtggaa agccgcggcg gaagaaccct   2100

caggagggct tgtacaacga gctgcaaaag gacaaaatgg ccgaagccta ctccgagatt   2160

ggcatgaagg gagagcgcag acgcgggaag ggacacgatg gactgtacca gggactgtca   2220

accgcgacta aggacactta cgacgccctg cacatgcagg ccctgccccc gcgc         2274
```

```
<210> SEQ ID NO 99
<211> LENGTH: 758
<212> TYPE: PRT
<213> ORGANISM: Artificial Sequence
<220> FEATURE:
<223> OTHER INFORMATION: D0206 (EF-1a-TSLPR-CD19 (FMC63)- CD8 BBz)

<400> SEQUENCE: 99

Met Leu Leu Leu Val Thr Ser Leu Leu Leu Cys Glu Leu Pro His Pro
1               5                   10                  15

Ala Phe Leu Leu Ile Pro Gln Val Thr Leu Lys Glu Ser Gly Pro Gly
            20                  25                  30
```

```
Ile Leu Lys Pro Ser Gln Thr Leu Ser Leu Thr Cys Ser Phe Ser Gly
        35                  40                  45

Phe Ser Leu Ser Thr Ser Gly Met Gly Val Gly Trp Ile Arg Gln Pro
    50                  55                  60

Ser Gly Lys Gly Leu Glu Trp Leu Ala His Ile Trp Trp Asp Asp Asp
65                  70                  75                  80

Lys Tyr Tyr Asn Pro Ser Leu Lys Ser Gln Leu Thr Ile Ser Lys Asp
                85                  90                  95

Thr Ser Arg Asn Gln Val Phe Leu Lys Ile Thr Ser Val Asp Thr Ala
            100                 105                 110

Asp Thr Ala Thr Tyr Tyr Cys Ser Arg Arg Pro Arg Gly Thr Met Asp
        115                 120                 125

Ala Met Asp Tyr Trp Gly Gln Gly Thr Ser Val Thr Val Ser Ser Gly
    130                 135                 140

Gly Gly Gly Ser Gly Gly Gly Gly Ser Gly Gly Gly Gly Ser Asp Ile
145                 150                 155                 160

Val Met Thr Gln Ala Ala Ser Ser Leu Ser Ala Ser Leu Gly Asp Arg
                165                 170                 175

Val Thr Ile Ser Cys Arg Ala Ser Gln Asp Ile Ser Lys Tyr Leu Asn
            180                 185                 190

Trp Tyr Gln Gln Lys Pro Asp Gly Thr Val Lys Leu Leu Ile Tyr Tyr
        195                 200                 205

Thr Ser Arg Leu His Ser Gly Val Pro Ser Arg Phe Ser Gly Ser Gly
    210                 215                 220

Ser Gly Thr Asp Tyr Ser Leu Thr Ile Arg Asn Leu Glu Gln Glu Asp
225                 230                 235                 240

Ile Ala Thr Tyr Phe Cys Gln Gln Val Tyr Thr Leu Pro Trp Thr Phe
                245                 250                 255

Gly Gly Gly Thr Lys Leu Glu Ile Lys Gly Gly Gly Gly Ser Gly Gly
            260                 265                 270

Gly Gly Ser Gly Gly Gly Gly Ser Gly Gly Gly Gly Ser Gly Gly Gly
        275                 280                 285

Gly Ser Asp Ile Gln Met Thr Gln Thr Thr Ser Ser Leu Ser Ala Ser
    290                 295                 300

Leu Gly Asp Arg Val Thr Ile Ser Cys Arg Ala Ser Gln Asp Ile Ser
305                 310                 315                 320

Lys Tyr Leu Asn Trp Tyr Gln Gln Lys Pro Asp Gly Thr Val Lys Leu
                325                 330                 335

Leu Ile Tyr His Thr Ser Arg Leu His Ser Gly Val Pro Ser Arg Phe
            340                 345                 350

Ser Gly Ser Gly Ser Gly Thr Asp Tyr Ser Leu Thr Ile Ser Asn Leu
        355                 360                 365

Glu Gln Glu Asp Ile Ala Thr Tyr Phe Cys Gln Gln Gly Asn Thr Leu
    370                 375                 380

Pro Tyr Thr Phe Gly Gly Gly Thr Lys Leu Glu Ile Thr Gly Gly Gly
385                 390                 395                 400

Gly Ser Gly Gly Gly Gly Ser Gly Gly Gly Gly Ser Glu Val Lys Leu
                405                 410                 415

Gln Glu Ser Gly Pro Gly Leu Val Ala Pro Ser Gln Ser Leu Ser Val
            420                 425                 430

Thr Cys Thr Val Ser Gly Val Ser Leu Pro Asp Tyr Gly Val Ser Trp
        435                 440                 445
```

```
Ile Arg Gln Pro Pro Arg Lys Gly Leu Glu Trp Leu Gly Val Ile Trp
    450                 455                 460

Gly Ser Glu Thr Thr Tyr Tyr Asn Ser Ala Leu Lys Ser Arg Leu Thr
465                 470                 475                 480

Ile Ile Lys Asp Asn Ser Lys Ser Gln Val Phe Leu Lys Met Asn Ser
                485                 490                 495

Leu Gln Thr Asp Asp Thr Ala Ile Tyr Tyr Cys Ala Lys His Tyr Tyr
            500                 505                 510

Tyr Gly Gly Ser Tyr Ala Met Asp Tyr Trp Gly Gln Gly Thr Ser Val
        515                 520                 525

Thr Val Ser Ser Ala Ala Ala Thr Thr Thr Pro Ala Pro Arg Pro Pro
    530                 535                 540

Thr Pro Ala Pro Thr Ile Ala Ser Gln Pro Leu Ser Leu Arg Pro Glu
545                 550                 555                 560

Ala Cys Arg Pro Ala Ala Gly Gly Ala Val His Thr Arg Gly Leu Asp
                565                 570                 575

Phe Ala Cys Asp Ile Tyr Ile Trp Ala Pro Leu Ala Gly Thr Cys Gly
            580                 585                 590

Val Leu Leu Leu Ser Leu Val Ile Thr Leu Tyr Cys Lys Arg Gly Arg
        595                 600                 605

Lys Lys Leu Leu Tyr Ile Phe Lys Gln Pro Phe Met Arg Pro Val Gln
    610                 615                 620

Thr Thr Gln Glu Glu Asp Gly Cys Ser Cys Arg Phe Pro Glu Glu Glu
625                 630                 635                 640

Glu Gly Gly Cys Glu Leu Arg Val Lys Phe Ser Arg Ser Ala Asp Ala
                645                 650                 655

Pro Ala Tyr Gln Gln Gly Gln Asn Gln Leu Tyr Asn Glu Leu Asn Leu
            660                 665                 670

Gly Arg Arg Glu Glu Tyr Asp Val Leu Asp Lys Arg Arg Gly Arg Asp
        675                 680                 685

Pro Glu Met Gly Gly Lys Pro Arg Arg Lys Asn Pro Gln Glu Gly Leu
    690                 695                 700

Tyr Asn Glu Leu Gln Lys Asp Lys Met Ala Glu Ala Tyr Ser Glu Ile
705                 710                 715                 720

Gly Met Lys Gly Glu Arg Arg Arg Gly Lys Gly His Asp Gly Leu Tyr
                725                 730                 735

Gln Gly Leu Ser Thr Ala Thr Lys Asp Thr Tyr Asp Ala Leu His Met
            740                 745                 750

Gln Ala Leu Pro Pro Arg
        755
```

<210> SEQ ID NO 100
<211> LENGTH: 2626
<212> TYPE: DNA
<213> ORGANISM: Artificial Sequence
<220> FEATURE:
<223> OTHER INFORMATION: LTG2282 (EF-1a-TSLPR (3G11) CD8 BBz)

<400> SEQUENCE: 100

```
atggcactgc ccgtgaccgc cctgcttctg ccgcttgcac ttctgctgca cgccgctagg     60

ccccaagtca ccctcaaaga gtcagggcca ggaatcctca agccctcaca gactctgtct    120

cttacttgct cattcagcgg attcagcctt tccacctctg gtatgggcgt ggggtggatt    180

aggcaaccta gcggaaaggg gcttgaatgg ctggcccaca tctggtggga cgacgacaag    240

tactacaacc cctcactgaa gtcccagctc actatttcca aagatacttc ccggaatcag    300
```

```
gtgttcctca agattacctc tgtcgacacc gctgataccg ccacttacta ttgttcacgc    360
agaccgagag gtaccatgga cgcaatggac tactggggac agggcaccag cgtgaccgtg    420
tcatctggcg gtggagggtc aggaggtgga ggtagcggag gcggtgggtc cgacattgtc    480
atgacccagg ccgccagcag cctgagcgct tcactgggcg acagggtgac catcagctgt    540
cgcgcatcac aagatatctc taagtatctt aattggtacc agcaaaagcc ggatggaacc    600
gtgaagctgc tgatctacta cacctcacgg ctgcattctg gagtgcctag ccgctttagc    660
ggatctgggt ccggtactga ctacagcctc accattagaa accttgaaca ggaggacatc    720
gcaacttatt tctgccaaca ggtctatact ctgccgtgga ccttcggcgg aggtaccaaa    780
ctggagatta aggcggccgc aactaccacc cctgcccctc ggccgccgac tccggcccca    840
accatcgcaa gccaacccct ctccttgcgc cccgaagctt gccgcccggc cgcgggtgga    900
gccgtgcata cccgggggct ggactttgcc tgcgatatct acatttgggc cccgctggcc    960
ggcacttgcg gcgtgctcct gctgtcgctg gtcatcaccc tttactgcaa gaggggccgg   1020
aagaagctgc tttacatctt caagcagccg ttcatgcggc ccgtgcagac gactcaggaa   1080
gaggacggat gctcgtgcag attccctgag gaggaagagg ggggatgcga actgcgcgtc   1140
aagttctcac ggtccgccga cgcccccgca tatcaacagg gccagaatca gctctacaac   1200
gagctgaacc tgggaaggag agaggagtac gacgtgctgg acaagcgacg cggacgcgac   1260
ccggagatgg gggggaaacc acggcggaaa aaccctcagg aaggactgta caacgaactc   1320
cagaaagaca agatggcgga agcctactca gaaatcggga tgaagggaga gcggaggagg   1380
ggaaagggtc acgacgggct gtaccaggga ctgagcaccg ccactaagga tacctacgat   1440
gccttgcata tgcaagcact cccaccccgg tctagagcta aacgctctgg gtctggtgaa   1500
ggacgaggta gccttcttac gtgcggagac gtggaggaaa acccaggacc catgctgctg   1560
cttgttacaa gccttttgct ctgcgaactc cccatccag ctttctcct gattccaagg    1620
aaggtttgca atggaatcgg tatagggag tttaaggatt cacttagcat aaacgctact    1680
aatattaaac acttcaaaaa ctgtacgagt ataagtggag atcttcacat tttgccggtt   1740
gcattccgag gcgattcatt cacccacacg ccaccgcttg acccacaaga attggatatt   1800
cttaaaaccg ttaaagaaat aacggggttt ttgctcattc aagcgtggcc agaaaatcgc   1860
actgacctcc atgctttcga gaacctggag attataagag gacgaactaa gcagcatggt   1920
caattctccc ttgctgtggt cagcctgaac atcaccagtc ttggtttgcg gtccctcaag   1980
gaaatttcag atggagatgt catcataagc ggcaacaaga atttgtgcta tgcaaatacc   2040
ataaactgga aaaaactgtt tggcacttcc ggccagaaaa ccaagattat ttcaaatcgg   2100
ggtgagaaca gctgcaaagc caccggccag gtttgtcatg ccttgtgctc tccggaaggc   2160
tgttgggggc cagaacccag ggactgcgtc agttgcagaa acgtctcaag aggccgcgaa   2220
tgcgttgaca agtgtaacct ccttgagggt gagccacgag agtttgttga gaacagcgag   2280
tgtatacaat gtcaccctga atgtttgccc caggctatga atataacctg cacaggccgc   2340
gggcctgata actgcatcca gtgtgctcat tacatagatg gacctcactg tgtgaaaacc   2400
tgcccggccg gagttatggg agaaaacaac actctggtgt ggaaatacgc tgatgcaggc   2460
cacgtgtgcc acctttgtca cccgaattgt acatatgggt gtaccggtcc tggacttgaa   2520
ggttgcccta ccaatggccc taaaataccc agtatcgcaa ctggcatggt aggcgctctt   2580
ctcttgctct tggtagttgc tctcggcata ggtcttttta tgtgac                  2626
```

<210> SEQ ID NO 101
<211> LENGTH: 874
<212> TYPE: PRT
<213> ORGANISM: Artificial Sequence
<220> FEATURE:
<223> OTHER INFORMATION: LTG2282 (EF-1a-TSLPR (3G11) CD8 BBz)

<400> SEQUENCE: 101

```
Met Ala Leu Pro Val Thr Ala Leu Leu Leu Pro Leu Ala Leu Leu Leu
1               5                   10                  15

His Ala Ala Arg Pro Gln Val Thr Leu Lys Glu Ser Gly Pro Gly Ile
            20                  25                  30

Leu Lys Pro Ser Gln Thr Leu Ser Leu Thr Cys Ser Phe Ser Gly Phe
        35                  40                  45

Ser Leu Ser Thr Ser Gly Met Gly Val Gly Trp Ile Arg Gln Pro Ser
    50                  55                  60

Gly Lys Gly Leu Glu Trp Leu Ala His Ile Trp Trp Asp Asp Asp Lys
65                  70                  75                  80

Tyr Tyr Asn Pro Ser Leu Lys Ser Gln Leu Thr Ile Ser Lys Asp Thr
                85                  90                  95

Ser Arg Asn Gln Val Phe Leu Lys Ile Thr Ser Val Asp Thr Ala Asp
            100                 105                 110

Thr Ala Thr Tyr Tyr Cys Ser Arg Arg Pro Arg Gly Thr Met Asp Ala
        115                 120                 125

Met Asp Tyr Trp Gly Gln Gly Thr Ser Val Thr Val Ser Ser Gly Gly
    130                 135                 140

Gly Gly Ser Gly Gly Gly Gly Ser Gly Gly Gly Gly Ser Asp Ile Val
145                 150                 155                 160

Met Thr Gln Ala Ala Ser Ser Leu Ser Ala Ser Leu Gly Asp Arg Val
                165                 170                 175

Thr Ile Ser Cys Arg Ala Ser Gln Asp Ile Ser Lys Tyr Leu Asn Trp
            180                 185                 190

Tyr Gln Gln Lys Pro Asp Gly Thr Val Lys Leu Leu Ile Tyr Tyr Thr
        195                 200                 205

Ser Arg Leu His Ser Gly Val Pro Ser Arg Phe Ser Gly Ser Gly Ser
    210                 215                 220

Gly Thr Asp Tyr Ser Leu Thr Ile Arg Asn Leu Glu Gln Glu Asp Ile
225                 230                 235                 240

Ala Thr Tyr Phe Cys Gln Gln Val Tyr Thr Leu Pro Trp Thr Phe Gly
                245                 250                 255

Gly Gly Thr Lys Leu Glu Ile Lys Ala Ala Ala Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365
```

```
Pro Glu Glu Glu Glu Gly Gly Cys Glu Leu Arg Val Lys Phe Ser Arg
    370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg Ser Arg Ala Lys Arg Ser
                485                 490                 495

Gly Ser Gly Glu Gly Arg Gly Ser Leu Leu Thr Cys Gly Asp Val Glu
            500                 505                 510

Glu Asn Pro Gly Pro Met Leu Leu Leu Val Thr Ser Leu Leu Leu Cys
        515                 520                 525

Glu Leu Pro His Pro Ala Phe Leu Leu Ile Pro Arg Lys Val Cys Asn
    530                 535                 540

Gly Ile Gly Ile Gly Glu Phe Lys Asp Ser Leu Ser Ile Asn Ala Thr
545                 550                 555                 560

Asn Ile Lys His Phe Lys Asn Cys Thr Ser Ile Ser Gly Asp Leu His
                565                 570                 575

Ile Leu Pro Val Ala Phe Arg Gly Asp Ser Phe Thr His Thr Pro Pro
            580                 585                 590

Leu Asp Pro Gln Glu Leu Asp Ile Leu Lys Thr Val Lys Glu Ile Thr
        595                 600                 605

Gly Phe Leu Leu Ile Gln Ala Trp Pro Glu Asn Arg Thr Asp Leu His
    610                 615                 620

Ala Phe Glu Asn Leu Glu Ile Ile Arg Gly Arg Thr Lys Gln His Gly
625                 630                 635                 640

Gln Phe Ser Leu Ala Val Val Ser Leu Asn Ile Thr Ser Leu Gly Leu
                645                 650                 655

Arg Ser Leu Lys Glu Ile Ser Asp Gly Asp Val Ile Ile Ser Gly Asn
            660                 665                 670

Lys Asn Leu Cys Tyr Ala Asn Thr Ile Asn Trp Lys Lys Leu Phe Gly
        675                 680                 685

Thr Ser Gly Gln Lys Thr Lys Ile Ile Ser Asn Arg Gly Glu Asn Ser
    690                 695                 700

Cys Lys Ala Thr Gly Gln Val Cys His Ala Leu Cys Ser Pro Glu Gly
705                 710                 715                 720

Cys Trp Gly Pro Glu Pro Arg Asp Cys Val Ser Cys Arg Asn Val Ser
                725                 730                 735

Arg Gly Arg Glu Cys Val Asp Lys Cys Asn Leu Leu Glu Gly Glu Pro
            740                 745                 750

Arg Glu Phe Val Glu Asn Ser Glu Cys Ile Gln Cys His Pro Glu Cys
        755                 760                 765

Leu Pro Gln Ala Met Asn Ile Thr Cys Thr Gly Arg Gly Pro Asp Asn
    770                 775                 780

Cys Ile Gln Cys Ala His Tyr Ile Asp Gly Pro His Cys Val Lys Thr
```

-continued

```
785                 790                 795                 800

Cys Pro Ala Gly Val Met Gly Glu Asn Asn Thr Leu Val Trp Lys Tyr
                805                 810                 815

Ala Asp Ala Gly His Val Cys His Leu Cys His Pro Asn Cys Thr Tyr
            820                 825                 830

Gly Cys Thr Gly Pro Gly Leu Glu Gly Cys Pro Thr Asn Gly Pro Lys
        835                 840                 845

Ile Pro Ser Ile Ala Thr Gly Met Val Gly Ala Leu Leu Leu Leu Leu
    850                 855                 860

Val Val Ala Leu Gly Ile Gly Leu Phe Met
865                 870
```